(12) United States Patent
Jun et al.

(10) Patent No.: US 12,378,228 B2
(45) Date of Patent: Aug. 5, 2025

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Ji-Song Jun, Gyeonggi-do (KR); Chi-Sik Kim, Gyeonggi-do (KR); Jin-Ri Hong, Gyeonggi-do (KR); Kyoung-Jin Park, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 902 days.

(21) Appl. No.: 17/318,973

(22) Filed: May 12, 2021

(65) Prior Publication Data

US 2021/0363133 A1    Nov. 25, 2021

(30) Foreign Application Priority Data

May 13, 2020  (KR) .................. 10-2020-0057013
Mar. 15, 2021  (KR) .................. 10-2021-0033234

(51) Int. Cl.
| | | |
|---|---|---|
| *C07D 405/04* | (2006.01) | |
| *C07D 251/24* | (2006.01) | |
| *C07D 403/04* | (2006.01) | |
| *C07D 405/10* | (2006.01) | |
| *C07D 409/04* | (2006.01) | |
| *C07D 409/10* | (2006.01) | |
| *C07D 495/04* | (2006.01) | |
| *H10K 50/11* | (2023.01) | |
| *H10K 85/30* | (2023.01) | |
| *H10K 85/60* | (2023.01) | |

(52) U.S. Cl.
CPC .......... *C07D 405/04* (2013.01); *C07D 409/04* (2013.01); *C07D 495/04* (2013.01); *H10K 85/615* (2023.02); *H10K 85/654* (2023.02); *H10K 85/6572* (2023.02); *H10K 85/6574* (2023.02); *H10K 85/6576* (2023.02)

(58) Field of Classification Search
None
See application file for complete search history.

(56) References Cited

U.S. PATENT DOCUMENTS

2017/0213968 A1    7/2017  Park et al.
2017/0279056 A1*   9/2017  Kim ............... H10K 85/626
2021/0179596 A1    6/2021  Park et al.

FOREIGN PATENT DOCUMENTS

| KR | 2015074603 A | * | 7/2015 | ........... C07D 209/82 |
|---|---|---|---|---|
| KR | 20150074603 A | | 7/2015 | |
| WO | 2015099507 A1 | | 7/2015 | |

OTHER PUBLICATIONS

Search Report from China National Intellectual Property Administration for China Patent application No. 202110527246.4; Application Date: May 12, 2021.

* cited by examiner

*Primary Examiner* — Ha S Nguyen
(74) *Attorney, Agent, or Firm* — G. Creston Campbell

(57) ABSTRACT

The present disclosure relates to a plurality of host materials comprising at least one first host compound represented by formula 1 and at least one second host compound represented by formula 2 and an organic electroluminescent device comprising the same. By comprising the host materials according to the present disclosure, an organic electroluminescent device having low driving voltage and/or high luminous efficiency and/or long lifespan can be provided.

10 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

An organic electroluminescent device (OLED) was first developed by Eastman Kodak in 1987, by using small aromatic diamine molecules and aluminum complexes as materials for forming a light-emitting layer [Appl. Phys. Lett. 51, 913, 1987].

An OLED changes electric energy into light by applying electricity to an organic electroluminescent material, and commonly comprises an anode, a cathode, and an organic layer formed between the two electrodes.

The most important factor determining luminous efficiency in an OLED is light-emitting materials. The light-emitting material is classified into a host material and a dopant material in a functional aspect. A light-emitting material can be used as a combination of a host and a dopant to improve color purity, luminous efficiency, and stability. Generally, a device having excellent electroluminescent (EL) characteristics has a structure comprising a light-emitting layer formed by doping a dopant to a host. When using such a dopant/host material system as a light-emitting material, their selection is important since host materials greatly influence the efficiency and lifespan of the EL device.

Recently, an urgent task is the development of an OLED having high efficiency and long lifespan. In particular, the development of highly excellent light-emitting material over conventional light-emitting materials is urgently required, considering the EL properties necessary for medium and large-sized OLED panels.

Korean Patent Application Laid-Open No. 2015-0074603 A discloses an organic light emitting device comprising a fluorene-based compound in the light-emitting layer. However, said reference does not specifically disclose a specific combination of host materials as described in the present disclosure. In addition, there is still a need for development of a light-emitting material having improved performances, such as improved driving voltage, luminous efficiency, power efficiency and/or lifespan properties, compared to the conventional specific combination of compounds disclosed in said reference.

DISCLOSURE OF THE INVENTION

Problems to be Solved

The object of the present disclosure is firstly, to provide a plurality of host materials which is able to produce an organic electroluminescent device having low driving voltage and/or high luminous efficiency and/or long lifespan, and secondly, to provide an organic electroluminescent device comprising the host materials.

Solution to Problems

As a result of intensive studies to solve the technical problem above, the present inventors found that the aforementioned objective can be achieved by a plurality of host materials comprising a first host material comprising a compound represented by the following formula 1 and a second host material comprising a compound represented by the following formula 2, so that the present invention was completed.

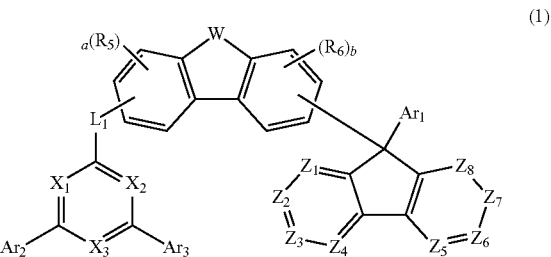

(1)

In formula 1,
W represents O, S, $CR_1R_2$, or $-N-L_2-R_3$;
$Z_1$ to $Z_8$ each independently represent, $CR_4$ or N;
$X_1$ to $X_3$ each independently represent, $CR_7$ or N;
$L_1$ and $L_2$ each independently represent, a single bond, a substituted or unsubstituted (C6-C30)arylene, or a substituted or unsubstituted (3- to 30-membered)heteroarylene;
$Ar_1$ to $Ar_3$ each independently represent, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;
$R_1$ to $R_7$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30) alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to the adjacent substituents to form a ring(s);

a and b each independently represent, an integer of 1 to 3; and when a and b are an integer of 2 or more, each of $R_5$ and each of $R_6$ may be the same or different;

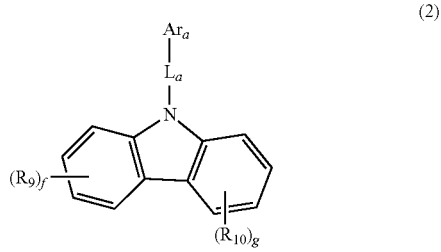

(2)

in formula 2, $L_a$ represents a single bond, a substituted or unsubstituted (C6-C30)arylene, or a substituted or unsubstituted (3- to 30-membered)heteroarylene;

$Ar_a$ represents a substituted or unsubstituted (C6-C30)aryl, or a substituted or unsubstituted (3- to 30-membered)heteroaryl;

$R_9$ and $R_{10}$ each independently represent, hydrogen, deuterium, halogen, cyano, a substituted or unsubstituted (C1-C30)alkyl, a substituted or unsubstituted (C6-C30)aryl, a substituted or unsubstituted (3- to 50-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, a substituted or unsubstituted mono- or di-(C6-C30)arylamino, a substituted or unsubstituted mono- or di-(3- to 30-membered)heteroarylamino, or a substituted or unsubstituted (C6-C30)aryl(3- to 30-membered)heteroarylamino; or may be linked to the adjacent substituents to form a ring(s);

f and g each independently represent, an integer of 1 to 4; and when f and g are an integer of 2 or more, each of $R_9$ and each of $R_{10}$ may be the same or different.

Advantageous Effects of Invention

By using the plurality of host materials according to the present disclosure, an organic electroluminescent device having low driving voltage and/or high luminous efficiency and/or long lifespan can be prepared.

EMBODIMENTS OF THE INVENTION

Hereinafter, the present disclosure will be described in detail. However, the following description is intended to explain the invention, and is not meant in any way to restrict the scope of the invention.

The present disclosure relates to a plurality of host materials comprising at least one first host material represented by the formula 1 and at least one second host material represented by the formula 2, and an organic electroluminescent device comprising the host materials.

In addition, the present disclosure relates to an organic electroluminescent compound represented by formula 1-1-1, and an organic electroluminescent device comprising the same.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, or an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such at least two compounds may be comprised in the same layer or different layers, and may be mixture-evaporated or co-evaporated, or may be individually evaporated.

The term "a plurality of host materials" in the present disclosure means an organic electroluminescent material comprising a combination of at least two host materials. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The at least two compounds comprised in a plurality of host materials may be comprised together in one light-emitting layer, or may each be comprised in separate light-emitting layers. When at least two host materials are comprised in one layer, the at least two host materials may be mixture-evaporated to form a layer or may be individually and simultaneously co-evaporated to form a layer.

The term "(C1-C30)alkyl" in the present disclosure is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. Herein, the term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(C6-C30)aryl(ene)" in the present disclosure is a monocyclic or fused ring radical derived from an aromatic hydrocarbon having 6 to 30 ring backbone carbon atoms, in which the number of the ring backbone carbon atoms is preferably 6 to 20, more preferably 6 to 15, and may be partially saturated. The aryl may comprise a spiro structure. Examples of the aryl specifically include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, tetramethyl-dihydrophenanthrenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-8-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc. Herein, "(3- to 30-membered)heteroaryl(ene)" is an aryl having 3 to 30 ring backbone atoms including at least one, preferably 1 to 4 heteroatoms selected from the group consisting of B, N, O, S, Si, P, Se, and Ge, in which the number of ring backbone atoms is preferably 3 to 30, more preferably 5 to 20. The above heteroaryl may be a monocyclic ring, or a fused ring condensed with at least one benzene ring; and may be partially saturated. Also, the above heteroaryl or heteroarylene herein may be one formed by linking at least one heteroaryl or aryl group to a heteroaryl group via a single bond(s) and may comprise a spiro structure. Examples of the heteroaryl specifically may include a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, dibenzoselenophenyl, benzofuroquinolinyl, benzofuroquinazolinyl, benzofuronaphthiridinyl, benzofuropyrimidinyl, naphthofuropyrimidinyl, benzothienoquinolinyl, benzothienoquinazolinyl, benzothienonaphthiridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acridinyl, silafluorenyl, germafluorenyl, benzotriazolyl, phenazinyl, imidazopyridinyl, chromenoquinazolinyl, thiochromenoquinazolinyl, dimethylbenzoperimidinyl, indolocarbazolyl, indenocarbazolyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazol-1-yl, azacarbazol-2-yl, azacarbazol-3-yl, azacarbazol-4-yl, azacarbazol-5-yl, azacarbazol-6-yl, azacarbazol-7-yl, azacarbazol-8-yl, azacarbazol-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Herein, the term "a fused ring of (C3-C30) aliphatic ring and (C6-C30) aromatic ring" means a ring formed by fusing at least one aliphatic ring having 3 to 30 ring backbone carbon atoms in which the carbon atoms number is preferably 3 to 25, more preferably 3 to 18, and at least one aromatic ring having 6 to 30 ring backbone carbon atoms in which the carbon atoms number is preferably 6 to 25, more preferably 6 to 18. For example, the fused ring may be a fused ring of at least one benzene and at least one cyclohexane, or a fused ring of at least one naphthalene and at least one cyclopentane, etc. Herein, the carbon atoms in the fused ring of (C3-C30) aliphatic ring and (C6-C30) aromatic ring may be replaced with at least one heteroatoms selected from B, N, O, S, Si and P, preferably at least one heteroatoms selected from N, O and S. The term "Halogen" in the present disclosure includes F, Cl, Br, and I.

In addition, "ortho (o)," "meta (m)," and "para (p)" in the present disclosure are meant to signify the substitution position of all substituents. Ortho position is a compound with substituents, which are adjacent to each other, i.e., at the 1 and 2 positions on benzene. Meta position is the next substitution position of the immediately adjacent substitution position, i.e., a compound with substituents at the 1 and 3 positions on benzene. Para position is the next substitution position of the meta position, i.e., a compound with substituents at the 1 and 4 positions on benzene.

Herein, "a ring formed in linking to an adjacent substituent" means a substituted or unsubstituted (3- to 30-membered) mono- or polycyclic, alicyclic, aromatic ring, or a combination thereof, formed by linking or fusing two or more adjacent substituents, preferably may be a substituted or unsubstituted (5- to 25-membered) mono- or polycyclic, alicyclic, aromatic ring, or a combination thereof. Further, the formed ring may be included at least one heteroatom selected from the group consisting of B, N, O, S, Si and P, preferably, N, O and S. According to one embodiment of the present disclosure, the number of atoms in the ring skeleton is 5 to 20; according to another embodiment of the present disclosure, the number of atoms in the ring skeleton is 5 to 15. In one embodiment, the fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, a substituted or unsubstituted carbazole ring, etc.

In addition, "substituted" in the expression "substituted or unsubstituted" means that a hydrogen atom in a certain functional group is replaced with another atom or functional group, i.e., a substituent, and substituted with a group to which two or more substituents are connected among the substituents. For example, "a substituent to which two or more substituents are connected" may be pyridine-triazine. That is, pyridine-triazine may be heteroaryl or may be interpreted as a substituent in which two heteroaryls are connected. Preferably, the substituent of the substituted (C1-C30)alkyl, the substituted (C6-C30)aryl(ene), the substituted (3- to 30-membered)heteroaryl(ene), the substituted (C3-C30)cycloalkyl, the substituted (C1-C30)alkoxy, the substituted fused ring of (C3-C30) aliphatic ring and (C6-C30) aromatic ring, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C2-C30)alkenylamino, the substituted (C1-C30)alkyl(C2-C30)alkenylamino, the substituted mono- or di-(C6-C30)arylamino, the substituted (C1-C30)alkyl(C6-C30)arylamino, the substituted mono- or di-(3- to 30-membered)heteroarylamino, the substituted (C1-C30)alkyl(3- to 30-membered)heteroarylamino, the substituted (C2-C30)alkenyl(C6-C30)arylamino, the substituted (C2-C30)alkenyl(3- to 30-membered)heteroarylamino, and the substituted (C6-C30)aryl(3- to 30-membered)heteroarylamino in the formulas of the present disclosure, each independently represents at least one selected from the group consisting of deuterium, halogen, cyano, carboxyl, nitro, hydroxy, phosphine oxide, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (5- to 30-membered)heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, a fused ring of (C3-C30) aliphatic ring and (C6-C30) aromatic ring, amino, mono- or di-(C1-C30)alkylamino, mono- or di-(C2-C30)alkenylamino, (C1-C30)alkyl(C2-C30)alkenylamino, a substituted or unsubstituted mono- or di-(C6-C30)arylamino, (C1-C30)alkyl(C6-C30)arylamino, mono- or di-(3- to 30-membered)heteroarylamino, (C1-C30)alkyl(3- to 30-membered)heteroarylamino, (C2-C30)alkenyl(C6-C30)arylamino, (C2-C30)alkenyl(3- to 30-membered)heteroarylamino, (C6-C30)aryl(3- to 30-membered)heteroarylamino, (C1-C30)alkylcarbonyl, (C1-C30)alkoxycarbonyl, (C6-C30)arylcarbonyl, (C6-C30)arylphosphinyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30)aryl. For example, the substituents may be deuterium, phenyl, biphenyl, naphthyl, or carbazolyl, etc.

Hereinafter, the host materials according to one embodiment will be described.

The plurality of host materials according to one embodiment comprise a first host material comprising a compound represented by the above formula 1 and a second host material comprising a compound represented by the above formula 2; and the plurality of host materials may be contained in the light-emitting layer of an organic electroluminescent device according to one embodiment.

The first host material as the host material according to one embodiment may be comprised a compound represented by the following formula 1.

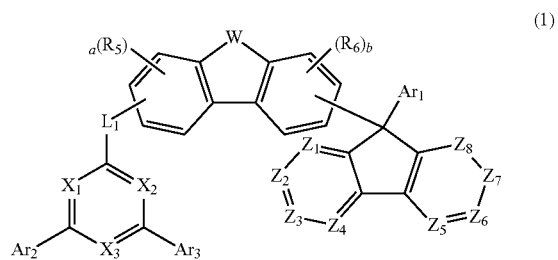

In formula 1,

W represents O, S, $CR_1R_2$, or $-N-L_2-R_3$;

$Z_1$ to $Z_8$ each independently represent, $CR_a$ or N;

$X_1$ to $X_3$ each independently represent, $CR_7$ or N;

$L_1$ and $L_2$ each independently represent, a single bond, a substituted or unsubstituted (C6-C30)arylene, or a substituted or unsubstituted (3- to 30-membered)heteroarylene;

$Ar_1$ to $Ar_3$ each independently represent, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

$R_1$ to $R_7$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to the adjacent substituents to form a ring(s);

a and b each independently represent, an integer of 1 to 3; and when a and b are an integer of 2 or more, each of $R_5$ and each of $R_6$ may be the same or different.

In one embodiment, W may be O, S, $CR_1R_2$, or —N-$L_2$-$R_3$.

$R_1$ to $R_3$ according to one embodiment each independently may be hydrogen, a substituted or unsubstituted (C1-C30)alkyl, or a substituted or unsubstituted (C6-C30)aryl, preferably hydrogen, a substituted or unsubstituted (C1-C10)alkyl, or a substituted or unsubstituted (C6-C25)aryl, more preferably, hydrogen, a substituted or unsubstituted (C1-C4)alkyl, or a substituted or unsubstituted (C6-C18)aryl. For example, $R_1$ to $R_3$ each independently may be a substituted or unsubstituted methyl, phenyl unsubstituted or substituted with naphthyl, a substituted or unsubstituted naphthyl, a substituted or unsubstituted m-biphenyl, a substituted or unsubstituted p-biphenyl, or a substituted or unsubstituted m-terphenyl.

$L_2$ according to one embodiment may be a single bond, or a substituted or unsubstituted (C6-C30)arylene, preferably, a single bond or a substituted or unsubstituted (C6-C25) arylene, more preferably, a single bond or a substituted or unsubstituted (C6-C18)arylene. For example, $L_2$ may be a substituted or unsubstituted phenylene or a substituted or unsubstituted biphenylene.

In one embodiment, $Z_1$ to $Z_8$ each independently may be $CR_4$ or N, preferably, all of $Z_1$ to $Z_8$ may be $CR_4$.

$R_4$ according to one embodiment may be hydrogen, deuterium, or may be linked to the adjacent substituents to form a ring(s), preferably, hydrogen, deuterium, or may be linked to the adjacent $R_4$(s) to form a substituted or unsubstituted (5- to 30-membered) mono- or polycyclic, alicyclic, aromatic ring, or a combination thereof, more preferably, hydrogen or deuterium, or may be linked to the adjacent $R_4$(s) to form a substituted or unsubstituted (5- to 25-membered) mono- or polycyclic, aromatic ring, or a combination thereof. For example, $R_4$ may be hydrogen, deuterium, or may be linked to the adjacent substituents to form a benzene ring, for example, a substituted or unsubstituted benzofluorene ring by fusing with a fluorine ring.

In one embodiment, $Ar_1$ may be a substituted or unsubstituted (C6-C30)aryl, preferably, a substituted or unsubstituted (C6-C25)aryl, more preferably, a substituted or unsubstituted (C6-C18)aryl. For example, $Ar_1$ may be a substituted or unsubstituted phenyl, a substituted or unsubstituted m-biphenyl, a substituted or unsubstituted p-biphenyl, or a substituted or unsubstituted m-terphenyl.

In one embodiment, $L_1$ may be a single bond, or a substituted or unsubstituted (C6-C30)arylene, preferably, a single bond or a substituted or unsubstituted (C6-C25) arylene, more preferably, a single bond or a substituted or unsubstituted (C6-C18)arylene. For example, $L_1$ may be a single bond or, a substituted or unsubstituted phenylene, a substituted or unsubstituted naphthylene, or a substituted or unsubstituted m-biphenylene.

In one embodiment, $Ar_2$ and $Ar_3$ each independently may be a substituted or unsubstituted (C6-C30)aryl, preferably, a substituted or unsubstituted (C6-C25)aryl, more preferably, a substituted or unsubstituted (C6-C18)aryl. For example, $Ar_2$ and $Ar_3$ each independently may be phenyl unsubstituted or substituted with naphthyl, a substituted or unsubstituted naphthyl, a substituted or unsubstituted m-biphenyl, a substituted or unsubstituted p-biphenyl, or a substituted or unsubstituted m-terphenyl.

In one embodiment, $X_1$ to $X_3$ each independently may be $CR_7$ or N, preferably, at least one of $X_1$ to $X_3$ may be N, more preferably, at least two of $X_1$ to $X_3$ may be N, even more preferably, all of $X_1$ to $X_3$ may be N.

In one embodiment, $R_5$ to $R_7$ each independently may be hydrogen, deuterium, halogen, cyano, or a substituted or unsubstituted (C1-C30)alkyl, preferably, hydrogen, deuterium, halogen, or cyano, more preferably, hydrogen or deuterium.

The compound represented by the above formula 1 may be represented by any one of the following formulas 1-1 to 1-16.

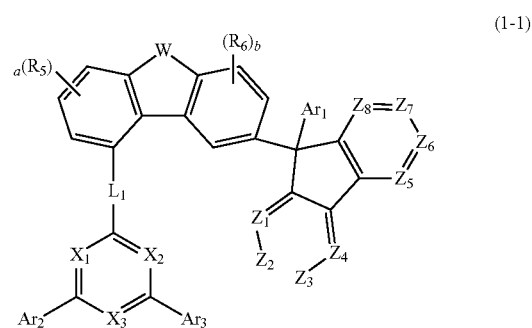

(1-1)

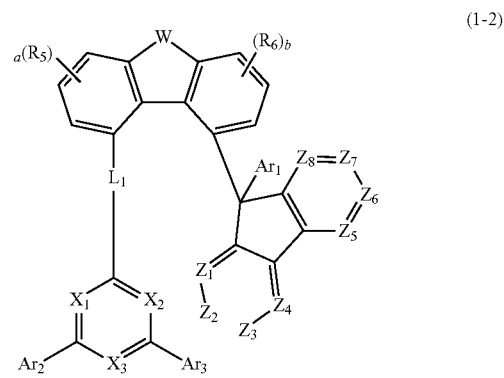

(1-2)

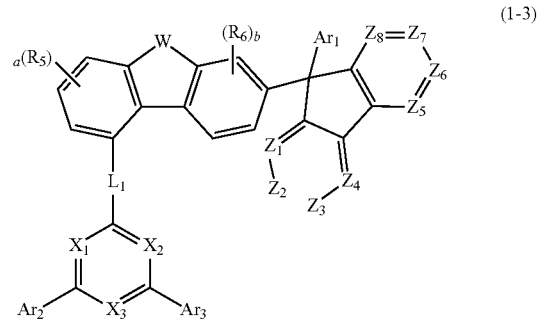

(1-3)

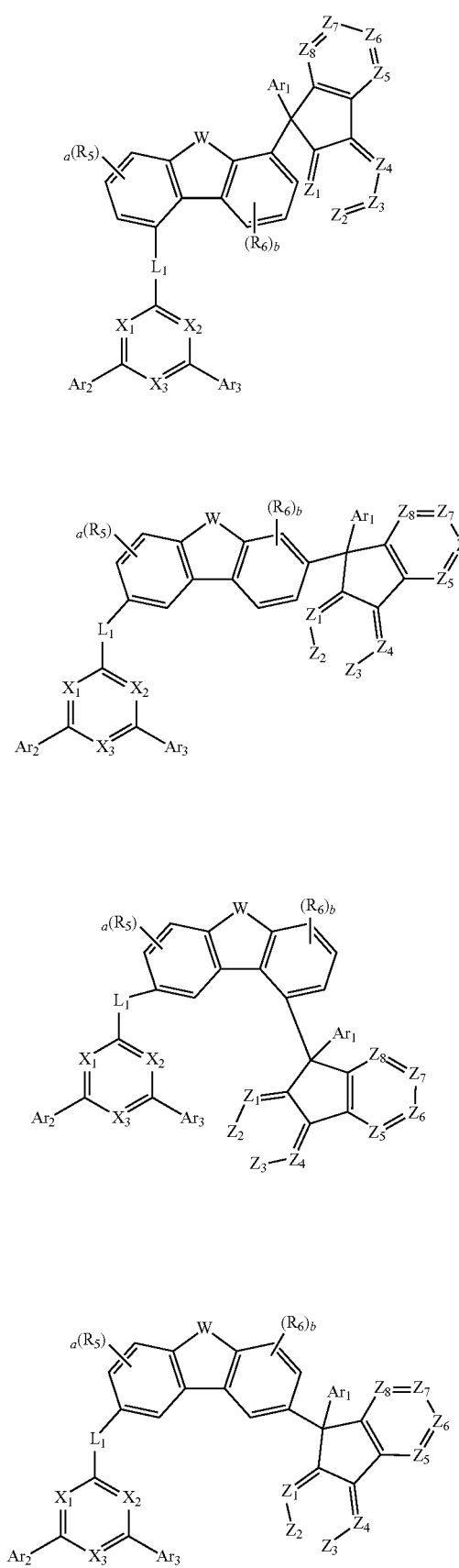
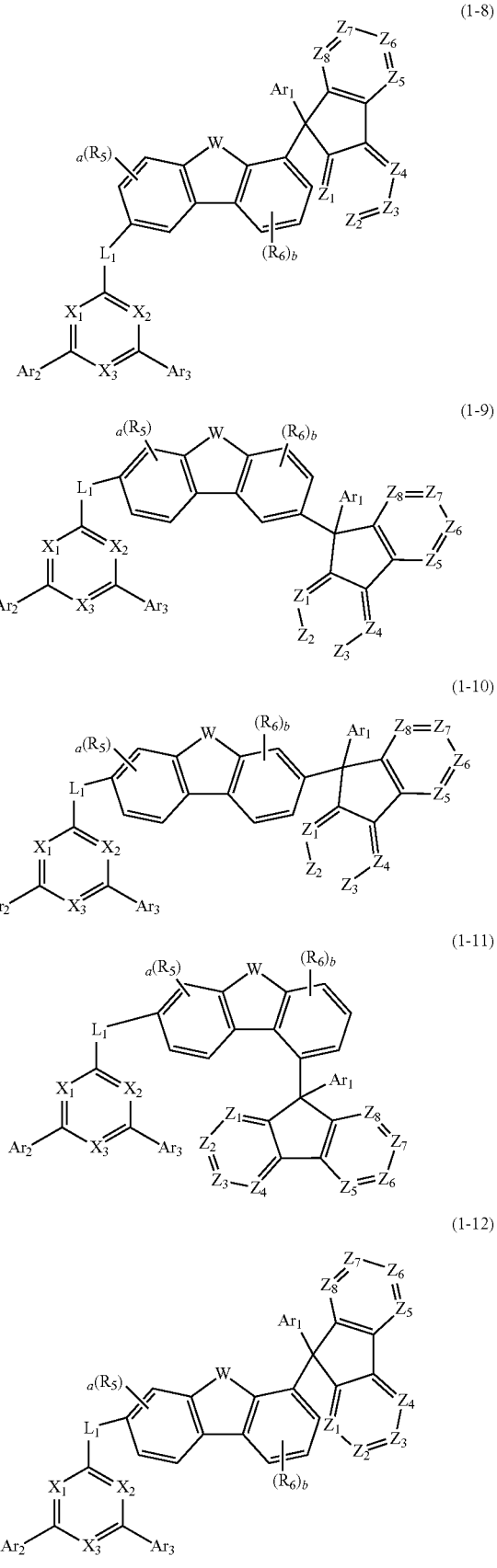

-continued
(1-13)
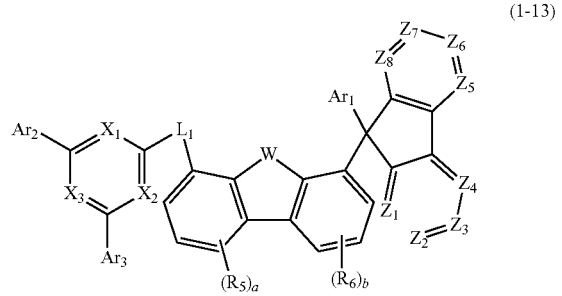
(1-14)
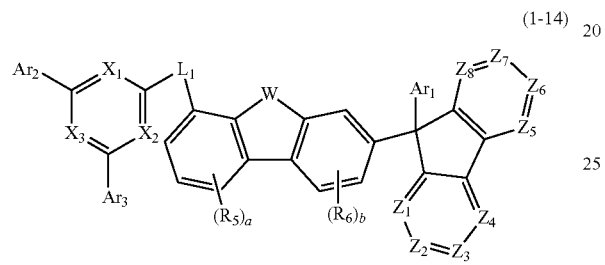
(1-15)
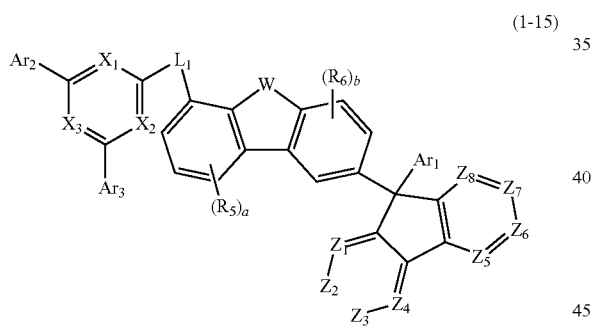
(1-16)
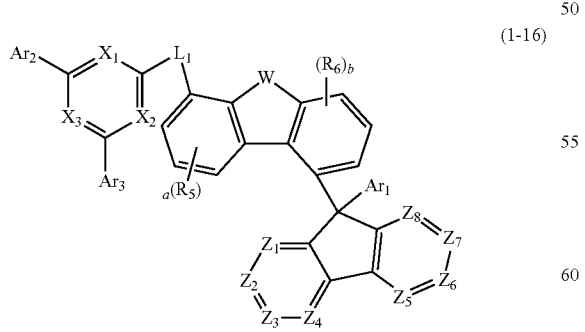
In formulas 1-1 to 1-16,
W, $Z_1$ to $Z_8$, $X_1$ to $X_3$, $Ar_1$ to $Ar_3$, $L_1$, $R_5$, $R_6$, a, and b are as defined in the formula 1.
In one embodiment, the first host material represented by the above formula 1 may be more specifically illustrated b the following compounds, but is not limited thereto.
H1-1
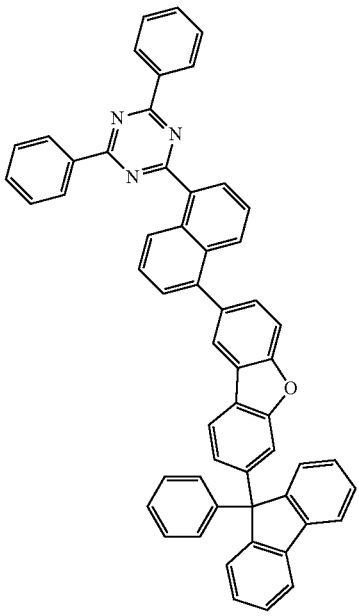
H1-2
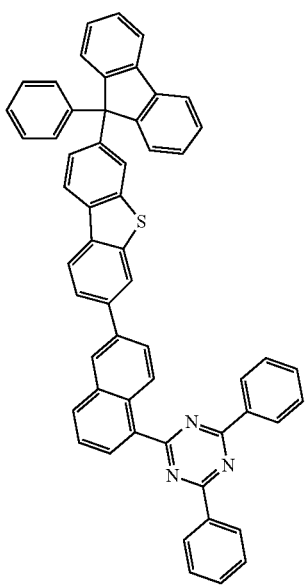

H1-3
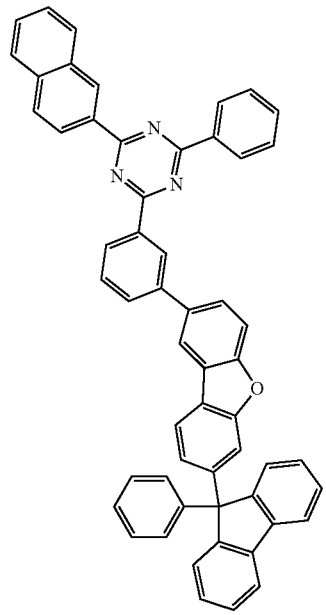
H1-4
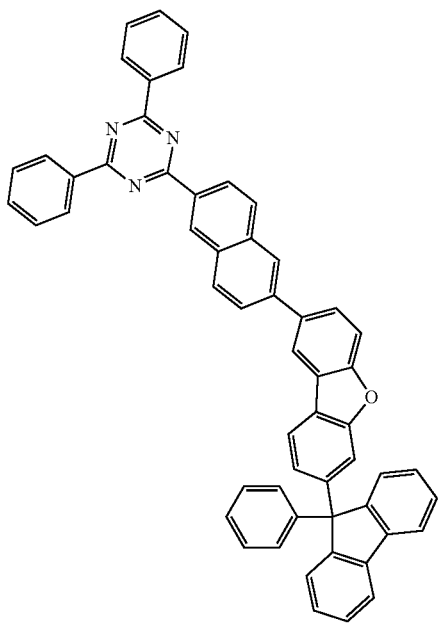
H1-5
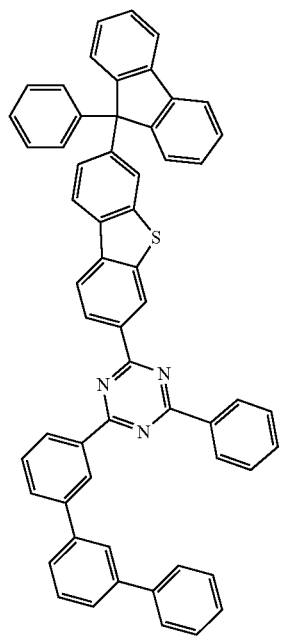
H1-6
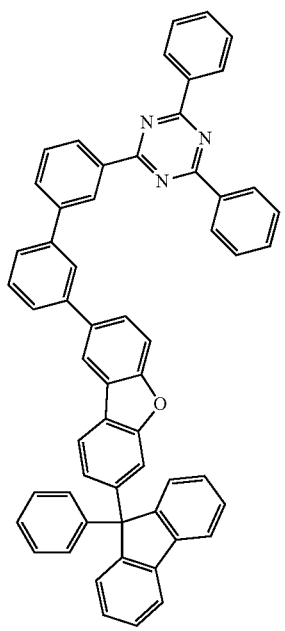

H1-7
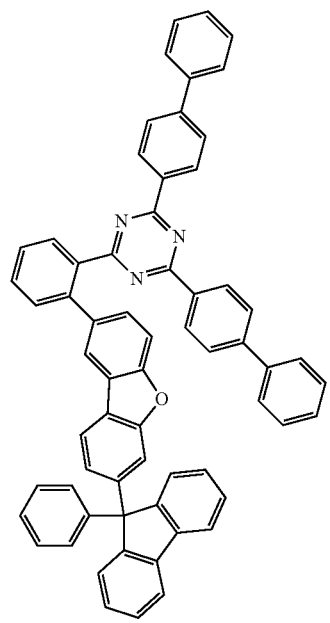
H1-8
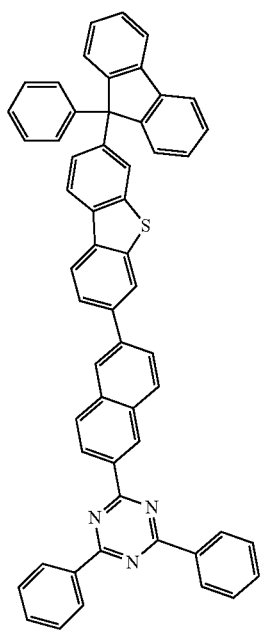
H1-9
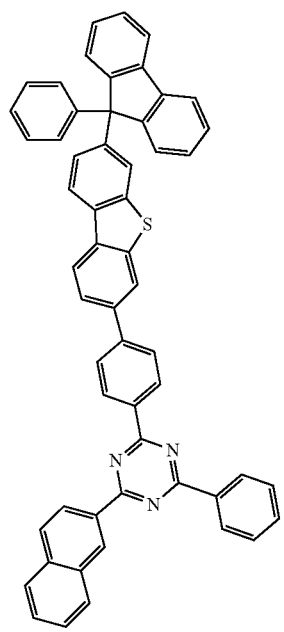
H1-10
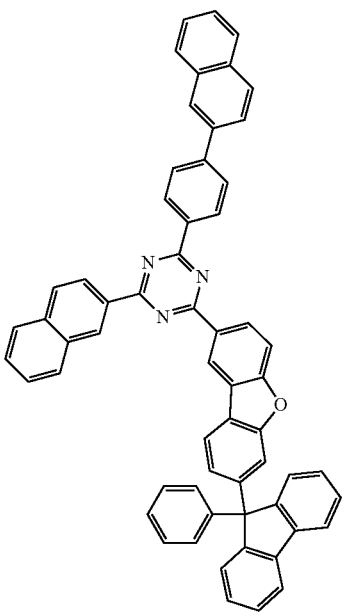

H1-11
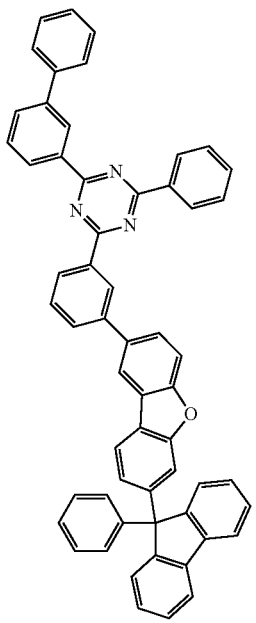
H1-13
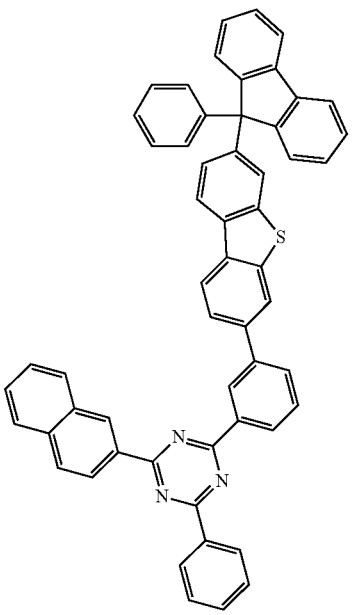
H1-12
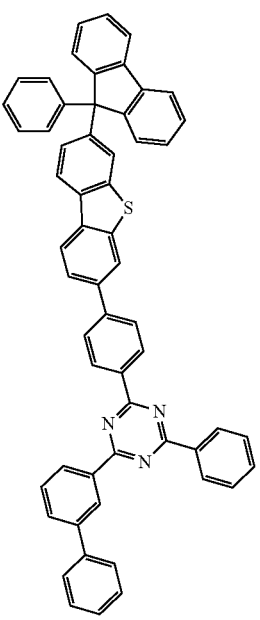
H1-14

H1-15
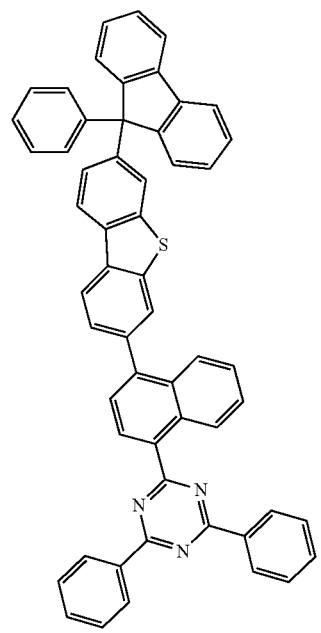
H1-17
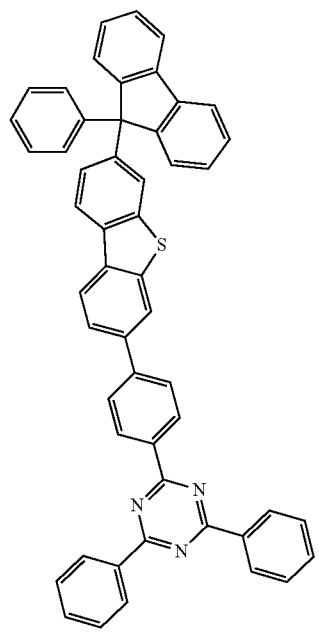
H1-16
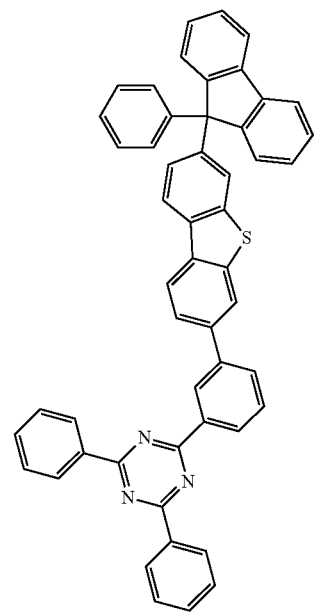
H1-18
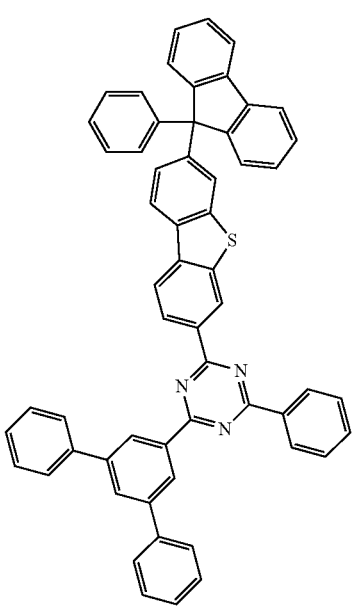

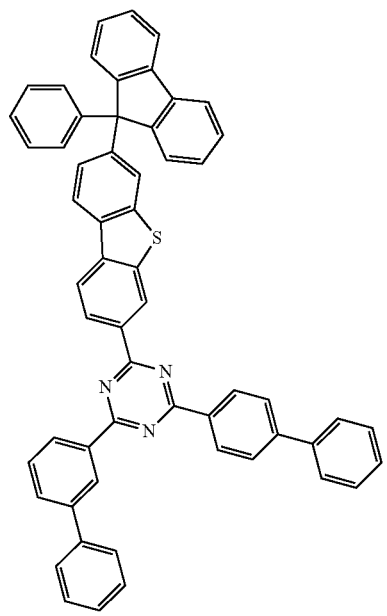
H1-19
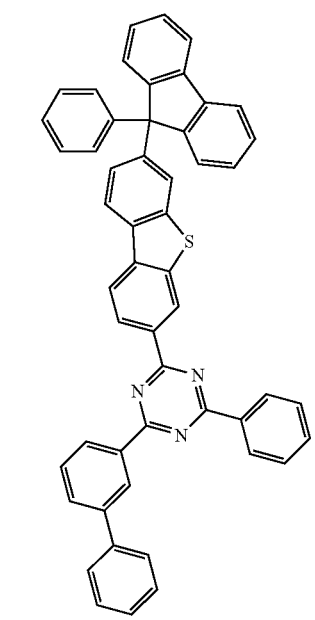
H1-21
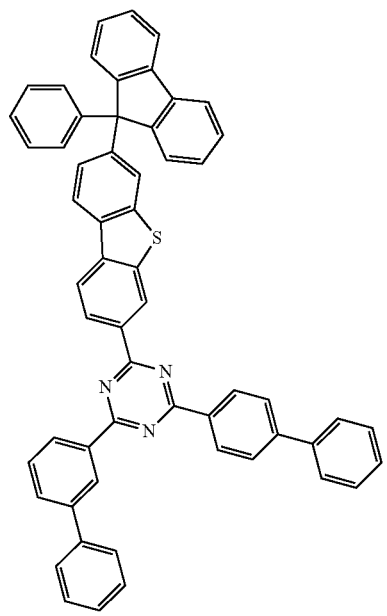
H1-20
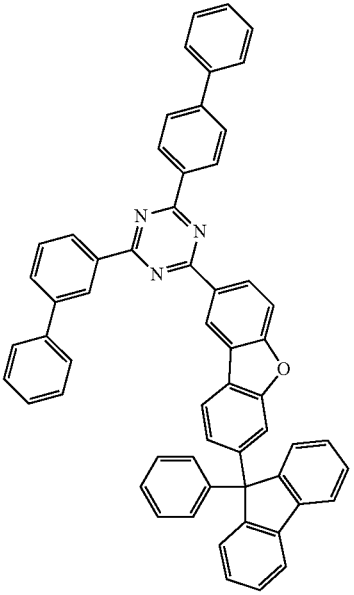
H1-22

H1-23
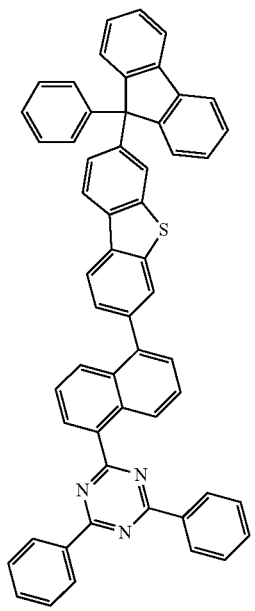
H1-25
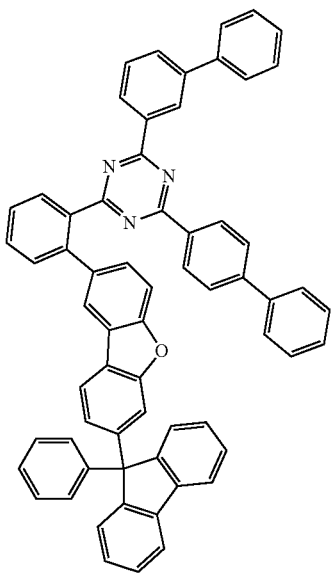
H1-24
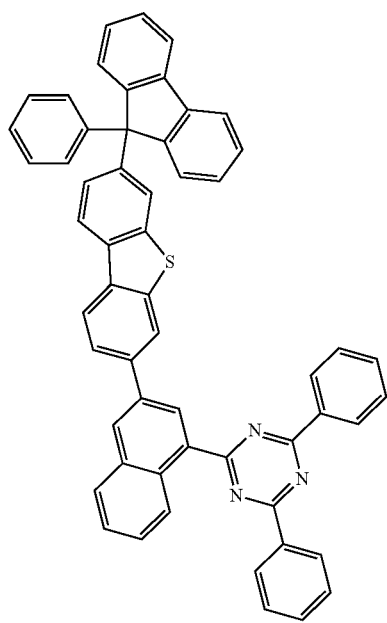
H1-26
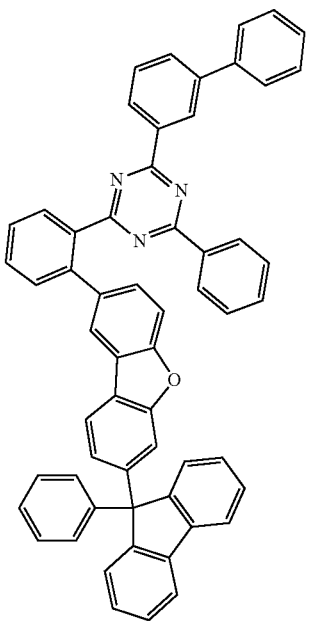

-continued
H1-27
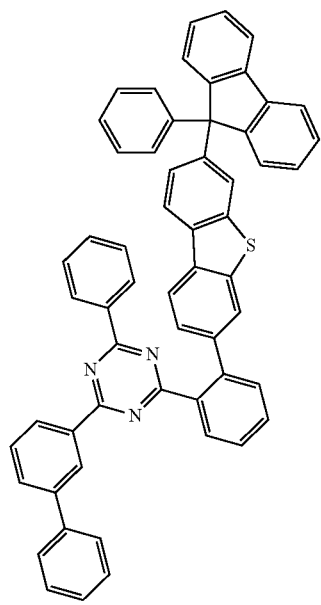
H1-28
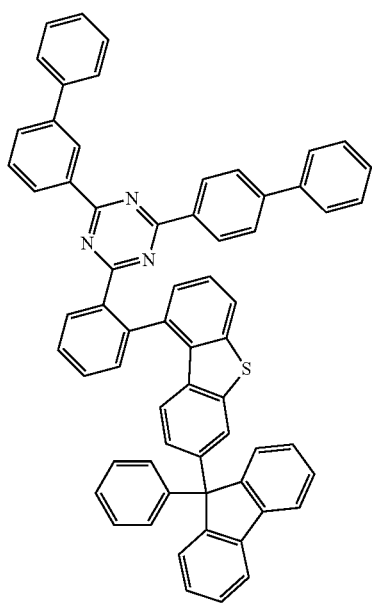
H1-29
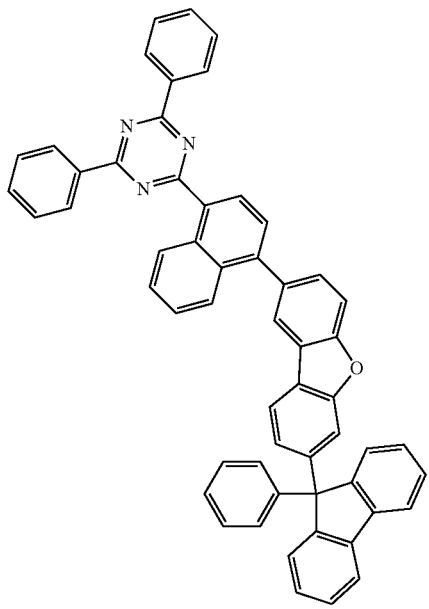
H1-30
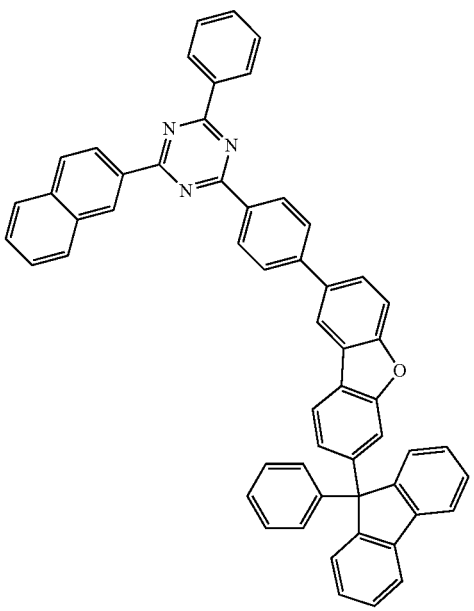

H1-31
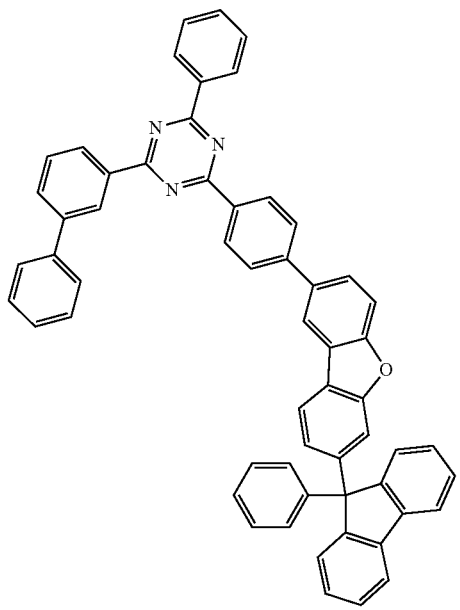
H1-33
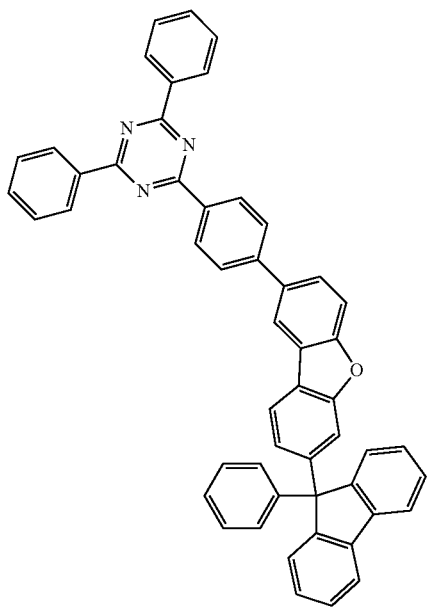
H1-32
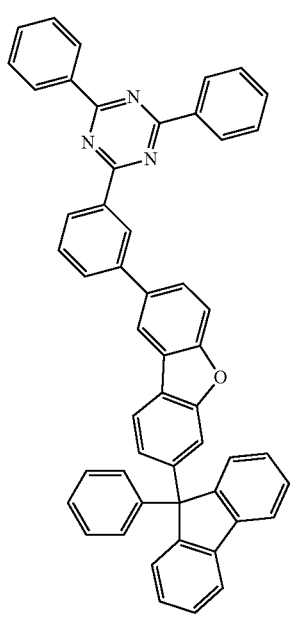
H1-34
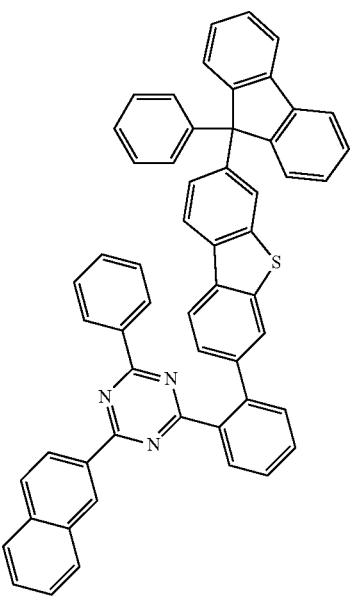

H1-35
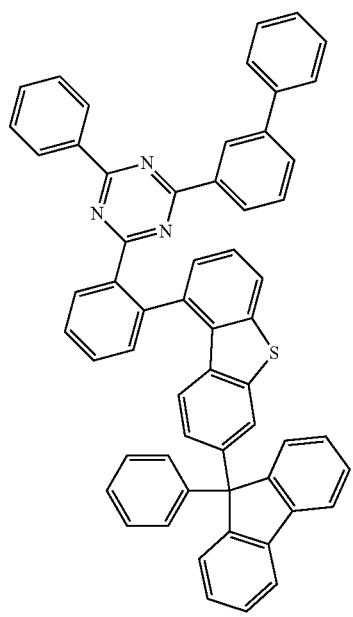
H1-36
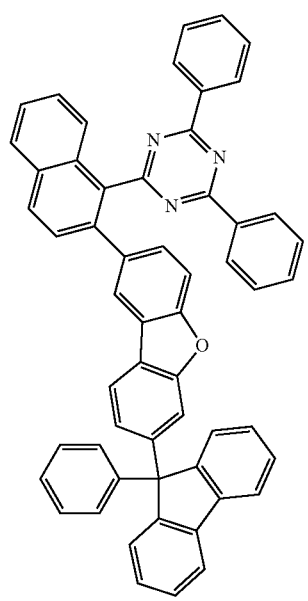
H1-37
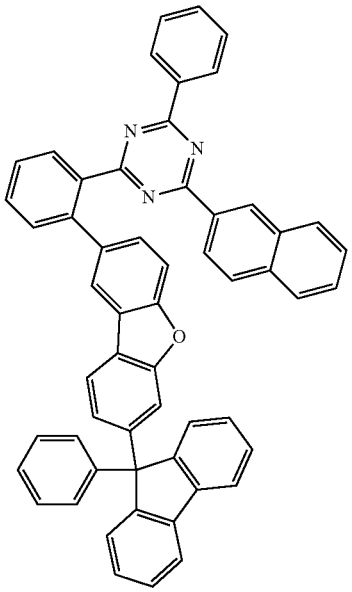
H1-38
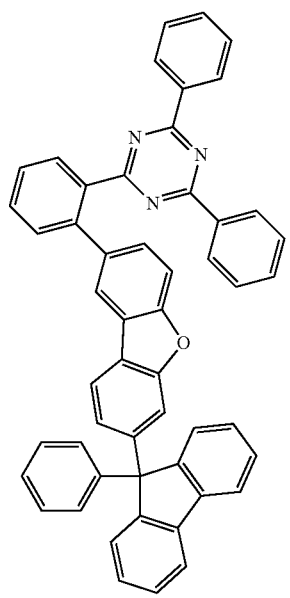

H1-39
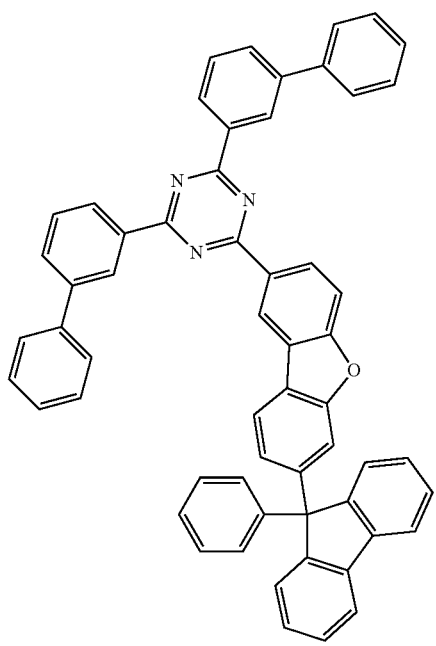
H1-40
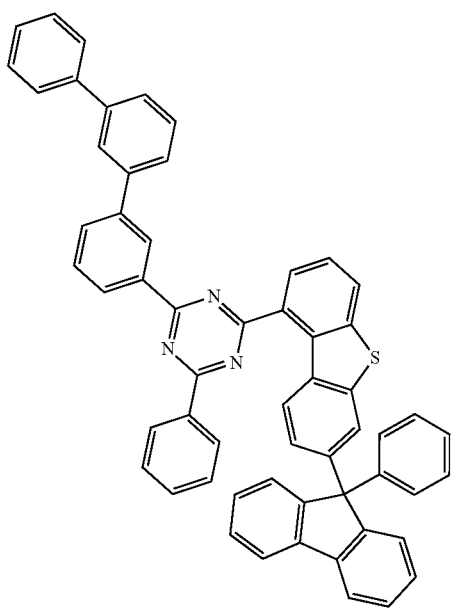
H1-41
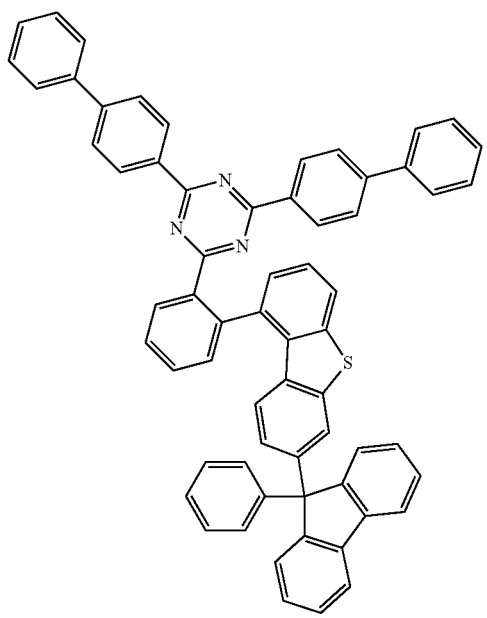
H1-42
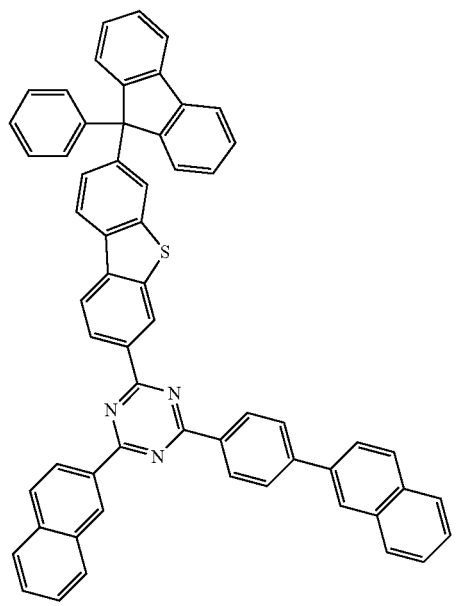

H1-43
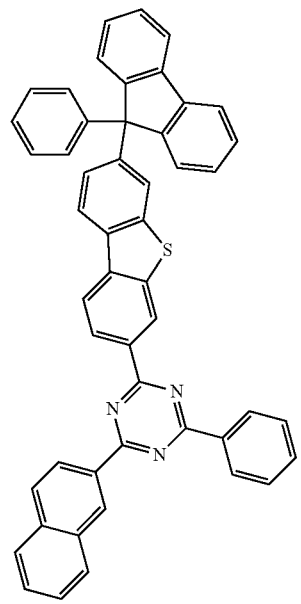
H1-45
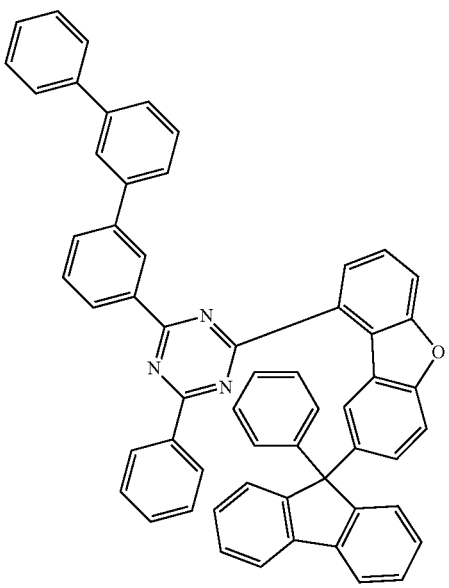
H1-44
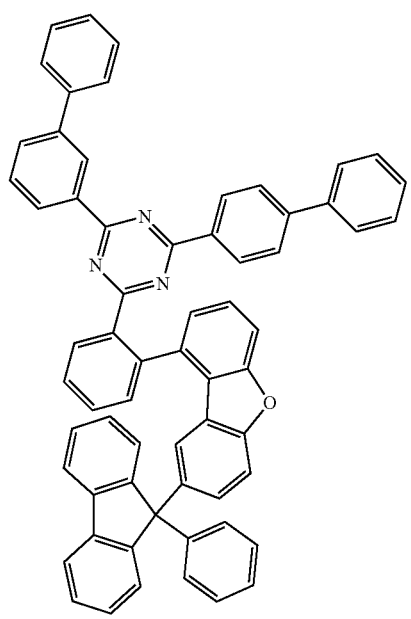
H1-46

H1-47
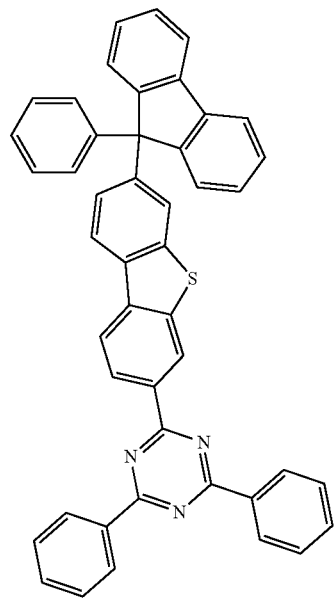
H1-49
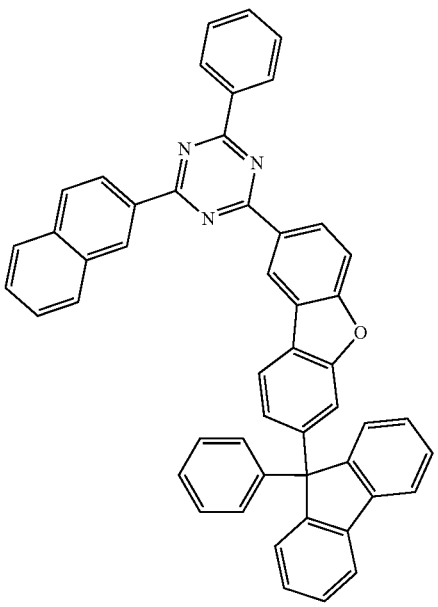
H1-48
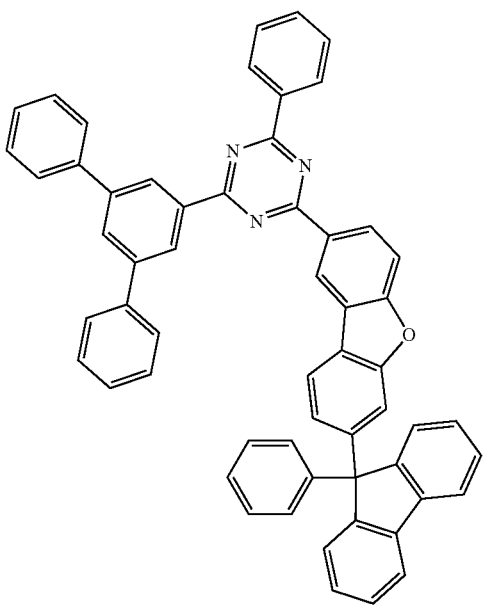
H1-50
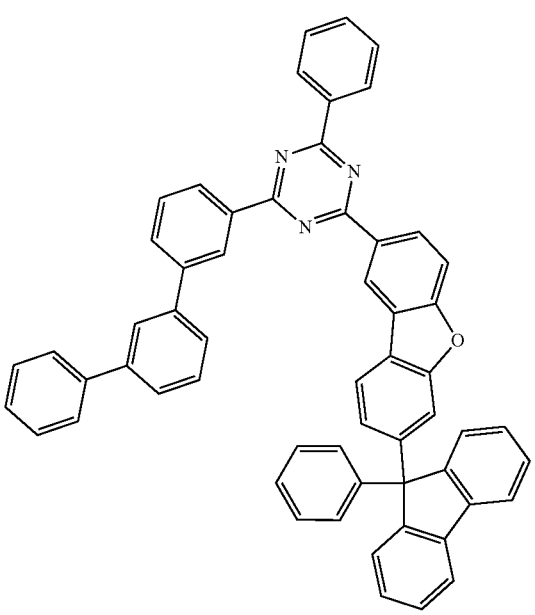

H1-51
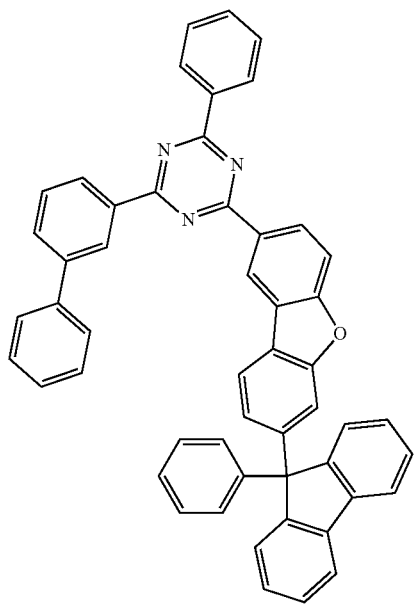
H1-52
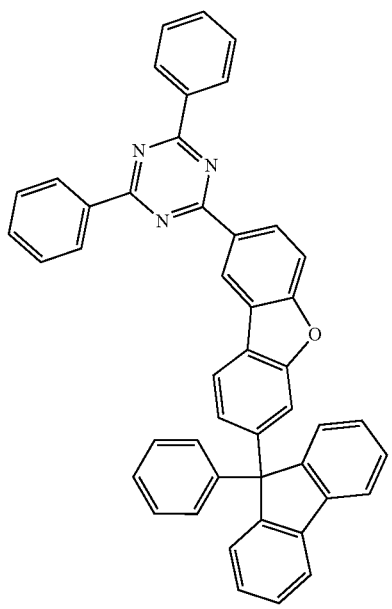
H1-53
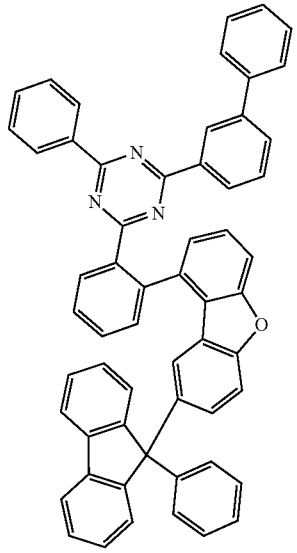
H1-54
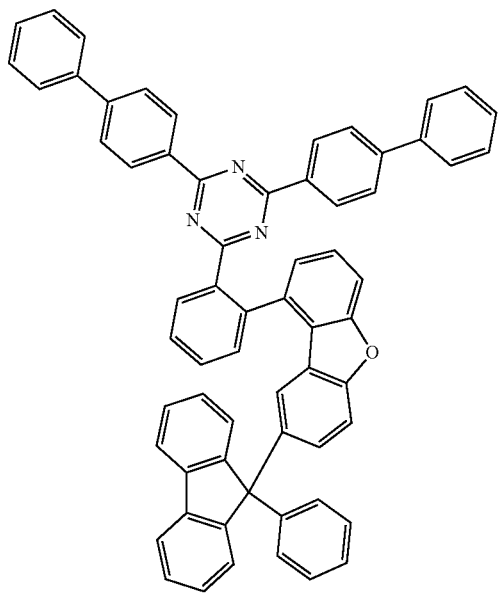

H1-55
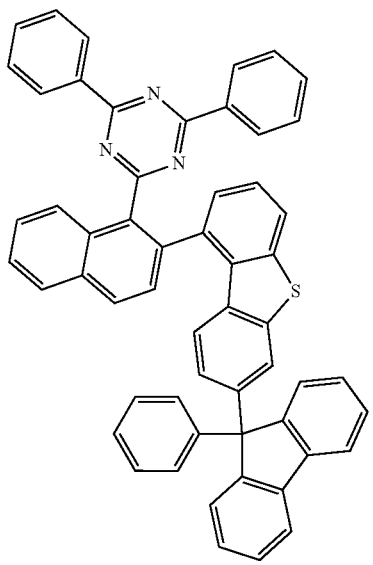
H1-58
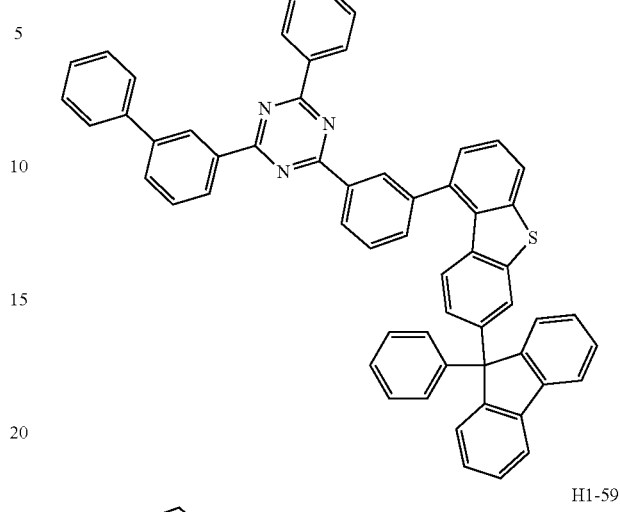
H1-56
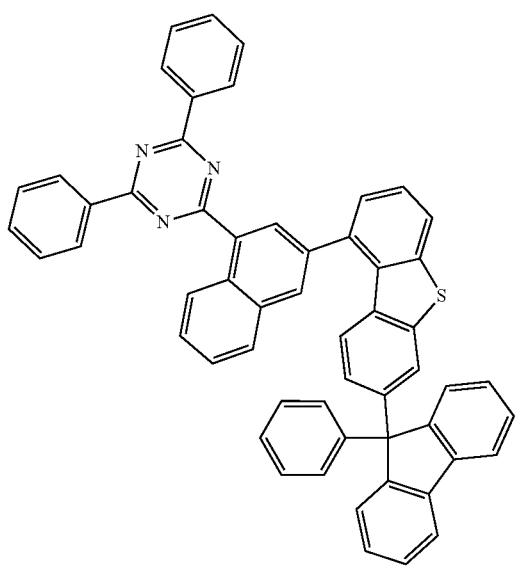
H1-59
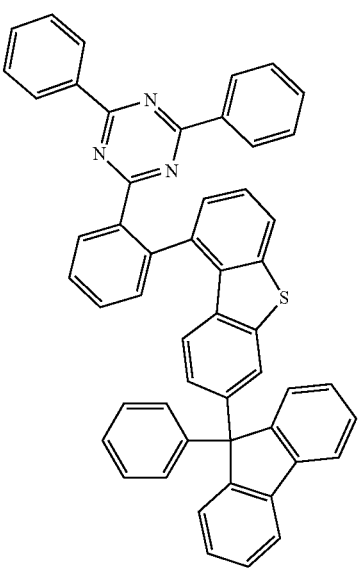
H1-57
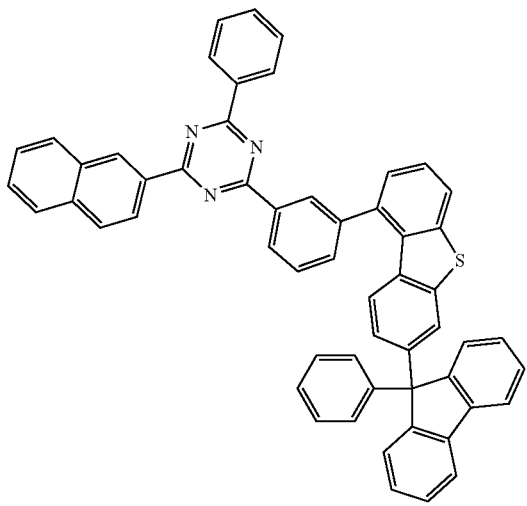
H1-60
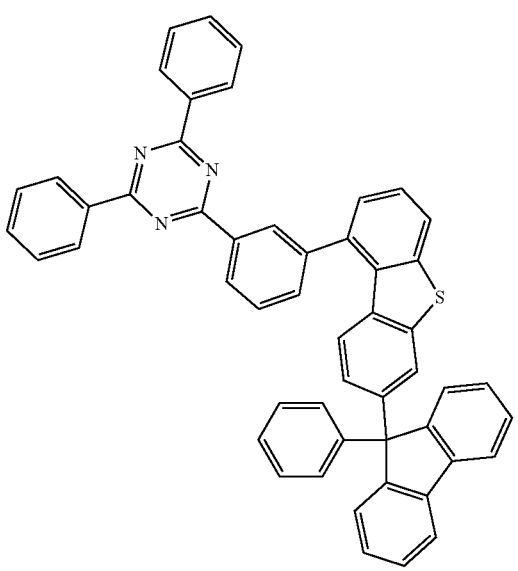

H1-61
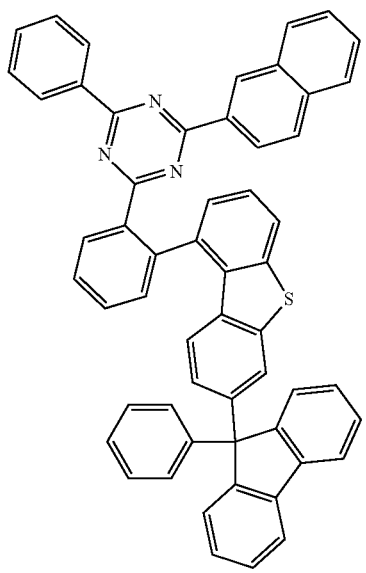
H1-62
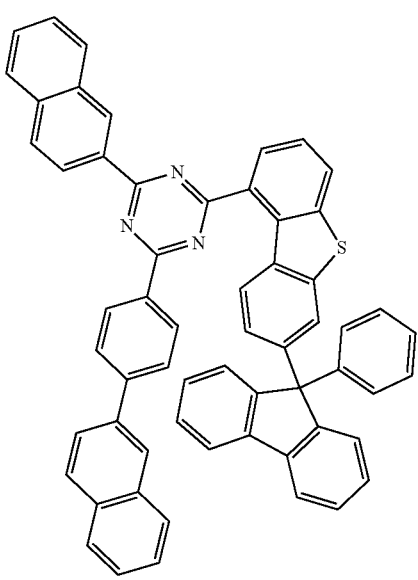
H1-63
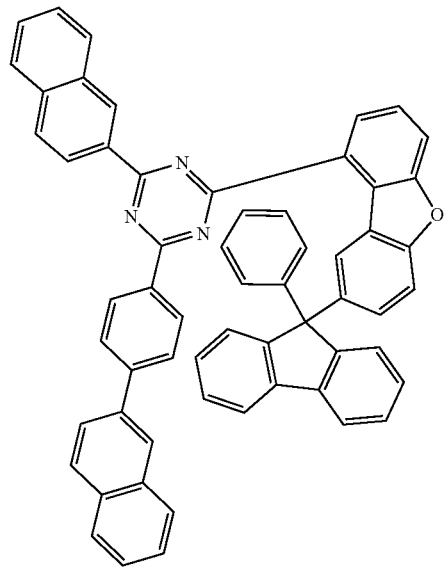
H1-64
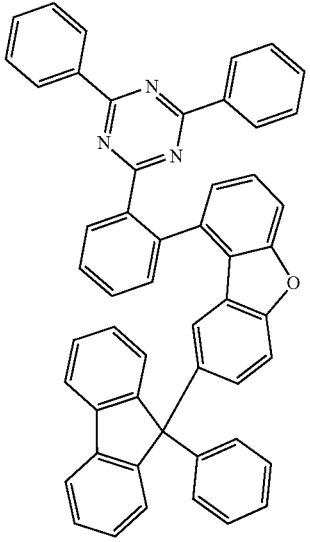
H1-65
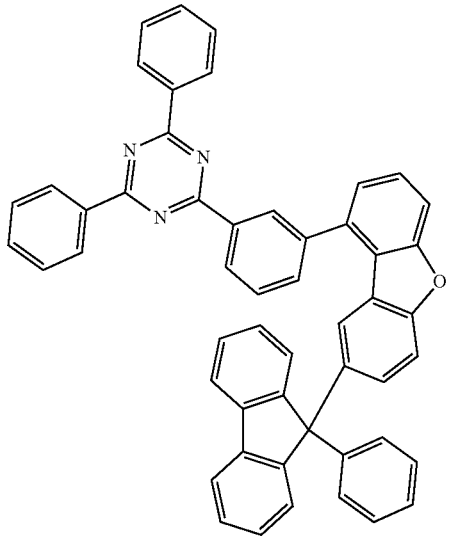

H1-66
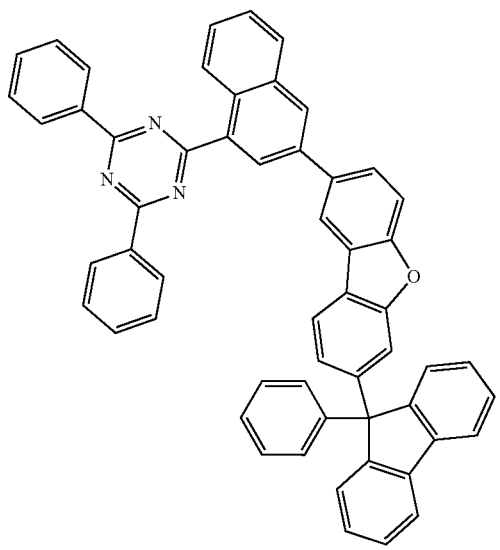
H1-67
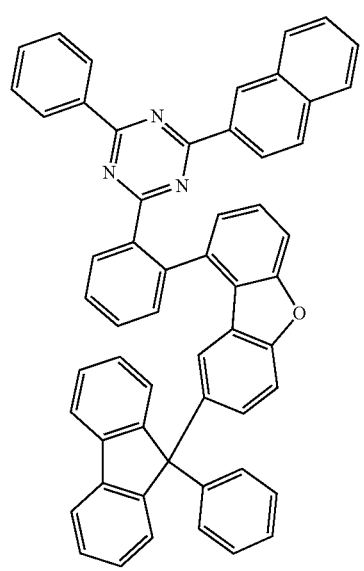
H1-68
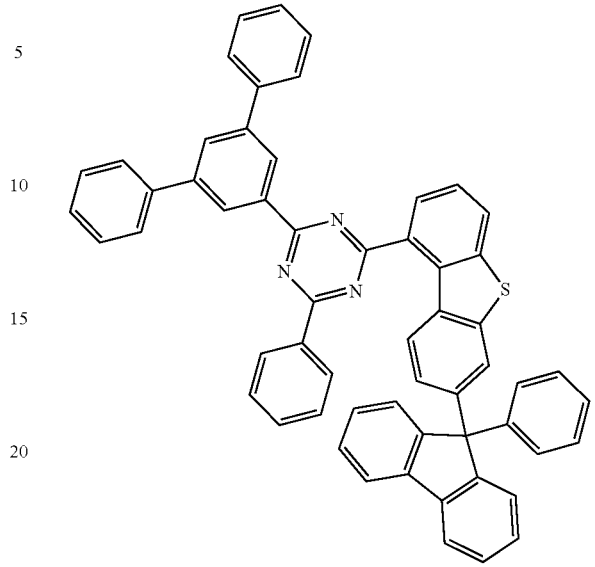
H1-69
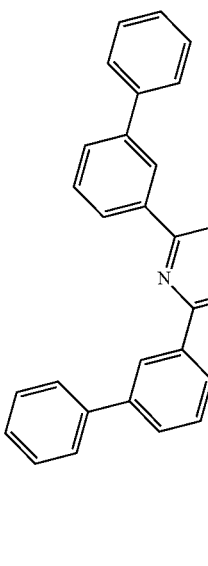

H1-70
H1-71
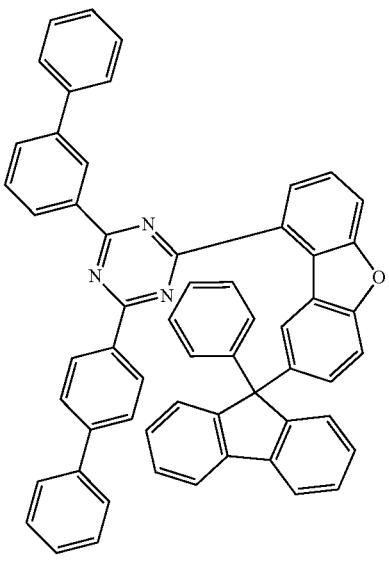
H1-72
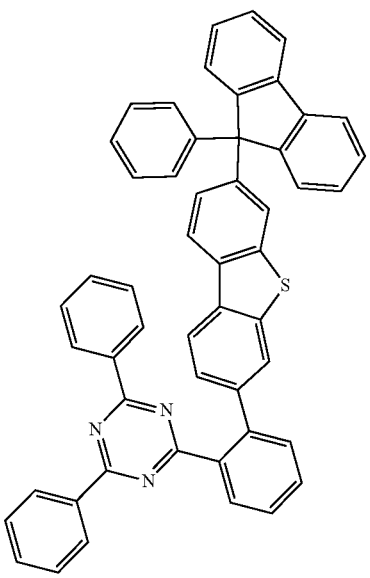
H1-73
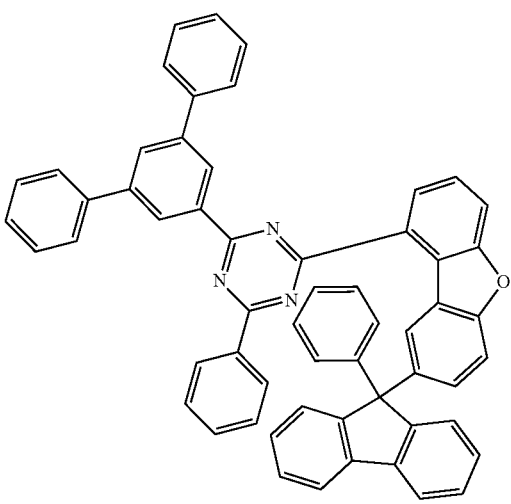
H1-74

H1-75
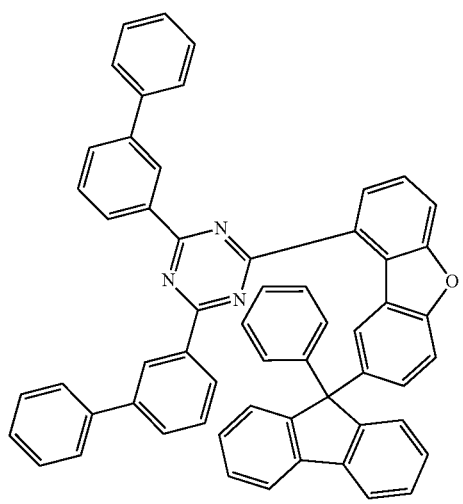
H1-76
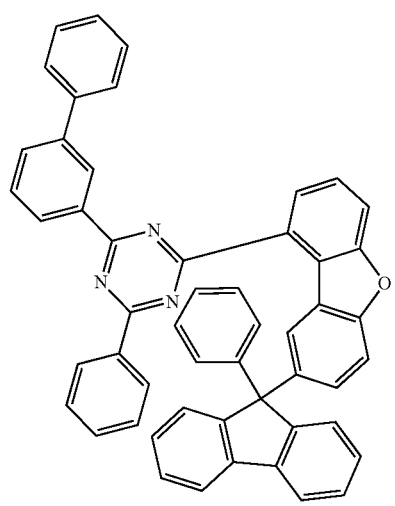
H1-77
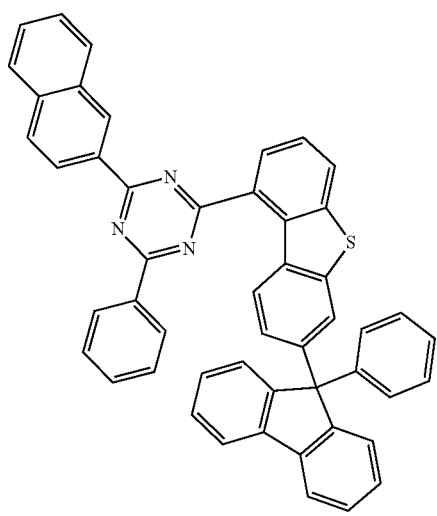
H1-78
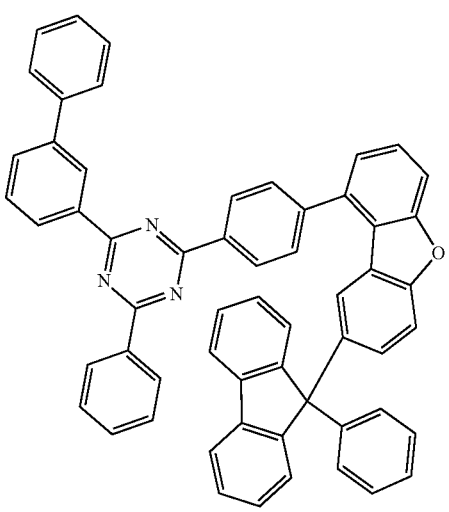
H1-79
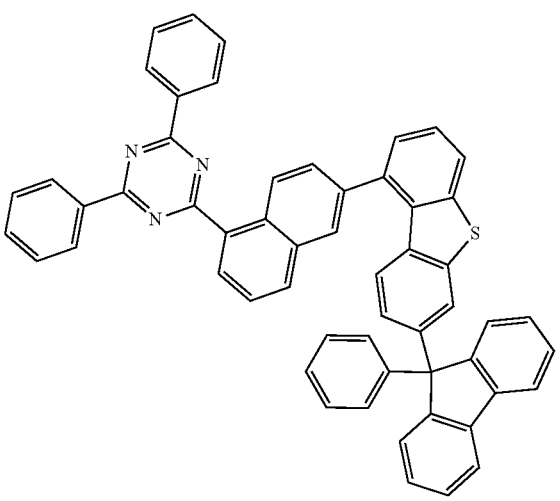
H1-80
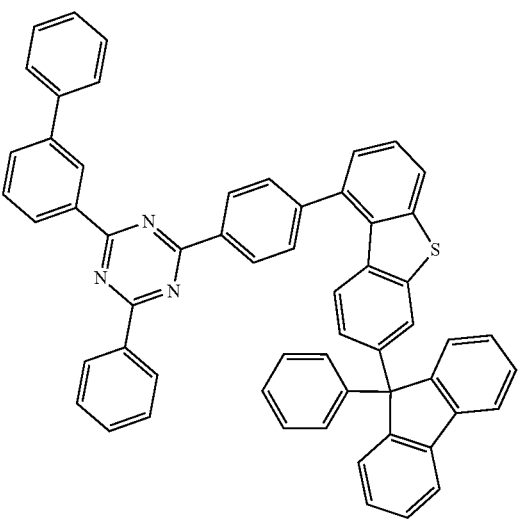

H1-81
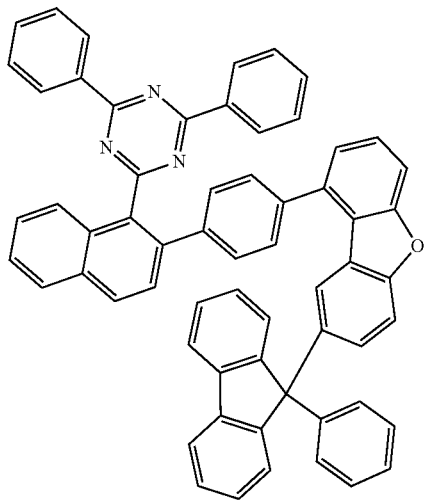
H1-82
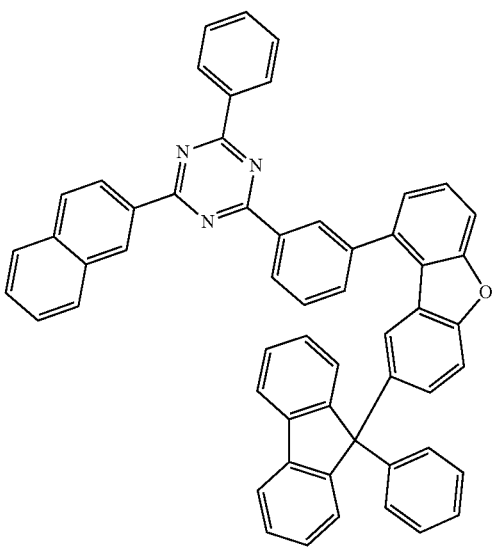
H1-83
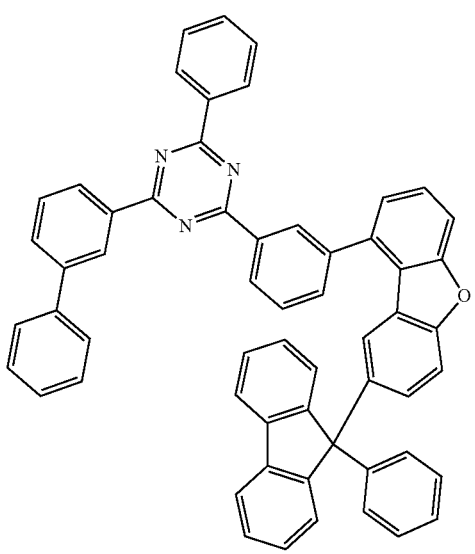
H1-84
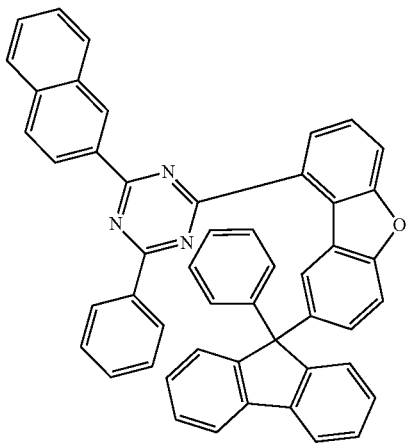
H1-85
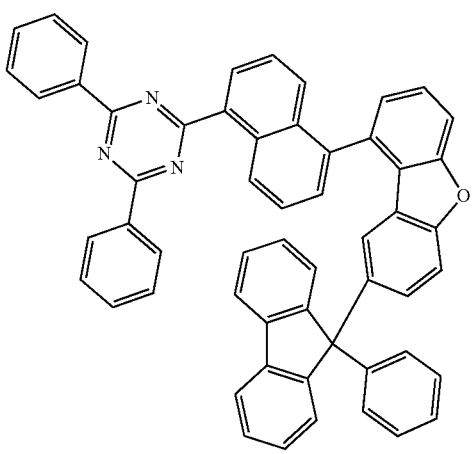
H1-86
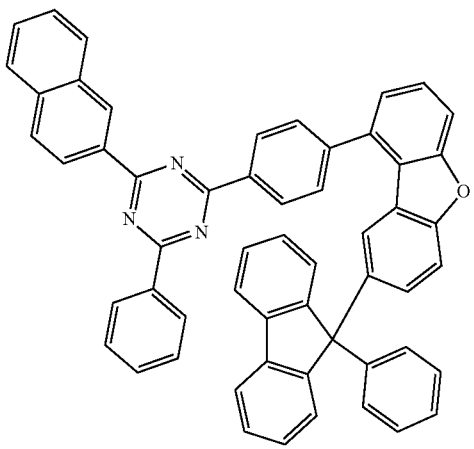

H1-87
H1-90
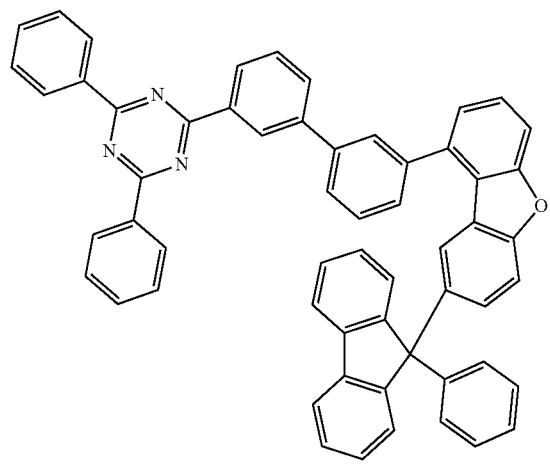
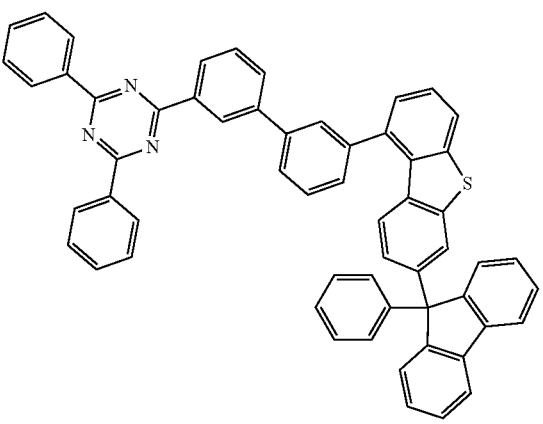
H1-88
H1-91
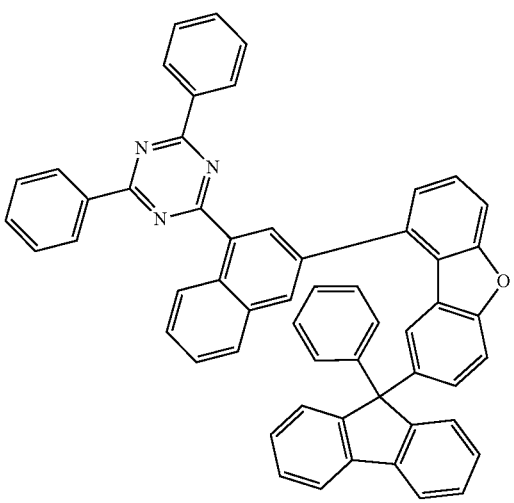
H1-89
H1-92
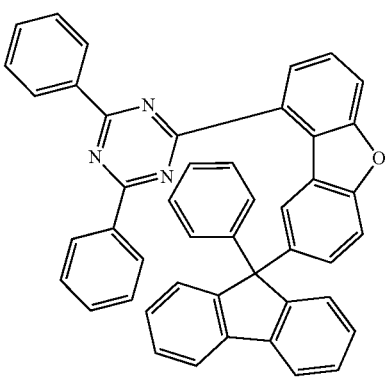

H1-93
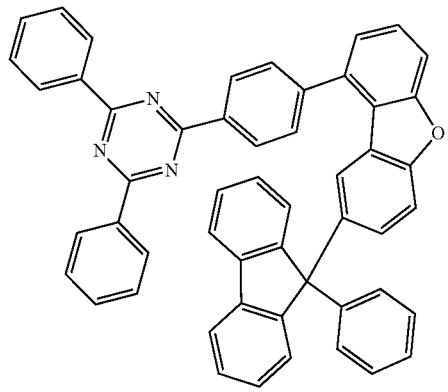
H1-94
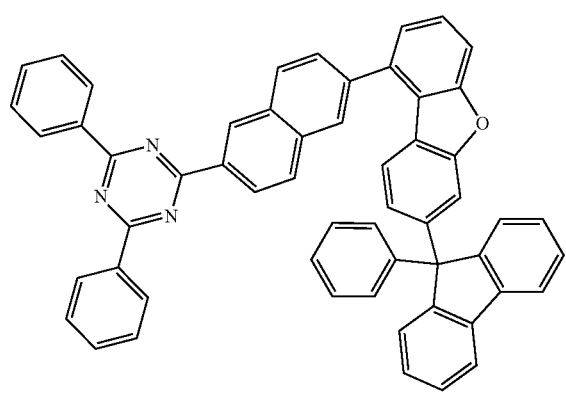
H1-95
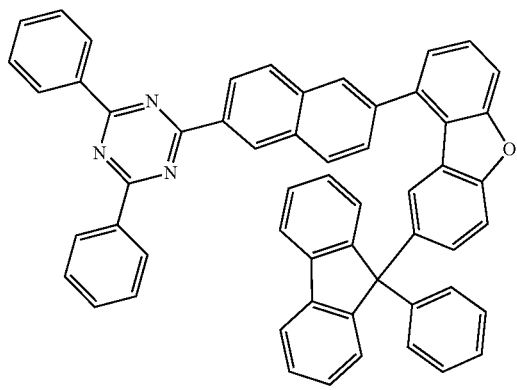
H1-96
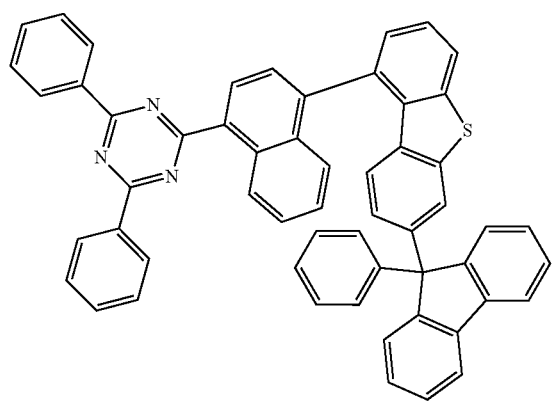
H1-97
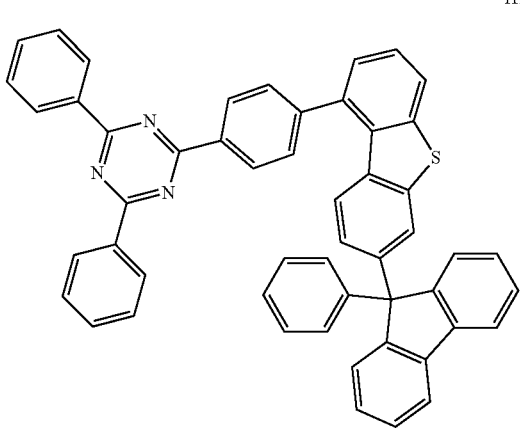
H1-98
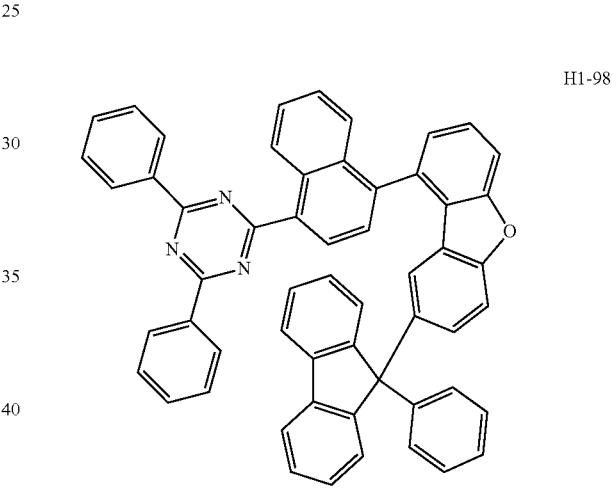
H1-99
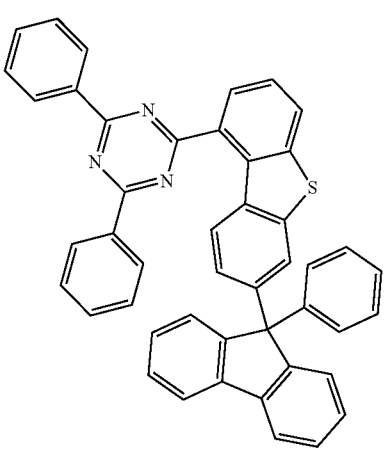

H1-100
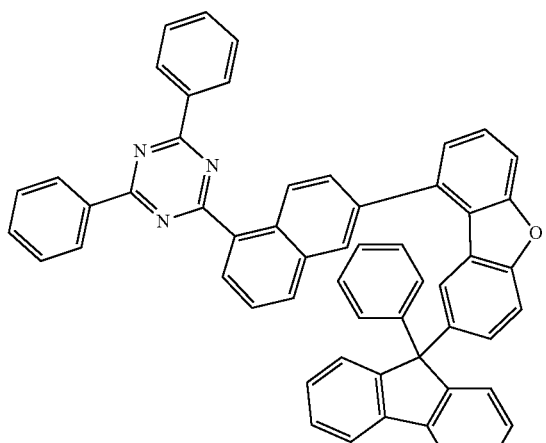
H1-101
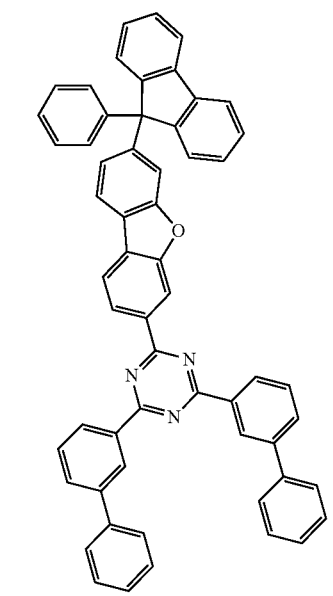
H1-102
H1-103
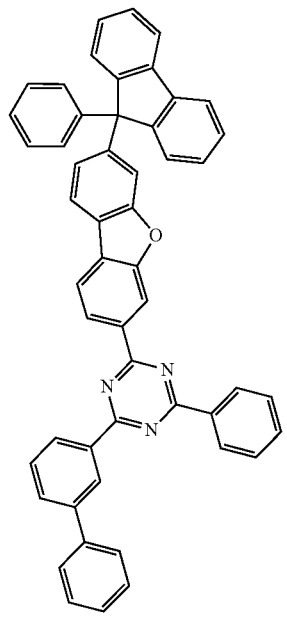
H1-104
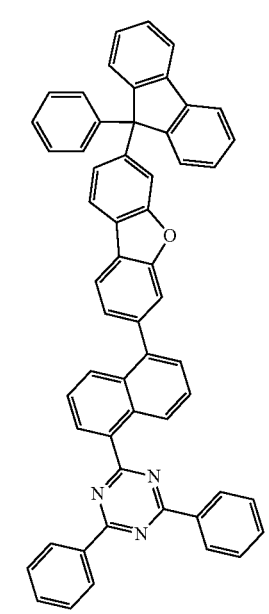

H1-105
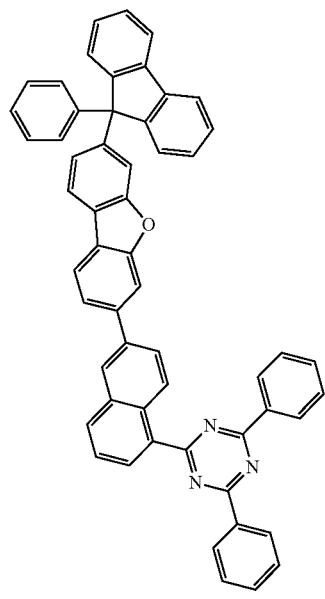
H1-107
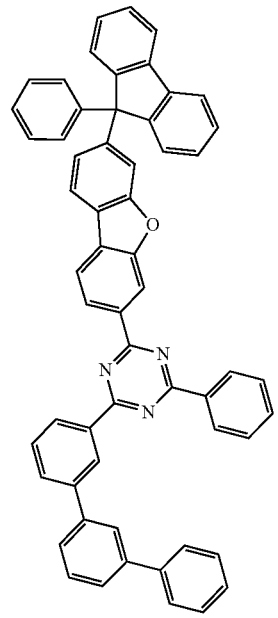
H1-106
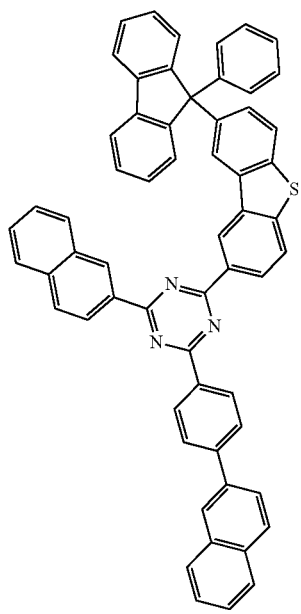
H1-108
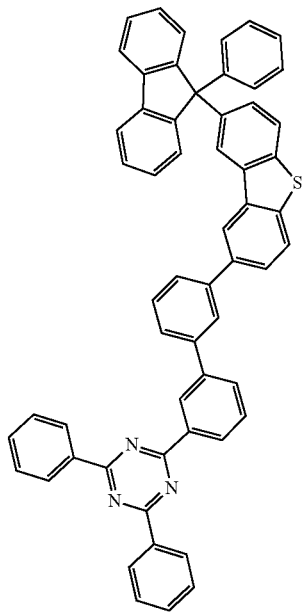

H1-109
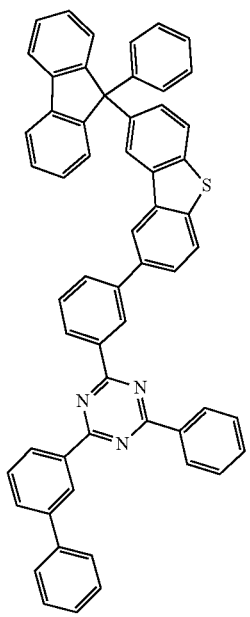
H1-110
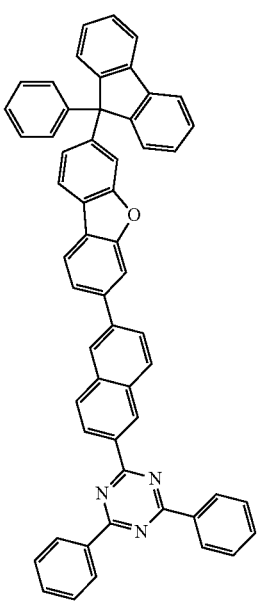
H1-111
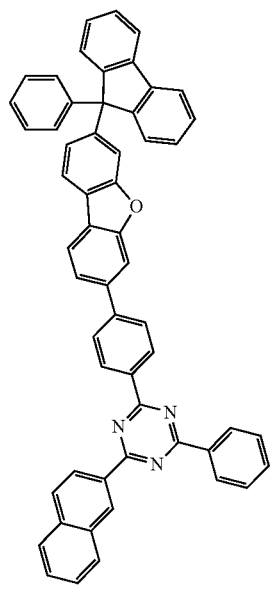
H1-112
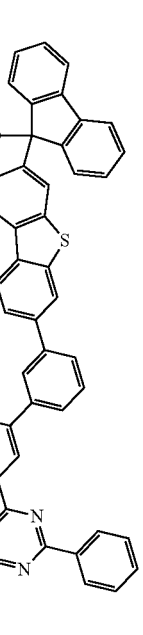

H1-113
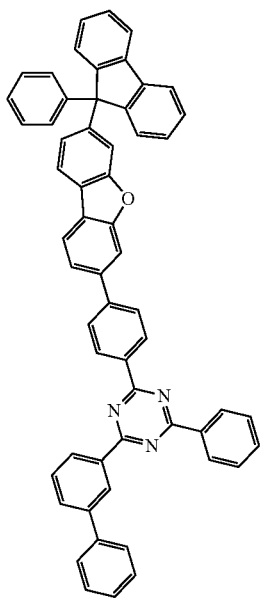
H1-114
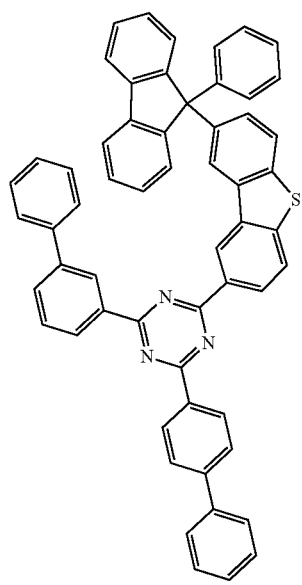
H1-115
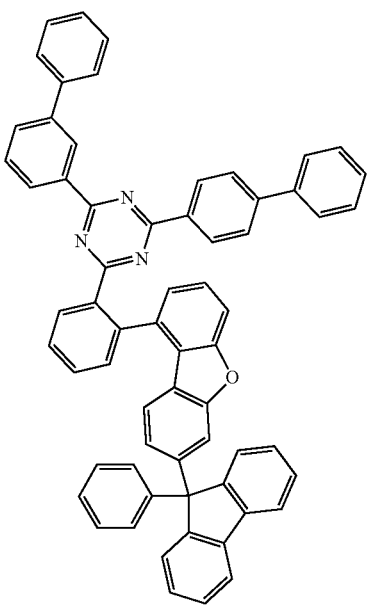
H1-116
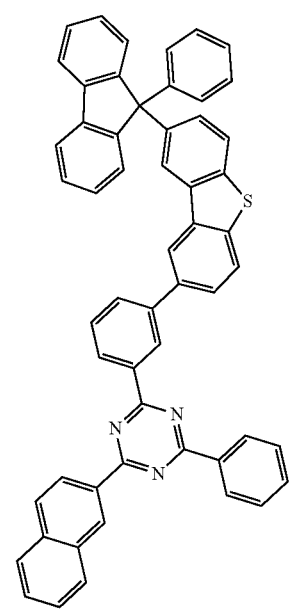

H1-117
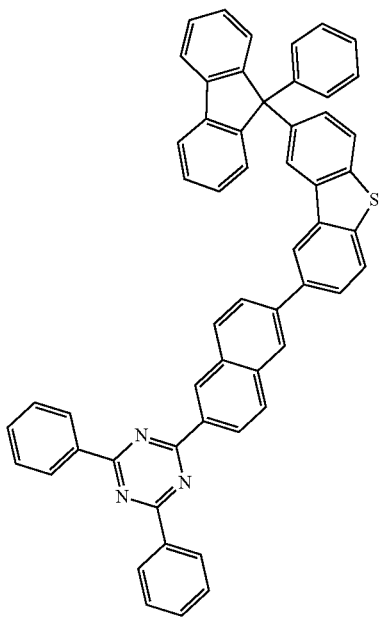
H1-118
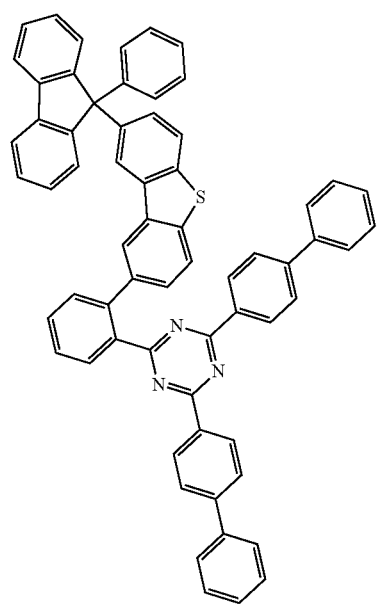
H1-119
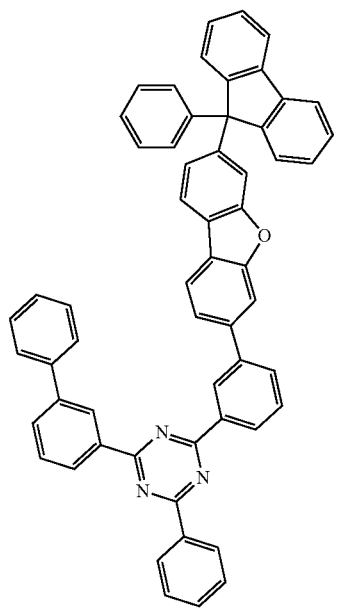
H1-120
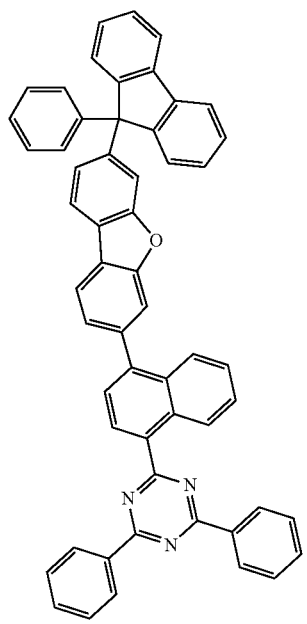

H1-121
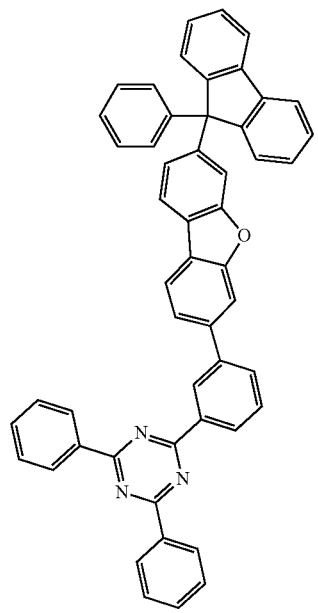
H1-122
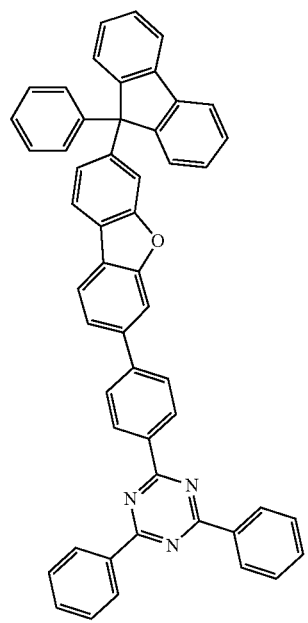
H1-123
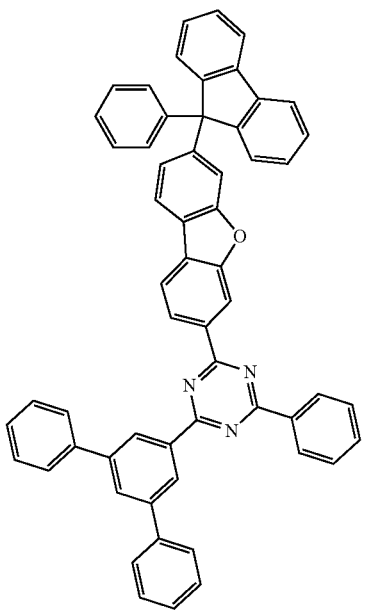
H1-124
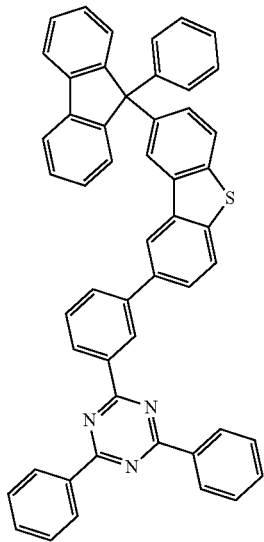

H1-125
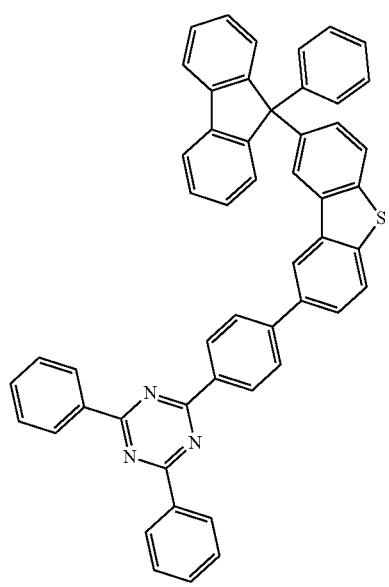
H1-126
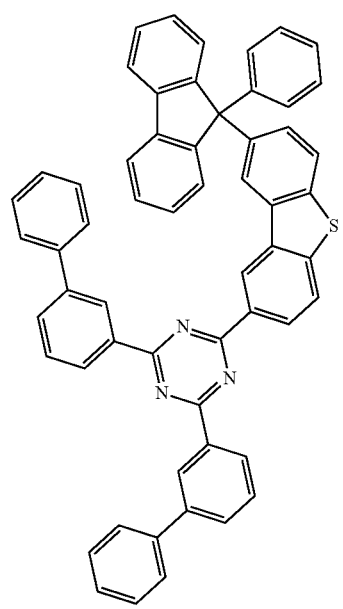
H1-127
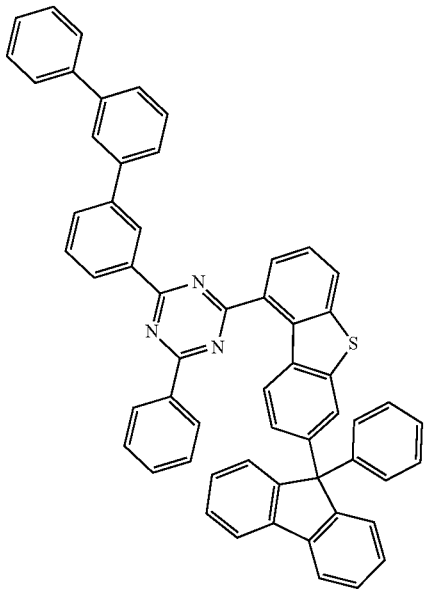
H1-128
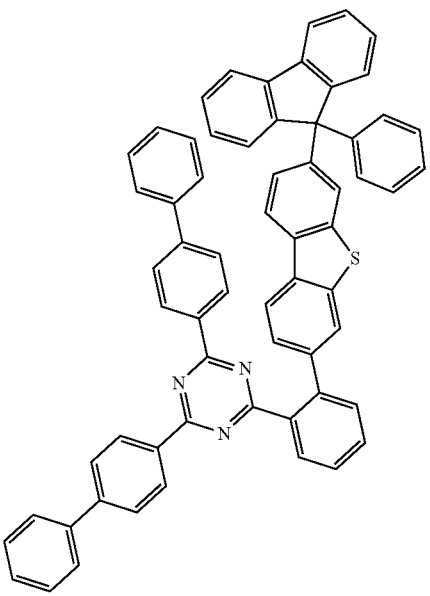

H1-129
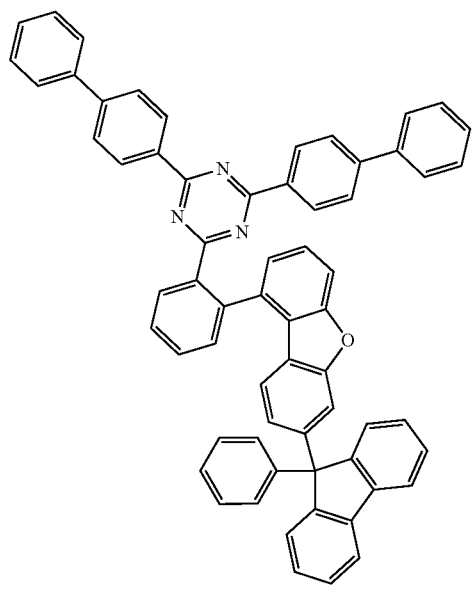
H1-131
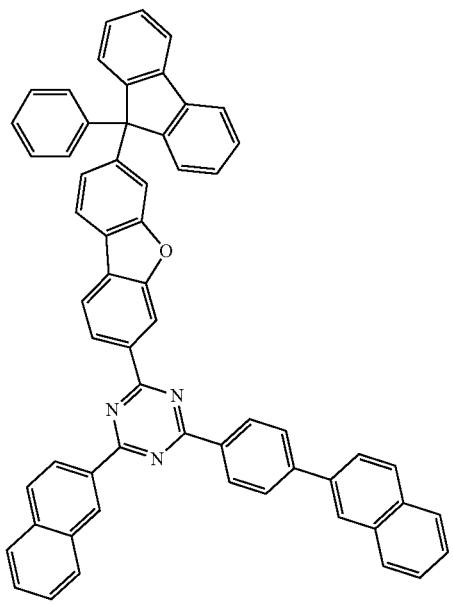
H1-130
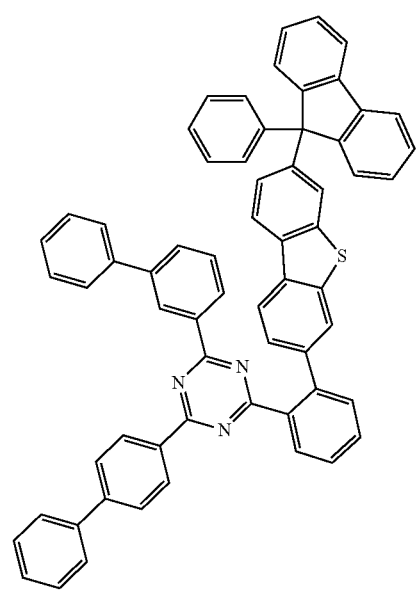
H1-132
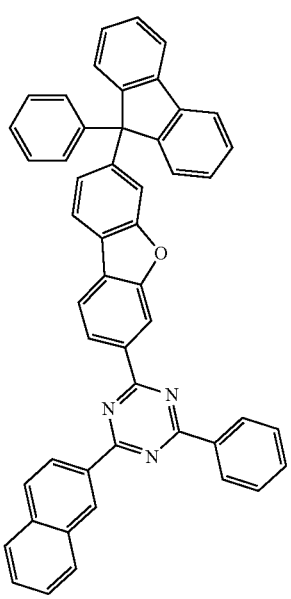

H1-133
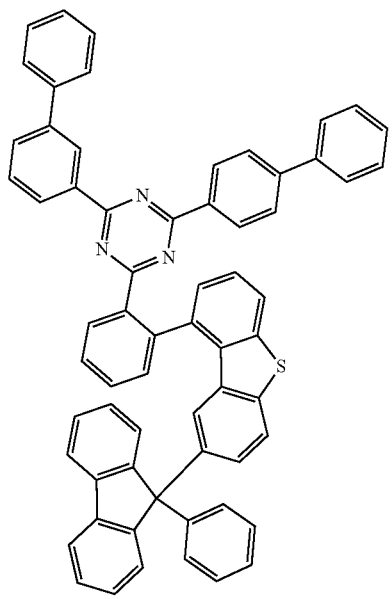
H1-134
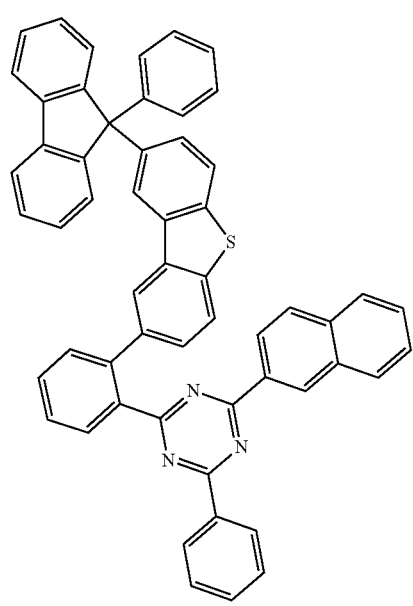
H1-135
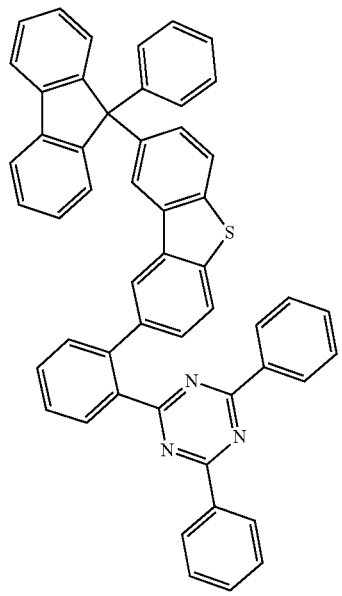
H1-136
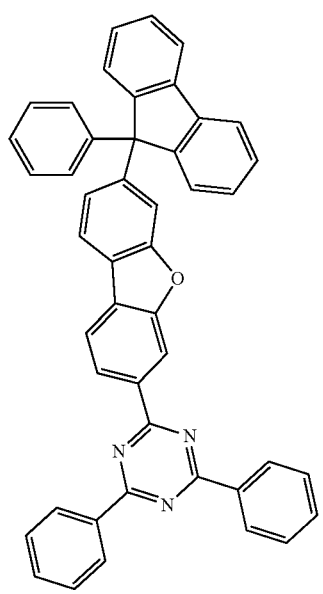

H1-137
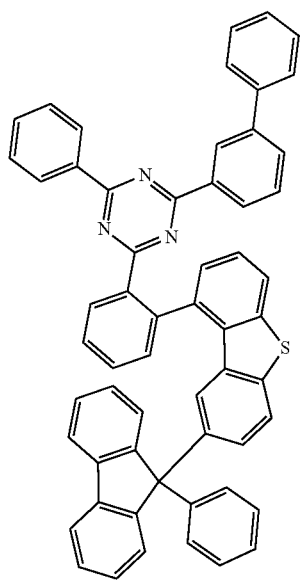
H1-138
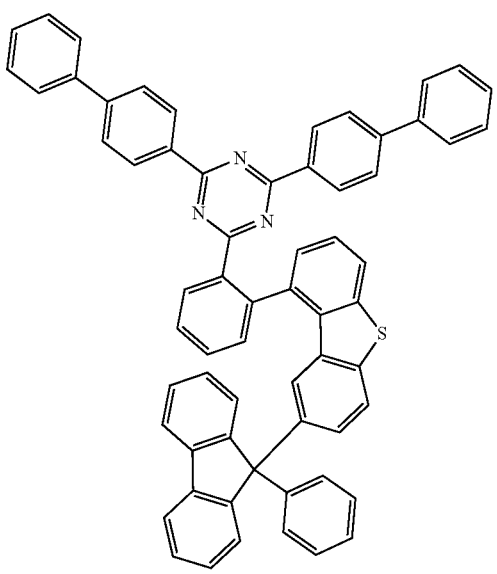
H1-139
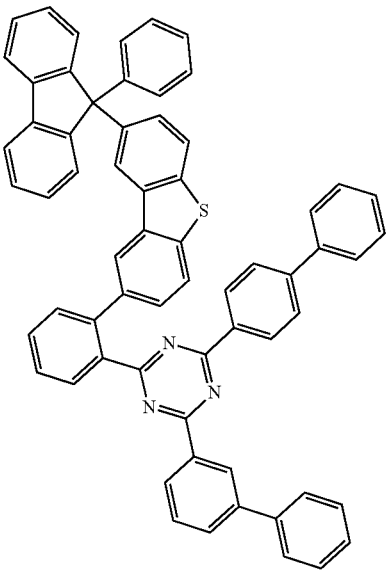
H1-140
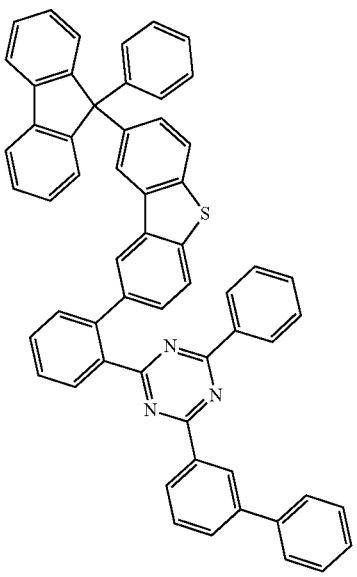

H1-141
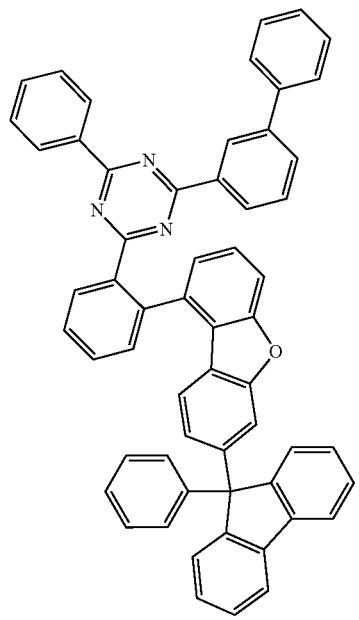
H1-142
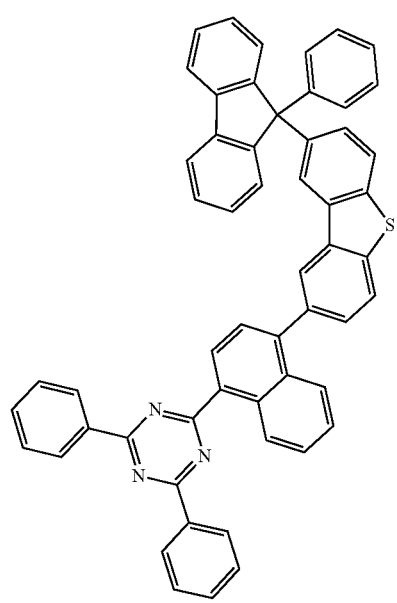
H1-143
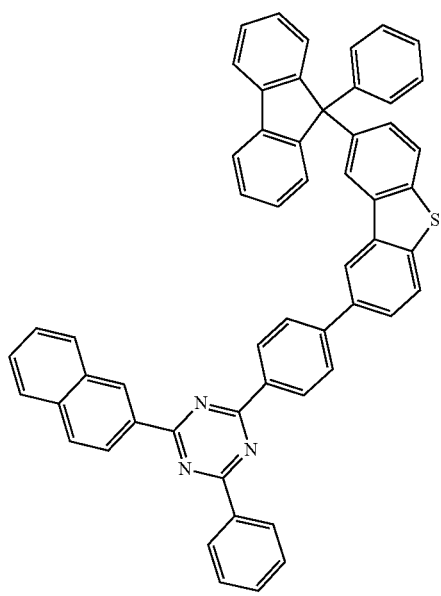
H1-144
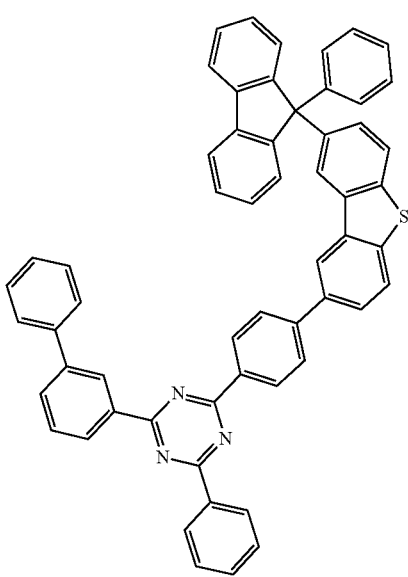

H1-145
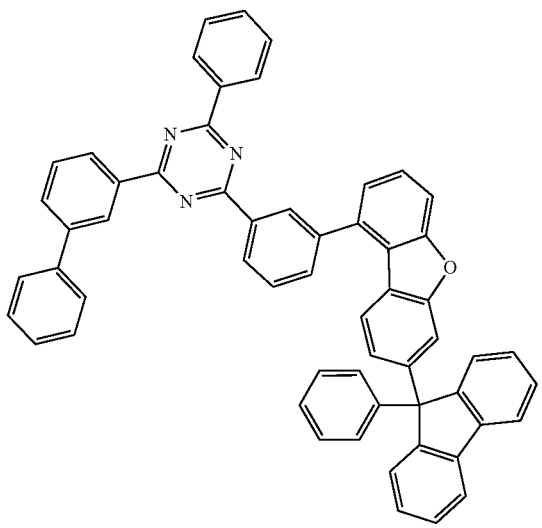
H1-146
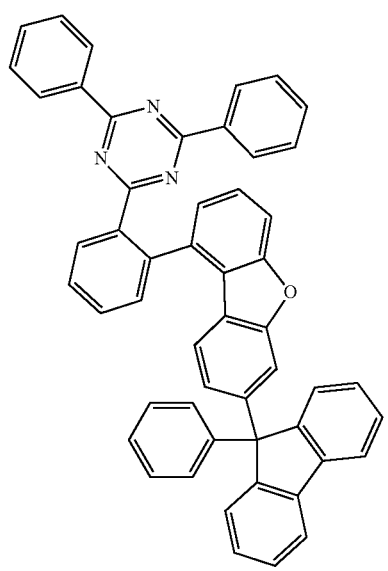
H1-147
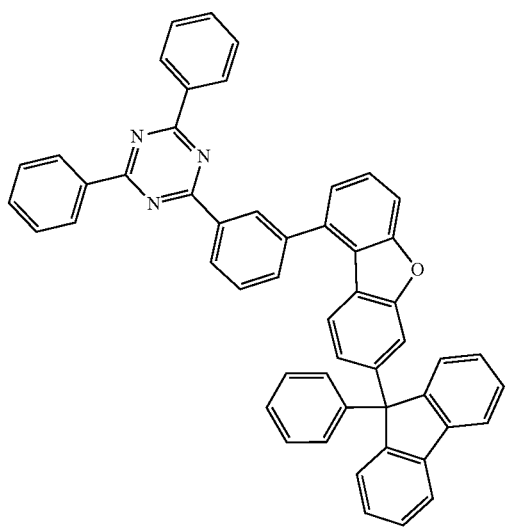
H1-148
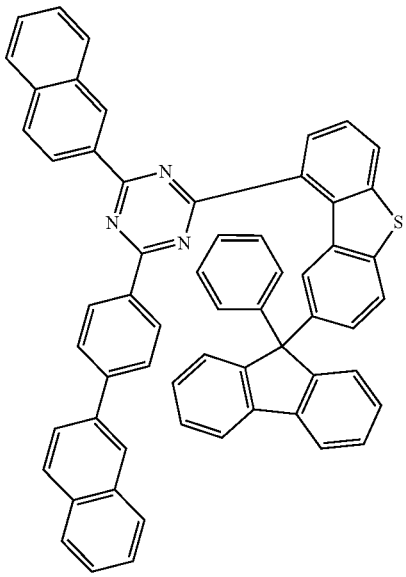
H1-149
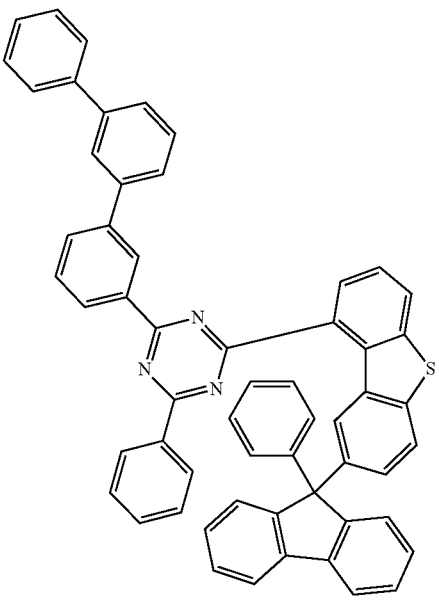

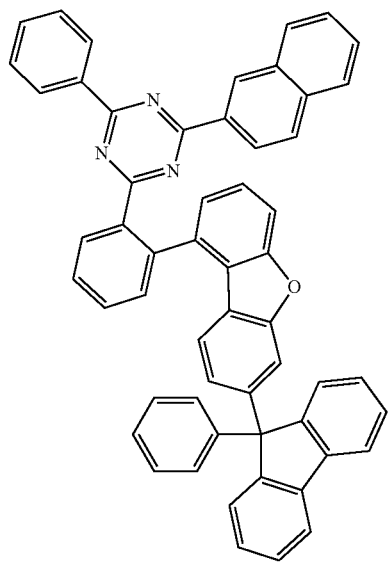 H1-150
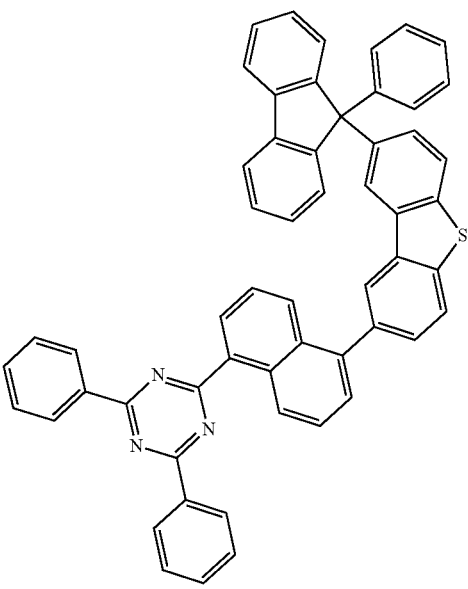 H1-152
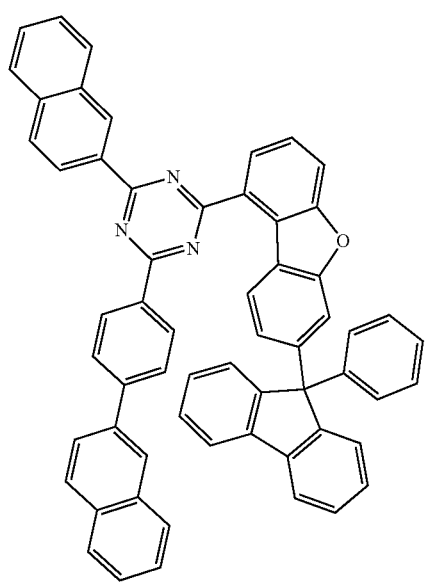 H1-151
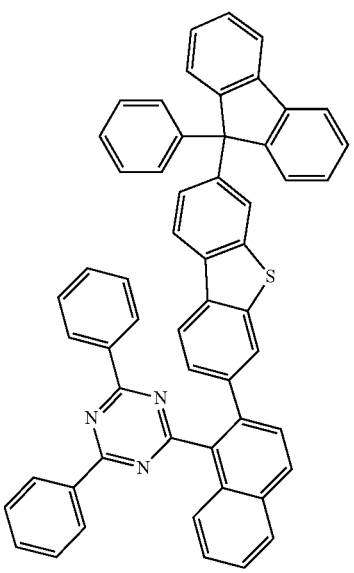 H1-153

H1-154
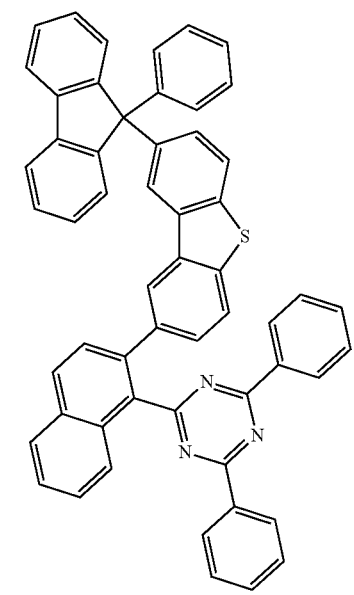
H1-155
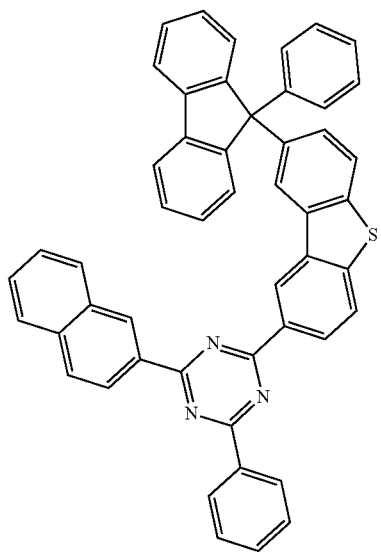
H1-156
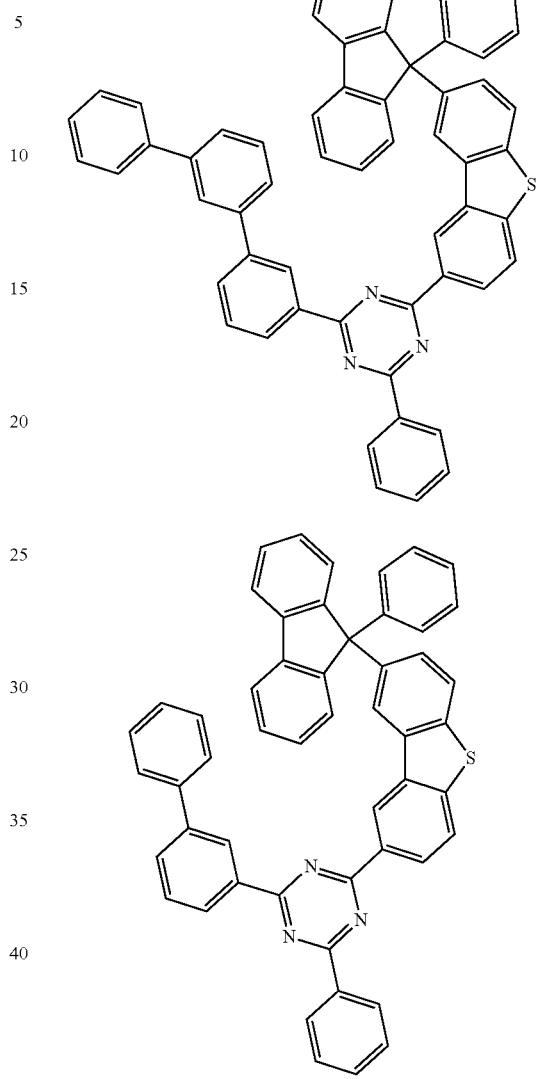
H1-157
H1-158
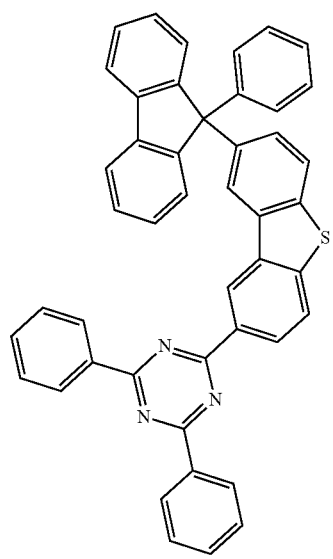

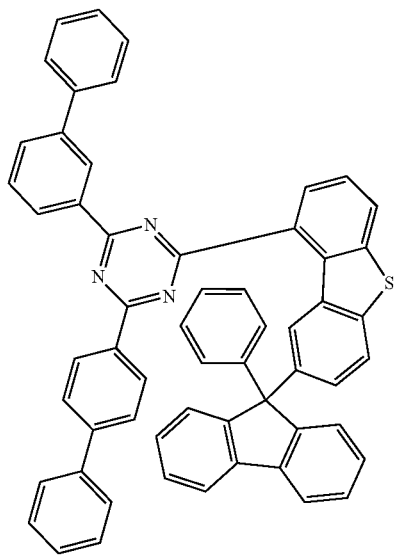
H1-159
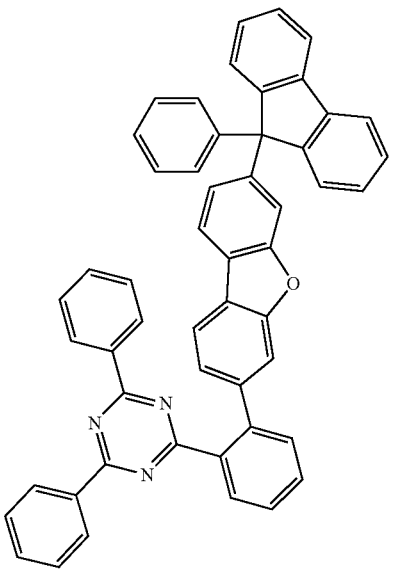
H1-161
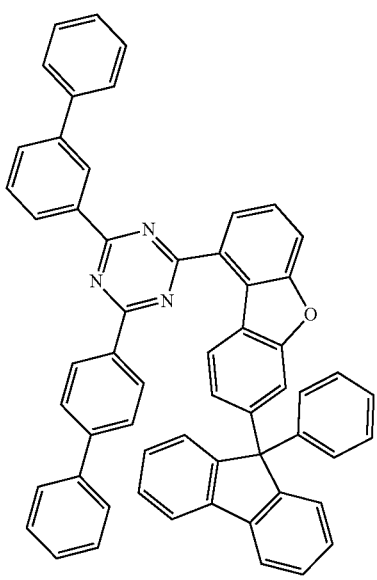
H1-160
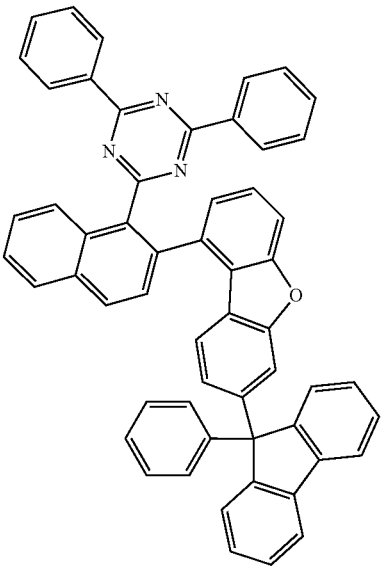
H1-162

H1-163
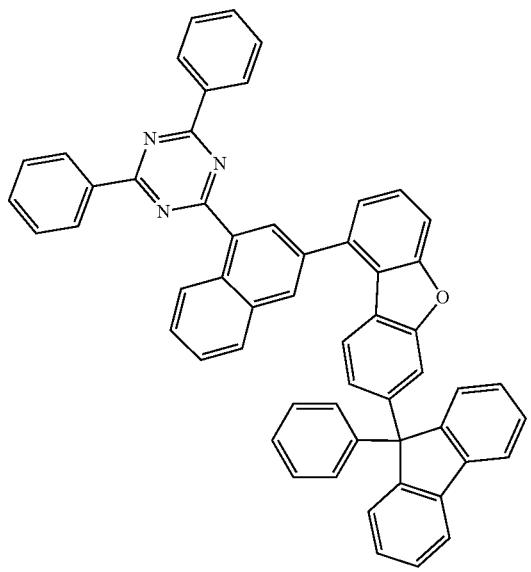
H1-164
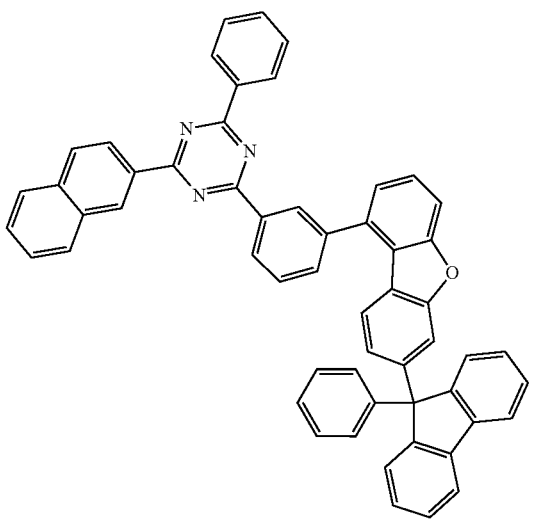
H1-165
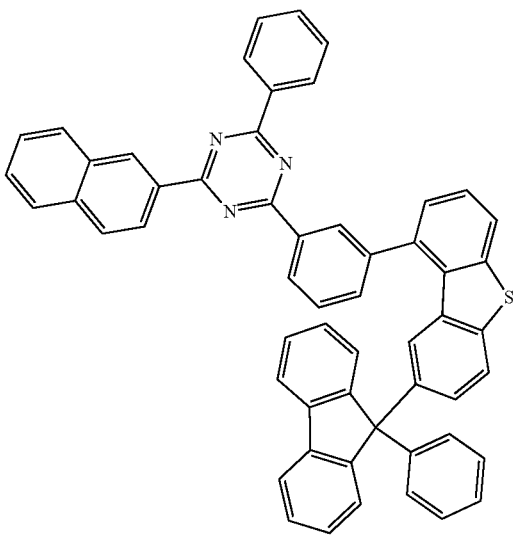
H1-166
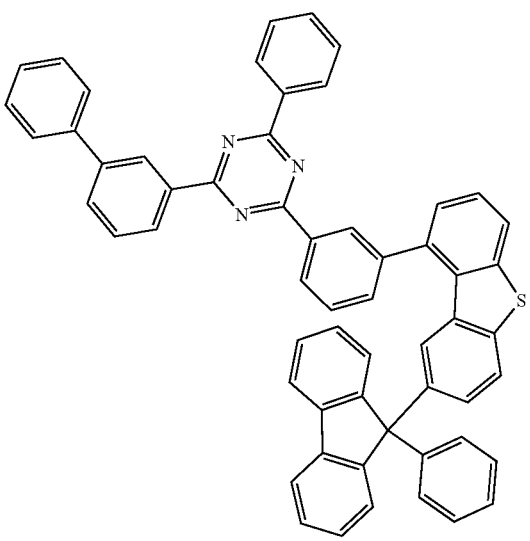
H1-167
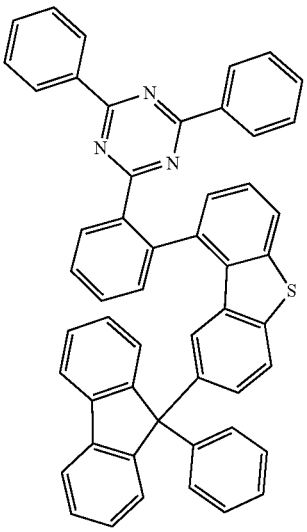

-continued
H1-168
H1-169
H1-170
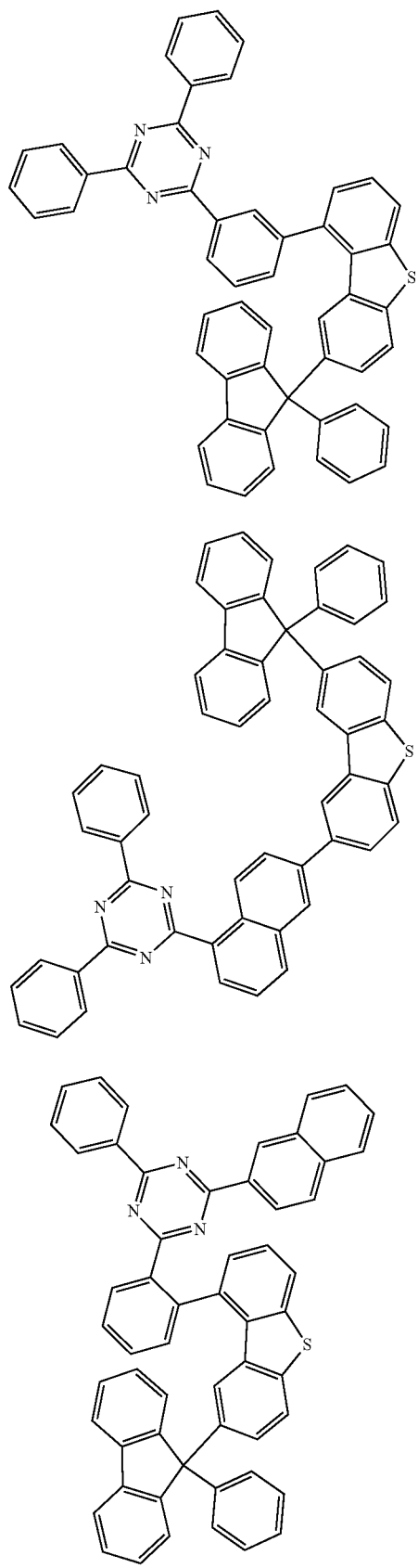
-continued
H1-171
H1-172
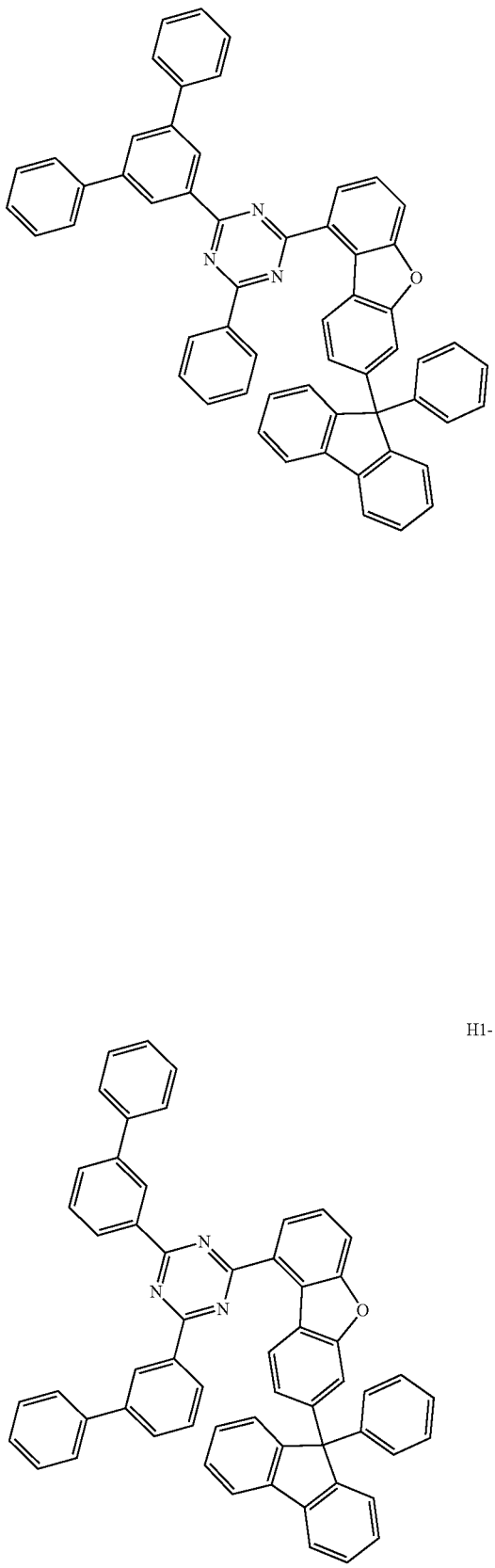

H1-173
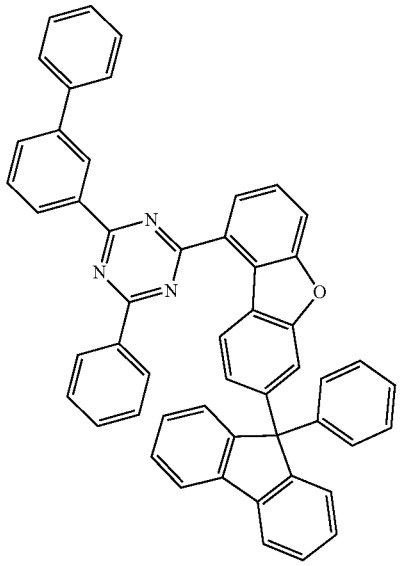
H1-174
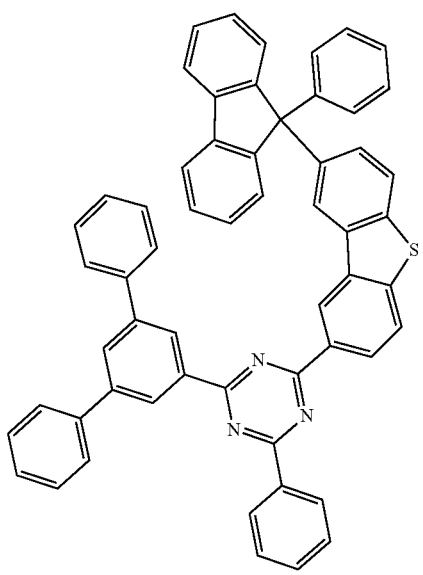
H1-175
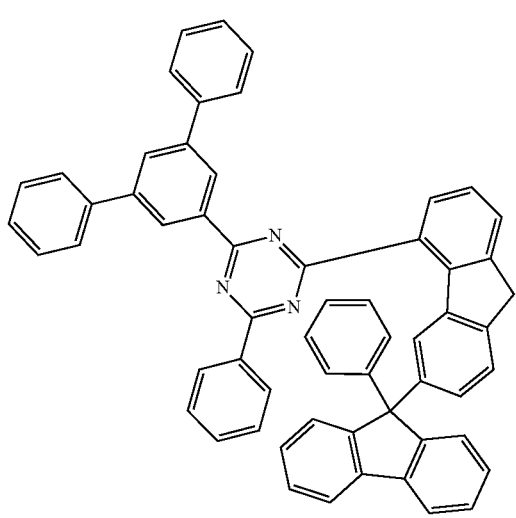
H1-176
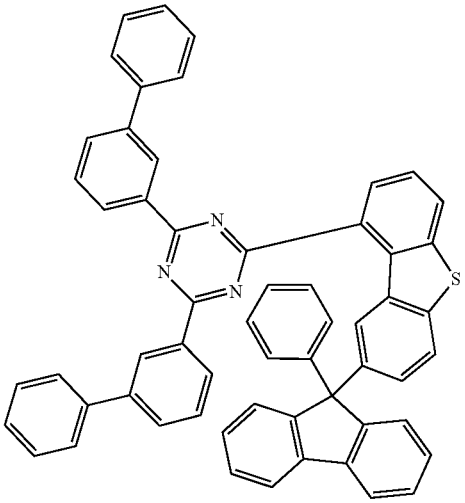
H1-177
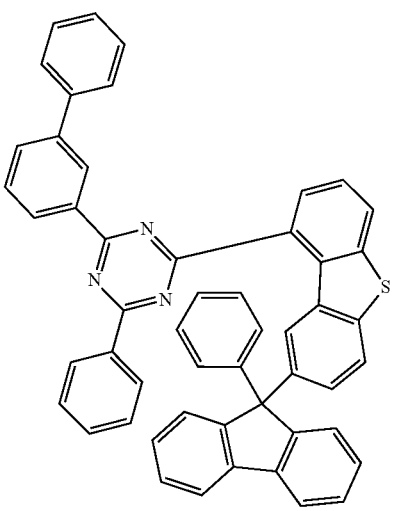
H1-178
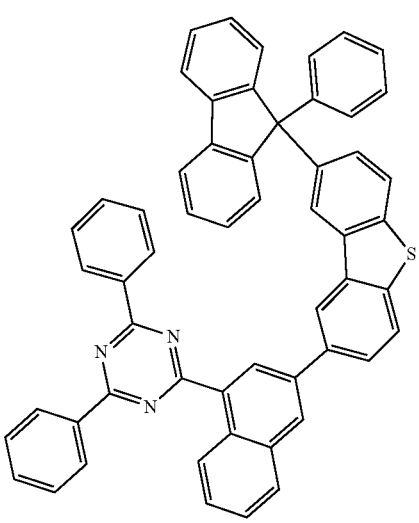

H1-179
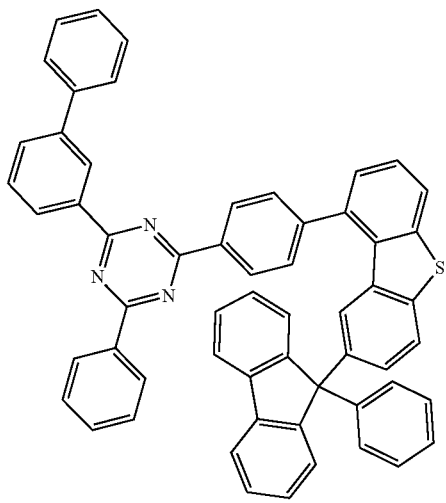
H1-180
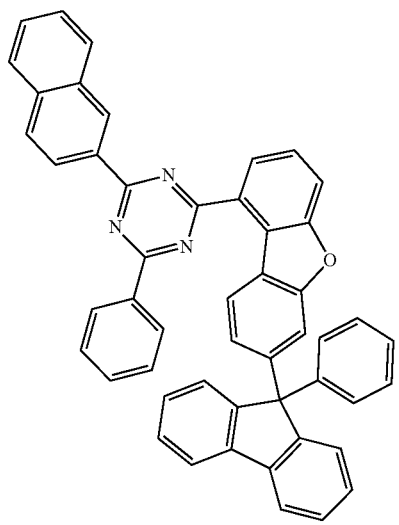
H1-181
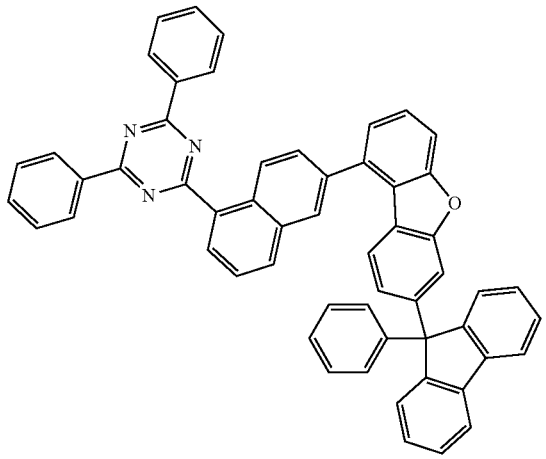
H1-182
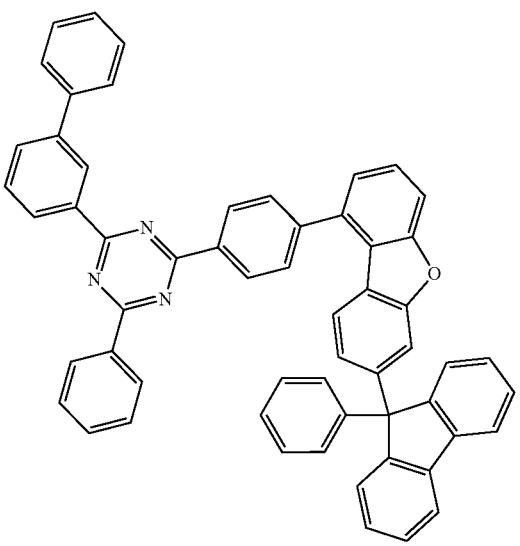
H1-183
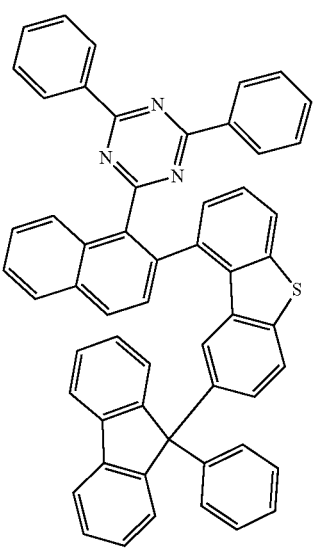
H1-184
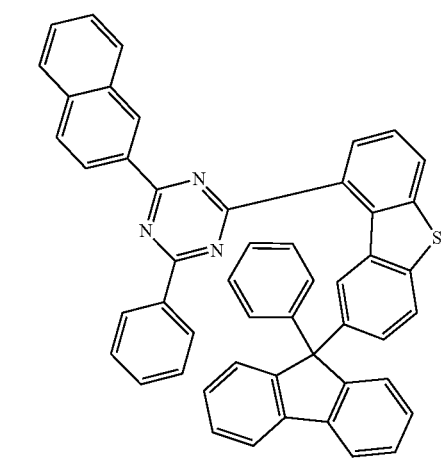

H1-185
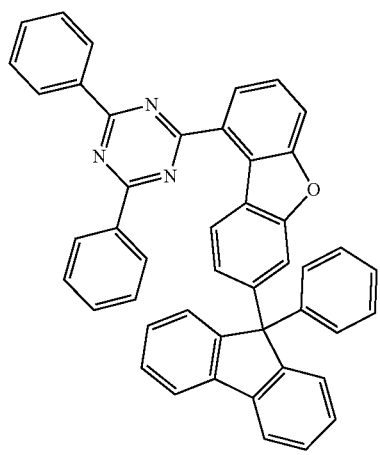
H1-188
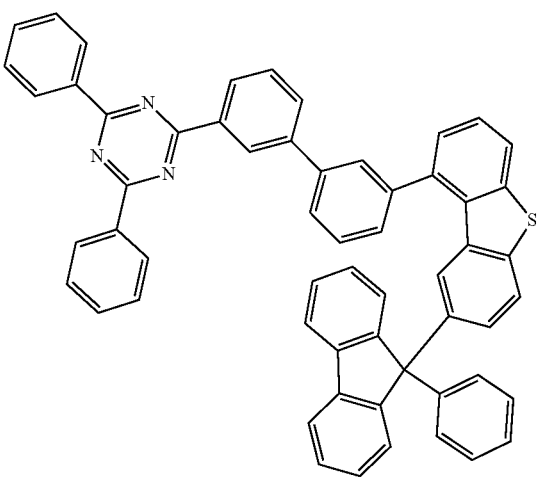
H1-186
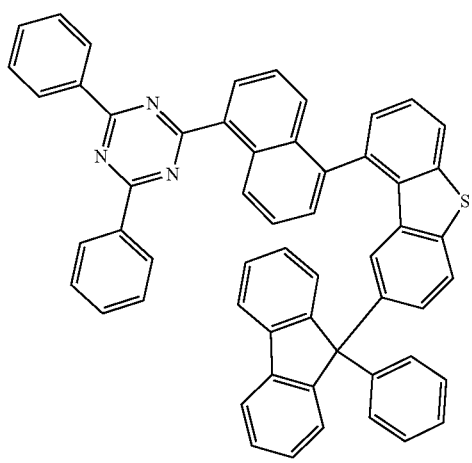
H1-189
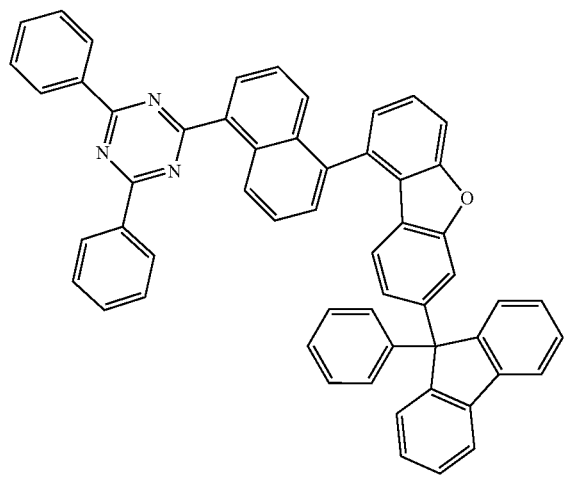
H1-187
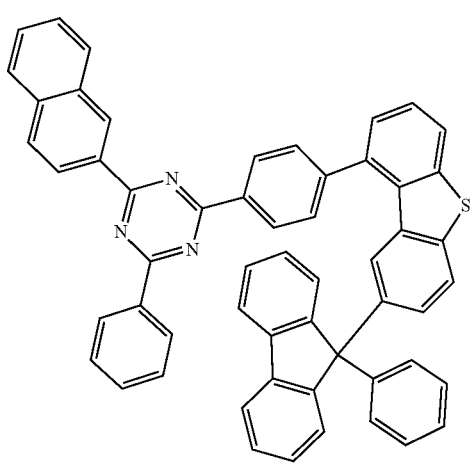
H1-190
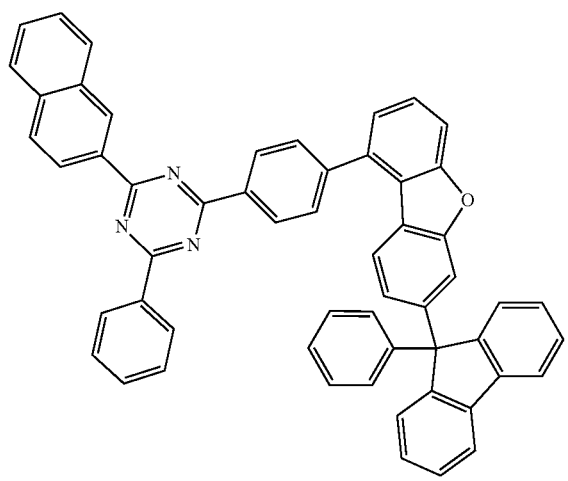

H1-191
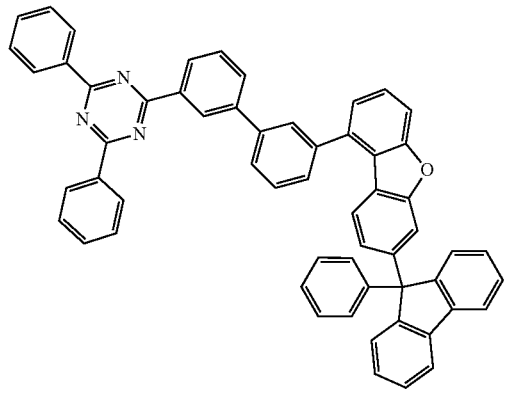
H1-194
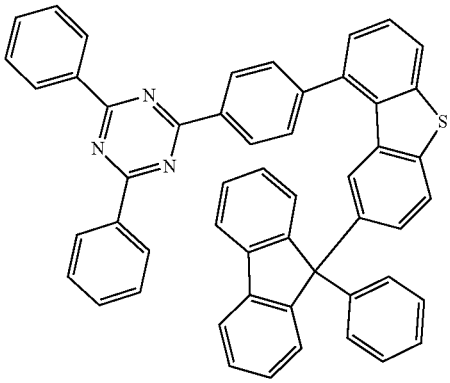
H1-192
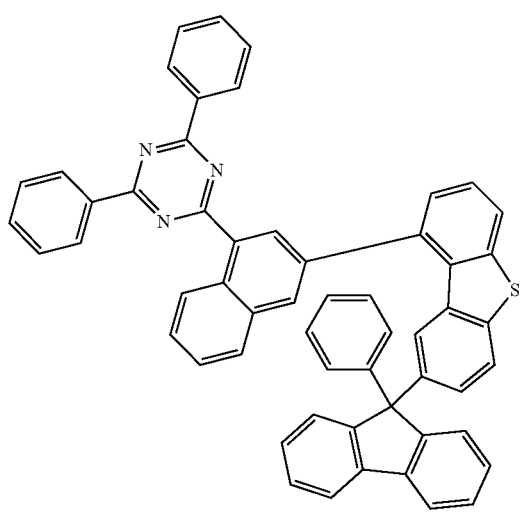
H1-195
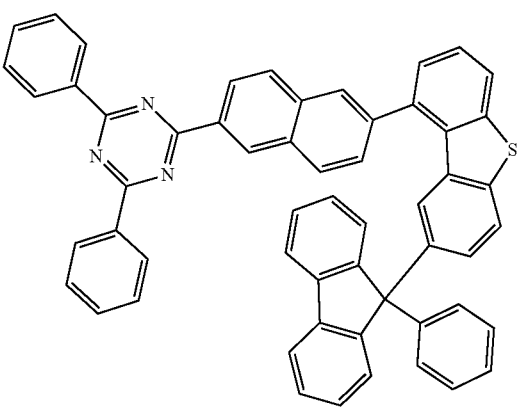
H1-196
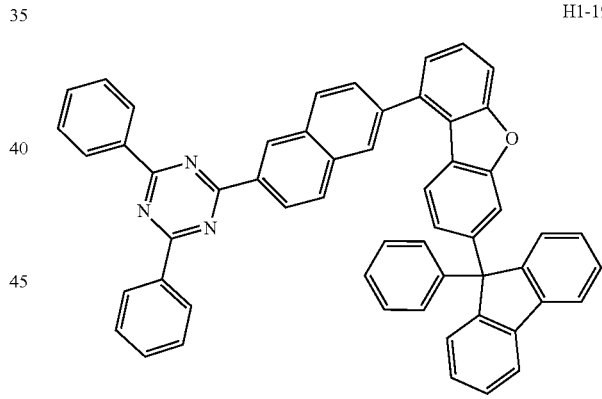
H1-193
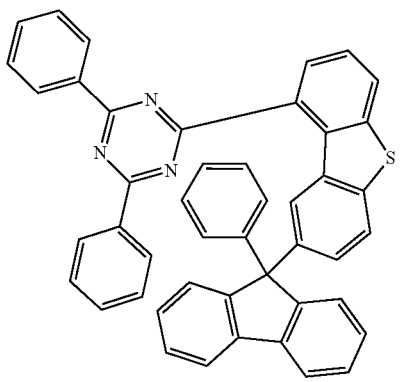
H1-197
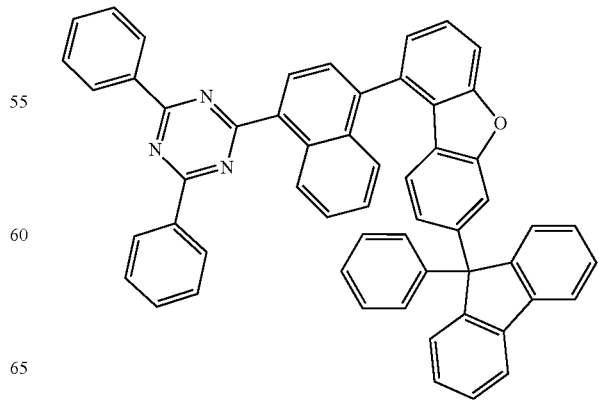

H1-198
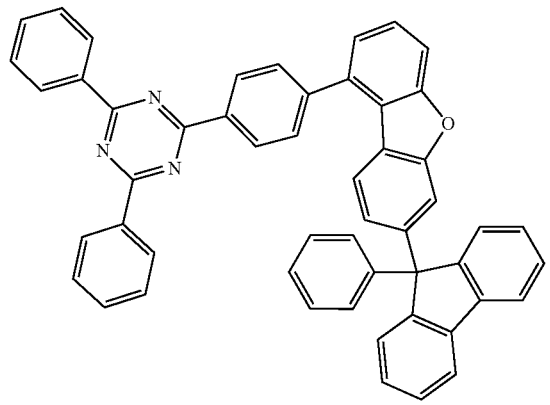
H1-199
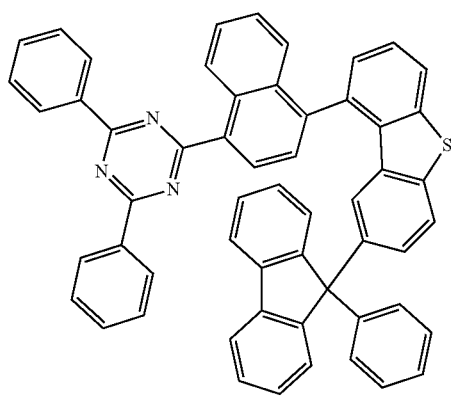
H1-200
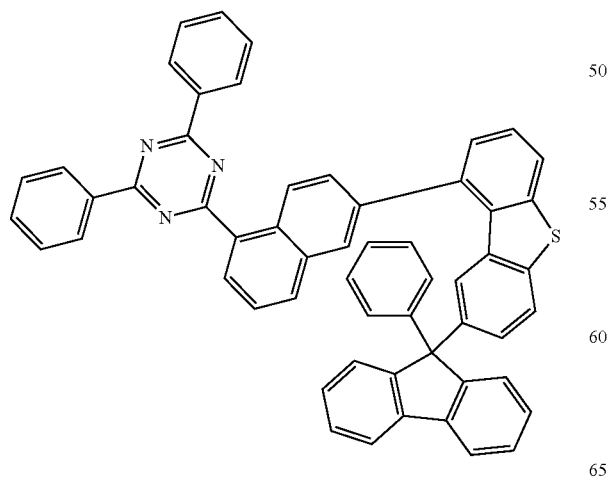
H1-201
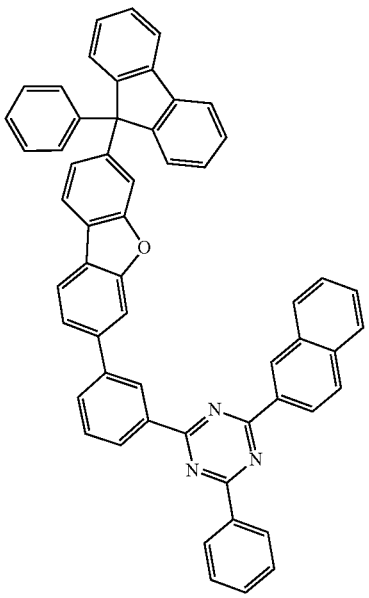
H1-202
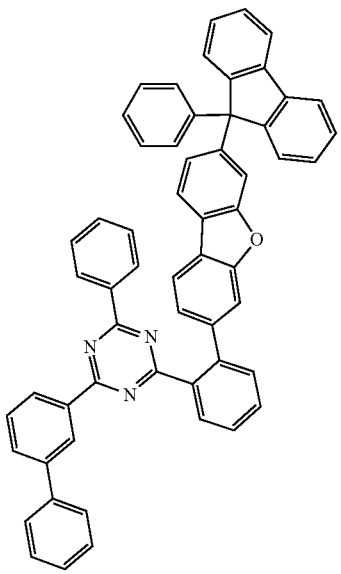

H1-203
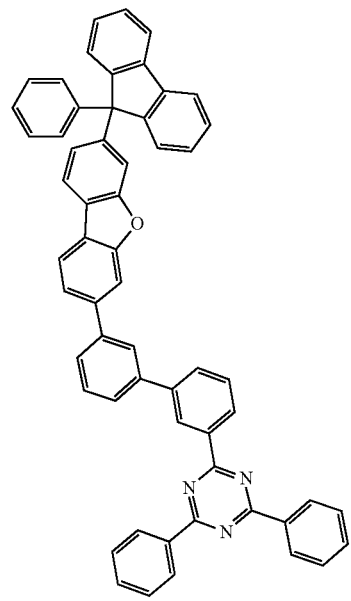
H1-205
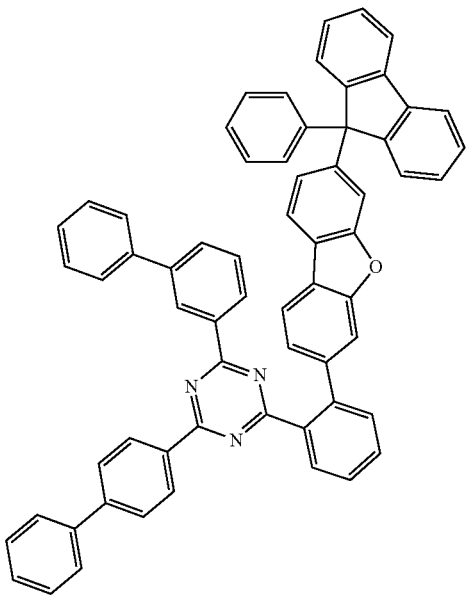
H1-204
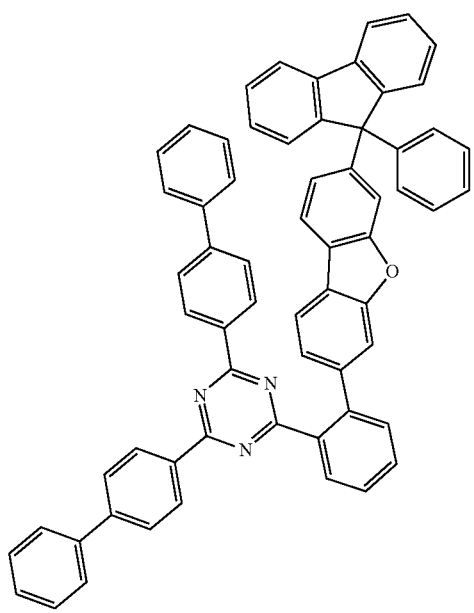
H1-206
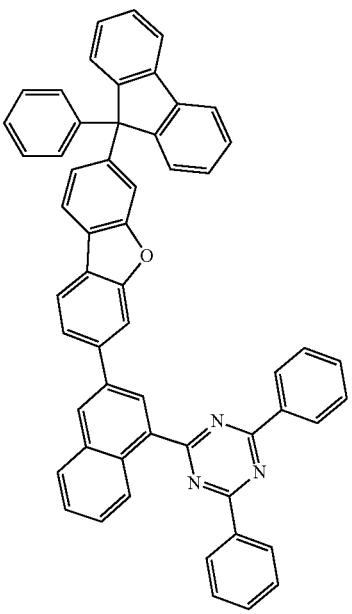

H1-207
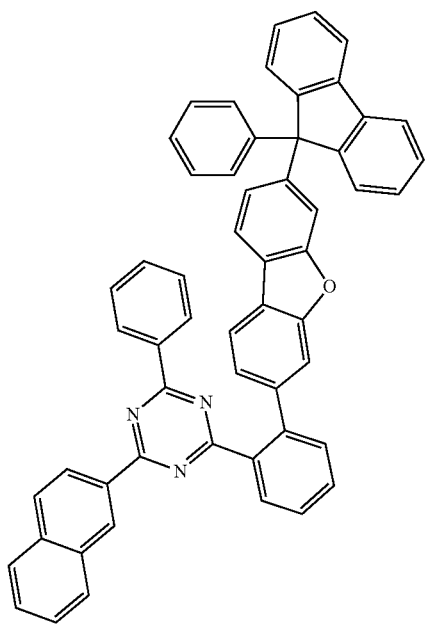
H1-209
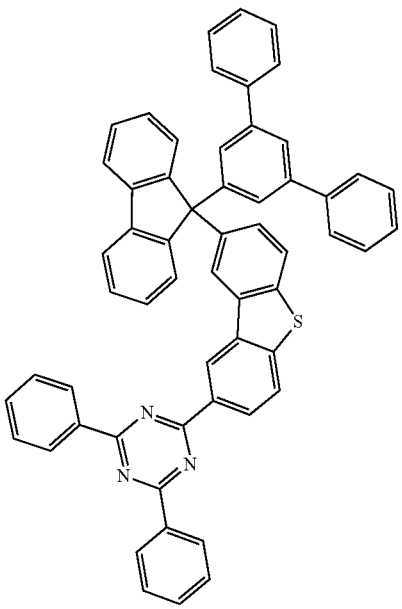
H1-208
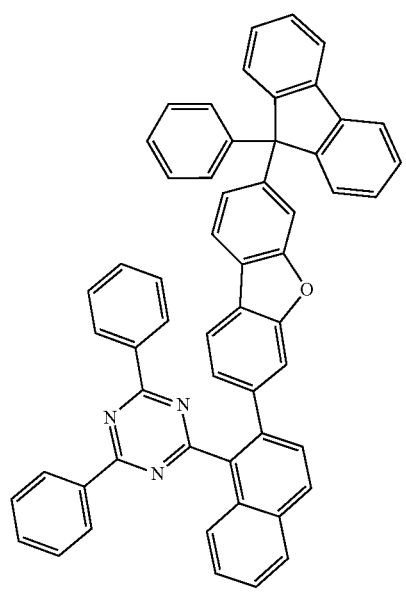
H1-210
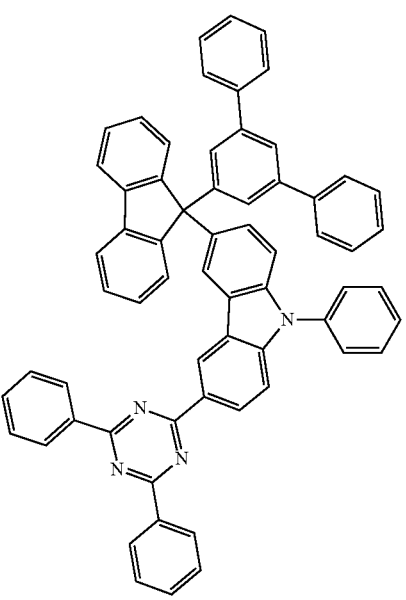

H1-211
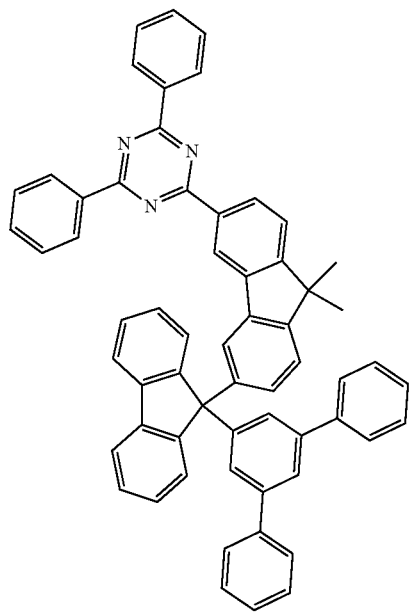
H1-212
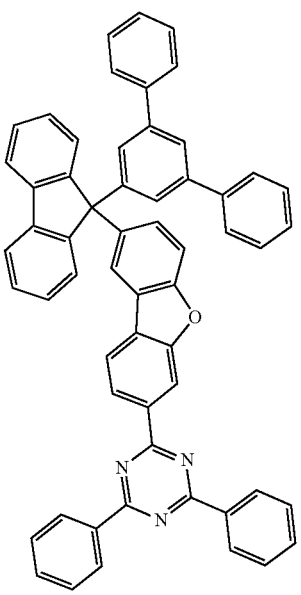
H1-213
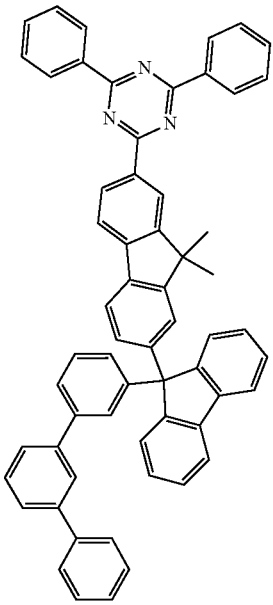
H1-214
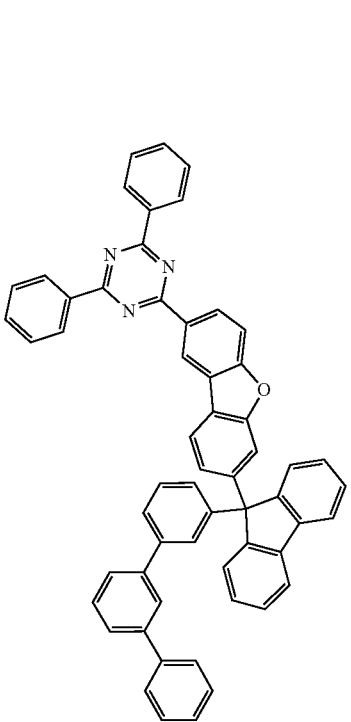

H1-215
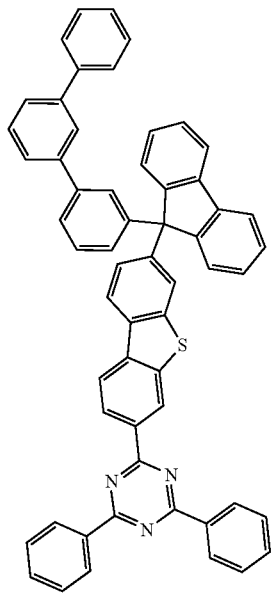
H1-217
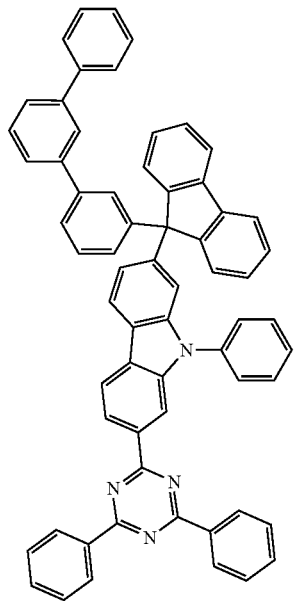
H1-216
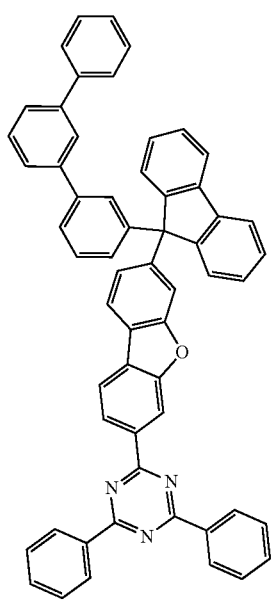
H1-218
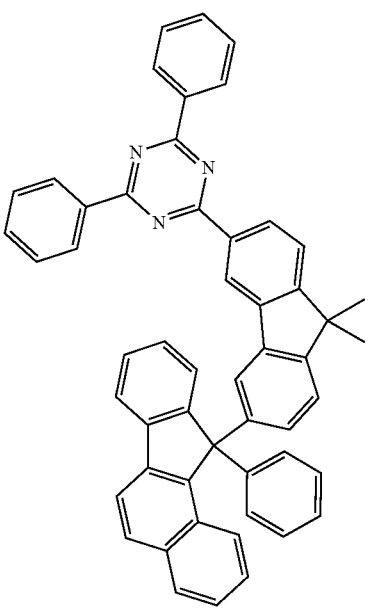

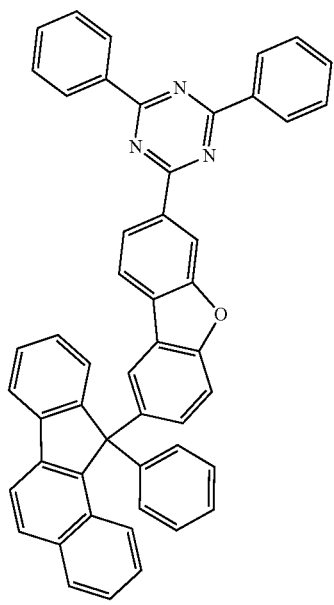
H1-219
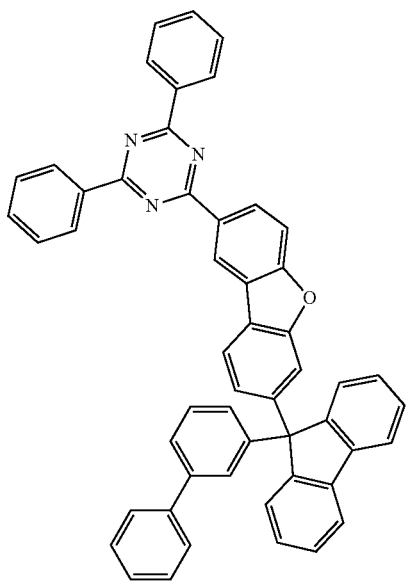
H1-221
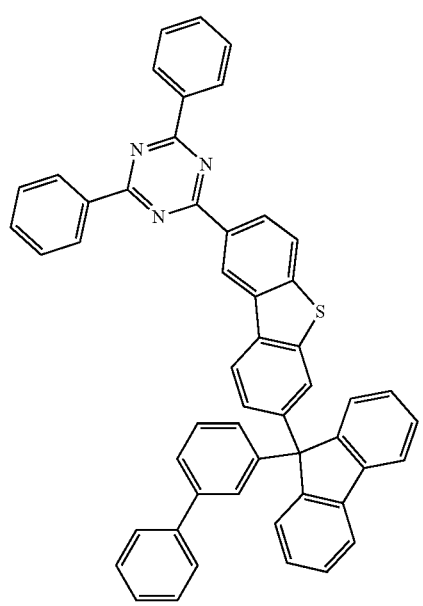
H1-220
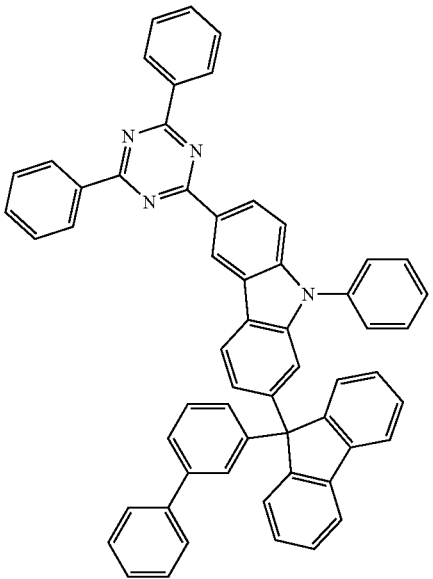
H1-222

H1-223
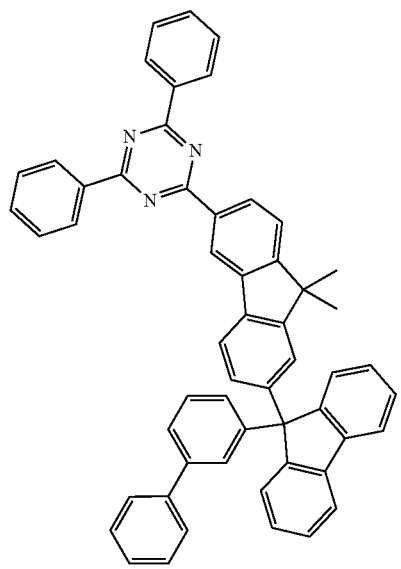
H1-225
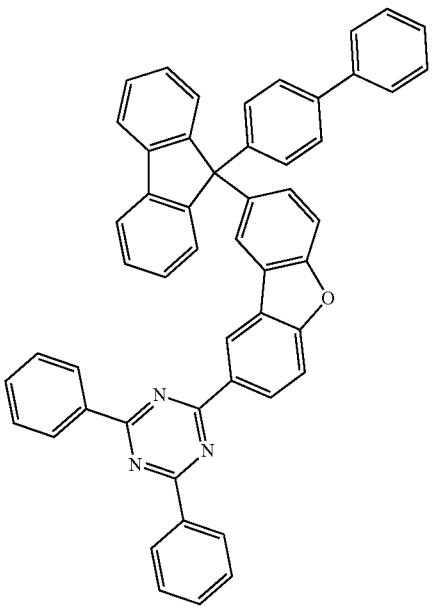
H1-224
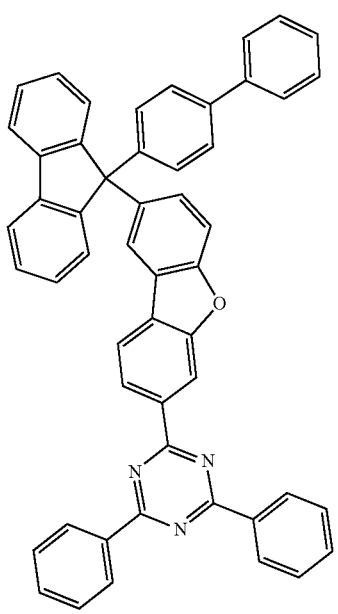
H1-226
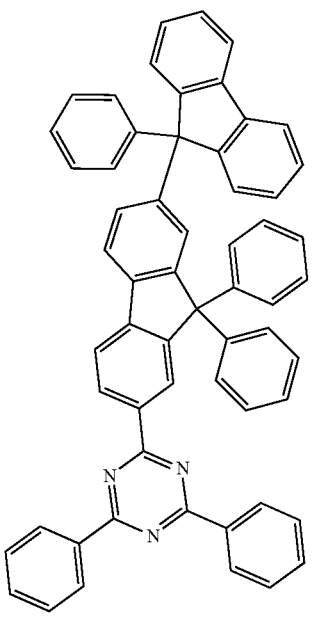

H1-227
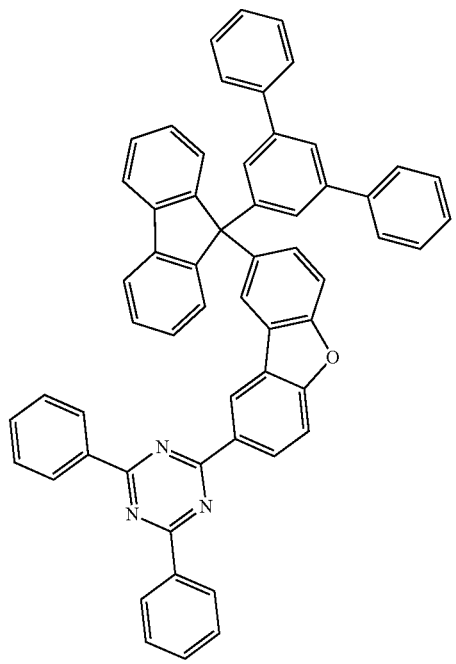
H1-229
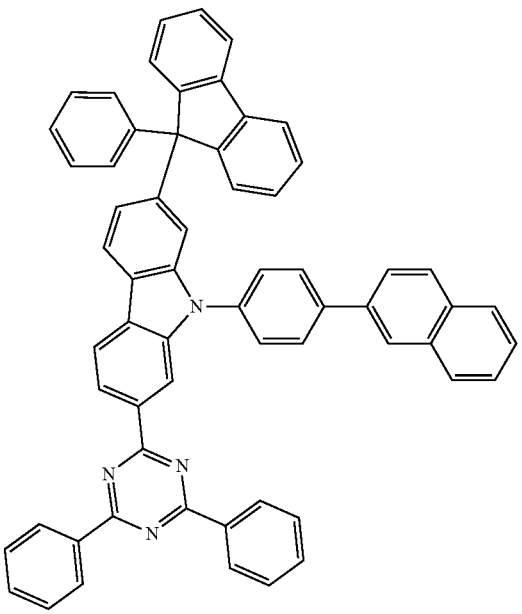
H1-228
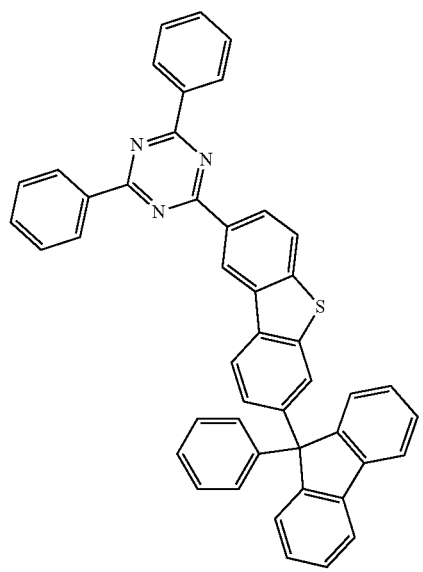
H1-230
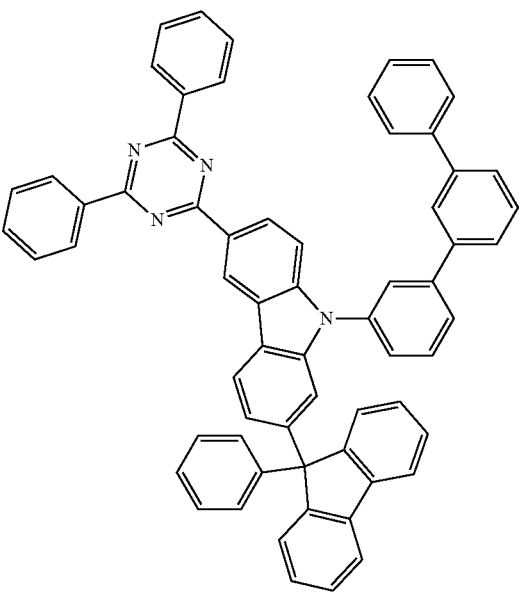

H1-231
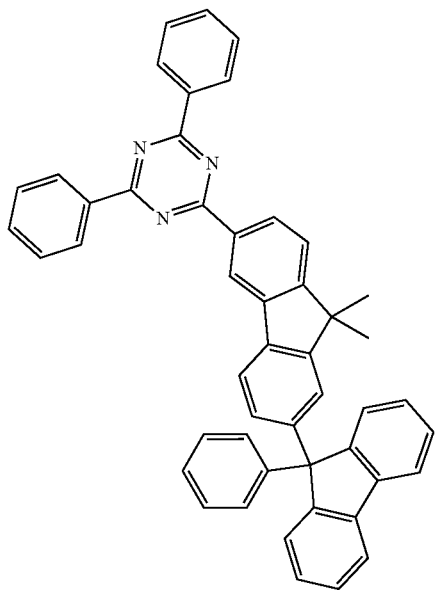
H1-232
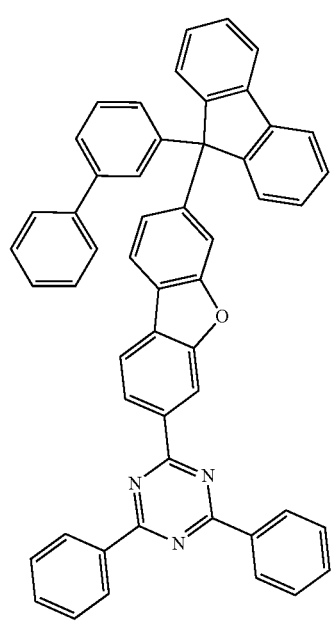
H1-233
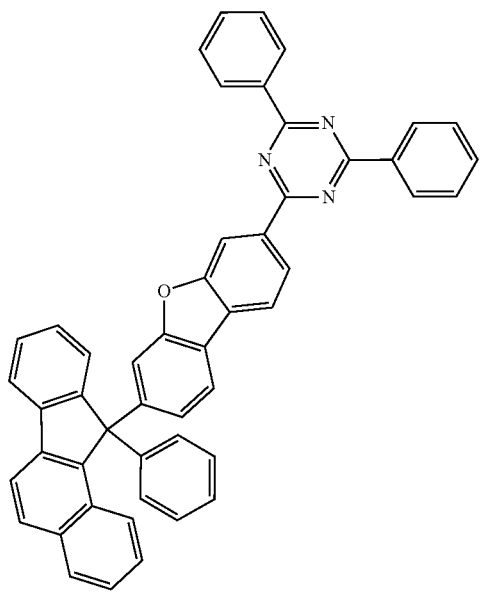
H1-234
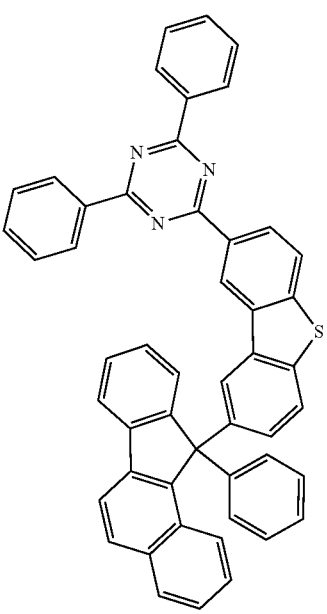

H1-235
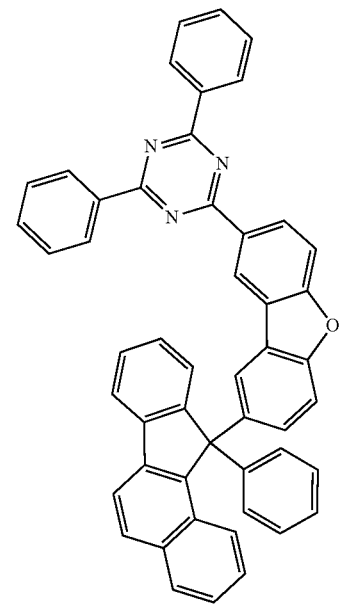
H1-236
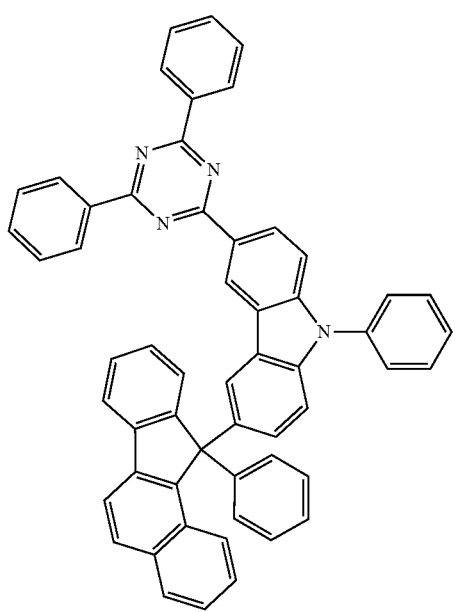
H1-237
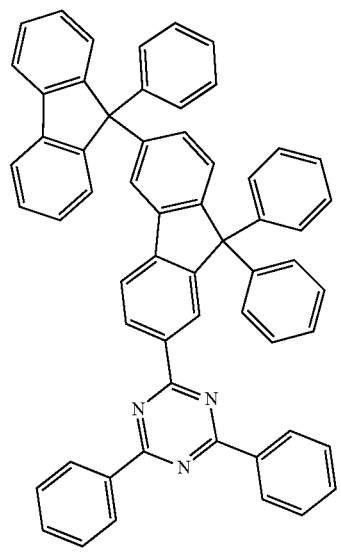
H1-238
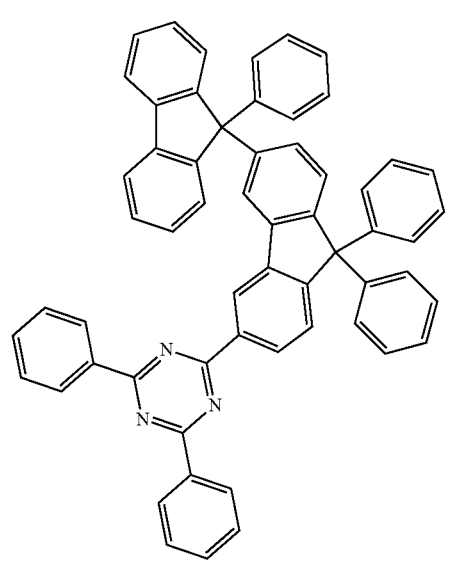
H1-239
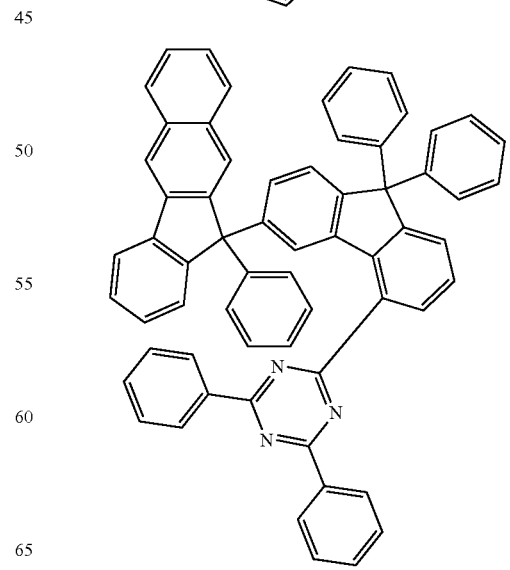

-continued
H1-240
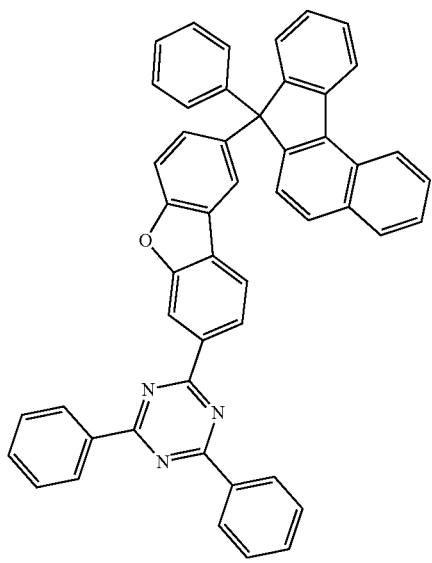
H1-241
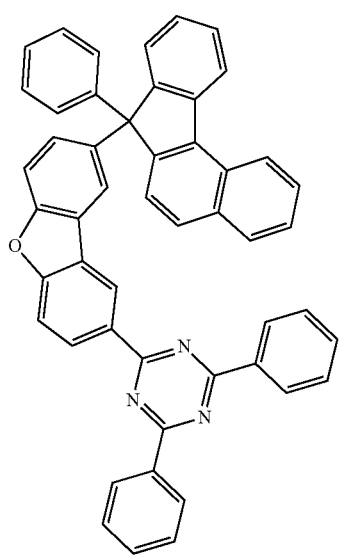
H1-242
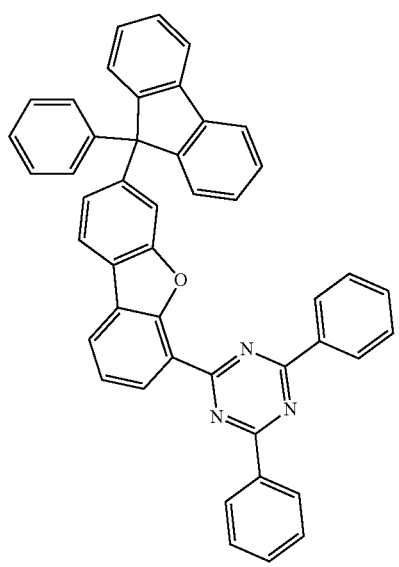
-continued
H1-243
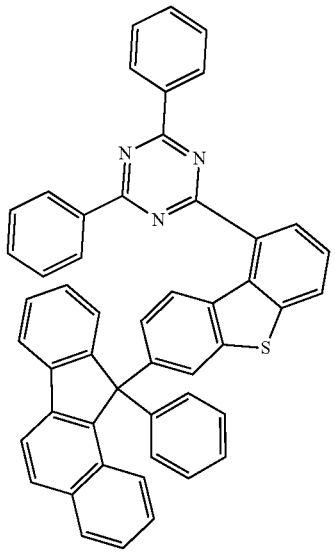
H1-244
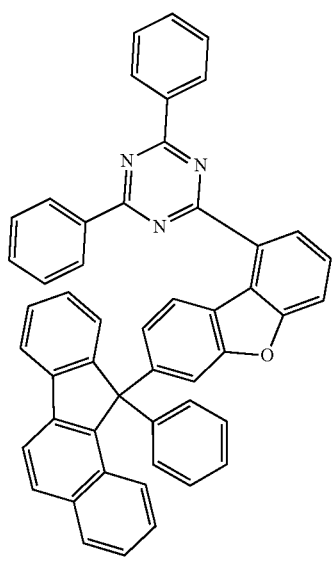
H1-245
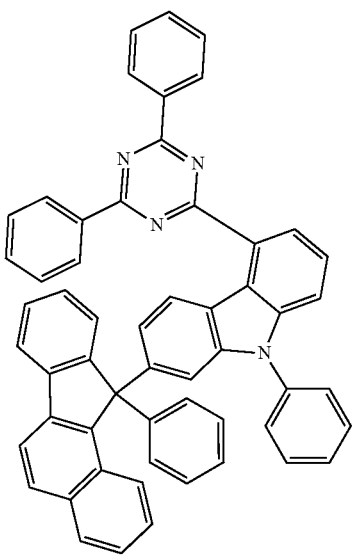

H1-246
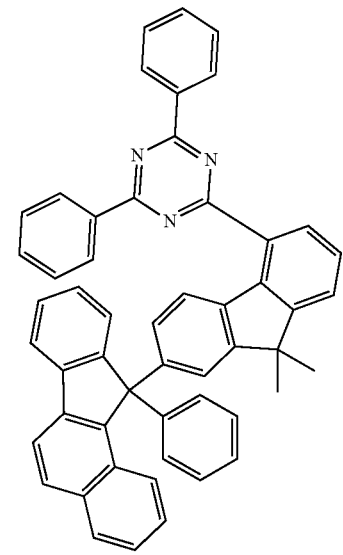
H1-247
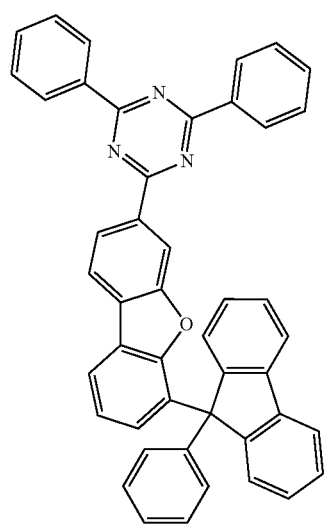
H1-248
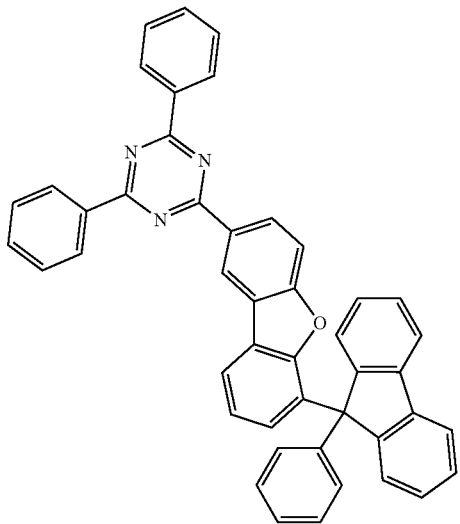
H1-249
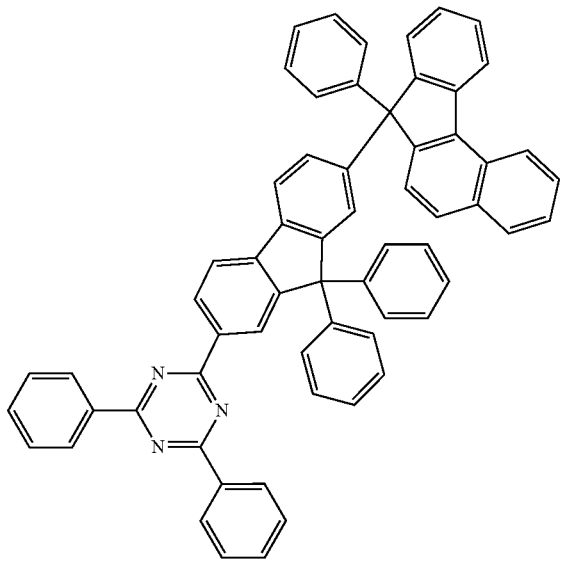
H1-250
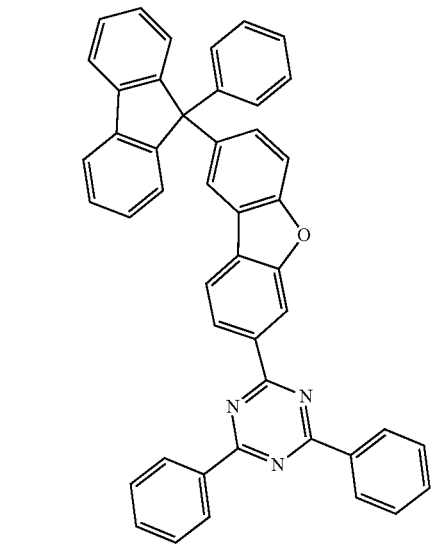

H1-251
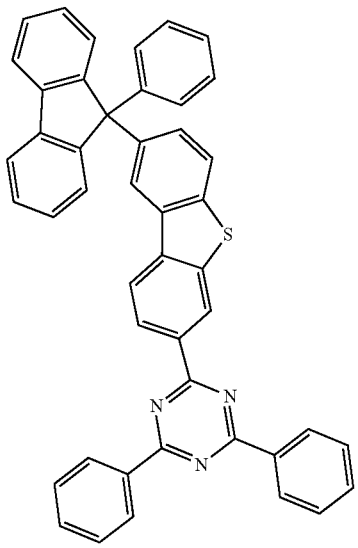
H1-252
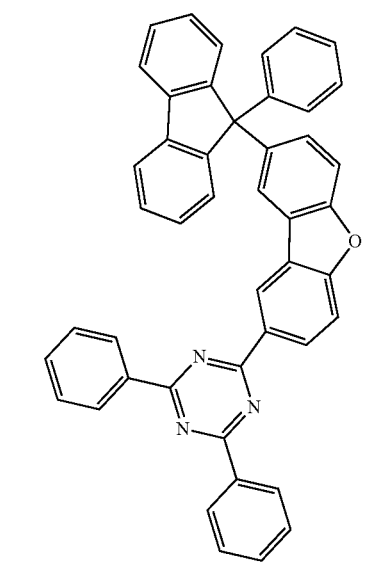
H1-253
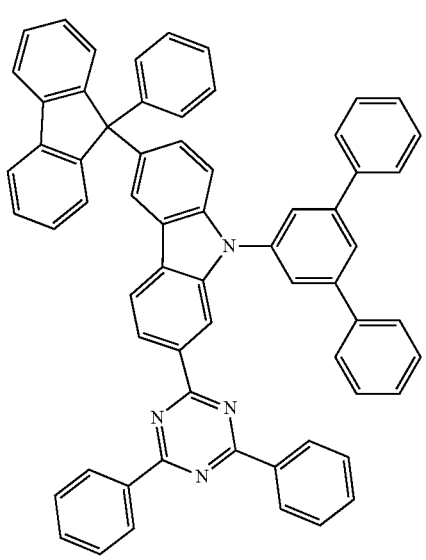
H1-254
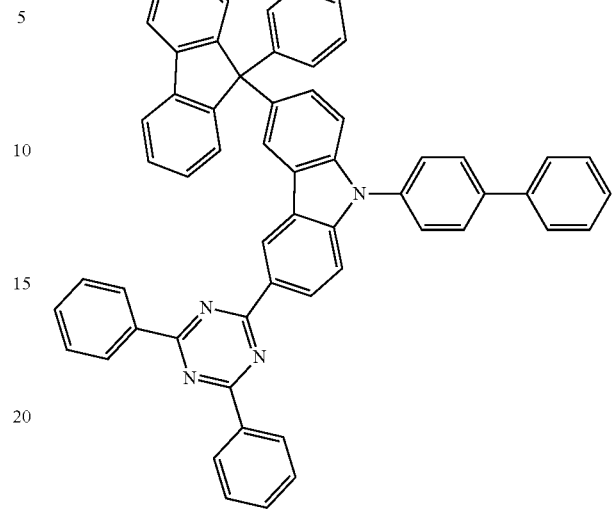
H1-255
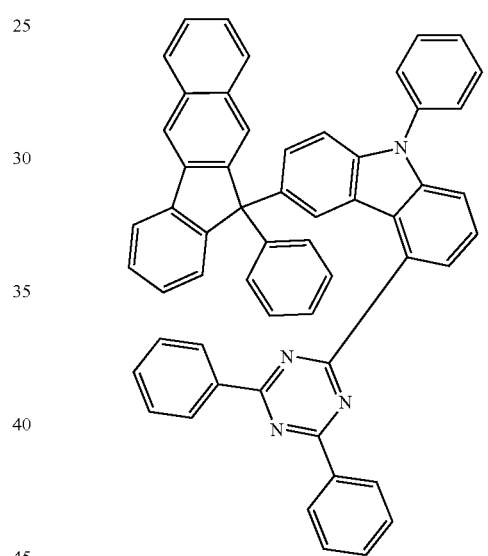
H1-256
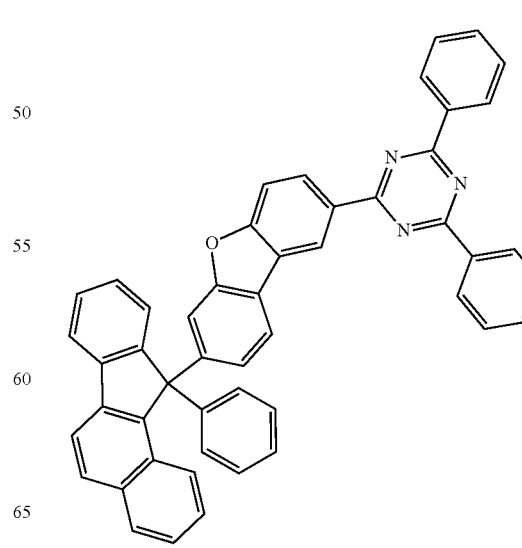

H1-257
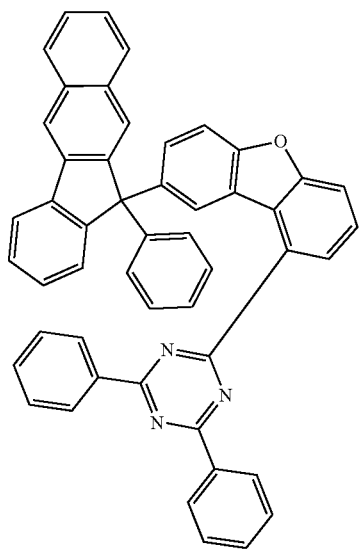
H1-258
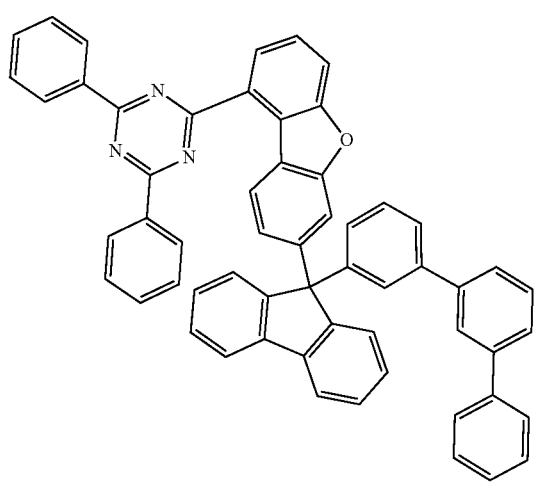
H1-259
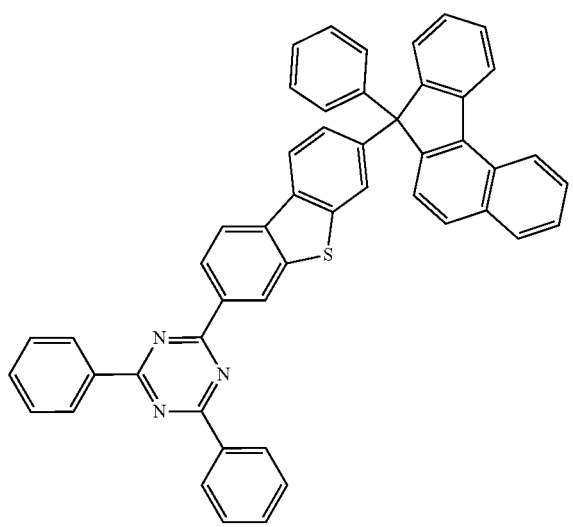
H1-260
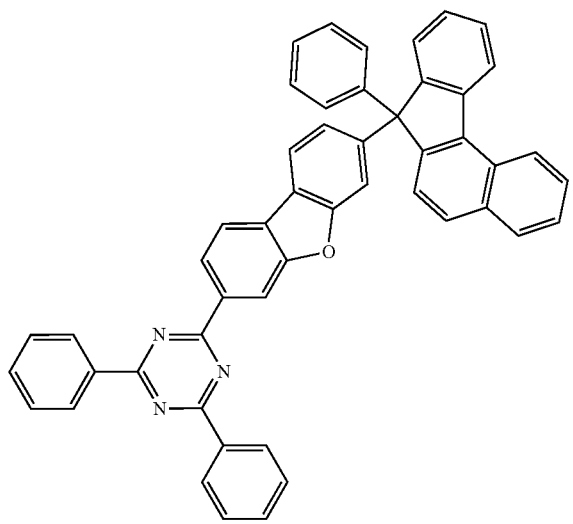
H1-261
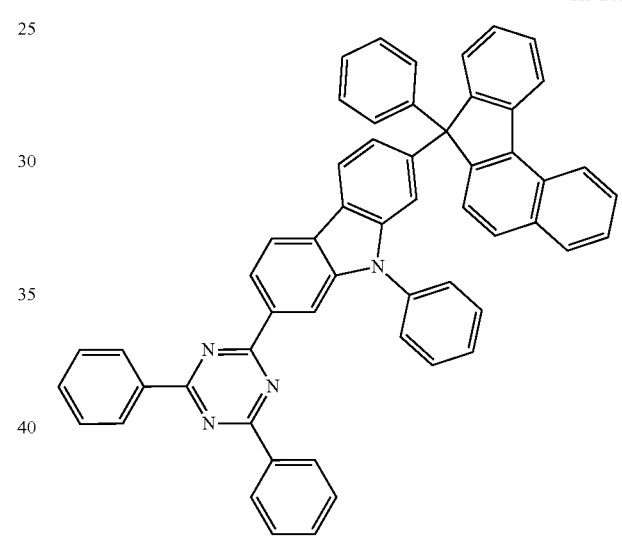
H1-262
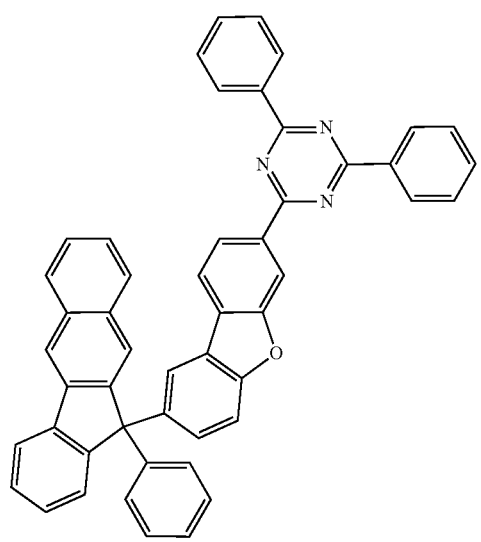

H1-263
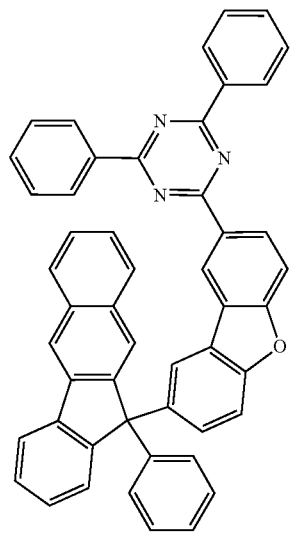
H1-264
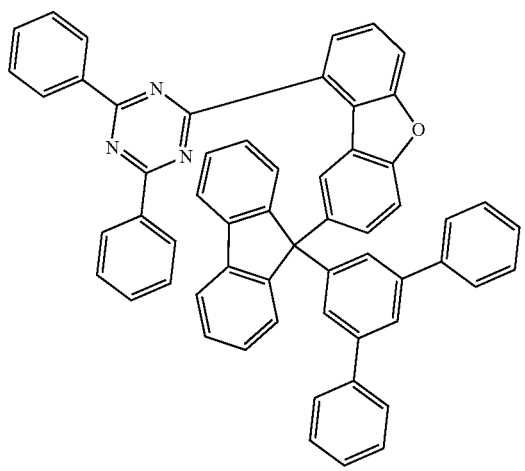
H1-265
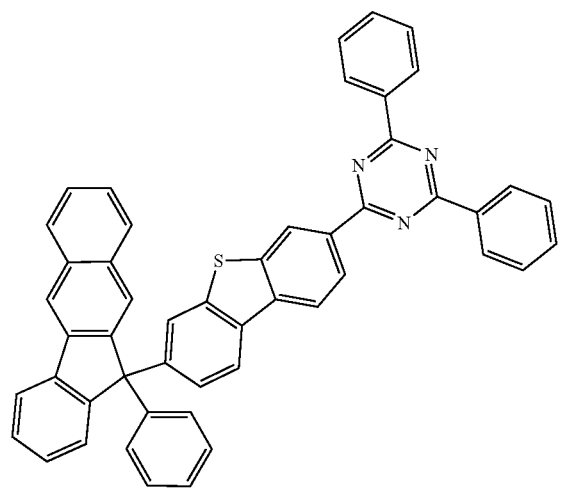
H1-266
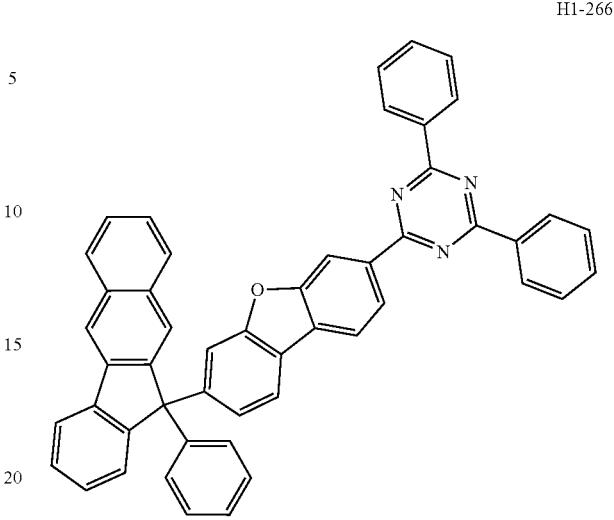
H1-267
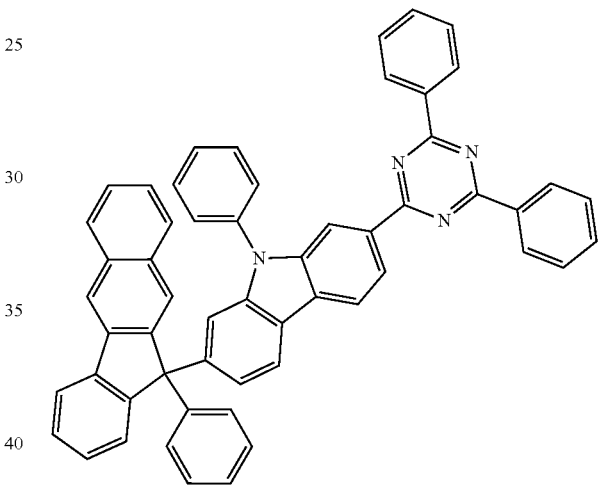
H1-268
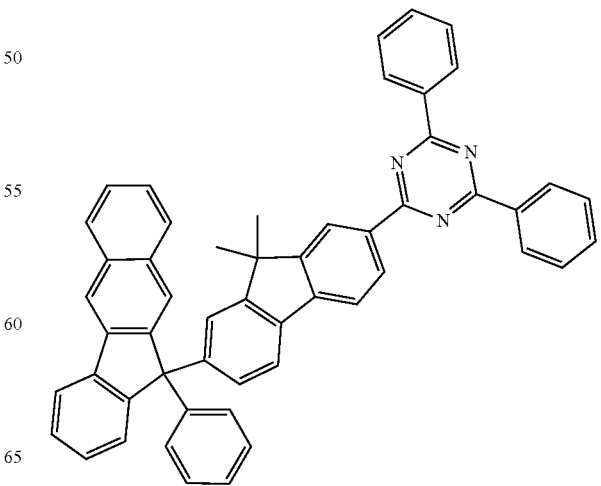

H1-269
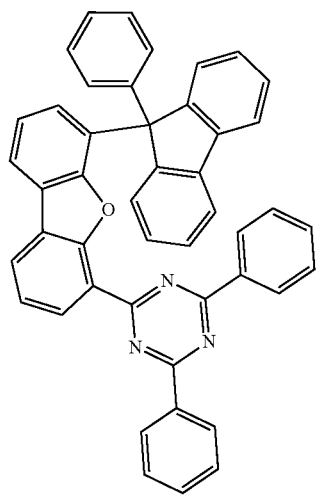
H1-270
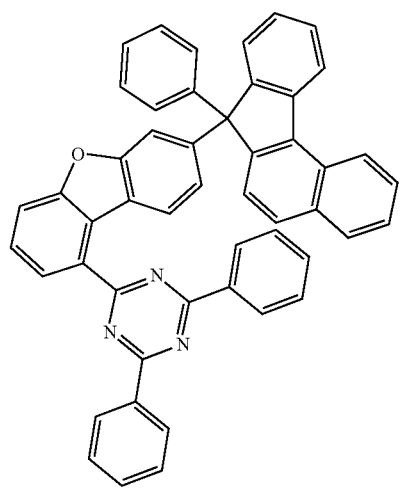
H1-271
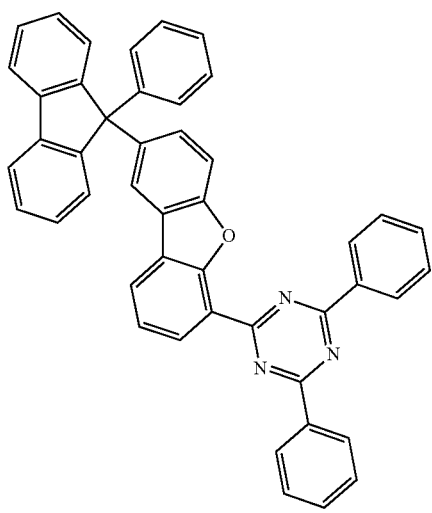
H1-272
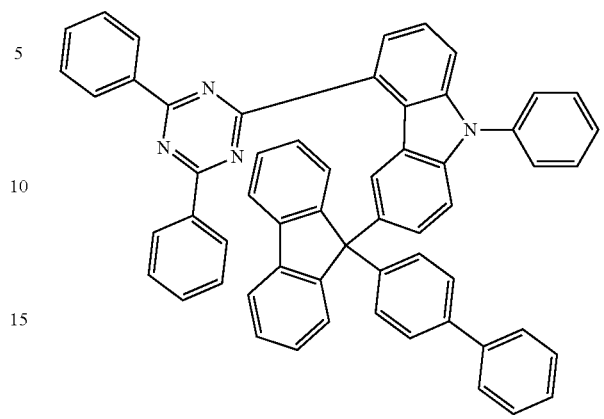
H1-273
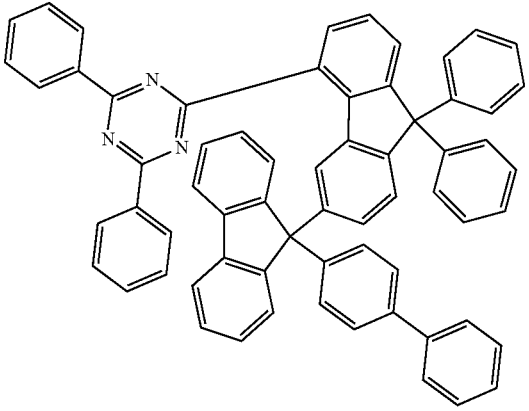
H1-274
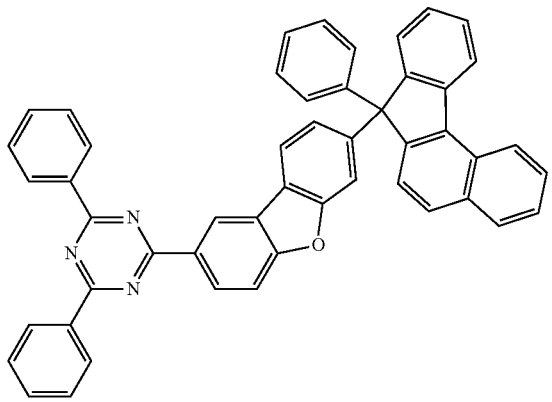

H1-275
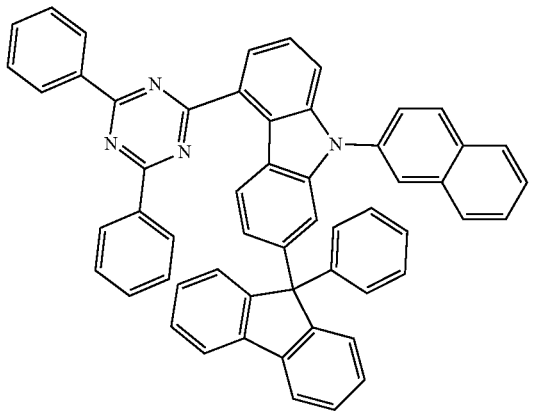
H1-276
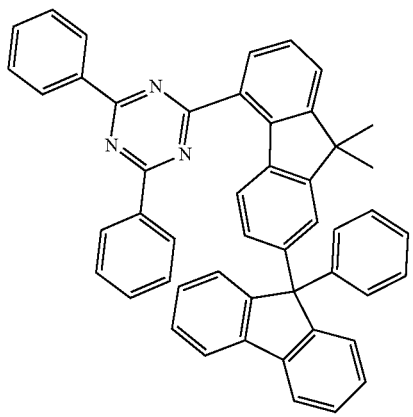
H1-277
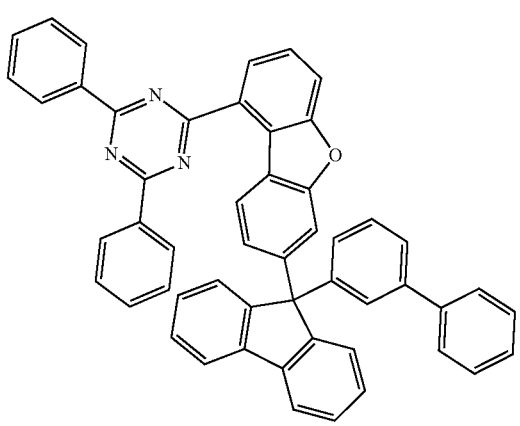
H1-278
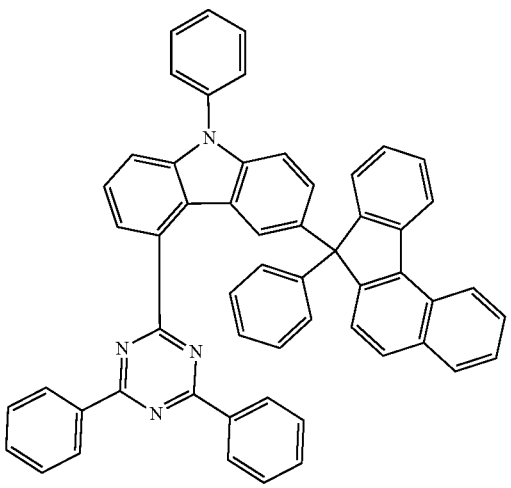
H1-279
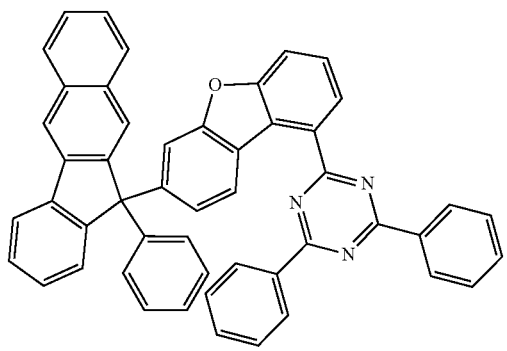
H1-280
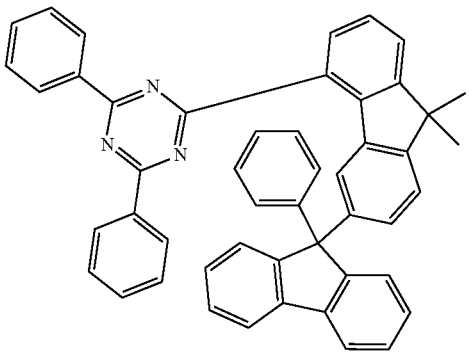
H1-281
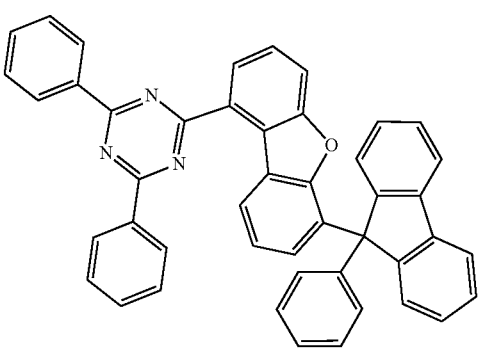

H1-282
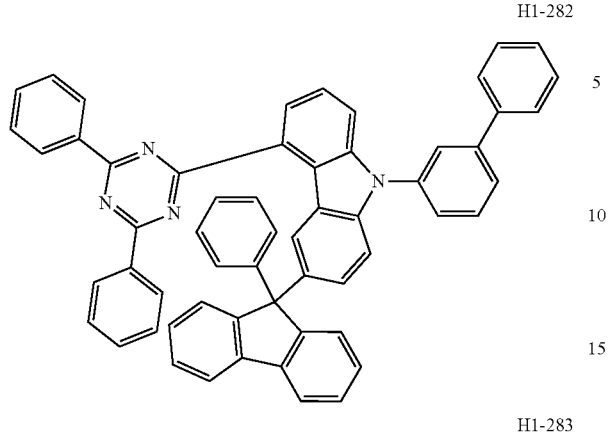
H1-286
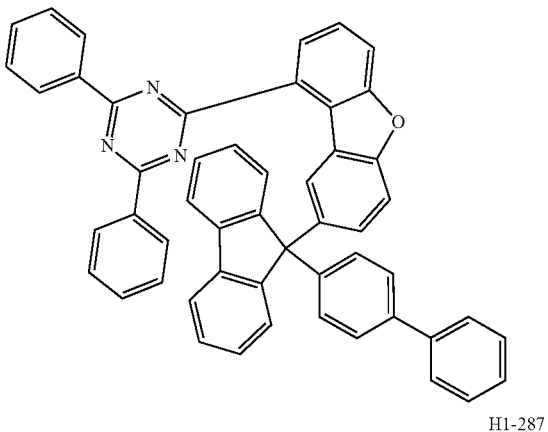
H1-283
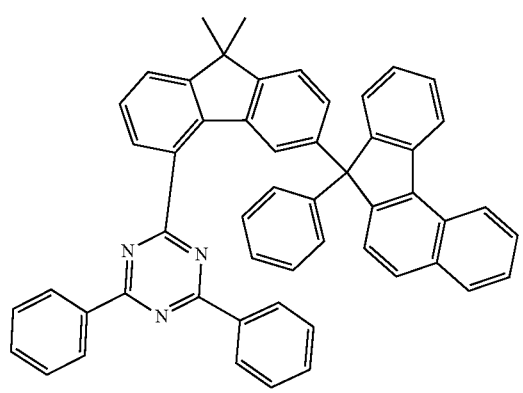
H1-287
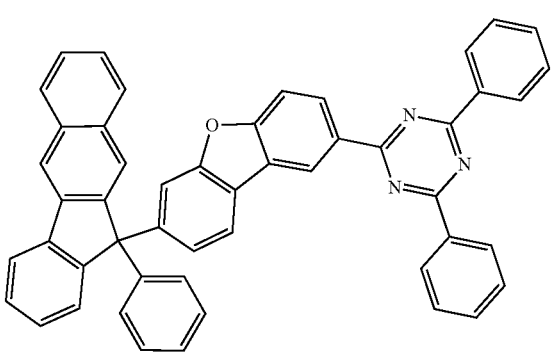
H1-284
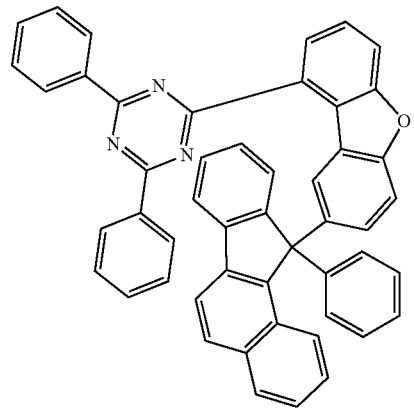
H1-288
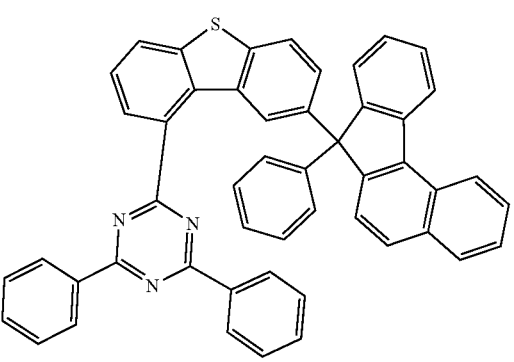
H1-285
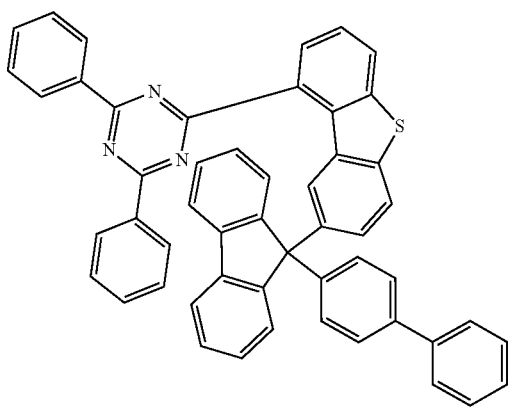
H1-289
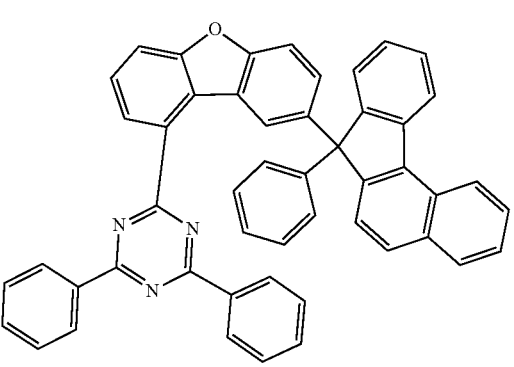

H1-290
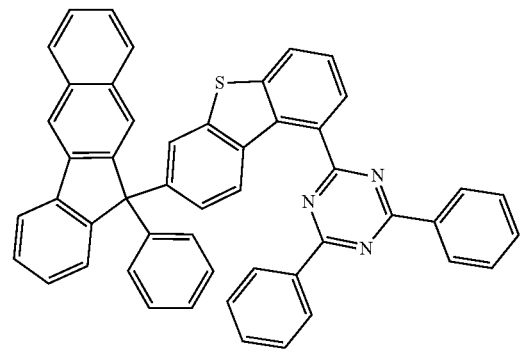
H1-293
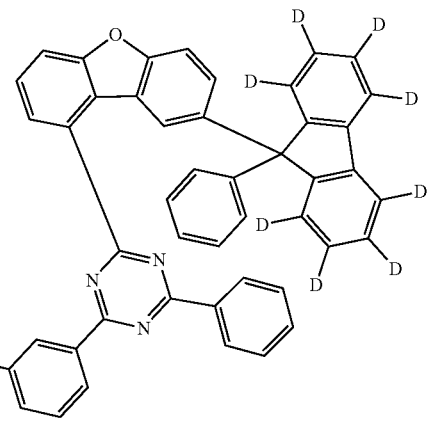
H1-291
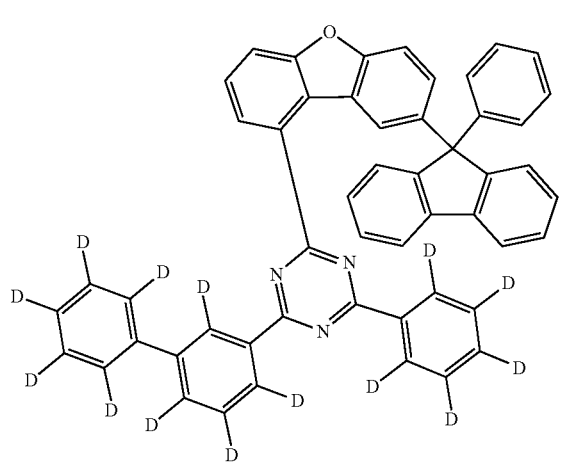
H1-294
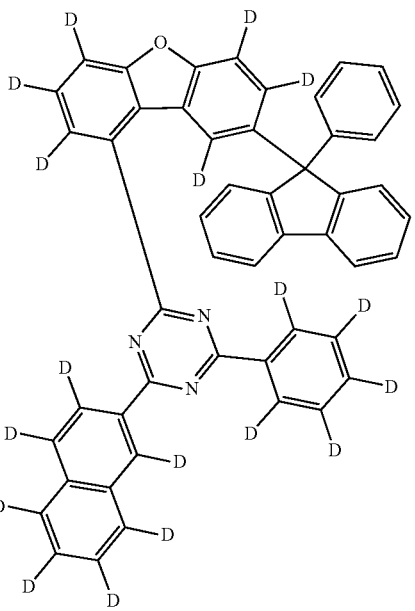
H1-292
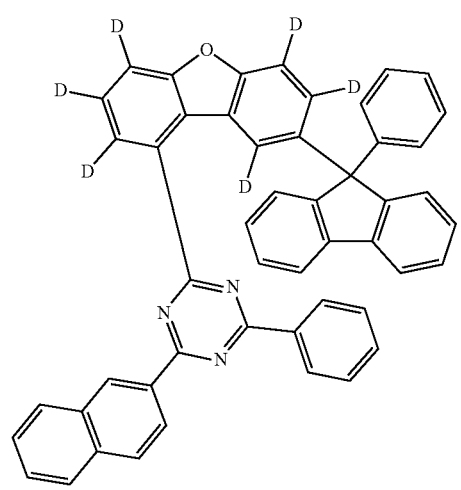
H1-295
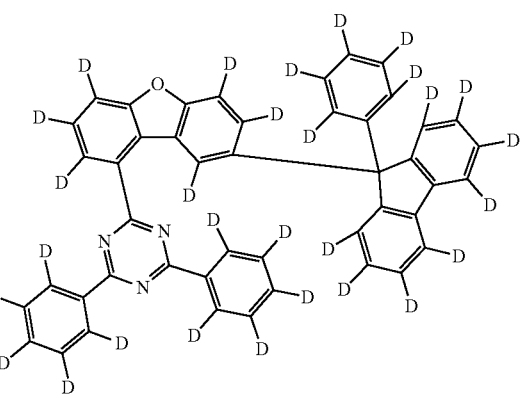
The compound represented by formula 1 of the present disclosure may be produced by a synthetic method known to a person skilled in the art. For example it may be prepared may be prepared by referring to the following reaction scheme 1 or 2, but is not limited thereto.

[Reaction Scheme 1]

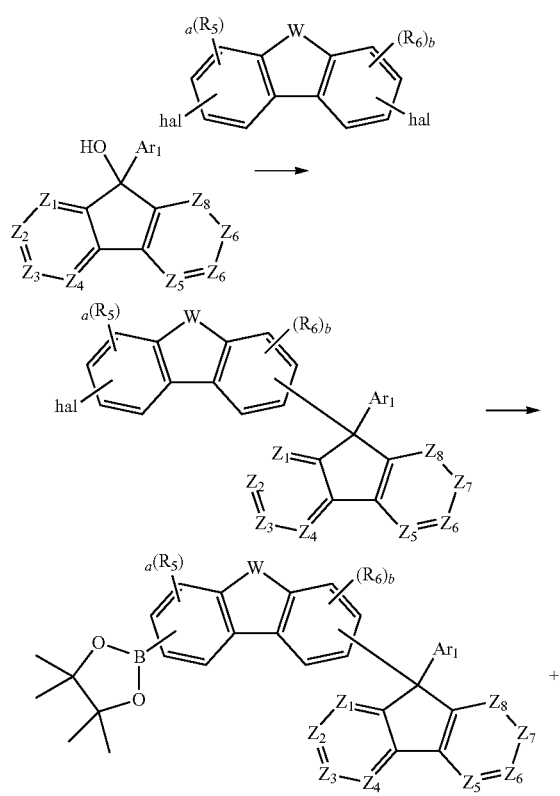

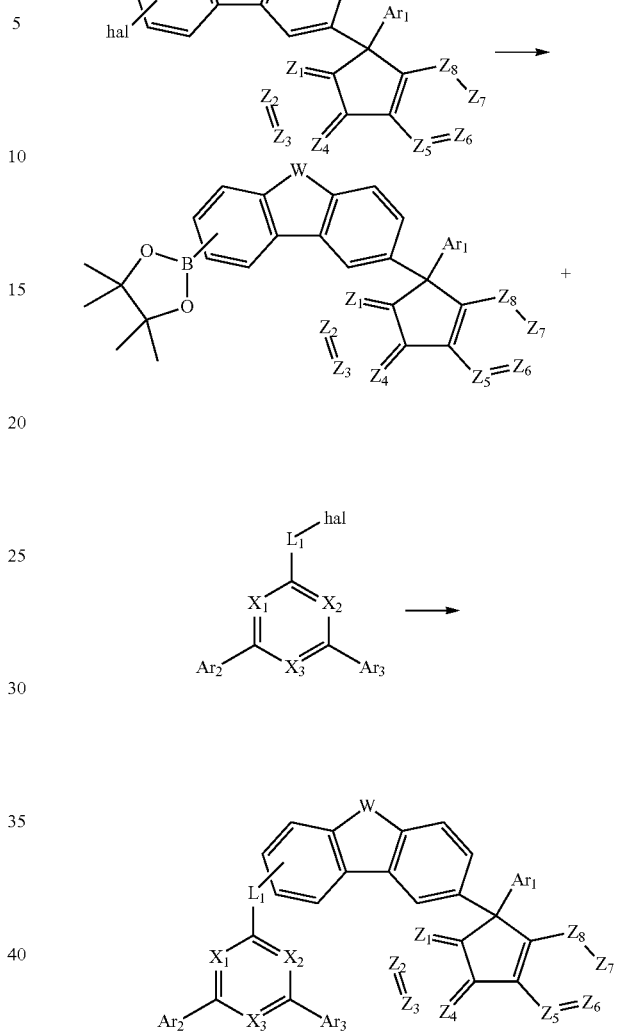

[Reaction Scheme 2]

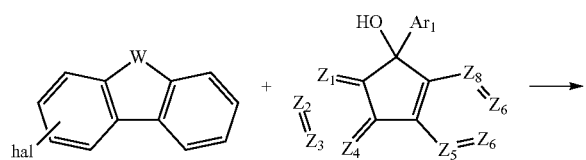

In reaction schemes 1 and 2 above, the definition of the respective substituents is as defined in formula 1, and hal means a halogen atom.

As described above, exemplary synthesis examples of the compounds represented by formula 1 according to one embodiment are described, but they are based on Buchwald-Hartwig cross coupling reaction, N-arylation reaction, H-mont-mediated etherification reaction, Miyaura borylation reaction, Suzuki cross-coupling reaction, Intramolecular acid-induced cyclization reaction, Pd(II)-catalyzed oxidative cyclization reaction, Grignard reaction, Heck reaction, Cyclic Dehydration reaction, SN1 substitution reaction, SN2 substitution reaction, and phosphine-mediated reductive cyclization reaction, etc. It will be understood by one skilled in the art that the above reaction proceeds even if other substituents defined in formula 1, other than the substituents described in the specific synthesis examples, are bonded.

The second host material as another host material according to one embodiment may be comprised a compound represented by the following formula 2.

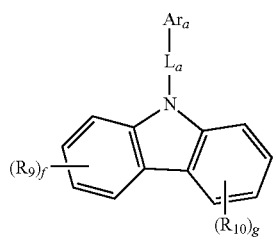

(2)

In formula 2, $L_a$ represents a single bond, a substituted or unsubstituted (C6-C30)arylene, or a substituted or unsubstituted (3- to 30-membered)heteroarylene;

$Ar_a$ represents a substituted or unsubstituted (C6-C30)aryl or a substituted or unsubstituted (3- to 30-membered)heteroaryl;

$R_9$ and $R_{10}$ each independently represent, hydrogen, deuterium, halogen, cyano, a substituted or unsubstituted (C1-C30)alkyl, a substituted or unsubstituted (C6-C30)aryl, a substituted or unsubstituted (3- to 50-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, a substituted or unsubstituted mono- or di-(C6-C30)arylamino, a substituted or unsubstituted mono- or di-(3- to 30-membered)heteroarylamino, or a substituted or unsubstituted (C6-C30)aryl(3- to 30-membered)heteroarylamino; or may be linked to the adjacent substituents to form a ring(s);

f and g each independently represent, an integer of 1 to 4; and when f and g are an integer of 2 or more, each of $R_9$ and each of $R_{10}$ may be the same or different.

In one embodiment, $R_9$ and $R_{10}$ each independently may be hydrogen, a substituted or unsubstituted (C6-C30)aryl, or a substituted or unsubstituted (3- to 50-membered)heteroaryl; or may be linked to the adjacent substituents to form a ring(s), preferably, hydrogen, a substituted or unsubstituted (C6-C25)aryl, or a substituted or unsubstituted (5- to 50-membered)heteroaryl; or may be linked to the adjacent substituents to form a substituted or unsubstituted (5- to 30-membered) mono- or polycyclic, alicyclic, aromatic ring, or a combination thereof, more preferably, hydrogen, a substituted or unsubstituted (C6-C18)aryl, or a substituted or unsubstituted (5- to 40-membered)heteroaryl; or may be linked to the adjacent substituents to form a substituted or unsubstituted (5- to 25-membered) mono- or polycyclic, aromatic ring, or a combination thereof. For example, $R_9$ and $R_{10}$ each independently may be hydrogen, a substituted or unsubstituted phenyl, or a substituted or unsubstituted carbazolyl; or may be linked to the adjacent substituents to form a substituted or unsubstituted indolocarbazole ring.

The second host material represented by the above formula 2 according to one embodiment may be represented by the following formula 2-1 or 2-2.

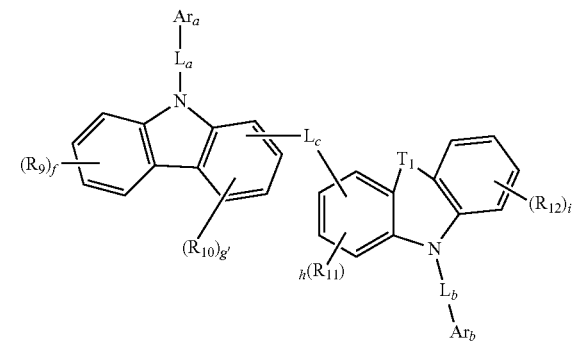

(2-1)

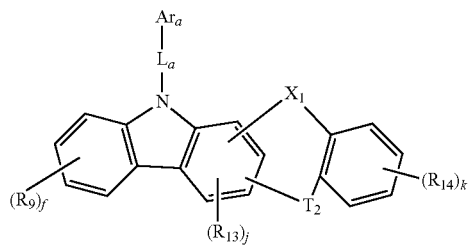

(2-2)

In formulas 2-1 and 2-2, $L_a$, $Ar_a$, $R_9$, $R_{10}$, and f are as defined in the formula 2;

$T_1$ and $T_2$ each independently represent, a single bond, O, or S;

$L_b$ and $L_c$ are as defined as $L_a$ in the formula 2;

$Ar_b$ is as defined as $Ar_a$ in the formula 2;

$R_{11}$ to $R_{14}$ each independently are as defined as $R_9$ in the formula 2;

$X_1$ represents O, S, or $NR_a$;

$R_a$ represents a substituted or unsubstituted (C6-C30)aryl;

g' and h each independently represent, an integer of 1 to 3, i and k each independently represent, an integer of 1 to 4, and j represents an integer of 1 or 2; and when g', h, i, j, and k are an integer of 2 or more, each of $R_{10}$, each of $R_{11}$, each of $R_{12}$, each of $R_{13}$, and each of $R_{14}$ may be the same or different.

In one embodiment, $L_a$ and $L_b$ each independently may be a single bond, a substituted or unsubstituted (C6-C30)arylene, or a substituted or unsubstituted (5- to 30-membered)heteroarylene, preferably, a single bond, a substituted or unsubstituted (C6-C25)arylene, or a substituted or unsubstituted (5- to 25-membered)heteroarylene, more preferably a single bond, a substituted or unsubstituted (C6-C18)arylene, or a substituted or unsubstituted (5- to 18-membered)heteroarylene. For example, $L_a$ and $L_b$ each independently may be a single bond, or a substituted or unsubstituted phenylene, a substituted or unsubstituted biphenylene, a substituted or unsubstituted pyridylene, or a substituted or unsubstituted pyrimidylene.

In one embodiment, $Ar_a$ and $Ar_b$ each independently may be a substituted or unsubstituted (C6-C30)aryl or a substituted or unsubstituted (5- to 30-membered)heteroaryl, preferably, a substituted or unsubstituted (C6-C25)aryl or a substituted or unsubstituted (5- to 25-membered)heteroaryl, more preferably, (C6-C18)aryl unsubstituted or substituted with (C6-C30)aryl or (5- to 30-membered)heteroaryl or (5- to 18-membered)heteroaryl unsubstituted or substituted with (C6-C30)aryl. For example. $Ar_a$ and $Ar_b$ each independently may be a substituted or unsubstituted phenyl, a substituted or unsubstituted o-biphenyl, a substituted or unsubstituted m-biphenyl, a substituted or unsubstituted p-biphenyl, a substituted or unsubstituted p-terphenyl, a substituted or unsubstituted m-terphenyl, a substituted or unsubstituted o-terphenyl, a substituted or unsubstituted naphthyl, a substituted or unsubstituted triphenylenyl, pyridyl unsubstituted or substituted with phenyl, or pyrimidyl unsubstituted or substituted with phenyl.

In one embodiment, $R_a$ may be a substituted or unsubstituted (C6-C30)aryl, preferably, a substituted or unsubstituted (C6-C25)aryl, more preferably, (C6-C25)aryl unsubstituted or substituted with (C6-C30)aryl. For example, $R_a$ may be a substituted or unsubstituted phenyl, a substituted or unsubstituted o-biphenyl, a substituted or unsubstituted m-biphenyl, a substituted or unsubstituted p-biphenyl, a substituted or unsubstituted m-terphenyl, a substituted or unsubstituted o-terphenyl, a substituted or unsubstituted naphthyl, or a substituted or unsubstituted triphenylenyl.

In one embodiment, $R_9$ to $R_{14}$ each independently may be hydrogen, a substituted or unsubstituted (C6-C30)aryl, or a substituted or unsubstituted (5- to 30-membered)heteroaryl, preferably, hydrogen, a substituted or unsubstituted (C6-C25)aryl, or a substituted or unsubstituted (5- to 25-membered)heteroaryl, more preferably, hydrogen, a substituted or unsubstituted (C6-C18)aryl, or (5- to 18-membered) heteroaryl unsubstituted or substituted with (C6-C30)aryl. For example, $R_9$ to $R_{14}$ each independently may be hydrogen, a substituted or unsubstituted phenyl, or carbazolyl unsubstituted or substituted with phenyl.

In one embodiment, the second host material represented by the above formula 2 may be more specifically illustrated by the following compounds, but is not limited thereto.

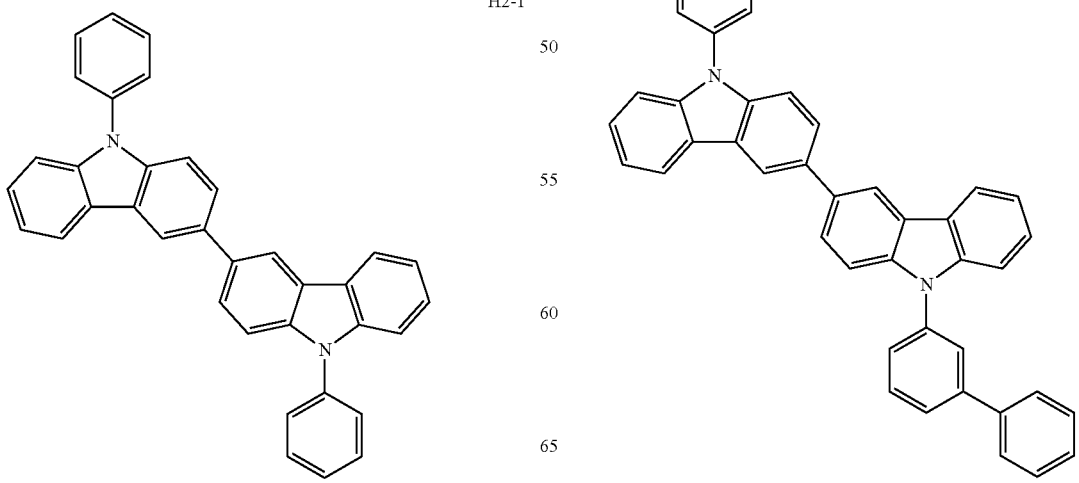

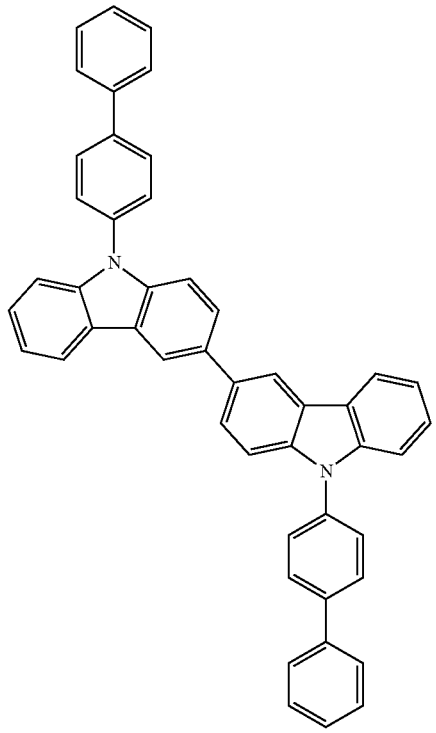

H2-4
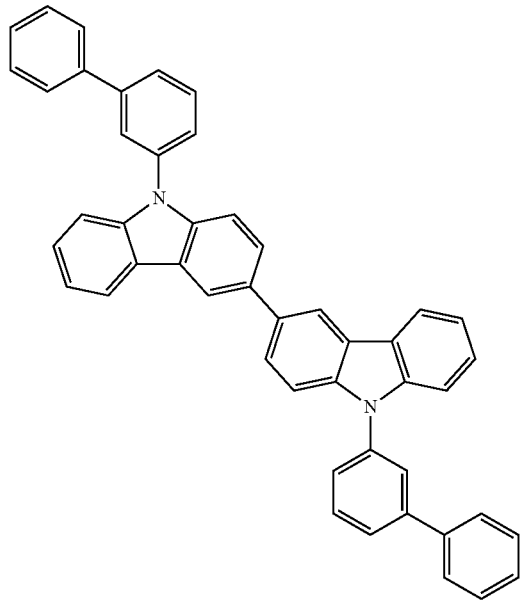
H2-5
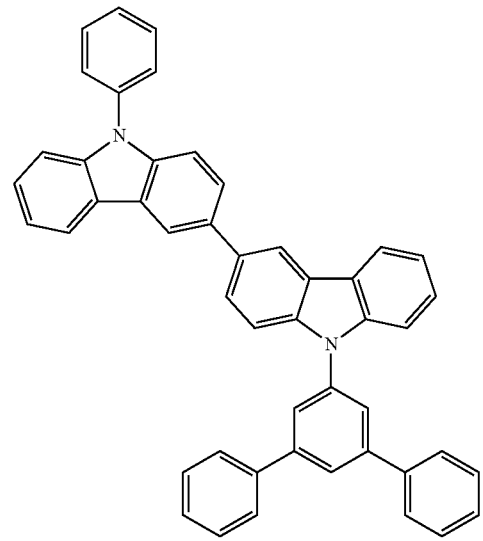
H2-6
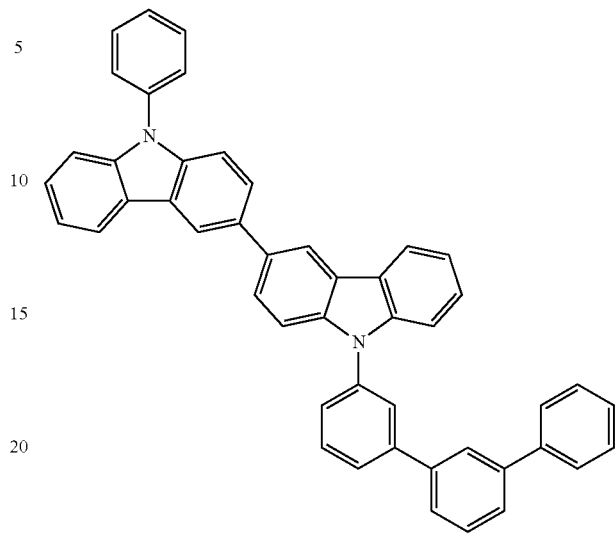
H2-7
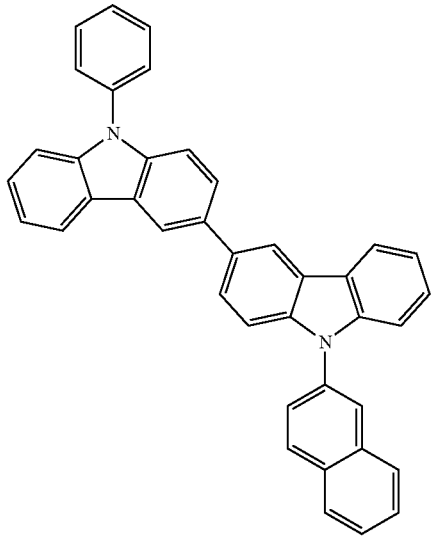

H2-8
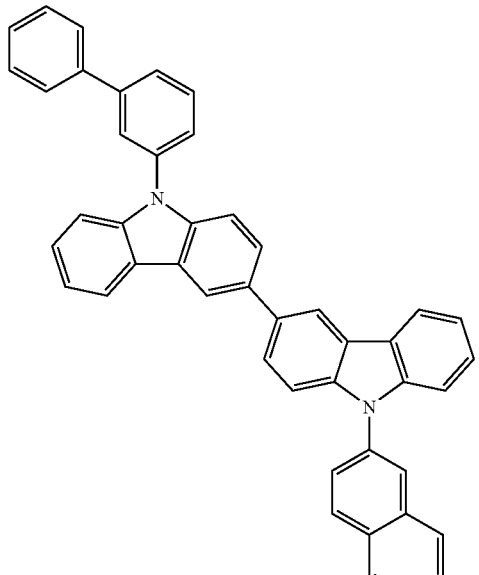
H2-11
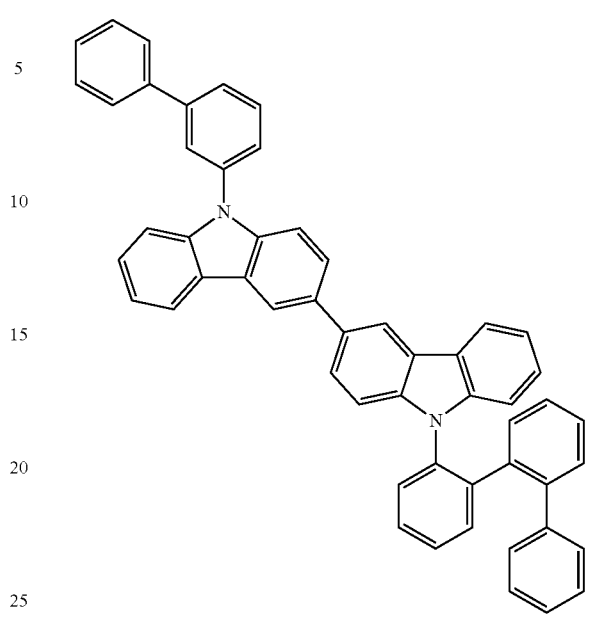
H2-9
H2-10
H2-12
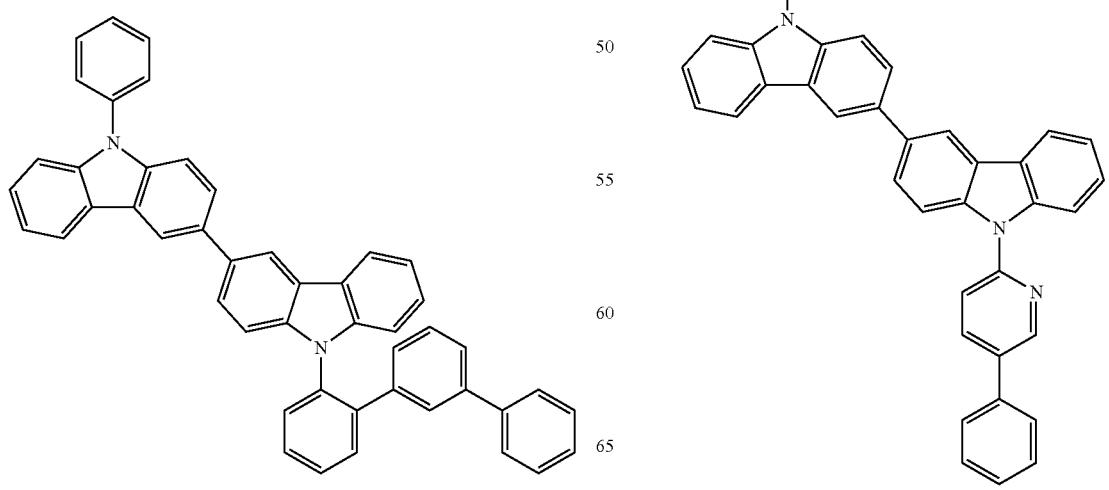

-continued
H2-13
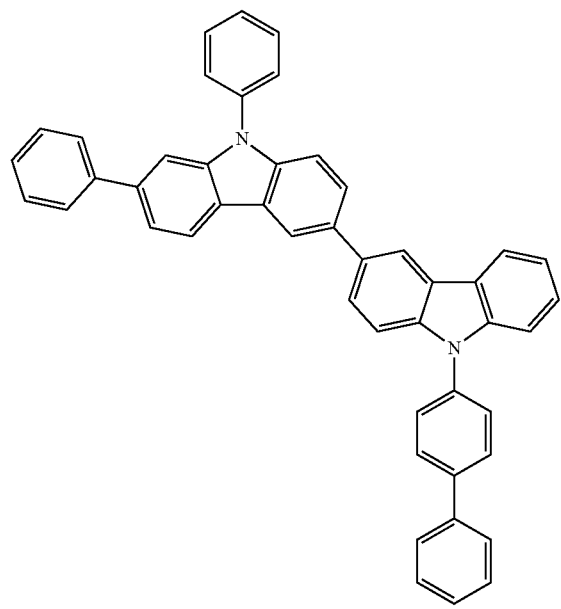
H2-15
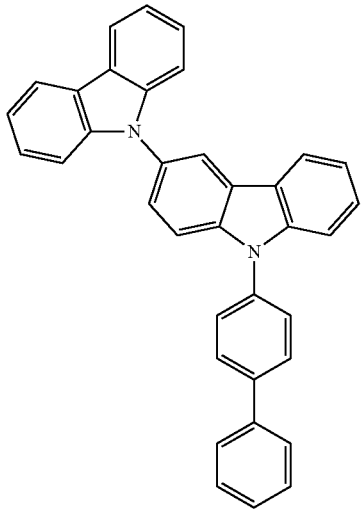
H2-16
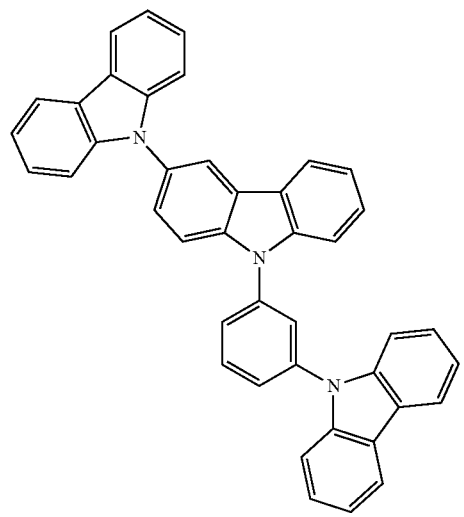
H2-14
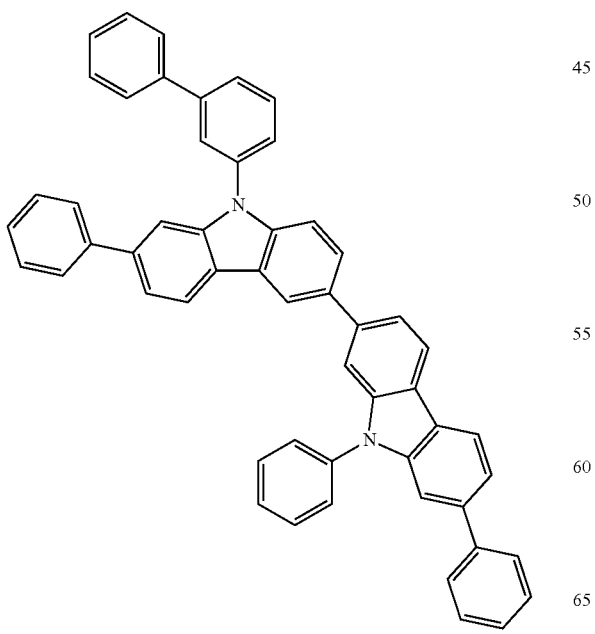
H2-17
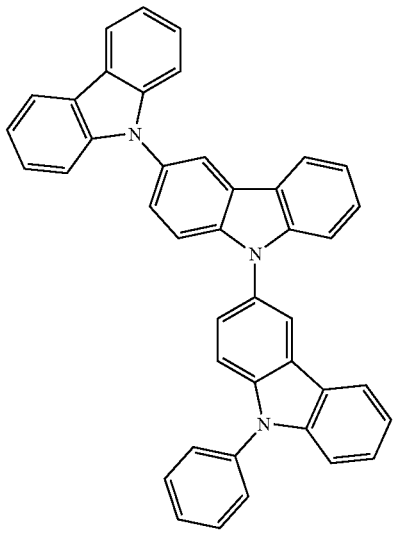

H2-18
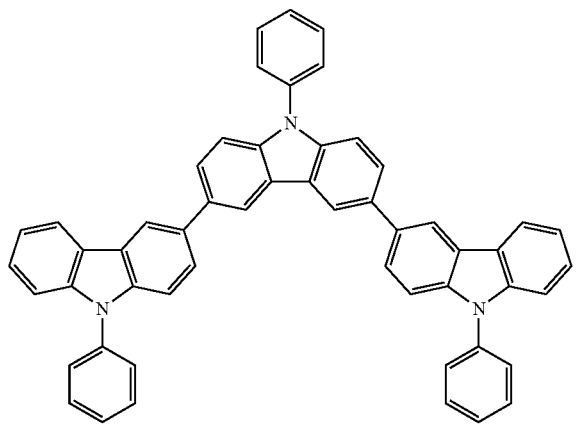
H2-19
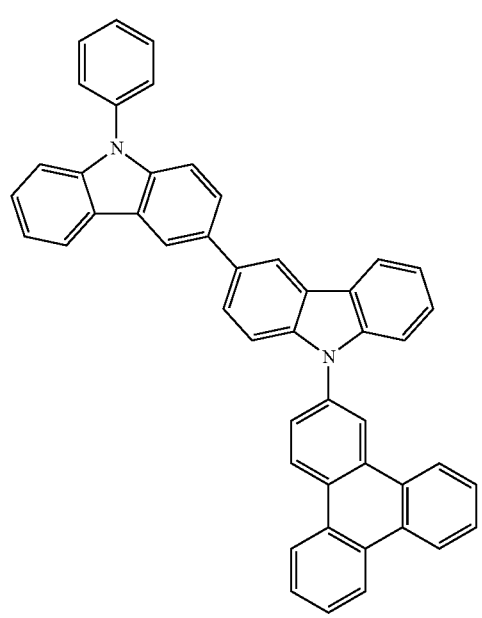
H2-20
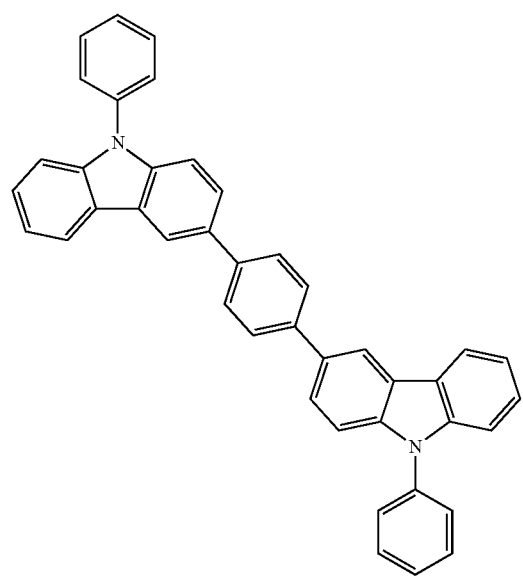
H2-21
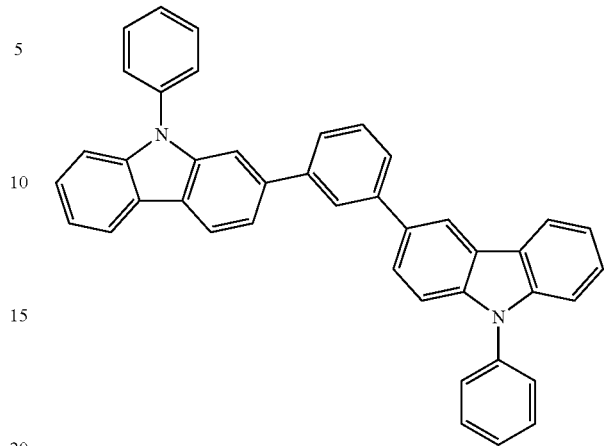
H2-22
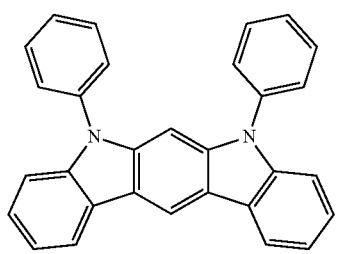
H2-23
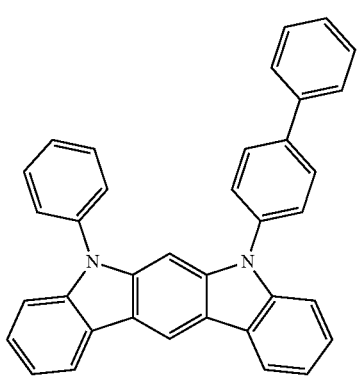
H2-24
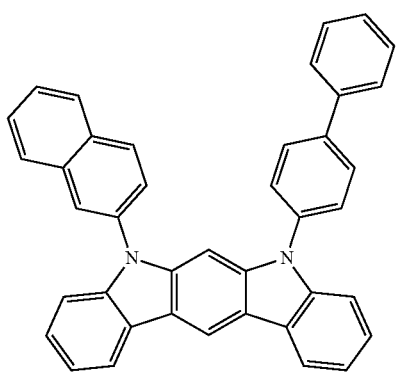

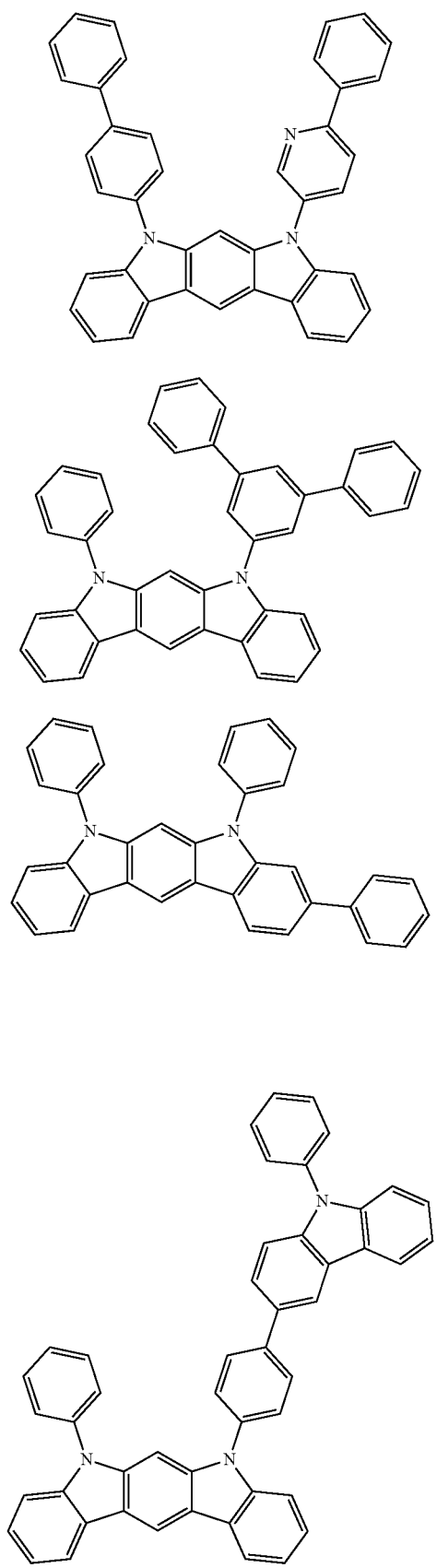
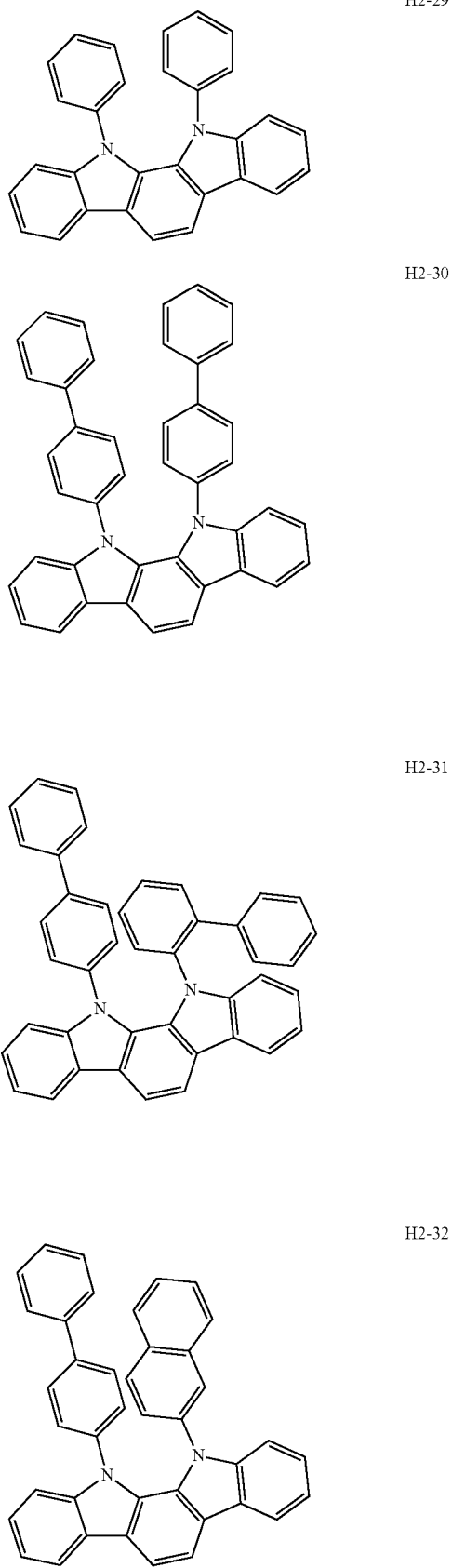

H2-33
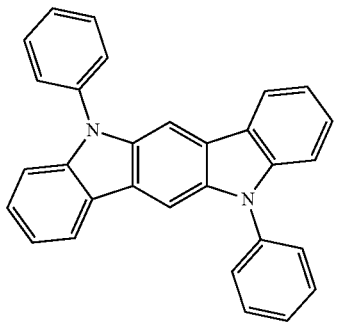
H2-36
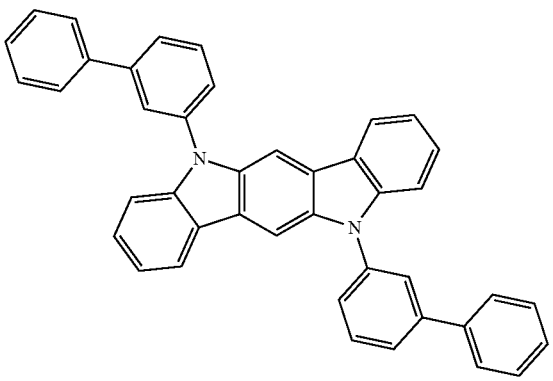
H2-34
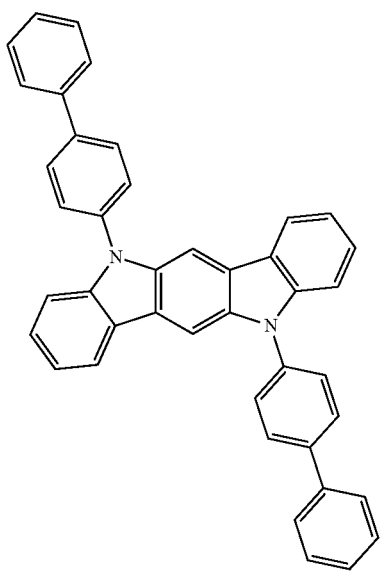
H2-37
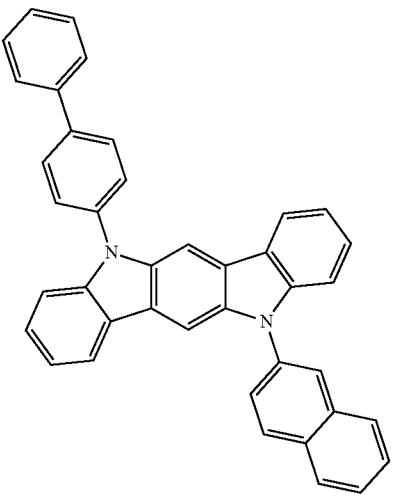
H2-35
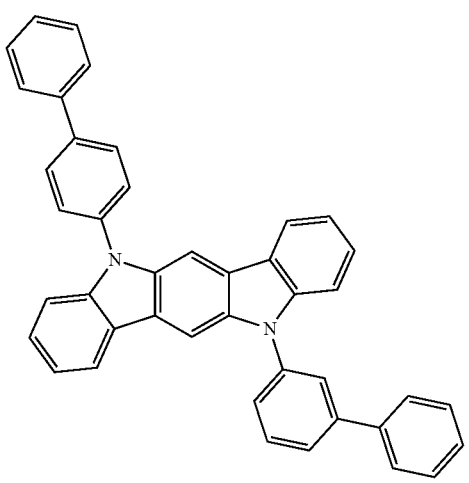
H2-38
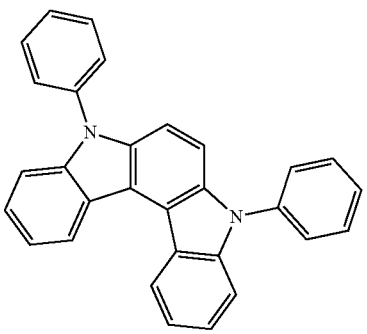

H2-39
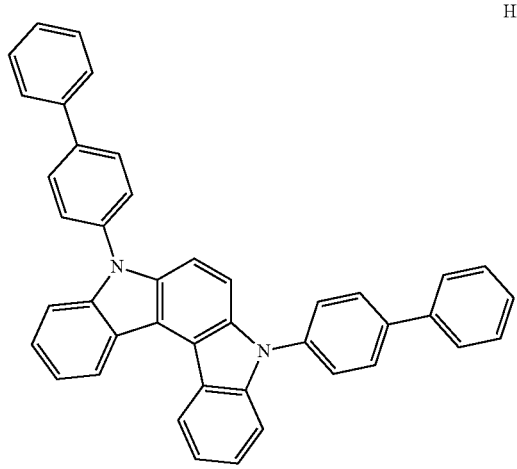
H2-40
H2-41
H2-42
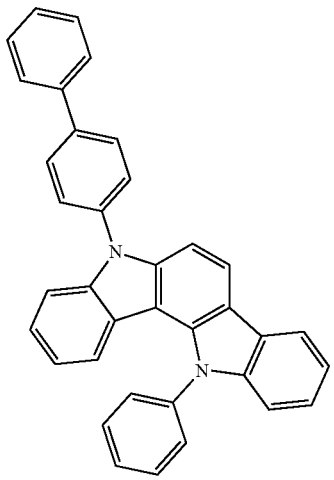
H-43
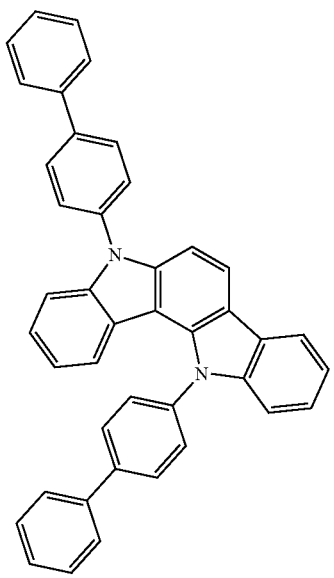
H-44
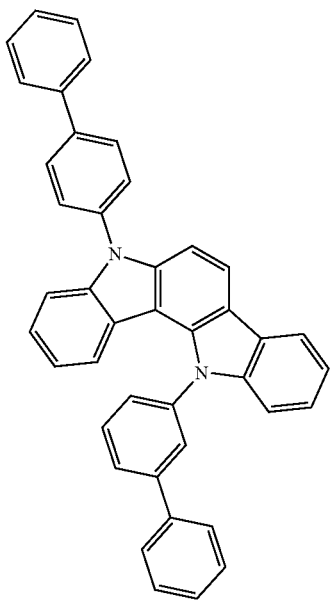

H2-45
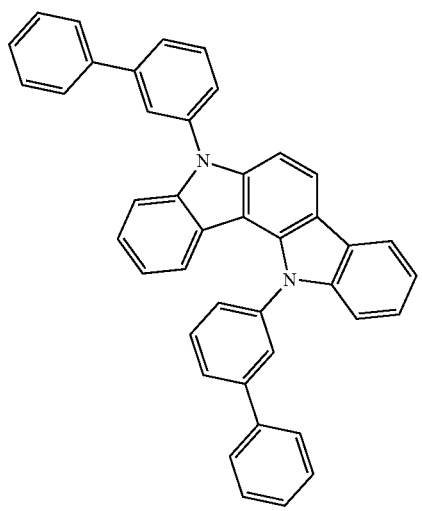
H2-46
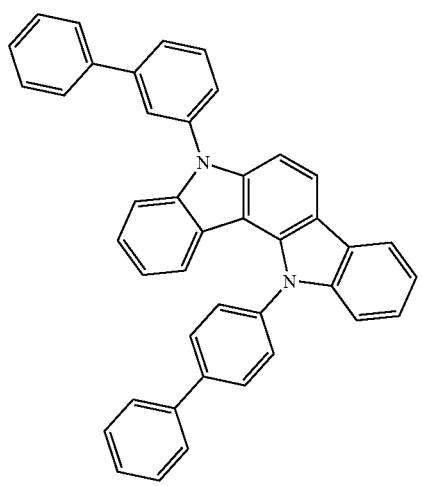
H2-47
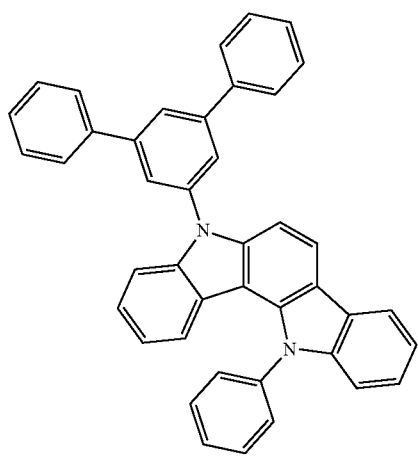
H2-48
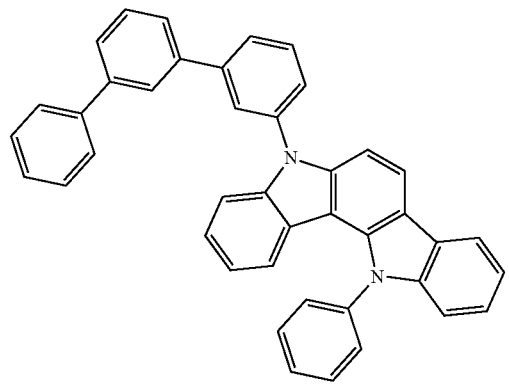
H2-49
H2-50
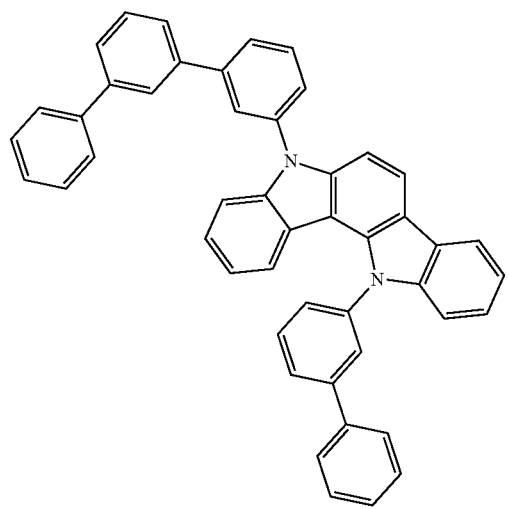

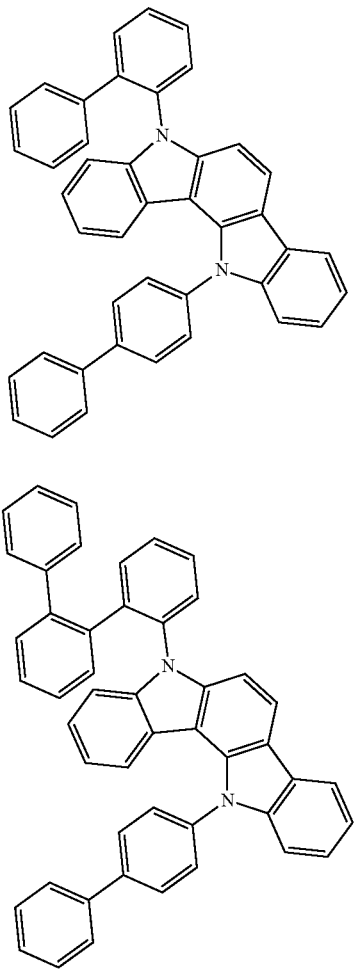
H2-51
H2-52
H2-53
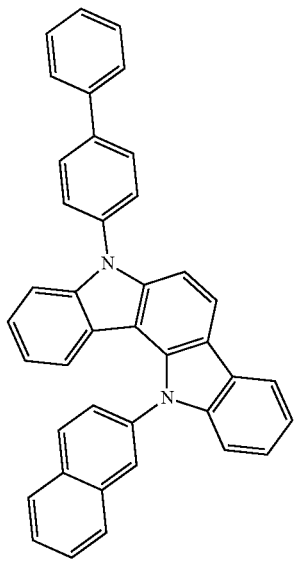
H2-54
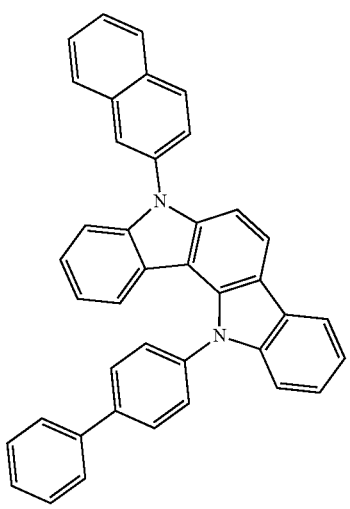
H2-55

H2-56
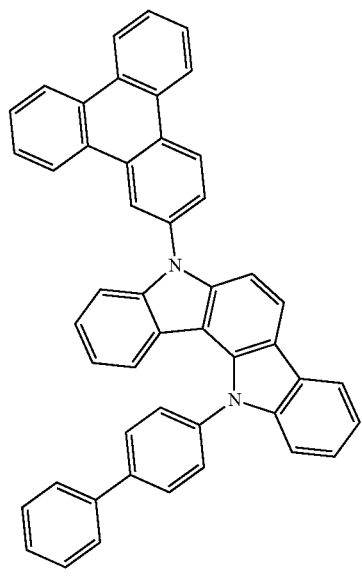
H2-57
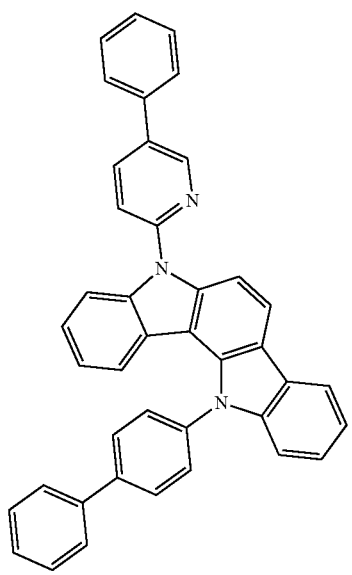
H2-58
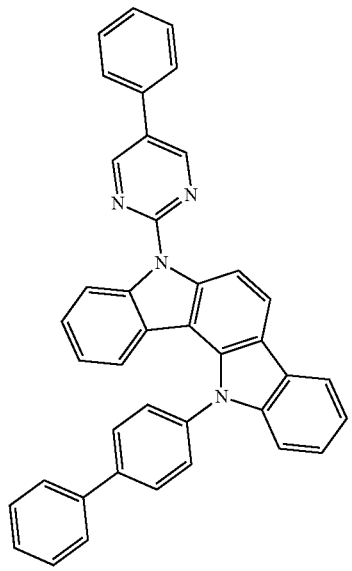
H2-59
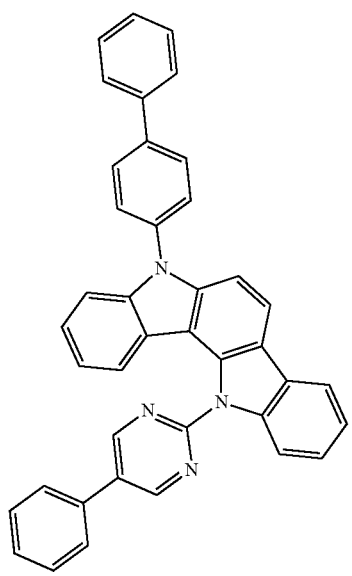
The compound represented by the formula 2 according to one embodiment may be produced by a synthetic method known to a person skilled in the art.
An organic electroluminescent compound according to another one embodiment of the present disclosure may be represented by the following formula 1-1-1.

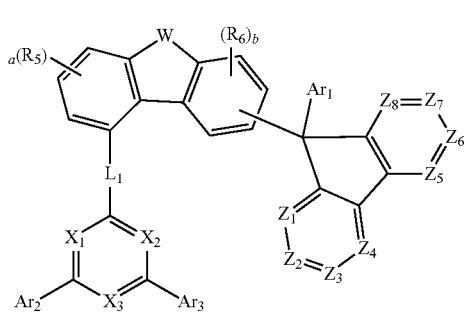

(1-1-1)

In formula 1-1-1,

W represents O or S;

$Z_1$ to $Z_8$ each independently represent, $CR_4$ or N;

$X_1$ to $X_3$ each independently represent, $CR_7$ or N;

$L_1$ represents a single bond or a substituted or unsubstituted (C6-C30)arylene;

$Ar_1$ represents an unsubstituted phenyl, an unsubstituted biphenyl, or an unsubstituted terphenyl;

$Ar_2$ and $Ar_3$ each independently represent, a substituted or unsubstituted (C6-C30)aryl or a substituted or unsubstituted (3- to 30-membered)heteroaryl;

$R_4$ to $R_7$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30) alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino; or may be linked to the adjacent substituents to form a ring(s);

a and b each independently represent, an integer of 1 to 3; and when a and b are an integer of 2 or more, each of $R_5$ and each of $R_6$ may be the same or different.

The compound represented by the above formula 1-1-1 may be more specifically illustrated by the following compounds, but is not limited thereto.

H1-40

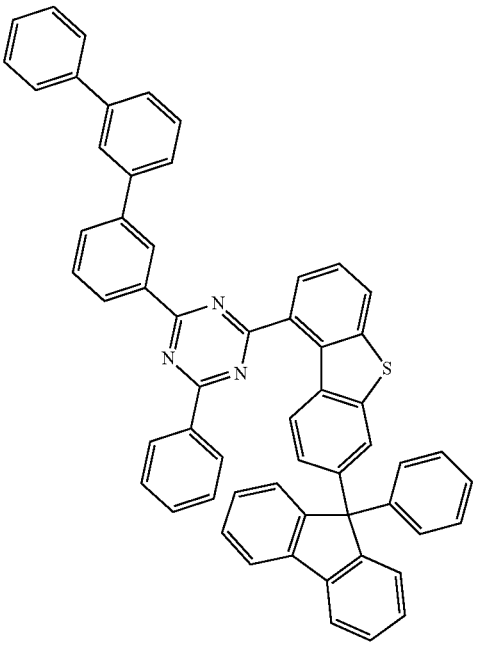

H1-45

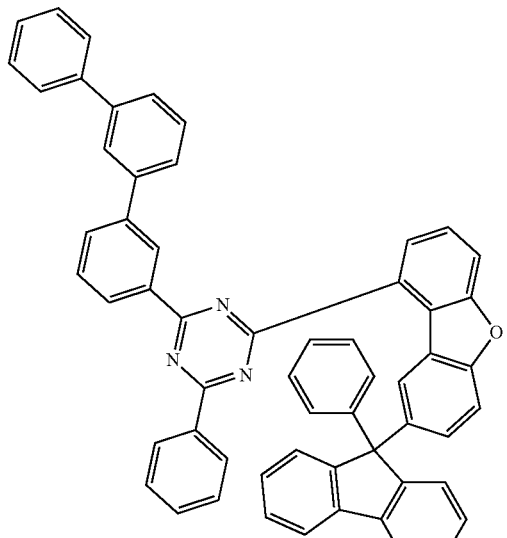

H1-53
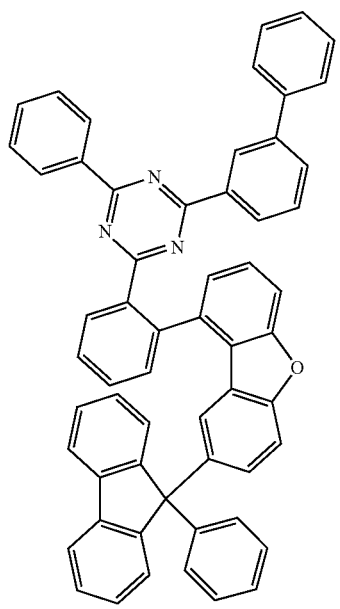
H1-54
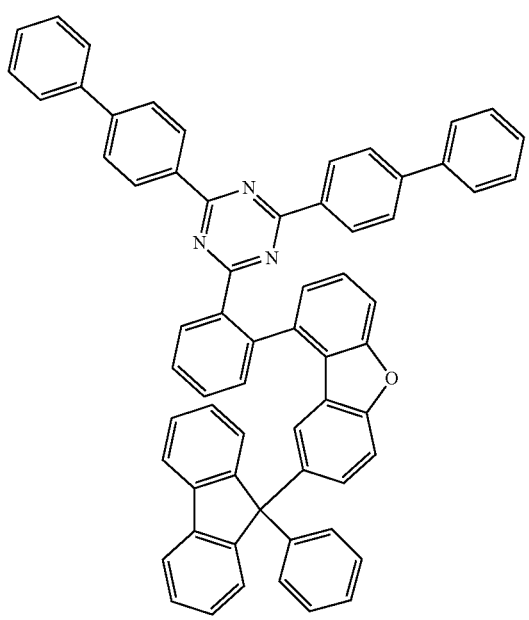
H1-55
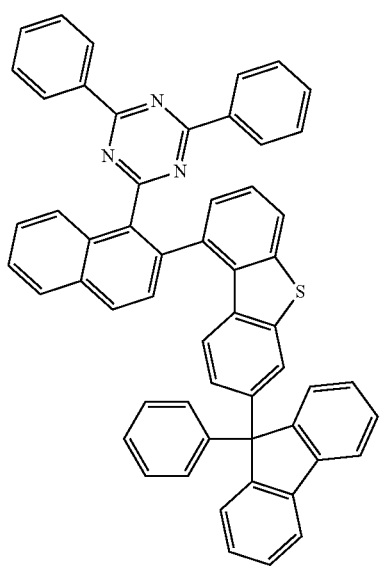
H1-56
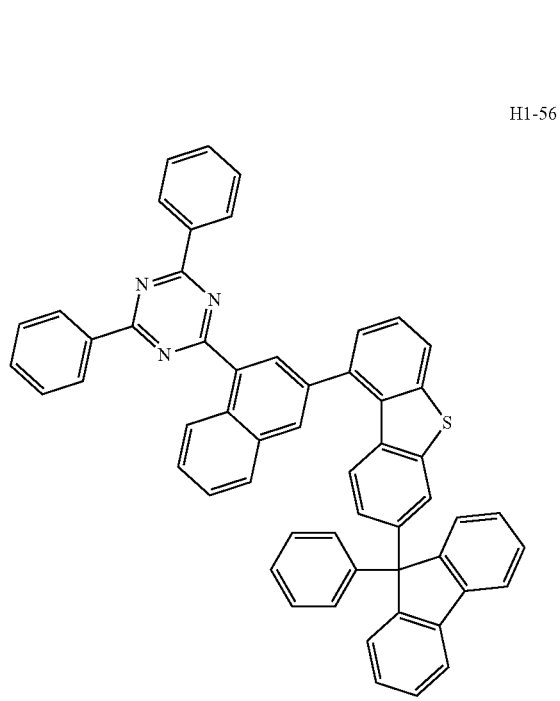

H1-57
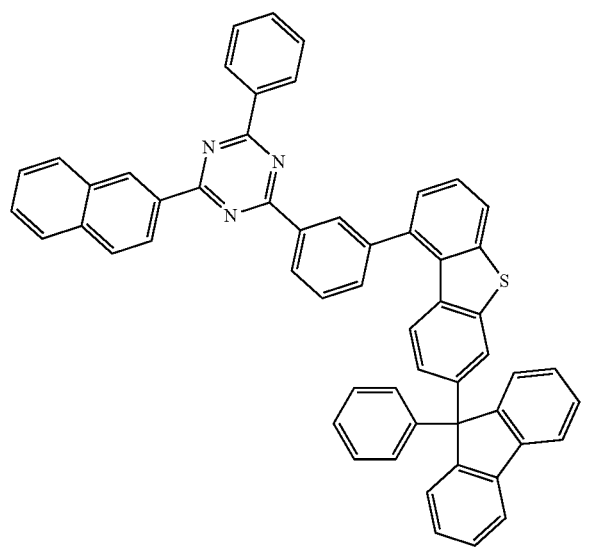
H1-60
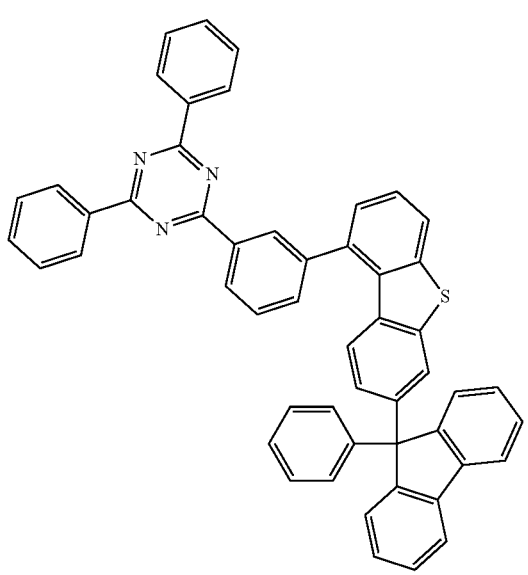
H1-58
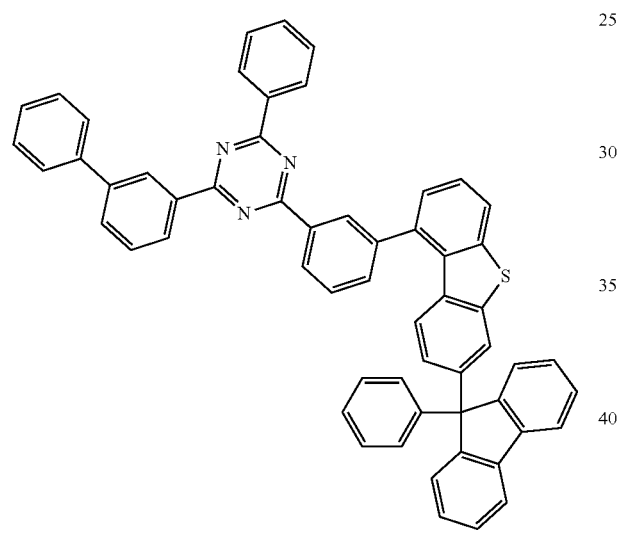
H1-59
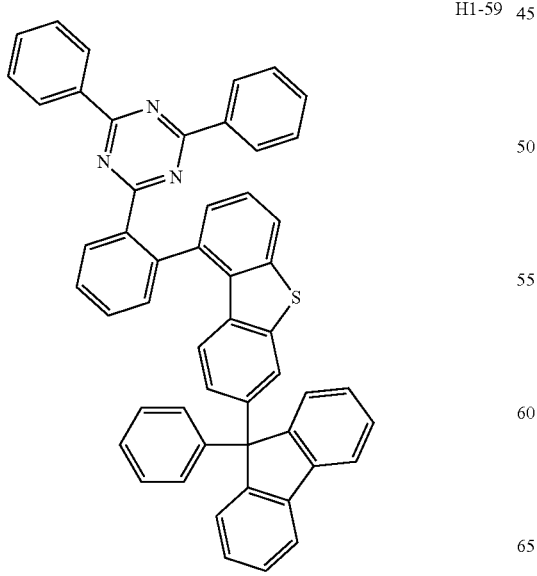
H1-61
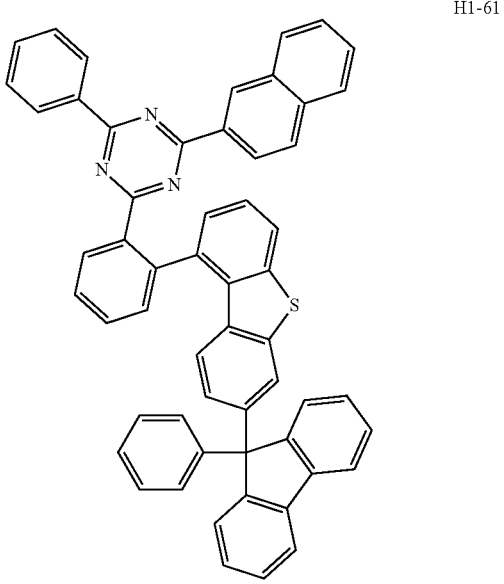

-continued
H1-62
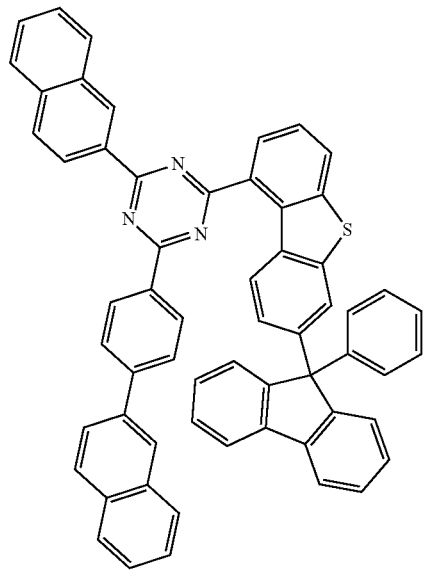
H1-63
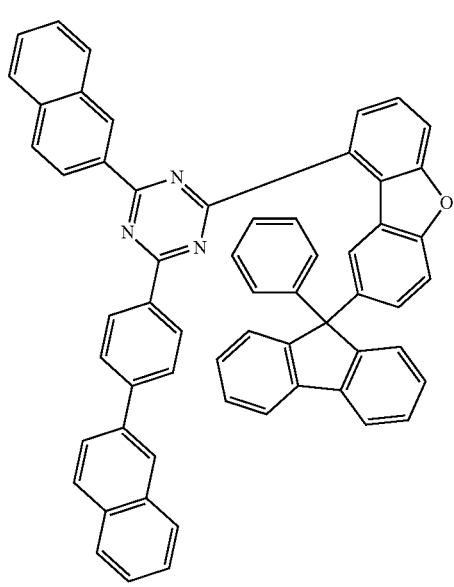
H1-64
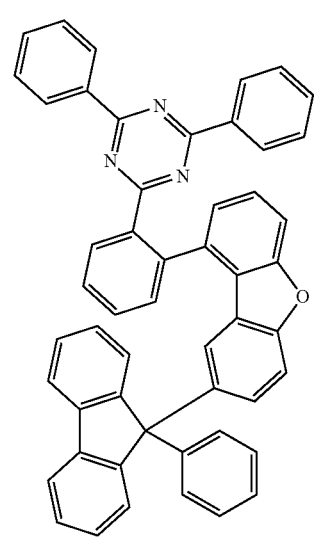
-continued
H1-65
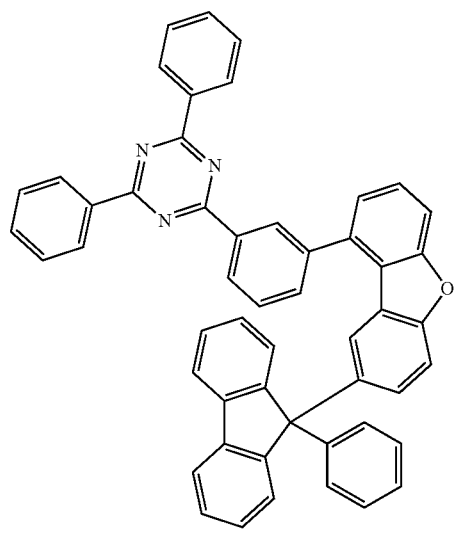
H1-67
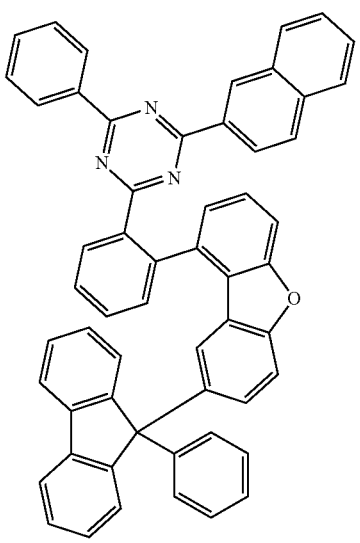
H1-68
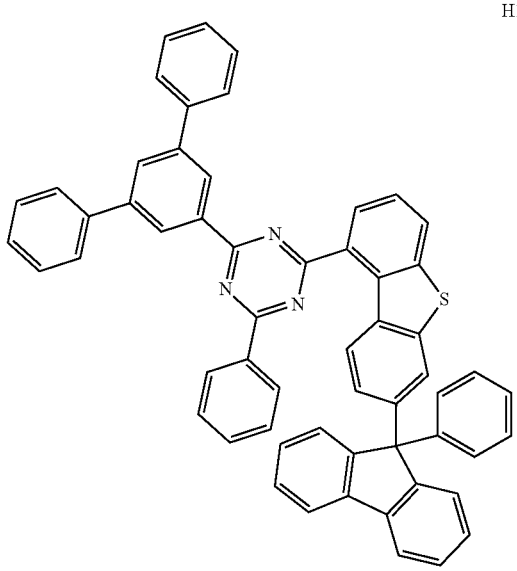

H1-69
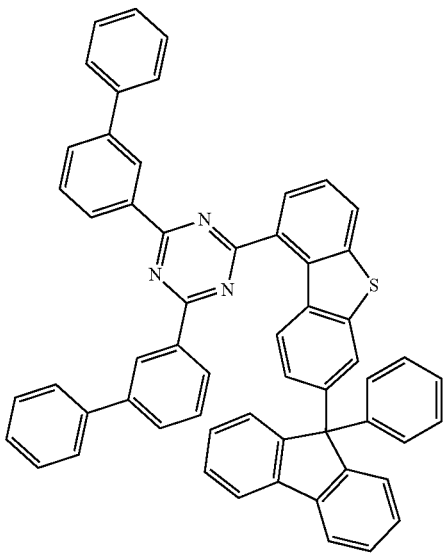
H1-71
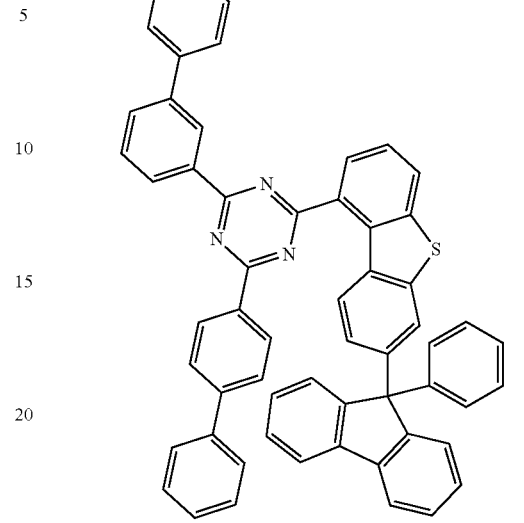
H1-70
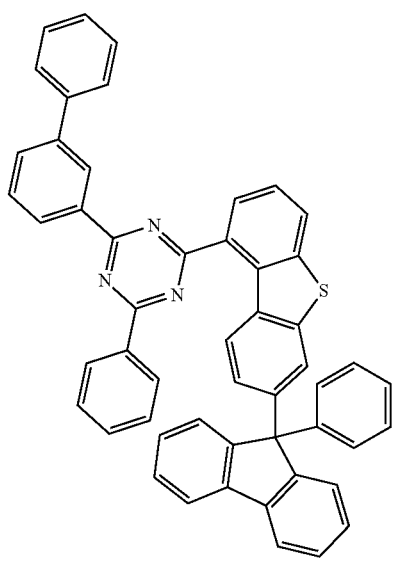
H1-72
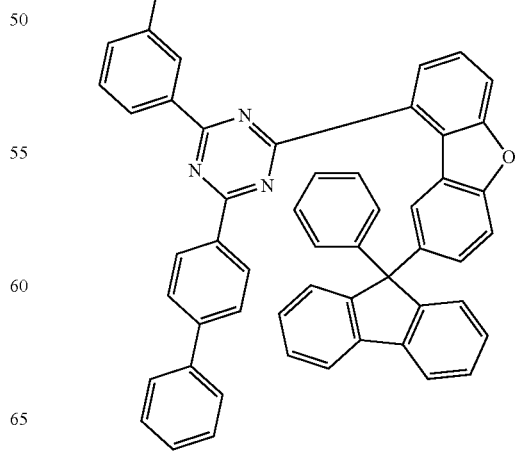

H1-73
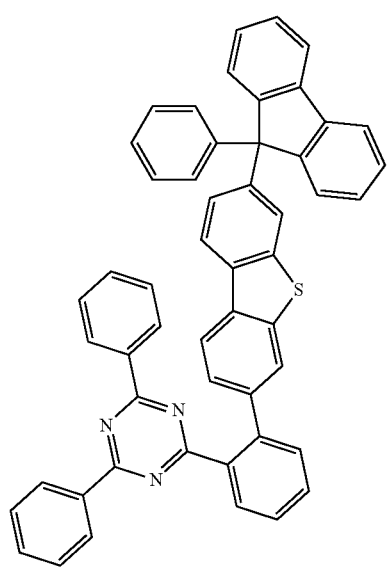
H1-74
H1-75
H1-76
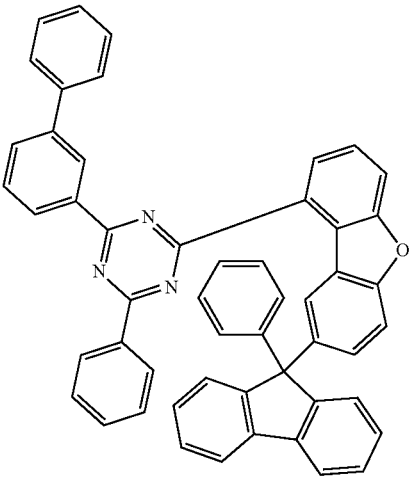
H1-77
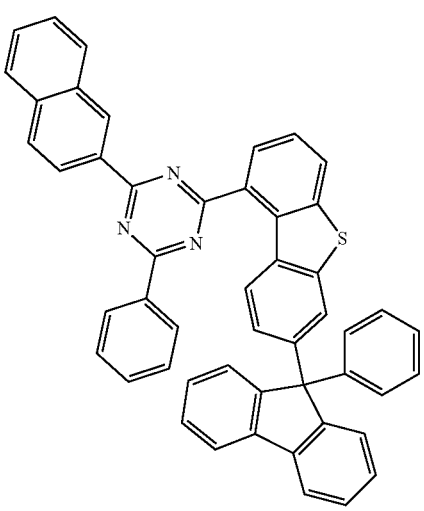
H1-78
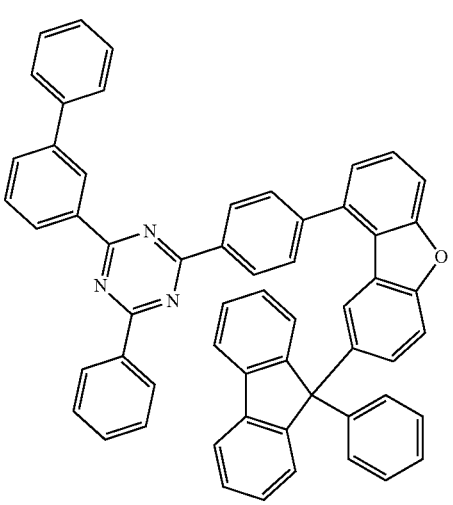

H-79
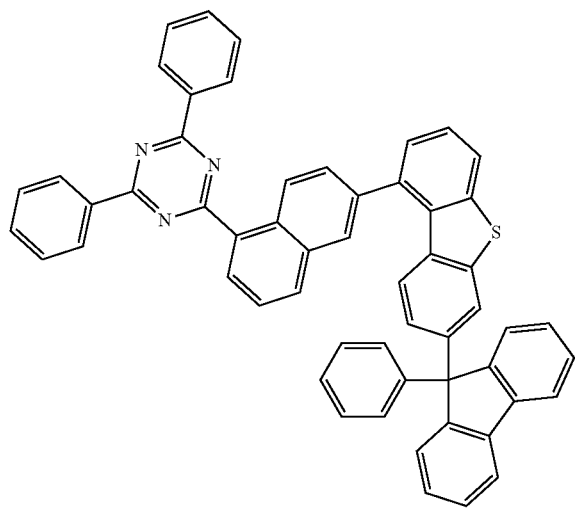
H1-80
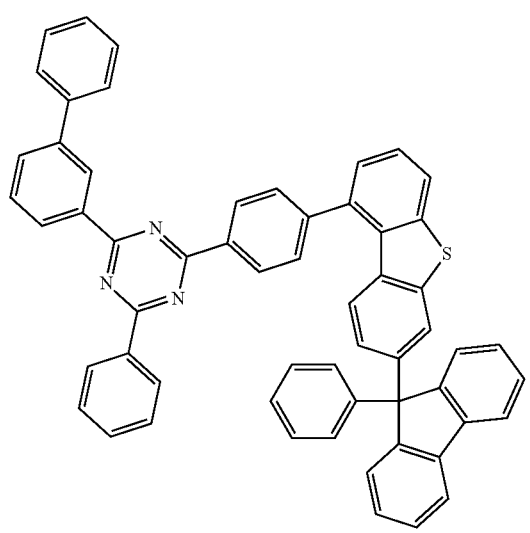
H1-81
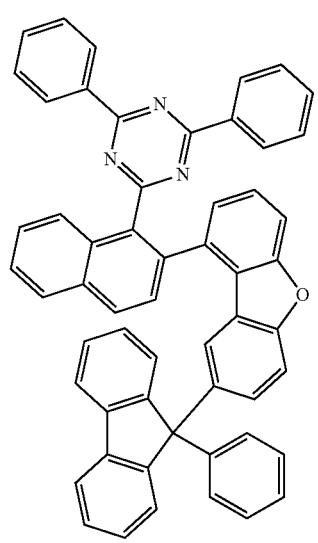
H1-82
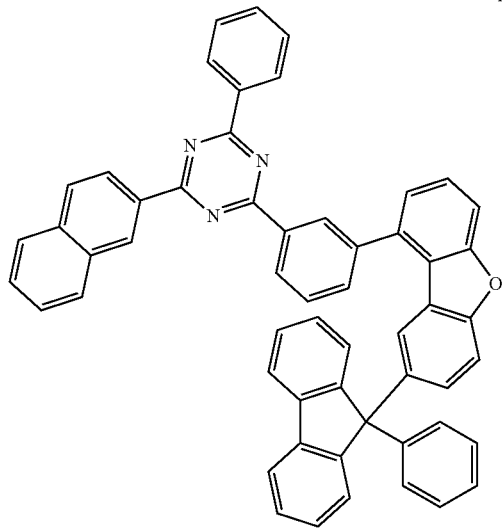
H1-83
H1-84

H1-85
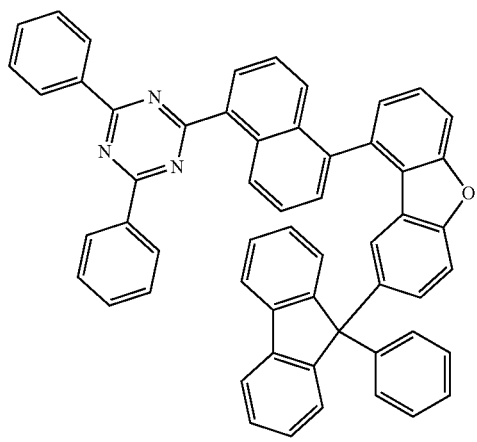
H1-86
H1-87
H1-88
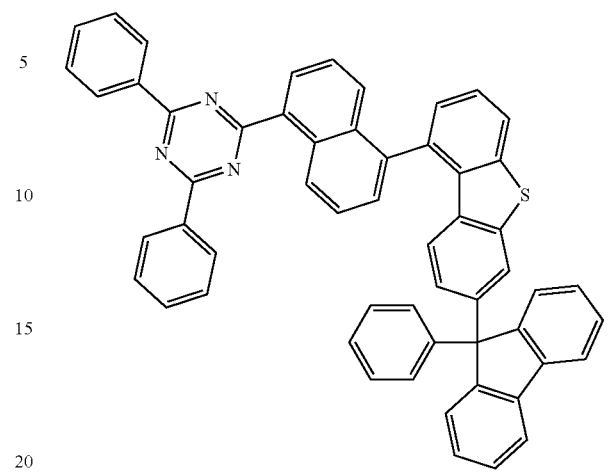
H1-89
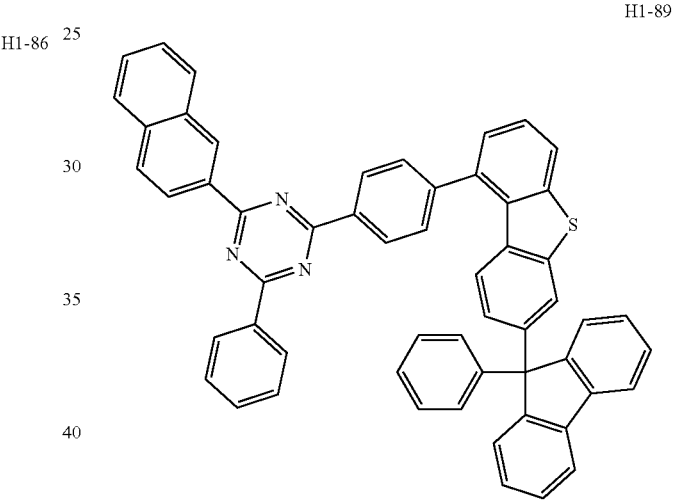
H1-90
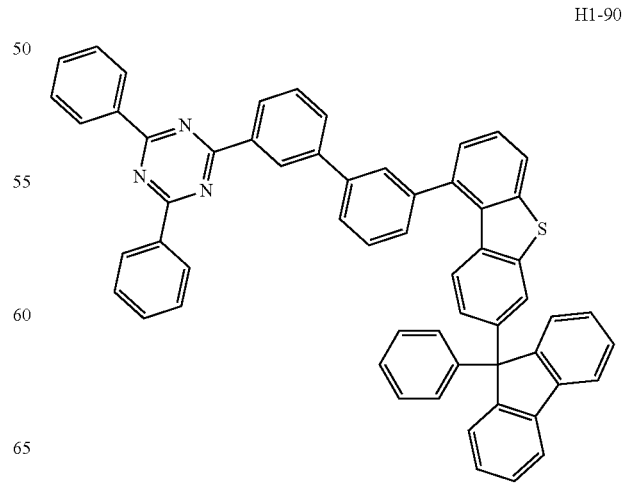

-continued
H1-91
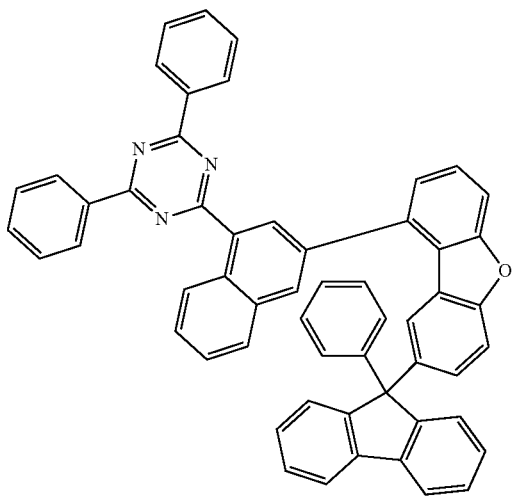
H1-92
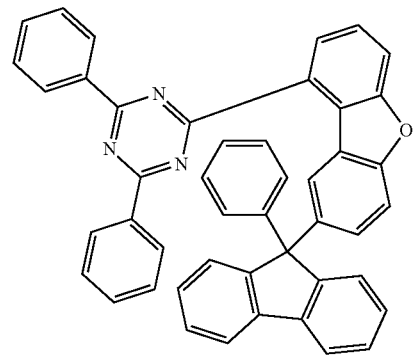
H1-93
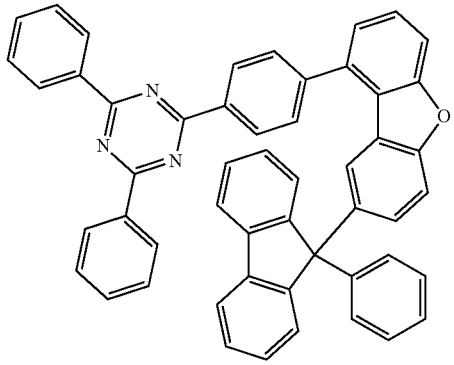
H1-94
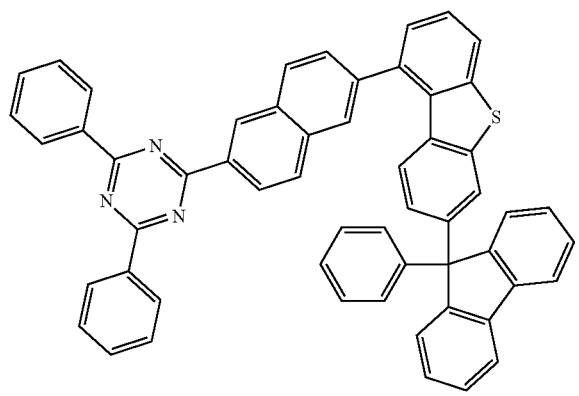
H1-95
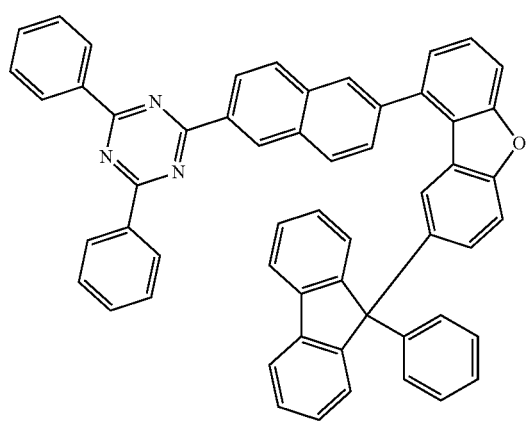
H1-96
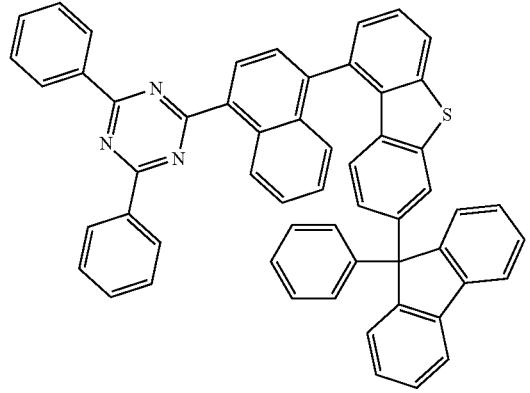
H1-97
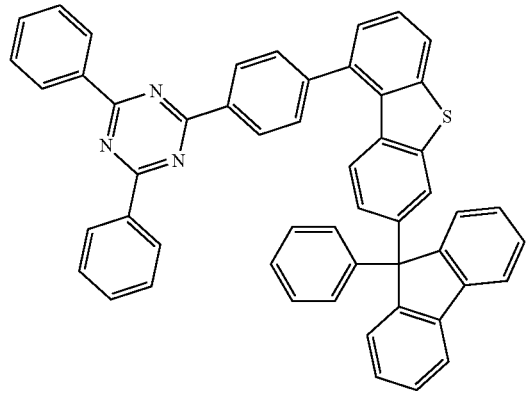

-continued
H1-98
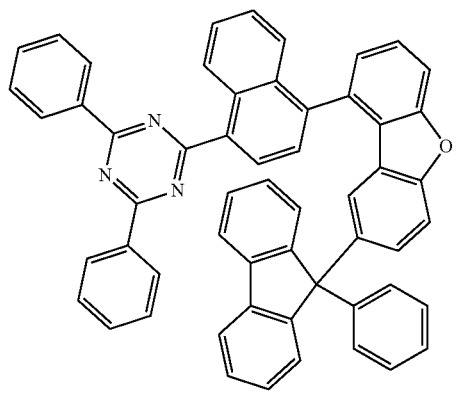
H1-99
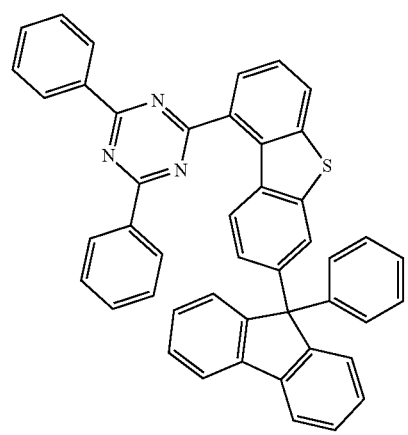
H1-100
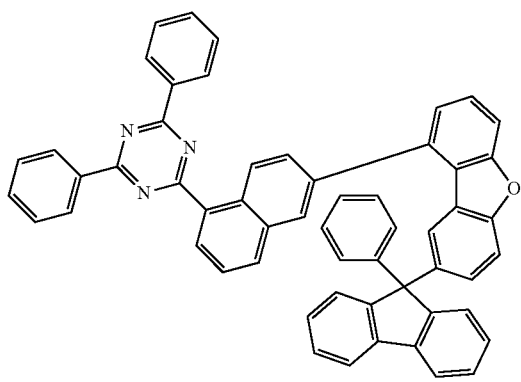
H1-115
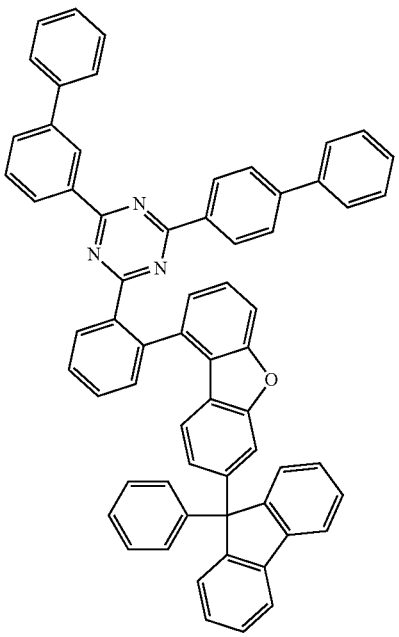
H1-127
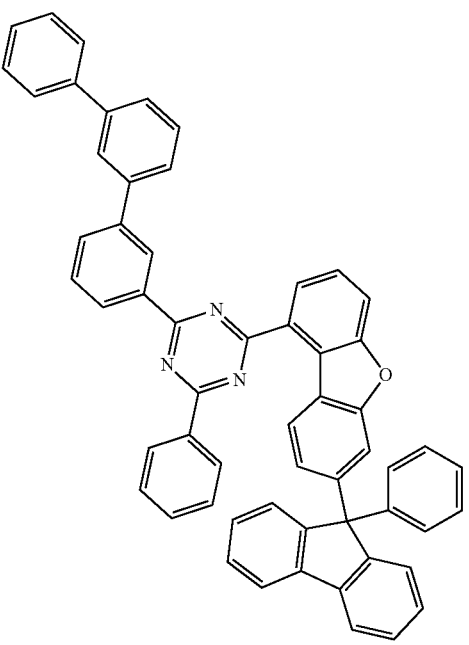

H1-128
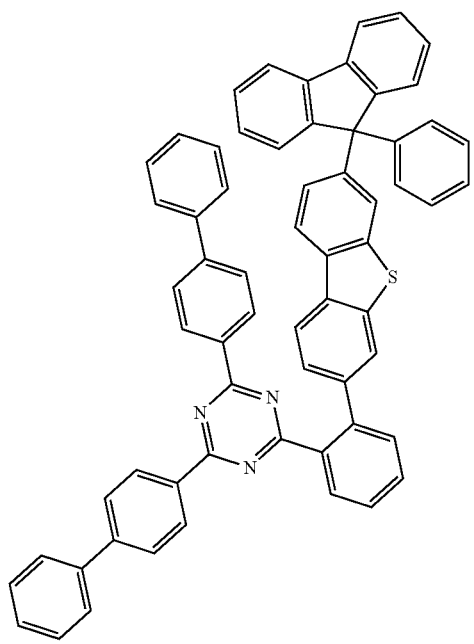
H1-133
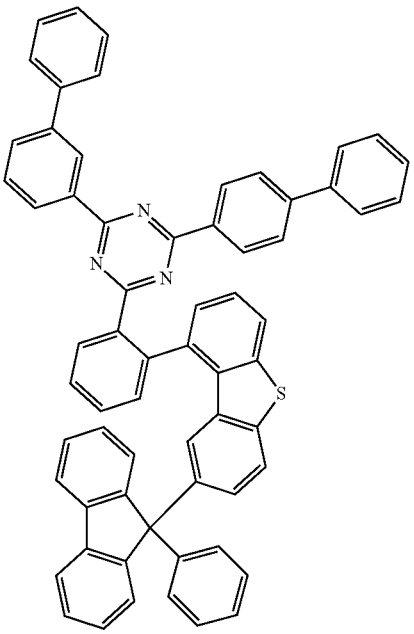
H1-129
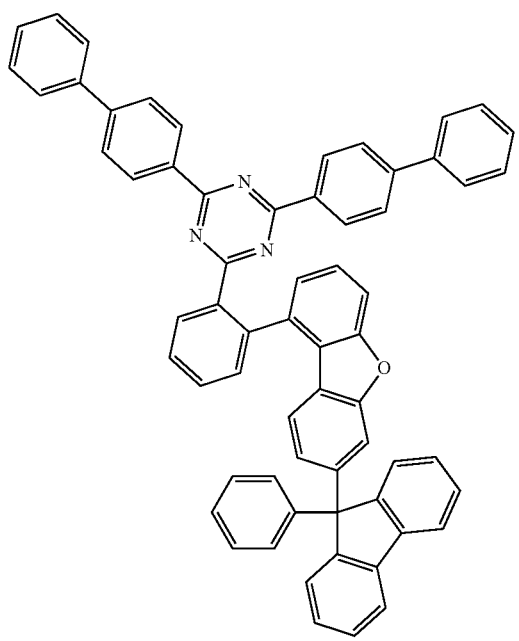
H1-141
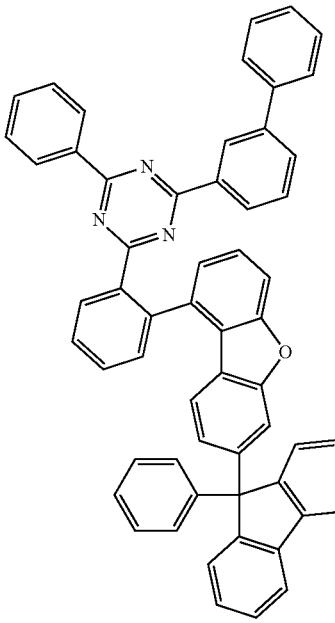

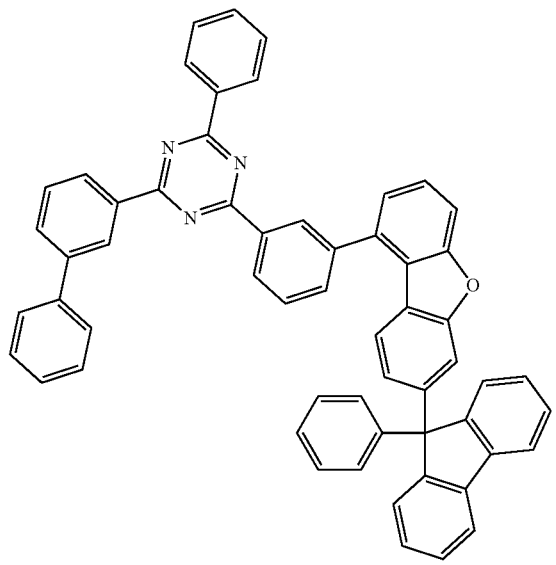
H1-145
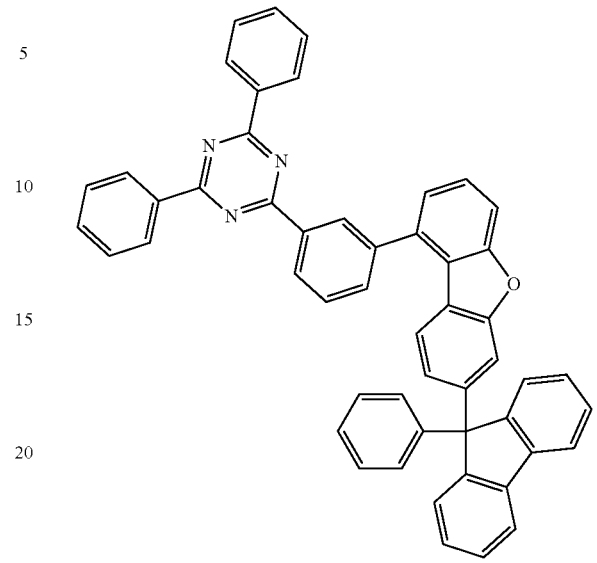
H1-147
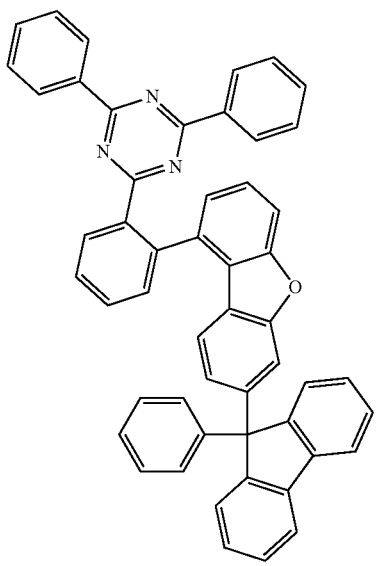
H1-146
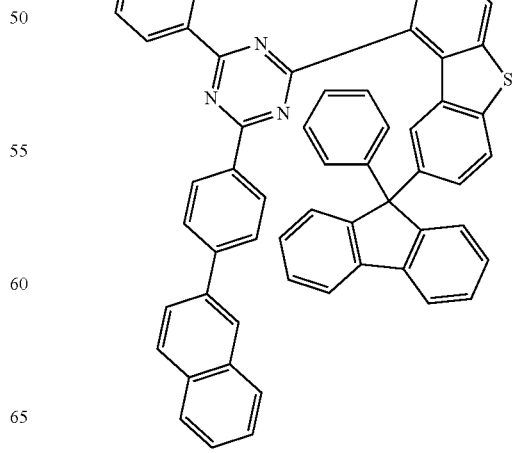
H1-148

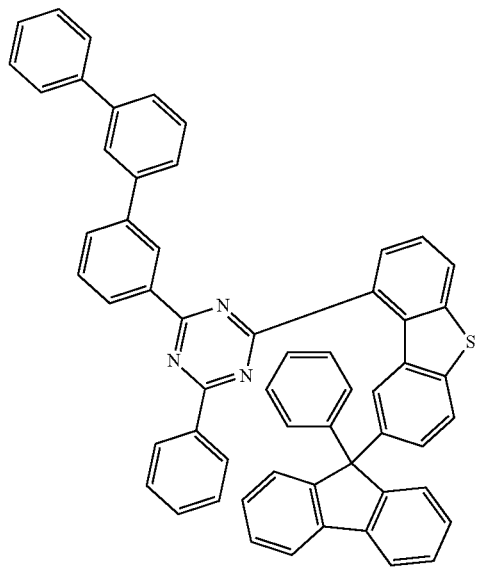
H1-149
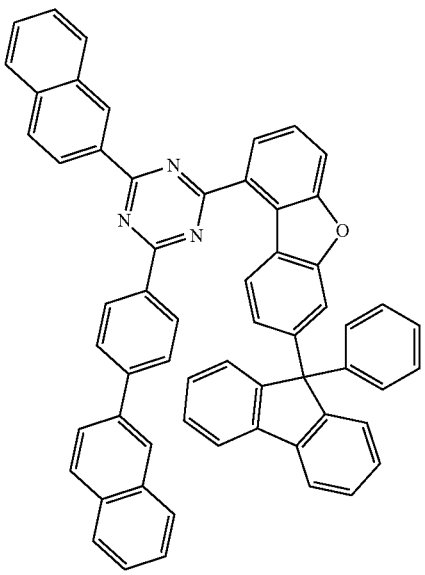
H1-151
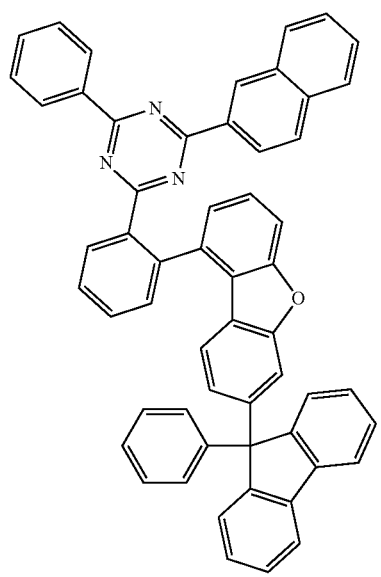
H1-150
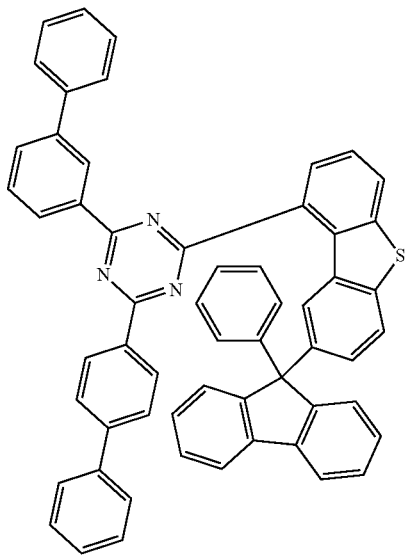
H1-159

H1-160
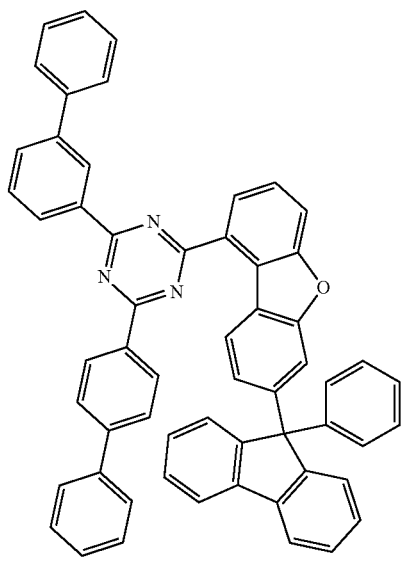
H1-162
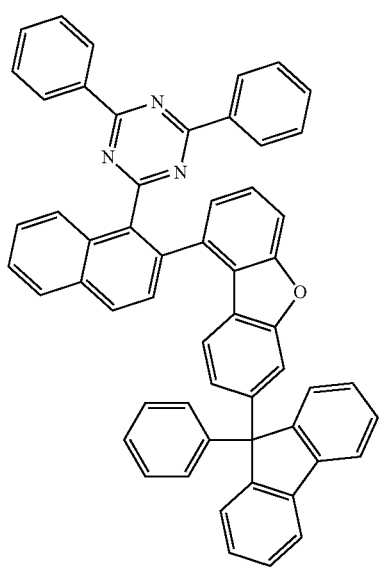
H1-163
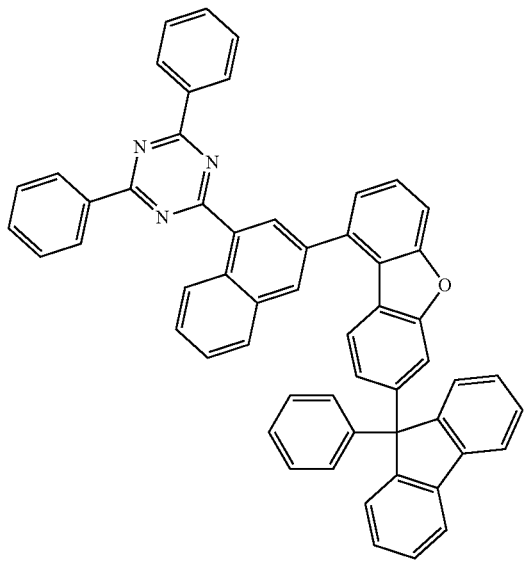
H1-164
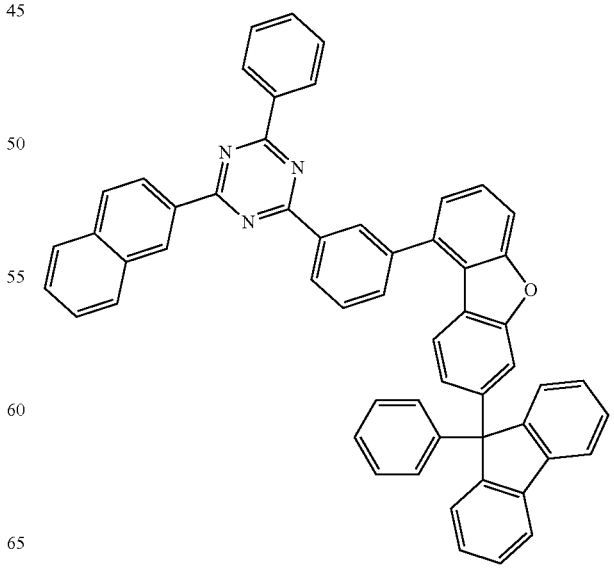

-continued
H1-165
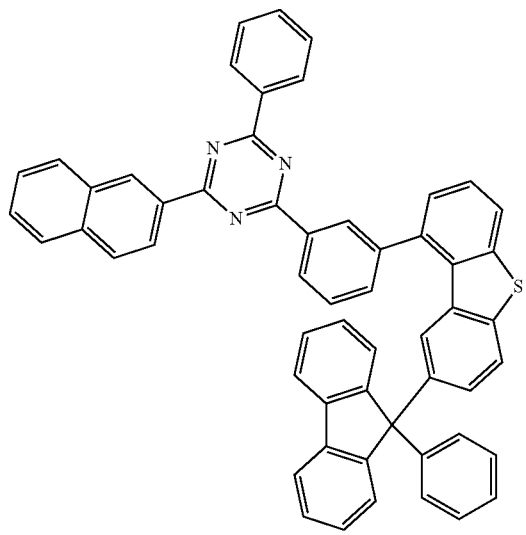
H1-166
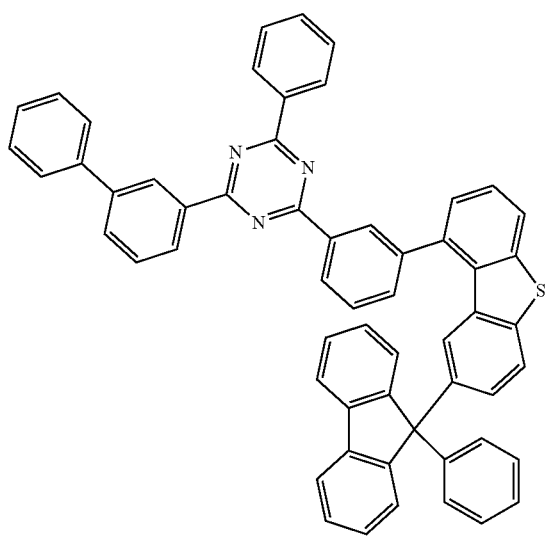
H1-167
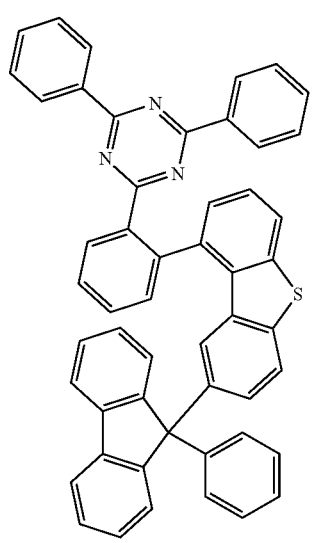
-continued
H1-168
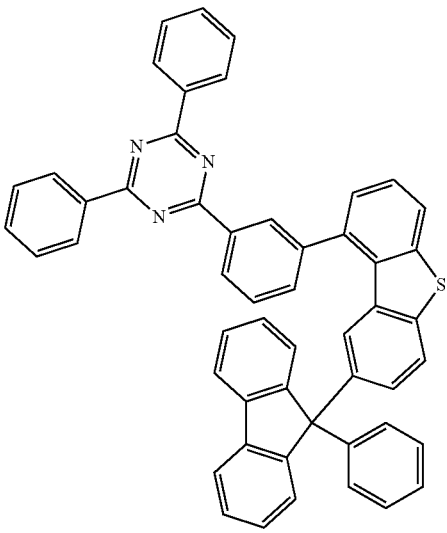
H1-170
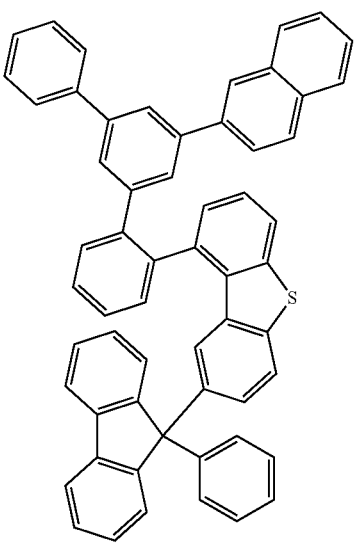
H1-171
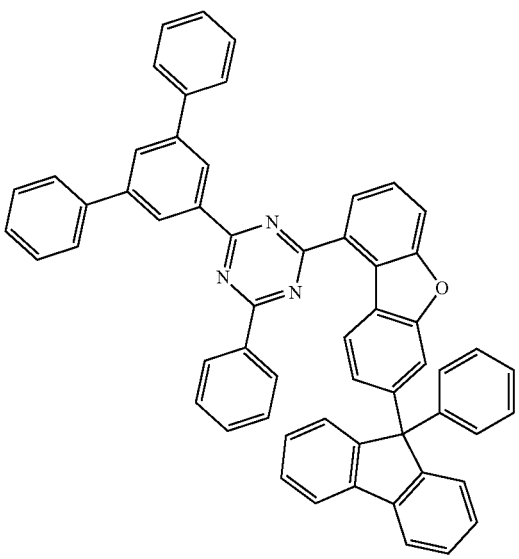

H1-172
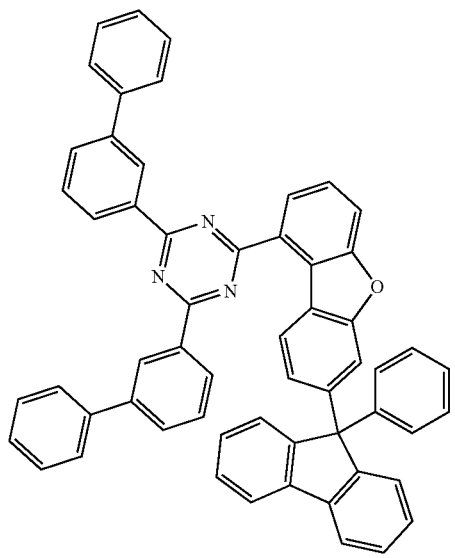
H1-173
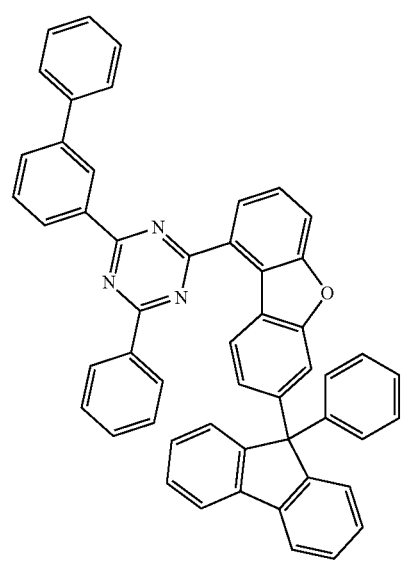
H1-175
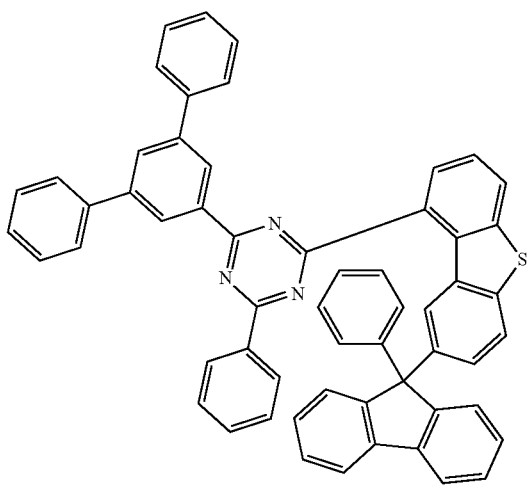
H1-176
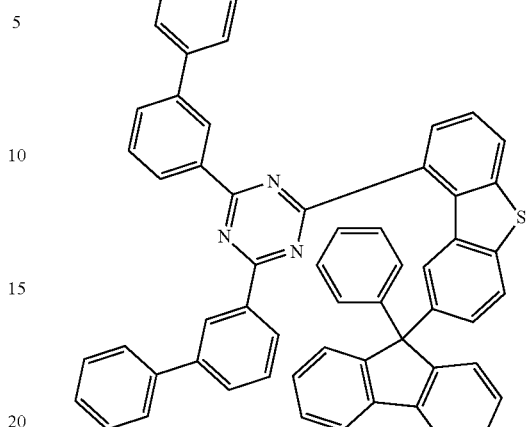
H1-177
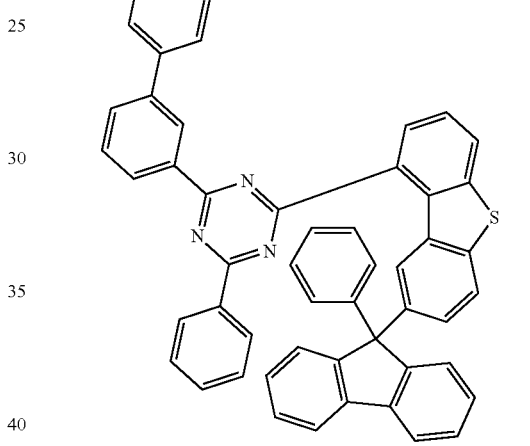
H1-179
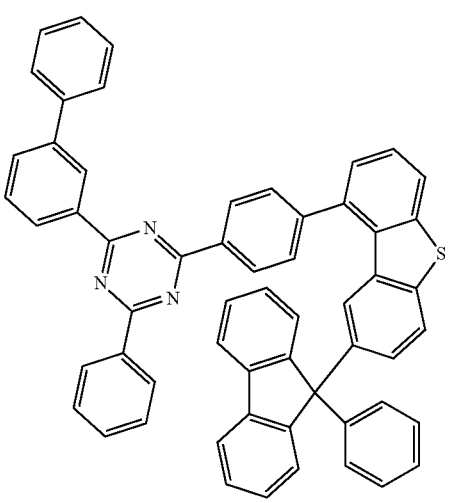

H1-180
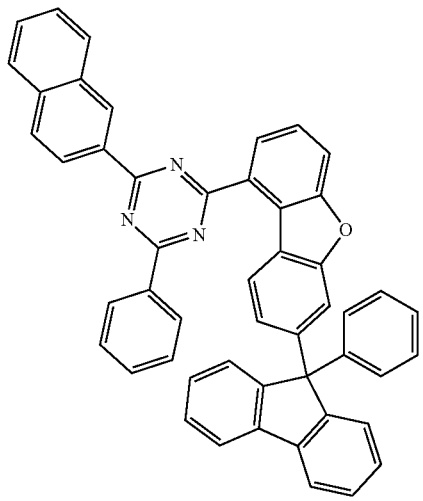
H1-181
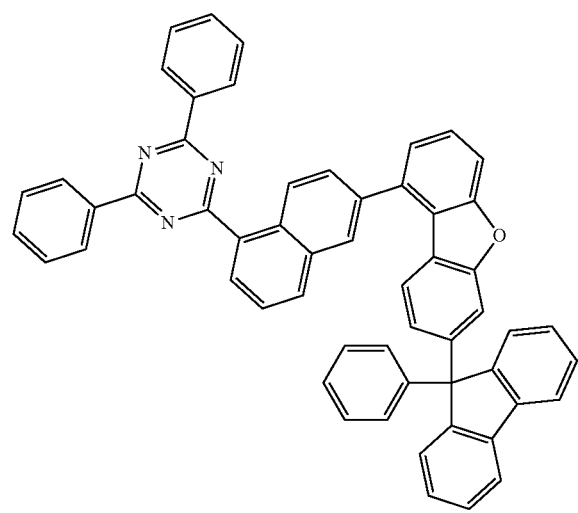
H1-182
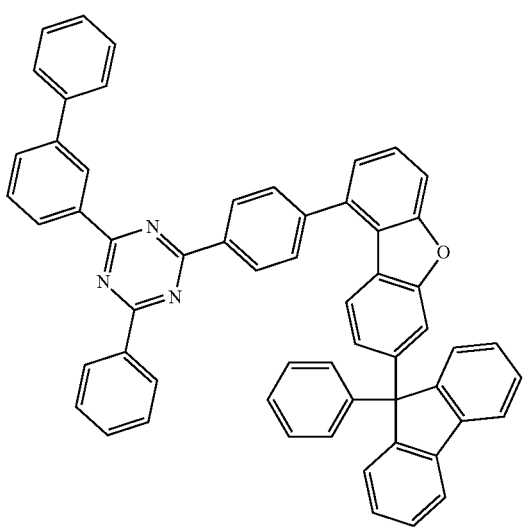
H1-183
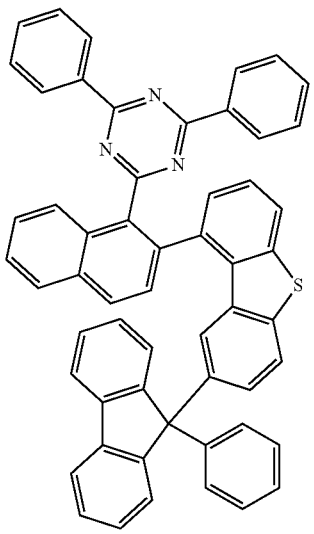
H1-184
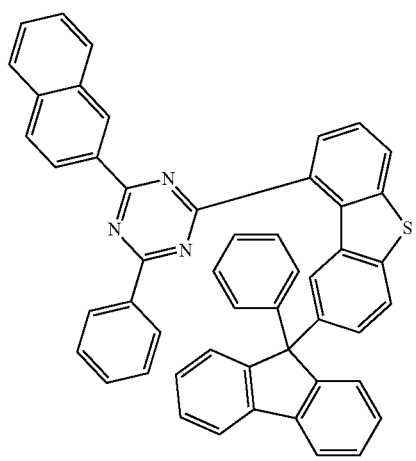
H1-186

H1-187
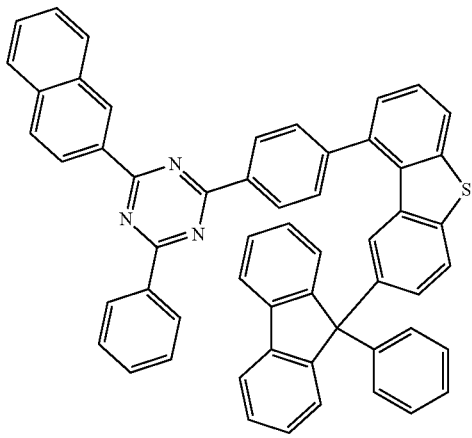
H1-188
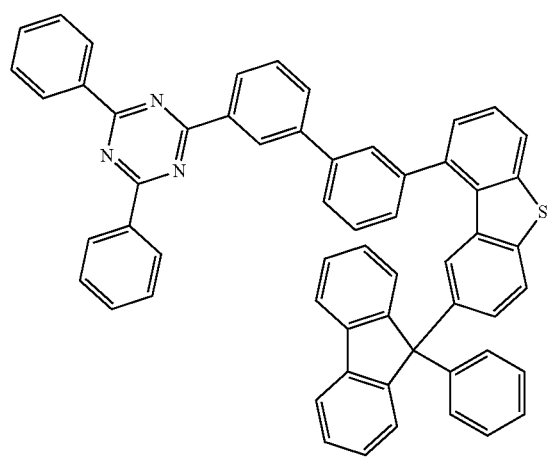
H1-189
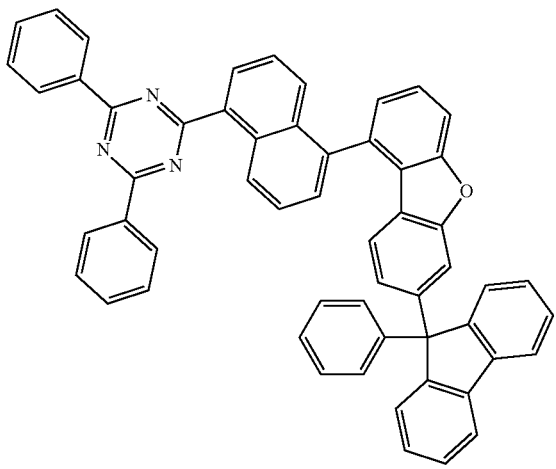
H1-190
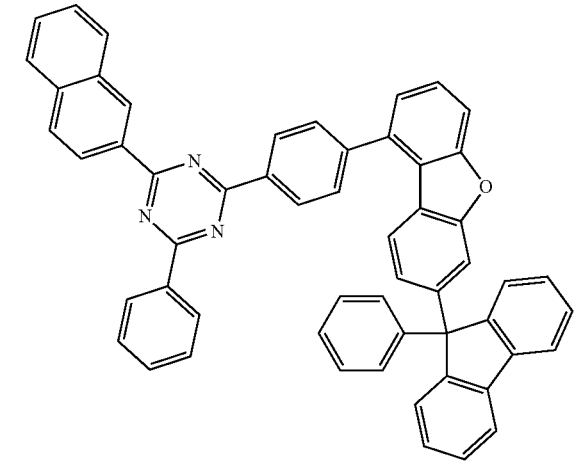
H1-191
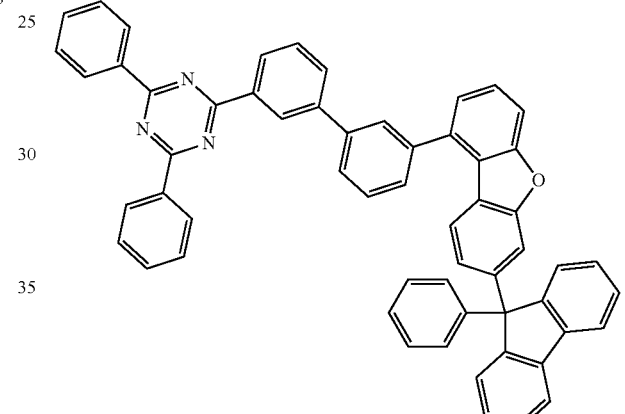
H1-192
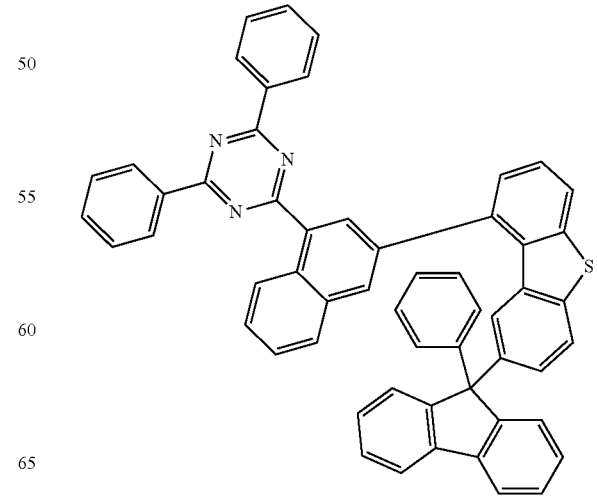

-continued
H1-193
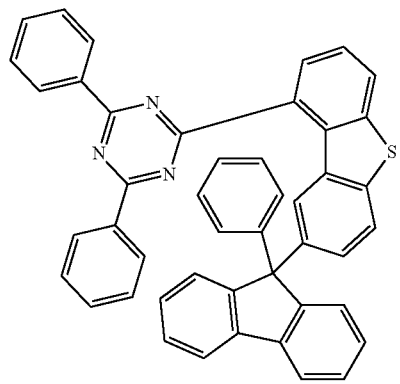
H1-194
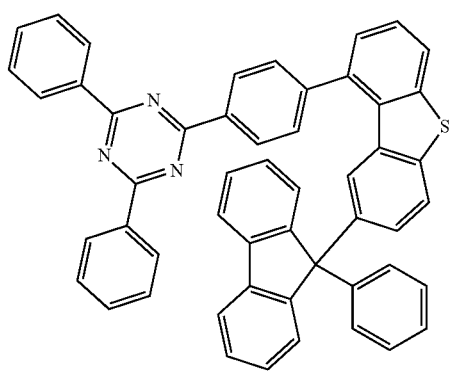
H1-195
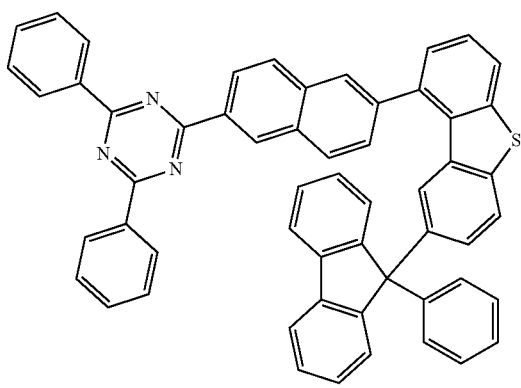
H1-196
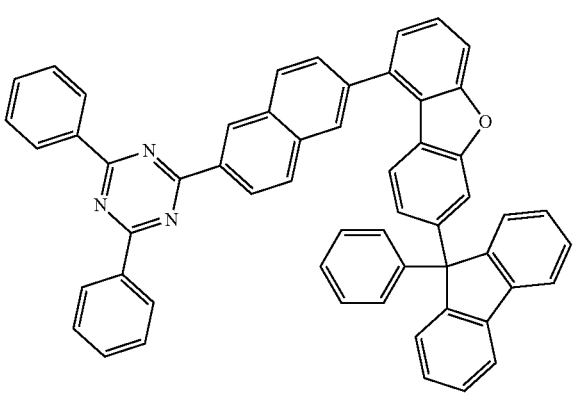
-continued
H1-197
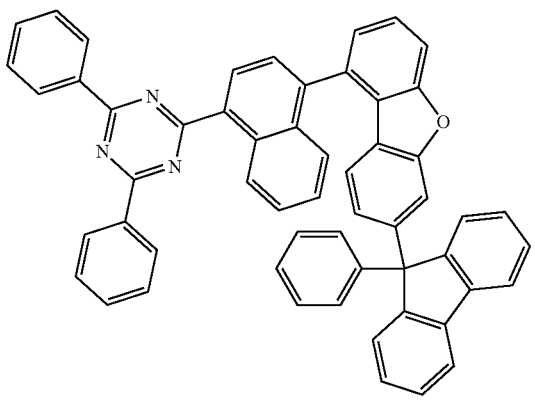
H1-198
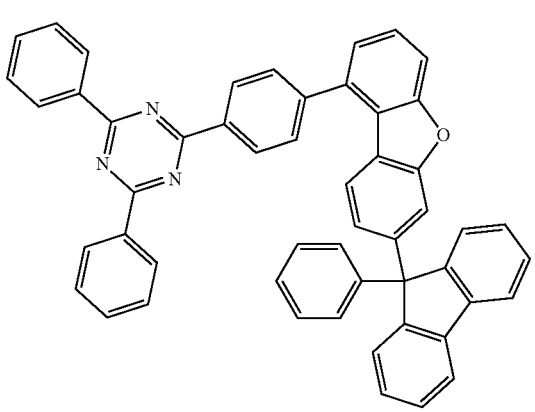
H1-199
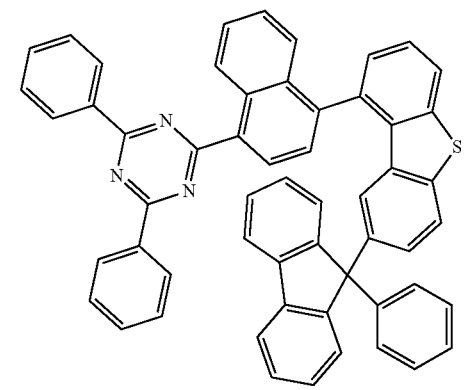

H1-200
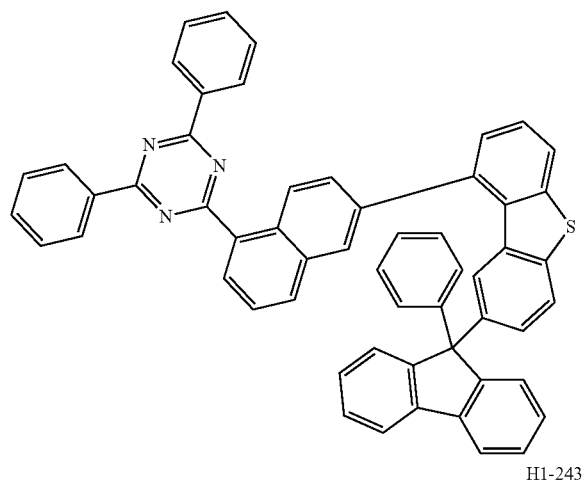
H1-243
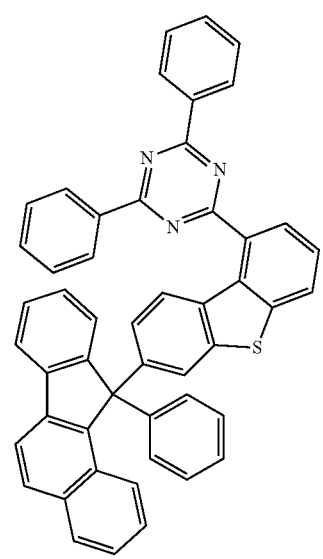
H1-244
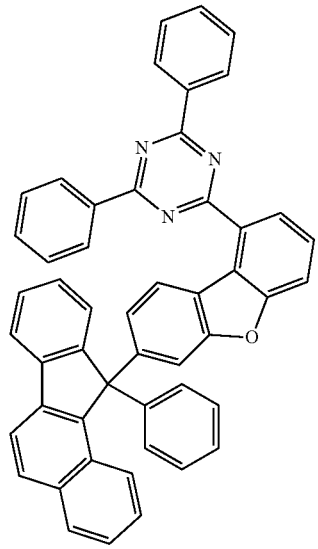
H1-257
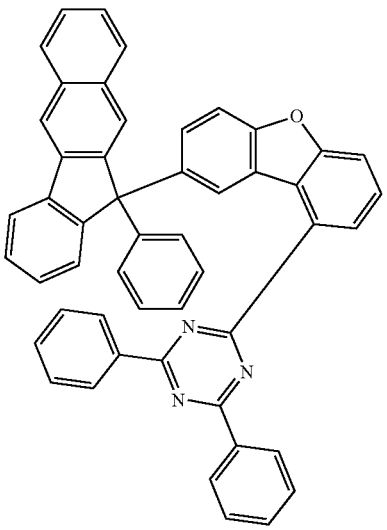
H1-258
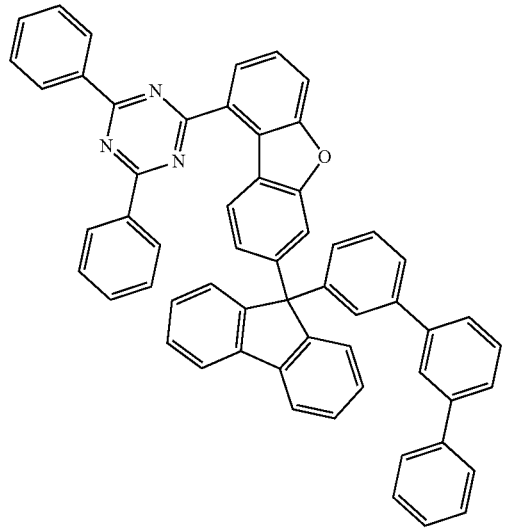
H1-264
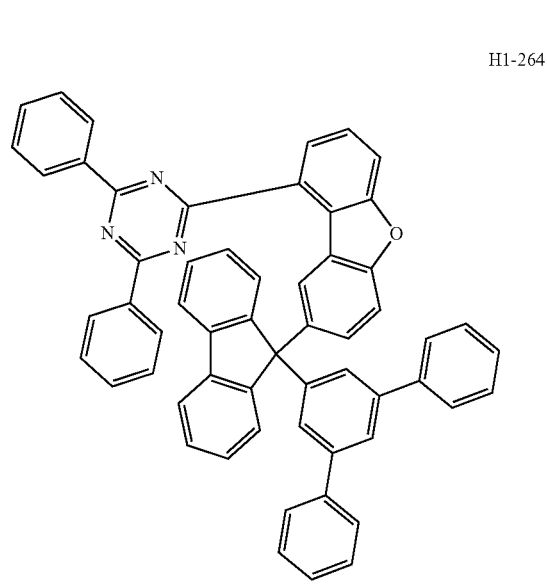

H1-270
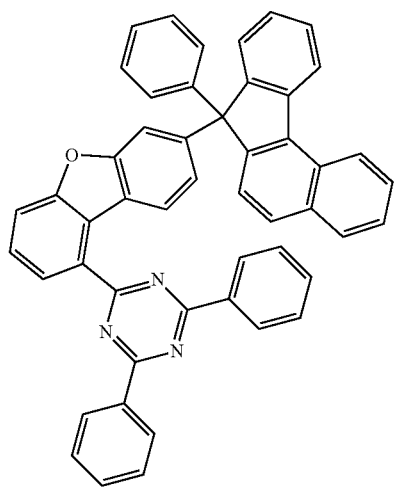
H1-281
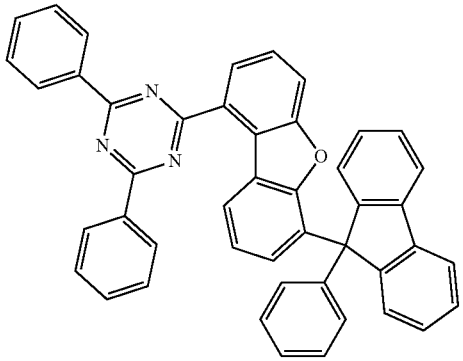
H1-277
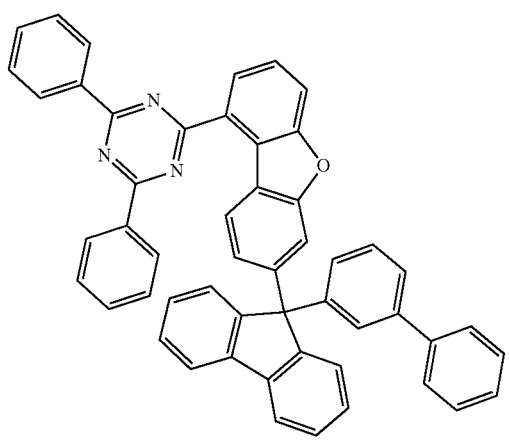
H1-284
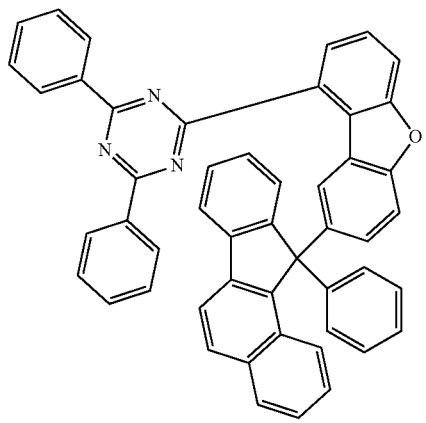
H1-279
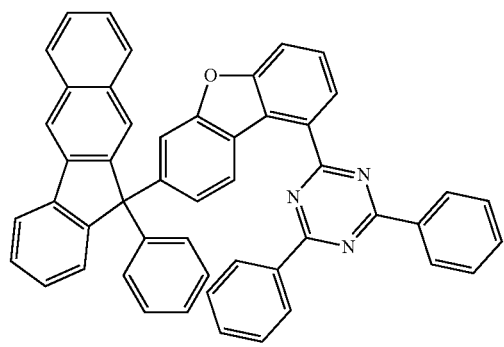
H1-285
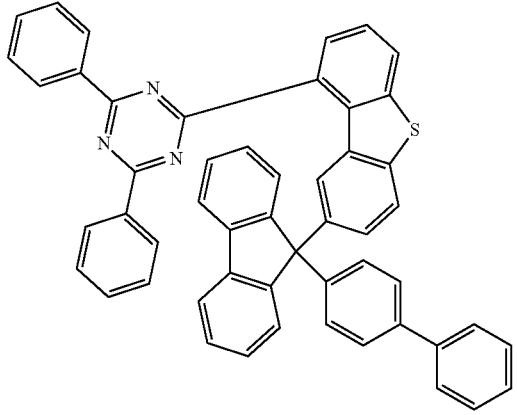

H1-286
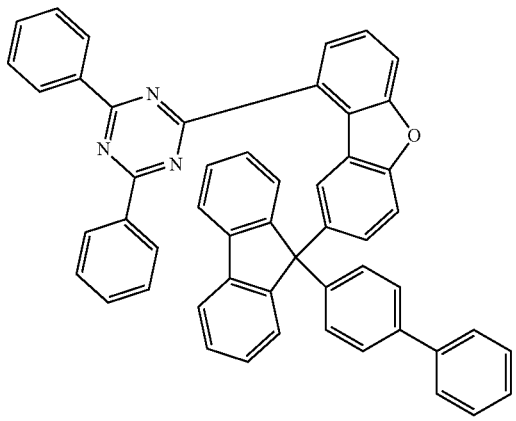
H1-288
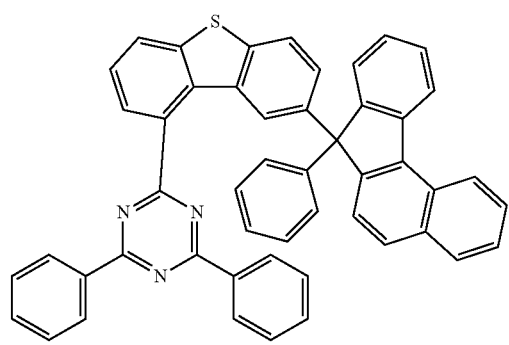
H1-289
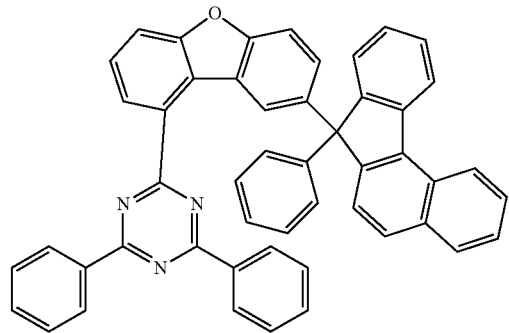
H1-290
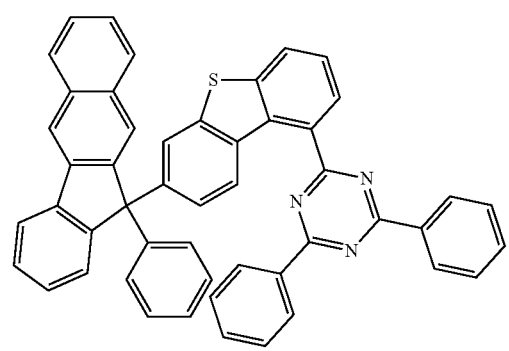
H1-291
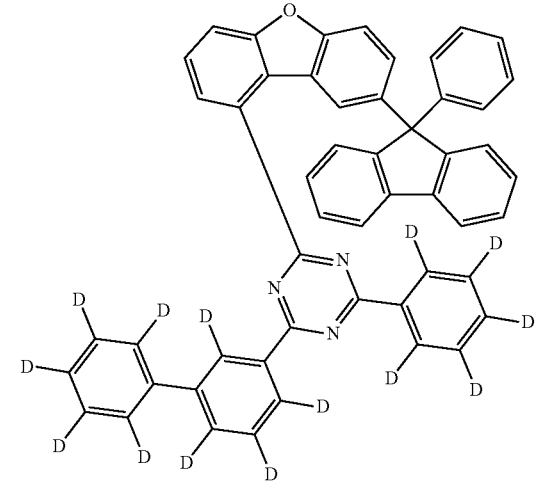
H1-292
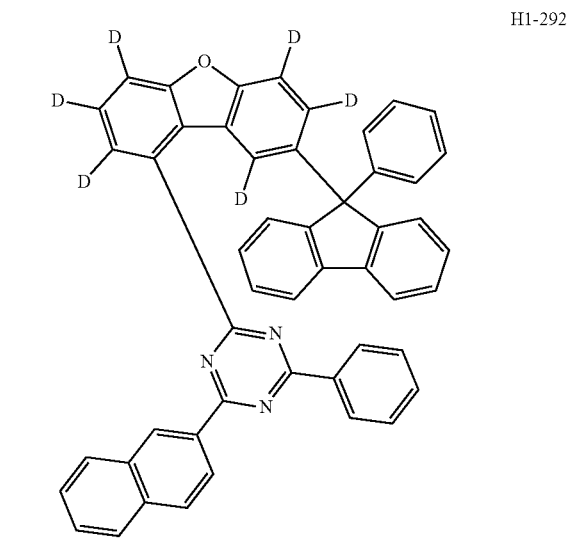
H1-293
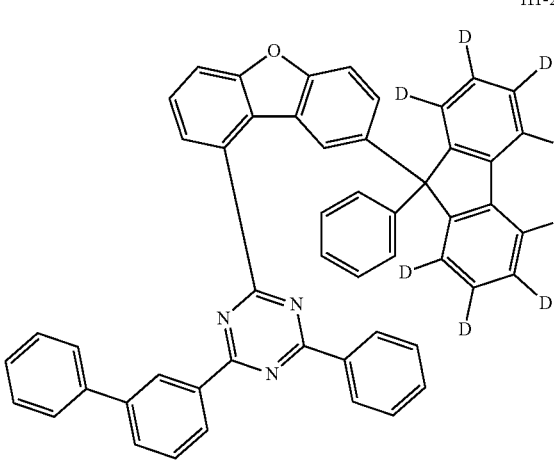

-continued

H1-294

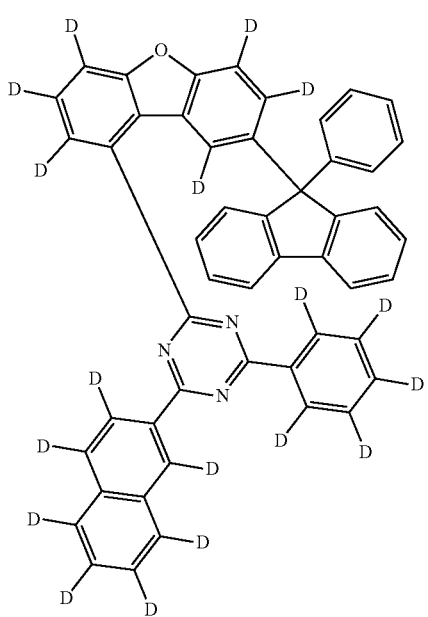

Hereinafter, an organic electroluminescent device to which the aforementioned plurality of host materials and/or the organic electroluminescent compound is(are) applied will be described.

The organic electroluminescent device according to one embodiment includes a first electrode; a second electrode; and at least one organic layer(s) interposed between the first electrode and the second electrode. The organic layer may include a light-emitting layer, and the light-emitting layer may comprise a plurality of host materials comprising a first host material comprising at least one compound represented by the above formula 1 and a second host material comprising at least one compound represented by the above formula 2. According to another embodiment of the present disclosure, the organic electroluminescent device according to the present disclosure includes a first electrode; a second electrode; and at least one light-emitting layer(s) interposed between the first electrode and the second electrode and the at least one light-emitting layer(s) may include a compound represented by the above formula 1-1-1.

According to one embodiment, the organic electroluminescent material of the present disclosure includes at least one of compounds H1-1 to H1-295 as the first host material represented by formula 1 and at least one of compounds H2-1 to H2-59 as the second host material represented by formula 2. The plurality of host materials may be included in the same organic layer, for example a light-emitting layer or may be included in different light-emitting layers, respectively. According to another embodiment, the organic electroluminescent material of the present disclosure includes a compound represented by formula 1-1-1 alone or in combination of two or more, and the organic electroluminescent material may be included in an organic layer, e.g., a light-emitting layer, of an organic electroluminescent device.

The organic layer may further comprise at least one layer selected from a hole injection layer, a hole transport layer, a hole auxiliary layer, a light-emitting auxiliary layer, an electron transport layer, an electron injection layer, an inter-layer, a hole blocking layer, an electron blocking layer, and an electron buffer layer, in addition to a light-emitting layer. The organic layer may further comprise an amine-based compound and/or an azine-based compound, in addition to the light-emitting material of the present disclosure. Specifically, the hole injection layer, the hole transport layer, the hole auxiliary layer, the light-emitting layer, the light-emitting auxiliary layer, or the electron blocking layer may comprise an amine-based compound, for example, arylamine-based compound, a styrylarylamine-based compound, etc., as a hole injection material, a hole transport material, a hole auxiliary material, a light-emitting material, a light-emitting auxiliary material, or an electron blocking material. In addition, the electron transport layer, the electron injection layer, the electron buffer layer, and the hole blocking layer may comprise an azine-based compound as an electron transport material, an electron injection material, an electron buffer material, and a hole blocking material. In addition, the organic layer further comprise at least one metal selected from the group consisting of metals of Group 1, metals of Group 2, transition metals of the 4$^{th}$ period, transition metals of the 5$^{th}$ period, lanthanides, and organic metals of the d-transition elements of the Periodic Table, or at least one complex compound comprising such a metal.

The plurality of host materials according to one embodiment may be used as light-emitting materials for a white organic light-emitting device. The white organic electroluminescent device has suggested various structures such as a parallel side-by-side arrangement method, a stacking arrangement method, or color conversion material (CCM) method, etc., according to the arrangement of R (Red), G (Green), YG (yellowish green), or B (Blue) light-emitting units. In addition, the organic electroluminescent material according to one embodiment may also be applied to the organic electroluminescent device comprising a QD (quantum dot).

One of the first electrode and the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. In addition, the hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer may be placed between the electron transport layer (or electron injection layer) and the light-emitting layer, and blocks the arrival of holes to the cathode, thereby improving the probability of recombination of electrons and holes in the light-emitting layer. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_x(1 \leq X \leq 2)$, $AlO_x(1 \leq X \leq 1.5)$, SiON, SiAlON, etc.; the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

Further, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent device according to one embodiment may further include at least one dopant in the light-emitting layer.

The dopant comprised in the organic electroluminescent device of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), as necessary; more preferably an ortho-metallated complex compound(s) of a metal atom(s) selected from iridium (Ir), osmium (Os), copper (Cu), and platinum (Pt), as necessary; and even more preferably ortho-metallated iridium complex compound(s), as necessary.

The dopant comprised in the organic electroluminescent device of the present disclosure may use the compound represented by the following formula 101, but is not limited thereto.

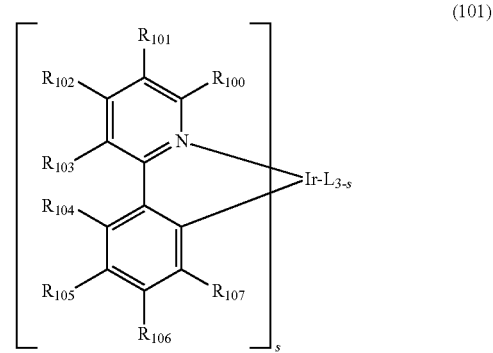

(101)

In formula 101,

L is selected from any one of the following structures 1 to 3;

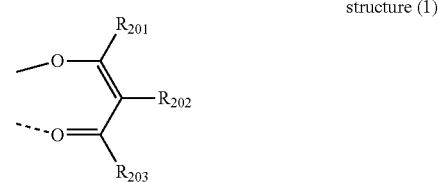

structure (1)

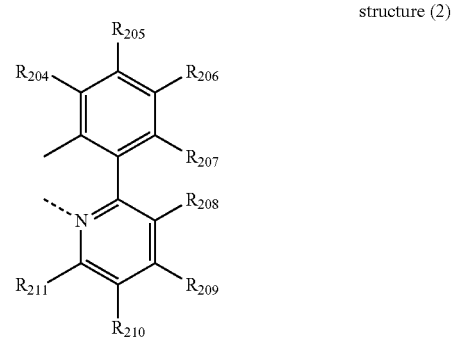

structure (2)

structure (3)

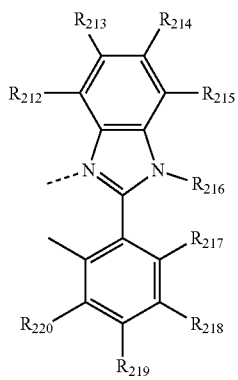

R<sub>100</sub> to R<sub>103</sub> each independently represent, hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or may be linked to the adjacent substituents to form a ring(s) e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$ each independently represent, hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy; or may be linked to the adjacent substituents to form a substituted or unsubstituted ring(s), e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted beznothienopyrdine together with benzene;

$R_{201}$ to $R_{220}$ each independently represent, hydrogen, deuterium, halogen, (C1-C30)alkyl unsubstituted or substituted with deuterium and/or halogen, a substituted or unsubstituted (C3-C30)cycloalkyl, or a substituted or unsubstituted (C6-C30)aryl; or may be linked to the adjacent substituents to form a substituted or unsubstituted ring(s); and s represents an integer of 1 to 3.

Specifically, the specific examples of the dopant compound include the following, but are not limited thereto.

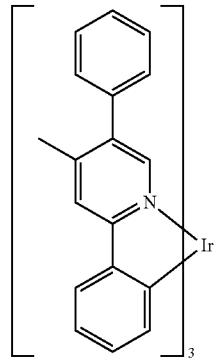

D-1

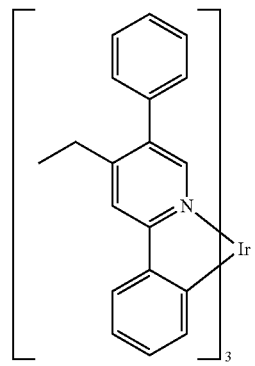

D-2

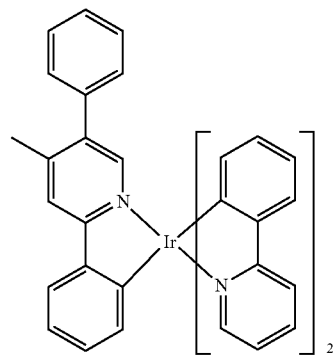

D-3

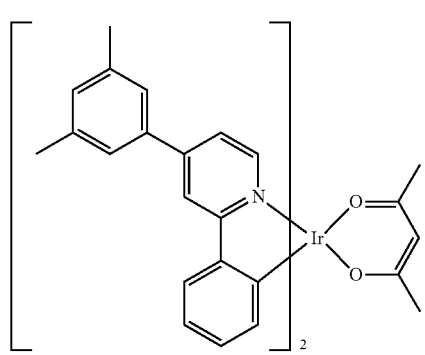

D-4

-continued
D-5
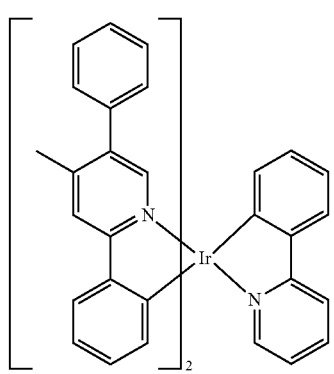
D-6
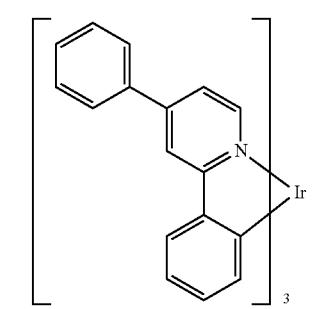
D-7
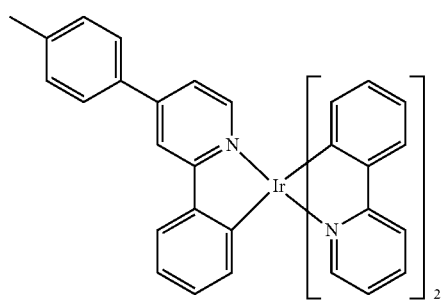
D-8
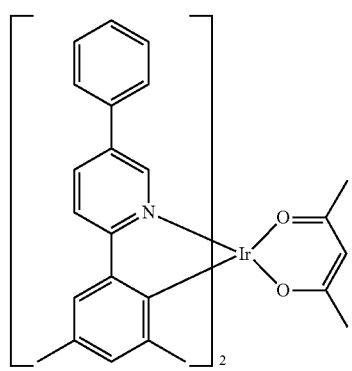
-continued
D-9
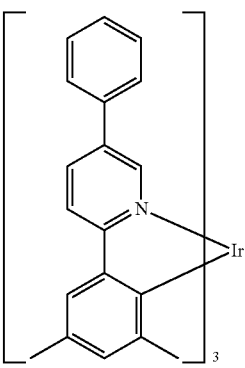
D-10
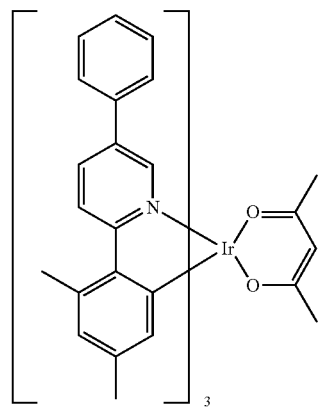
D-11
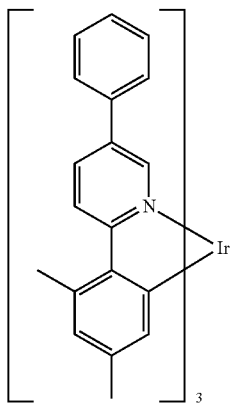
D-12
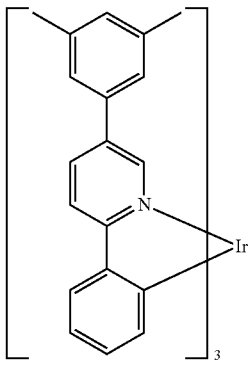

-continued
D-13
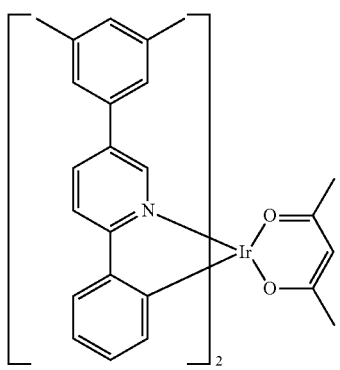
D-14
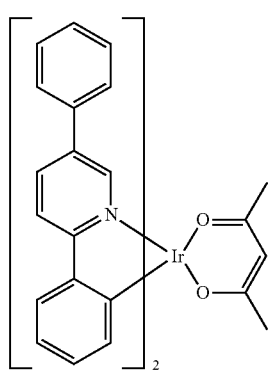
D-15
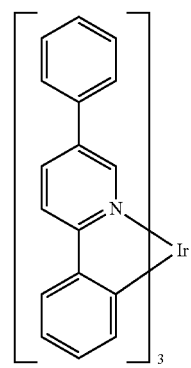
D-16
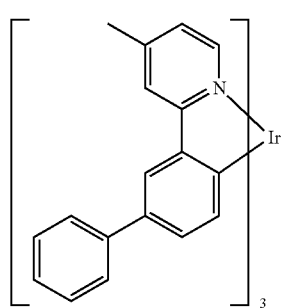
-continued
D-17
D-18
D-19
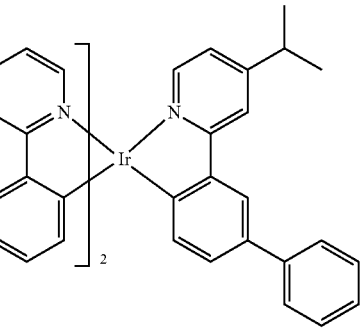
D-20
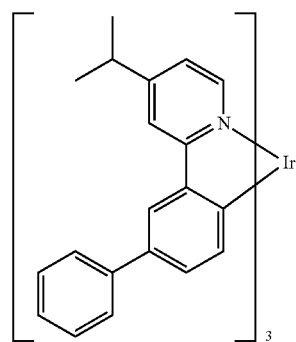

D-21 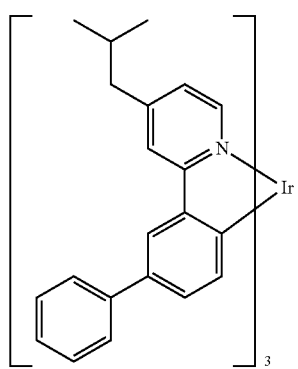
D-25 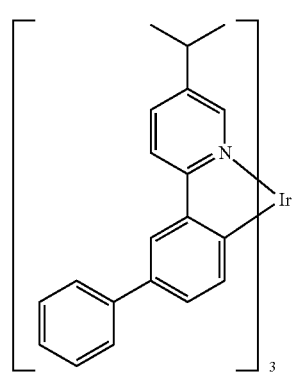
D-22 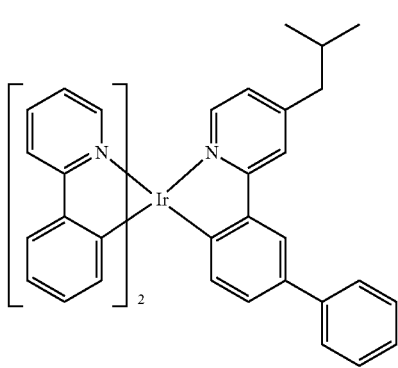
D-26 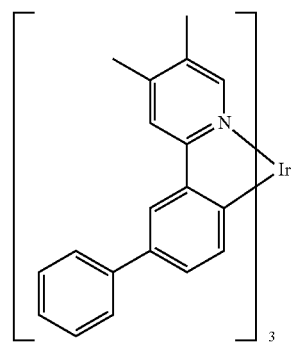
D-23 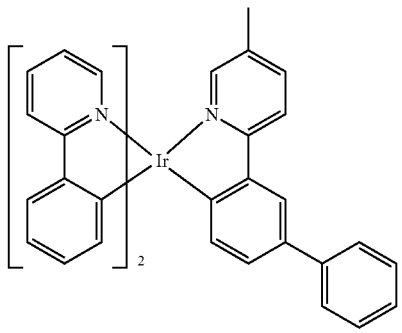
D-27 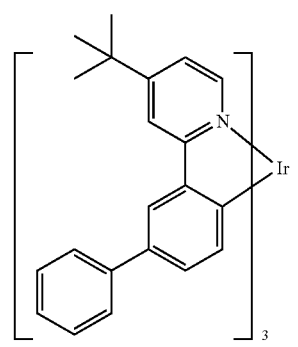
D-24 
D-28 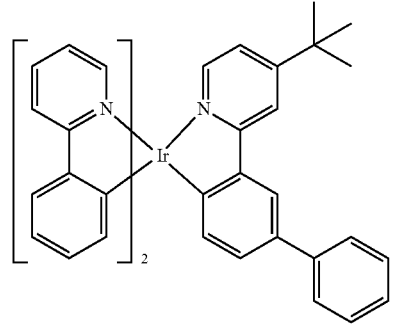

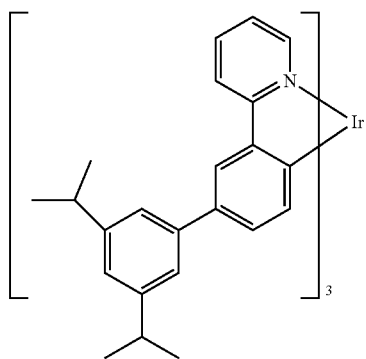 D-29
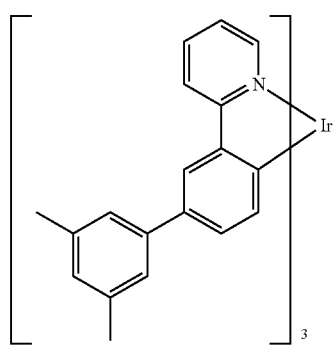 D-30
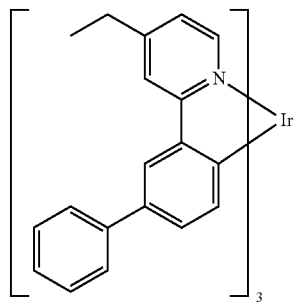 D-31
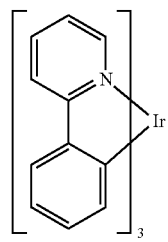 D-32
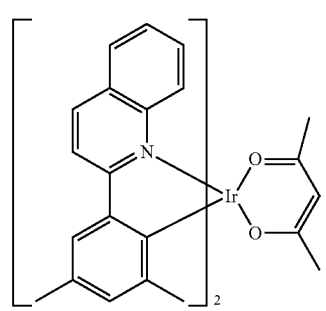 D-33
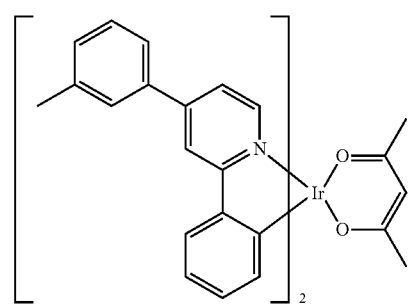 D-34
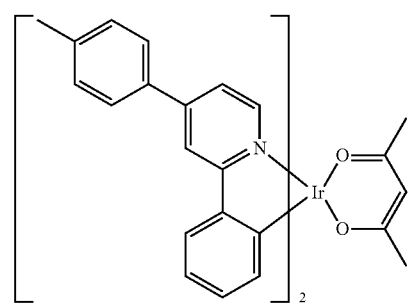 D-35
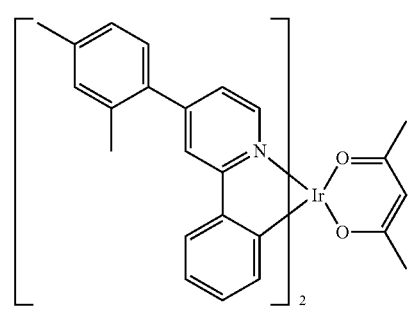 D-36
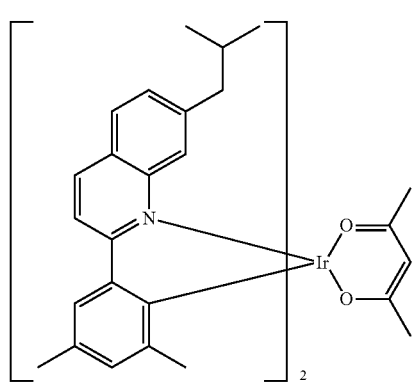 D-37
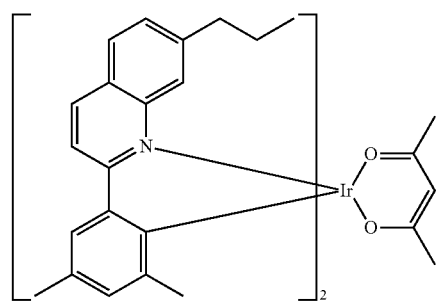 D-38

-continued
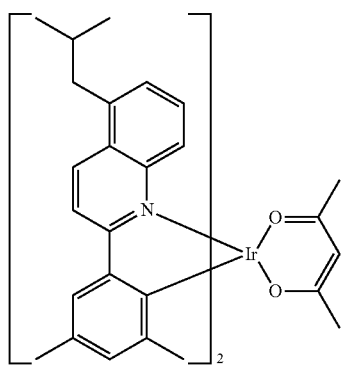
D-39
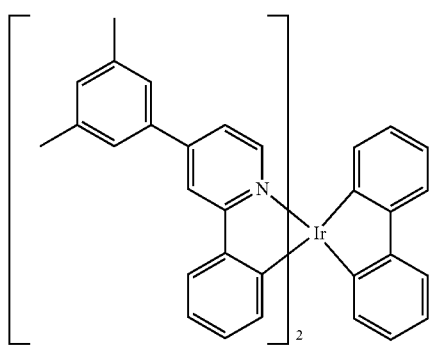
D-40
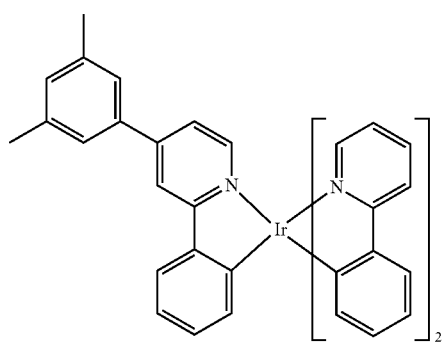
D-41
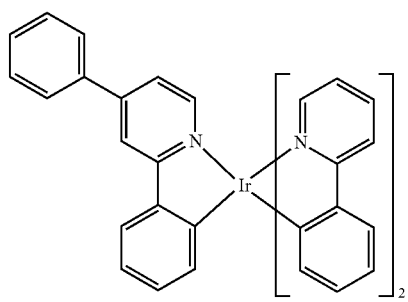
D-42
-continued
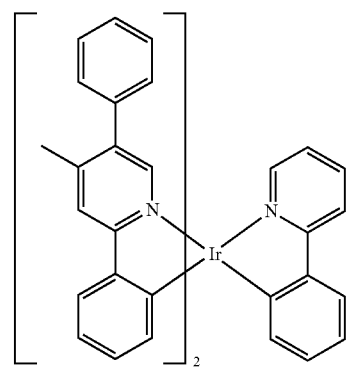
D-43
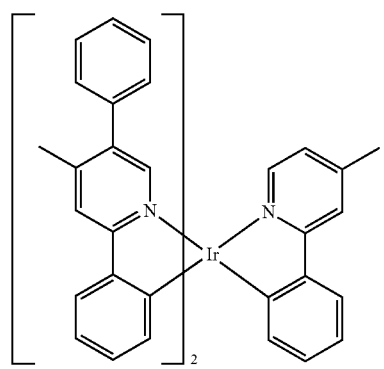
D-44
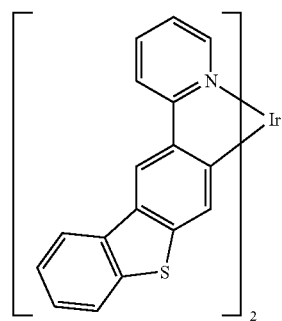
D-45
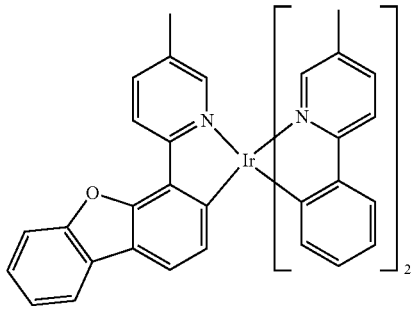
D-46

D-47
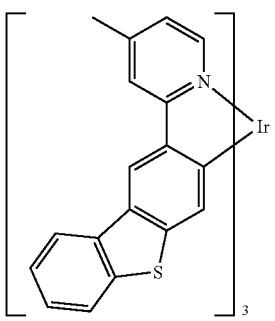
D-48
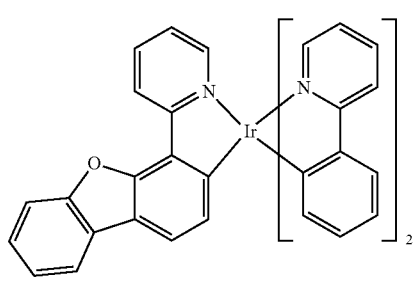
D-49
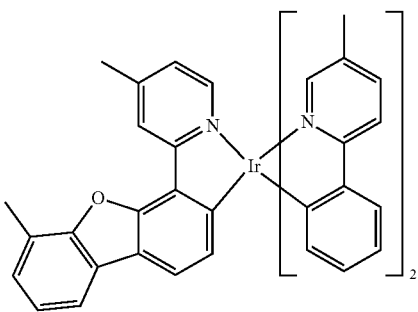
D-50
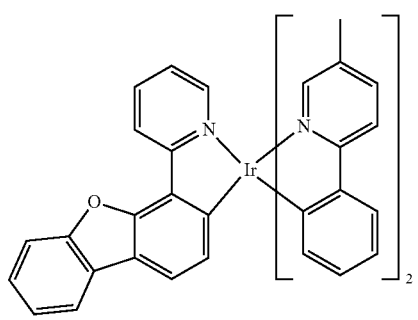
D-51
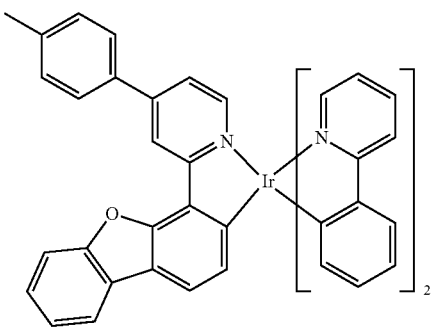
D-52
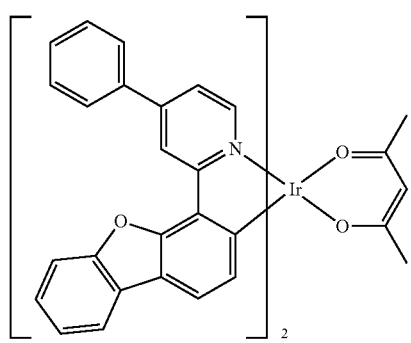
D-53
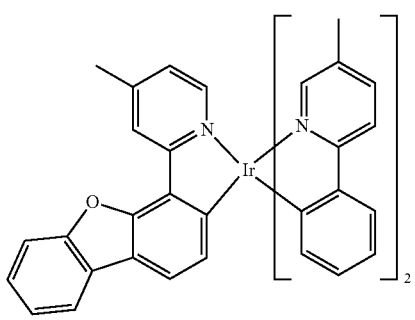
D-54
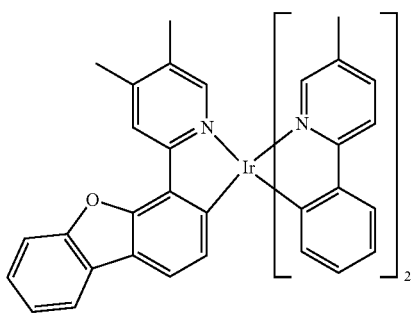
D-55
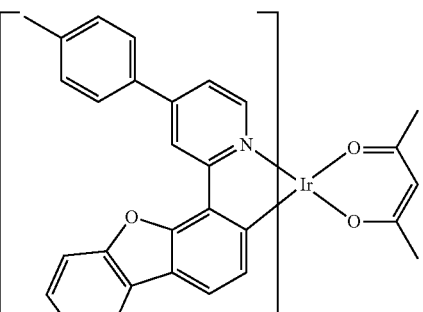
D-56
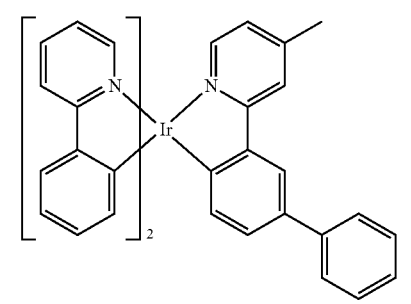

-continued
D-57
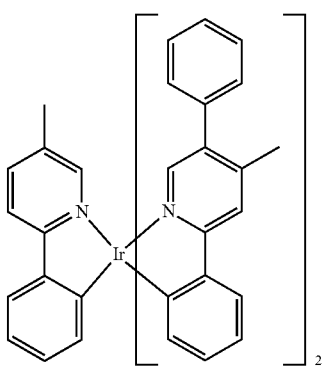
D-58
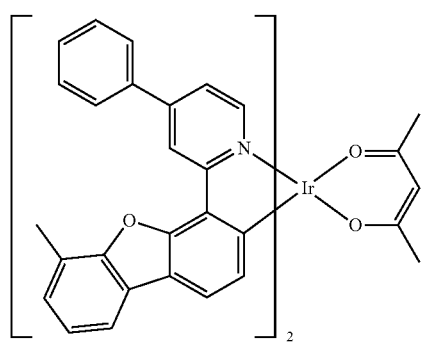
D-59
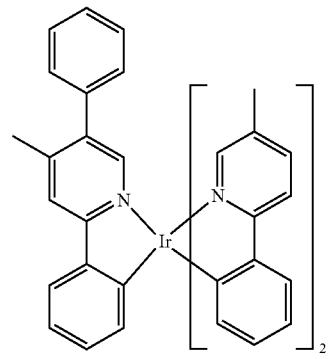
D-60
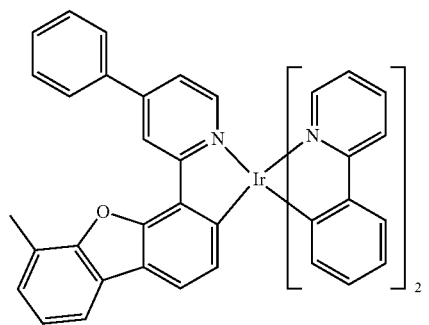
-continued
D-61
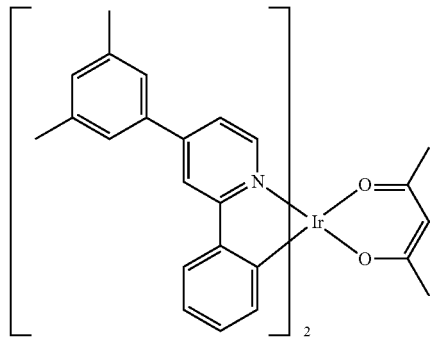
D-62
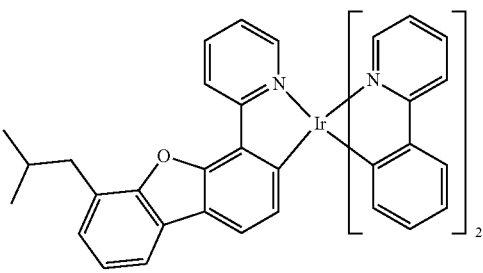
D-63
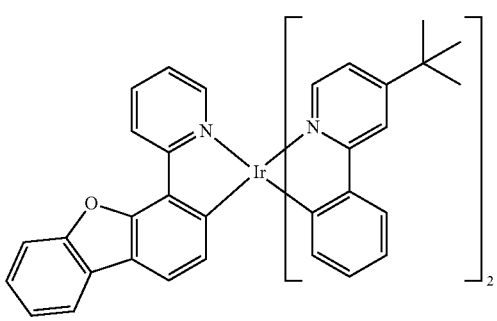
D-64
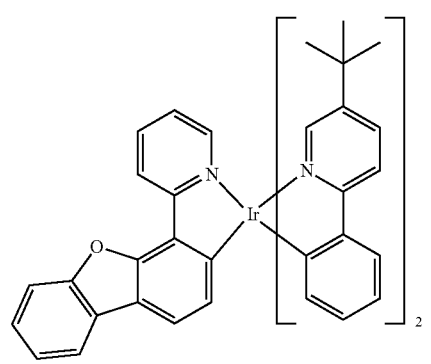
D-65
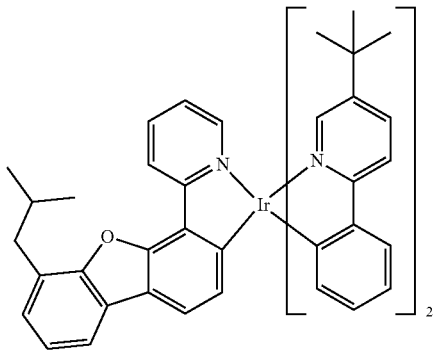

D-66 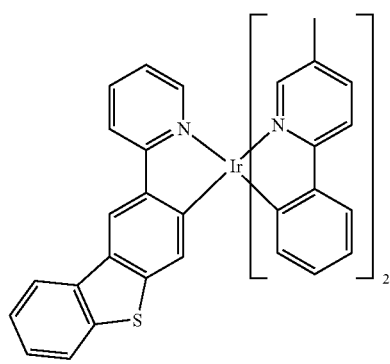
D-67 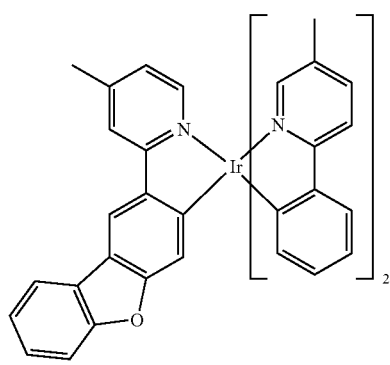
D-68 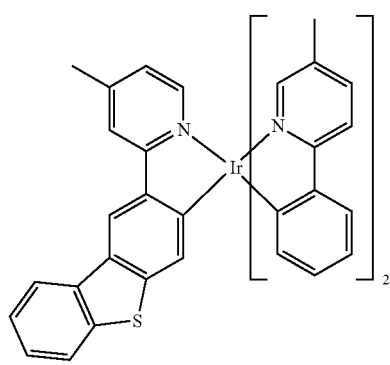
D-69 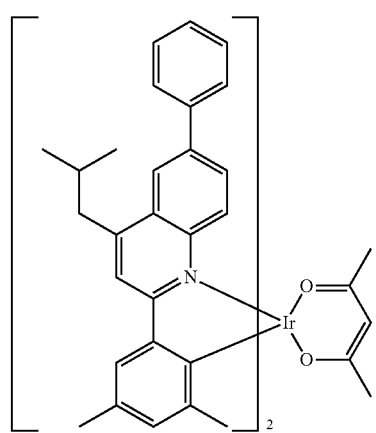
D-70 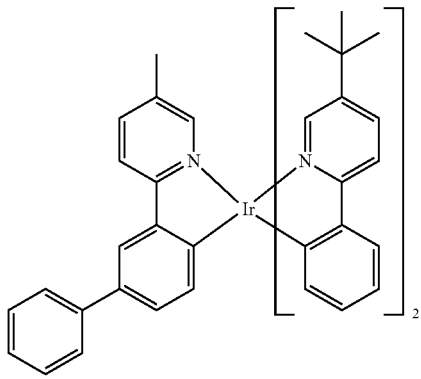
D-71 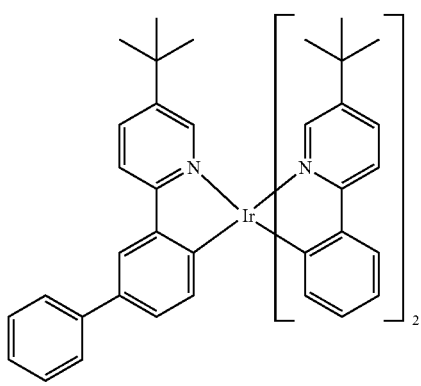
D-72 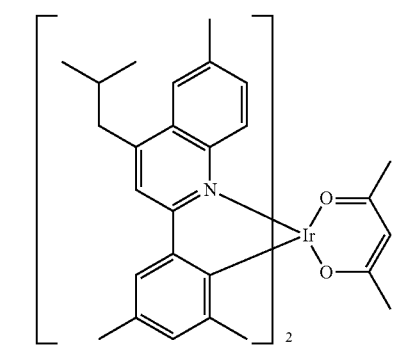
D-73 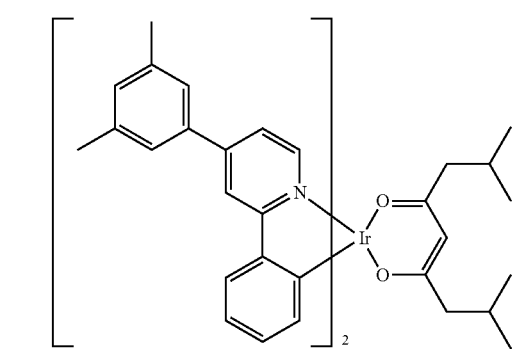

D-74
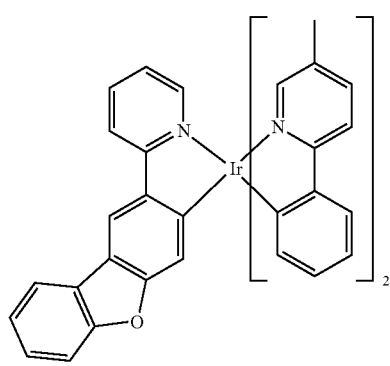
D-75
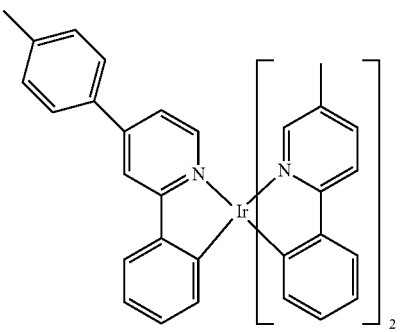
D-76
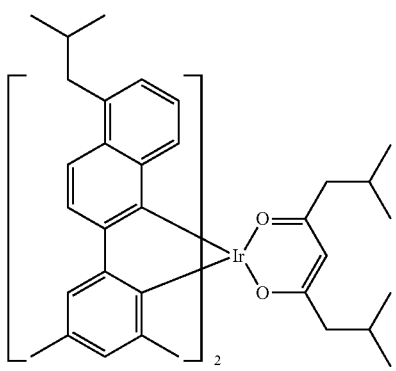
D-77
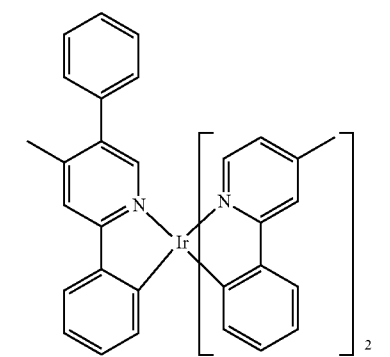
D-78
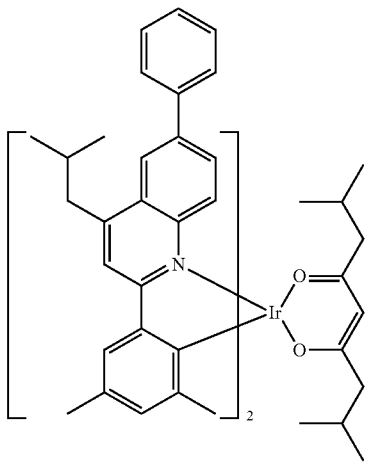
D-79
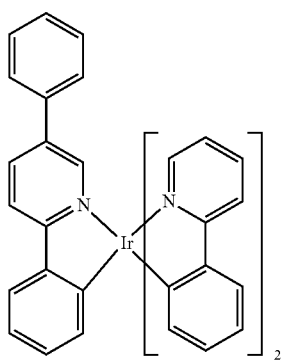
D-80

D-81
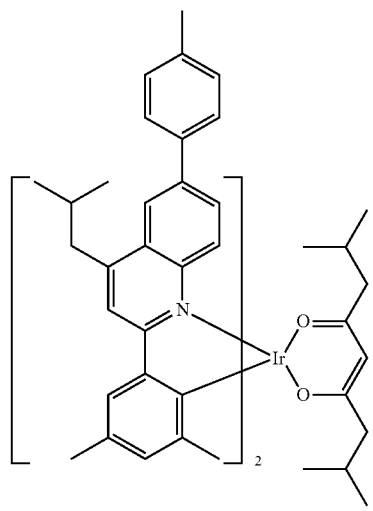
D-82
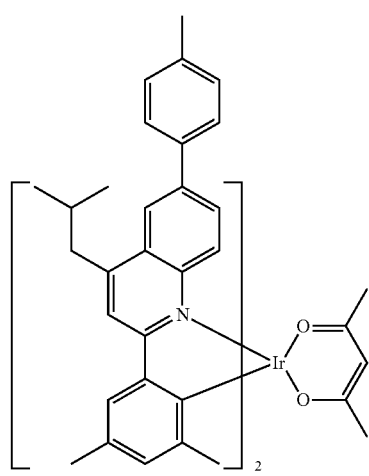
D-83
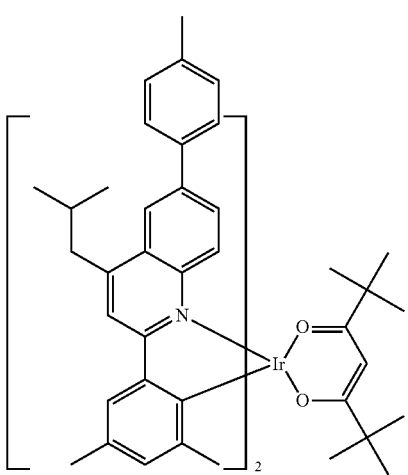
D-84
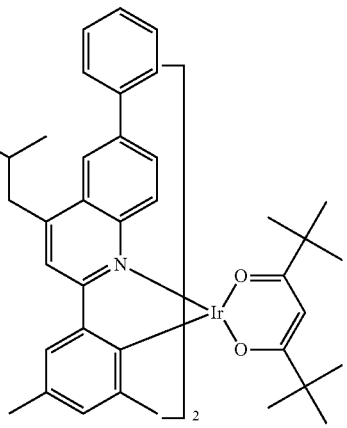
D-85
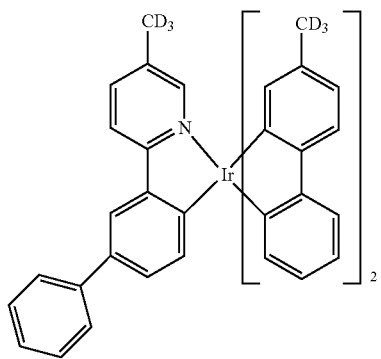
D-86
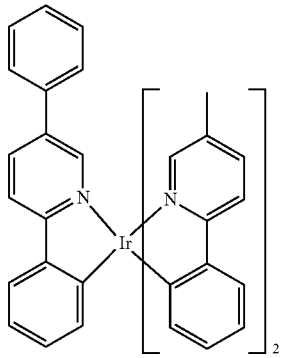
D-87
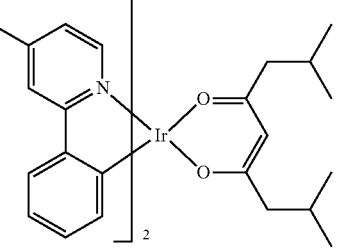

-continued
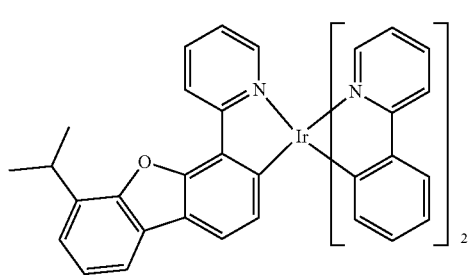
D-88
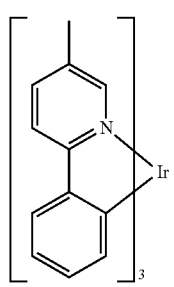
D-89
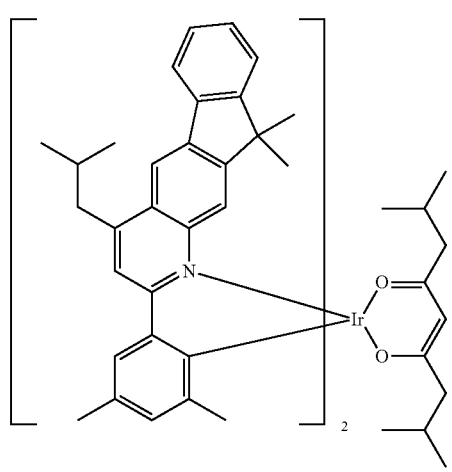
D-90
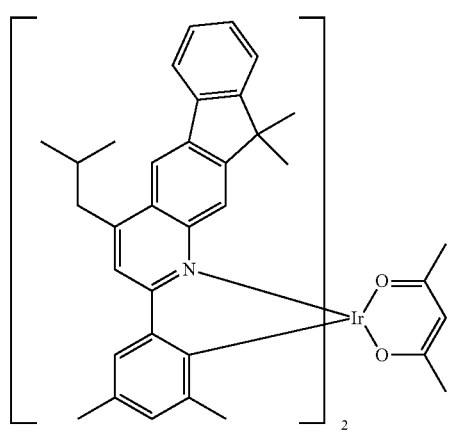
D-91
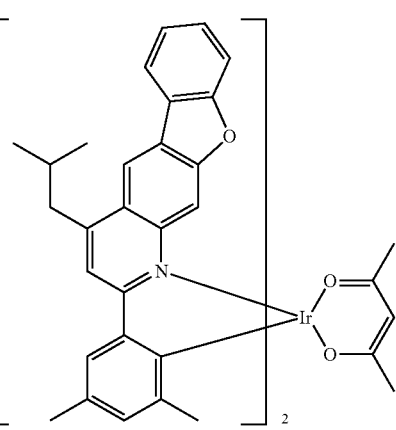
D-92
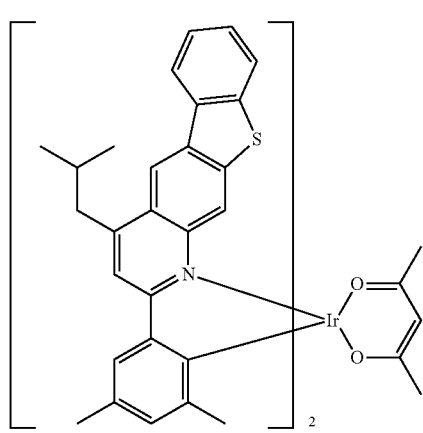
D-93
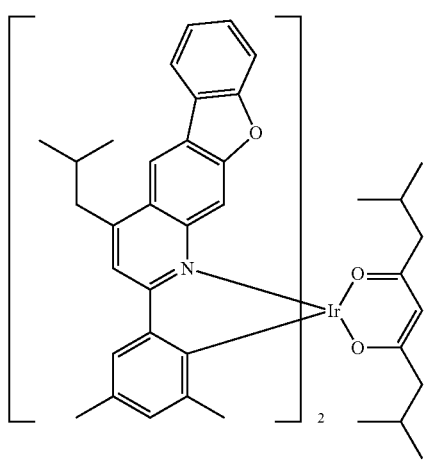
D-94

D-95
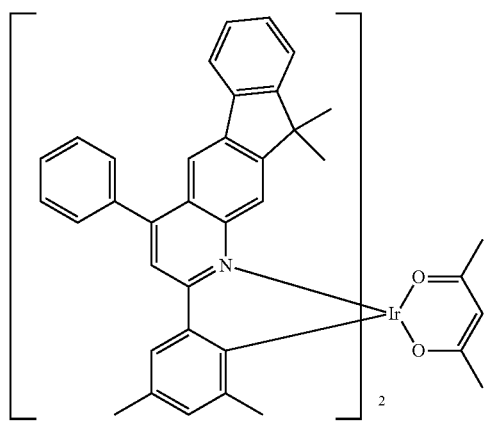
D-96
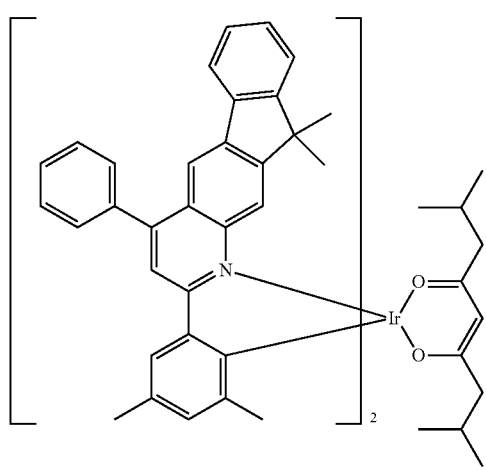
D-97
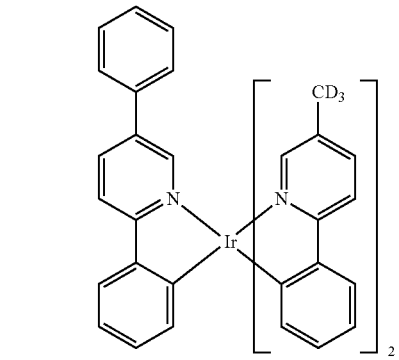
D-98
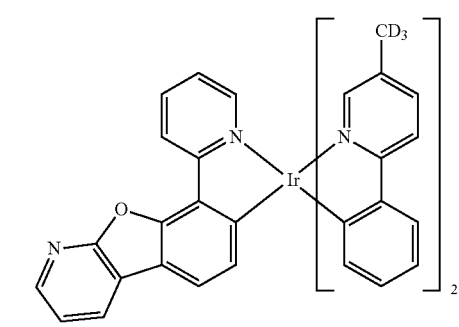
D-99
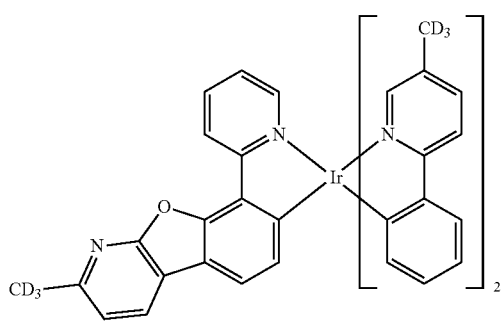
D-100
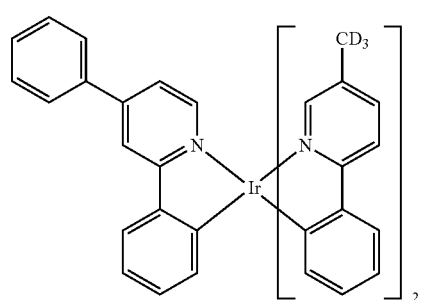
D-101
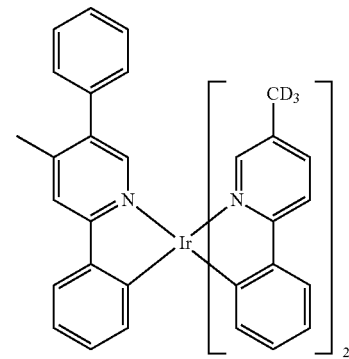
D-102
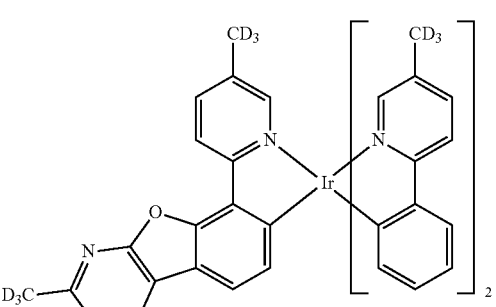

D-103
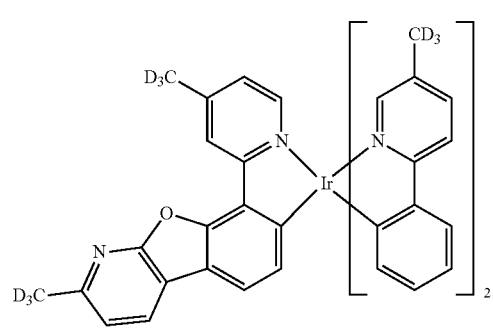
D-104
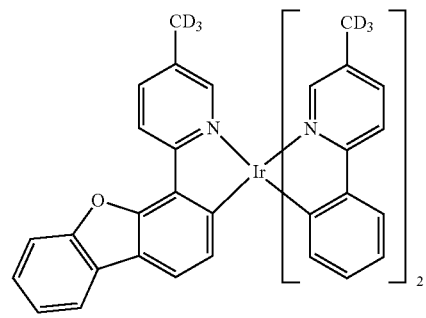
D-105
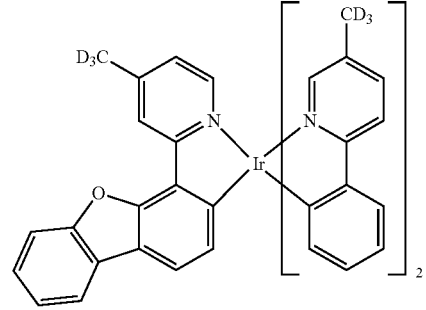
D-106
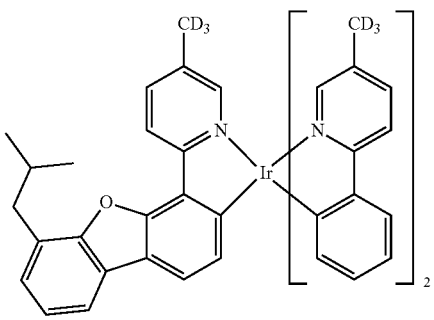
D-107
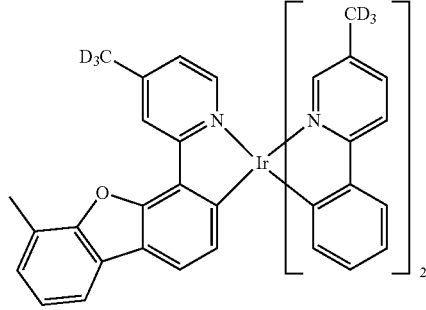
D-108
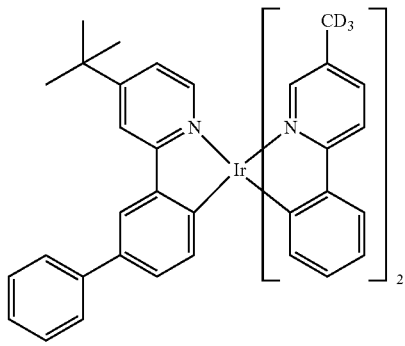
D-109
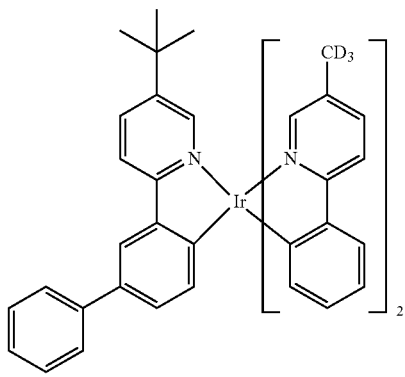
D-110
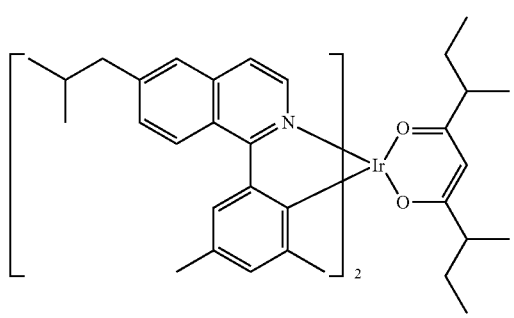
D-111
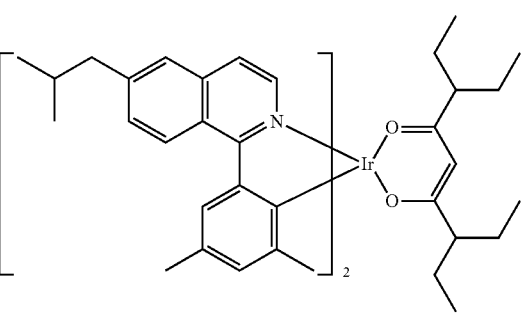

D-112
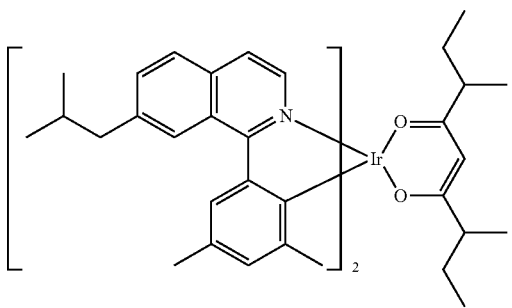
D-113
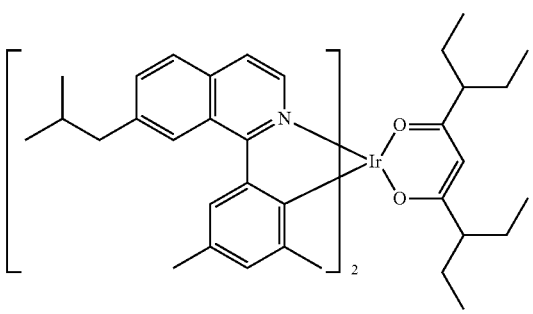
D-114
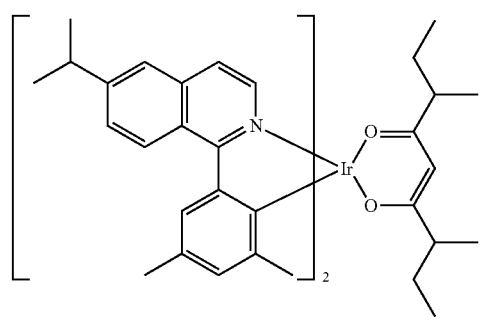
D-115
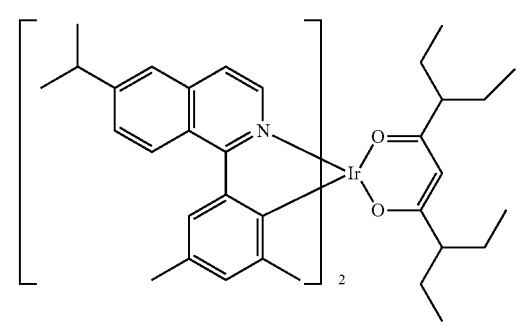
D-116
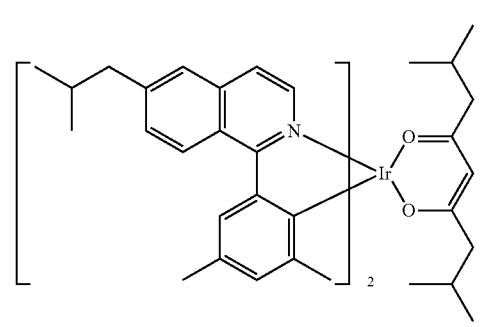
D-117
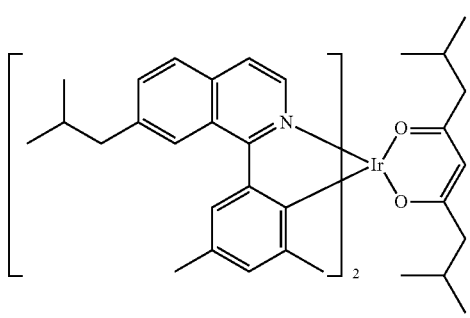
D-118
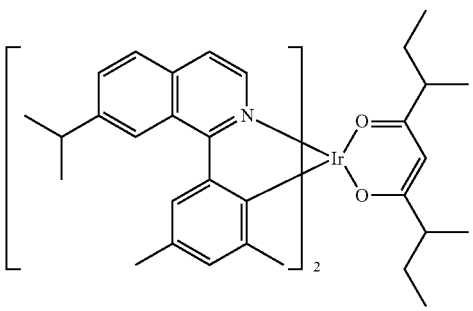
D-119
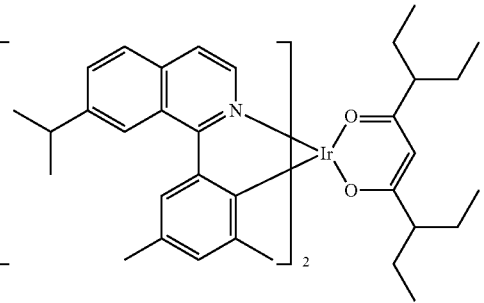
D-120
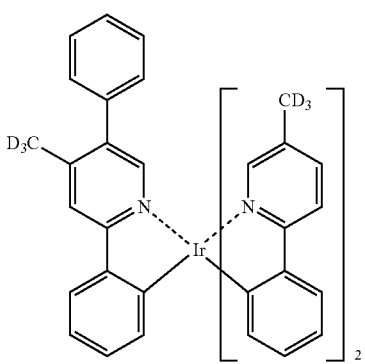

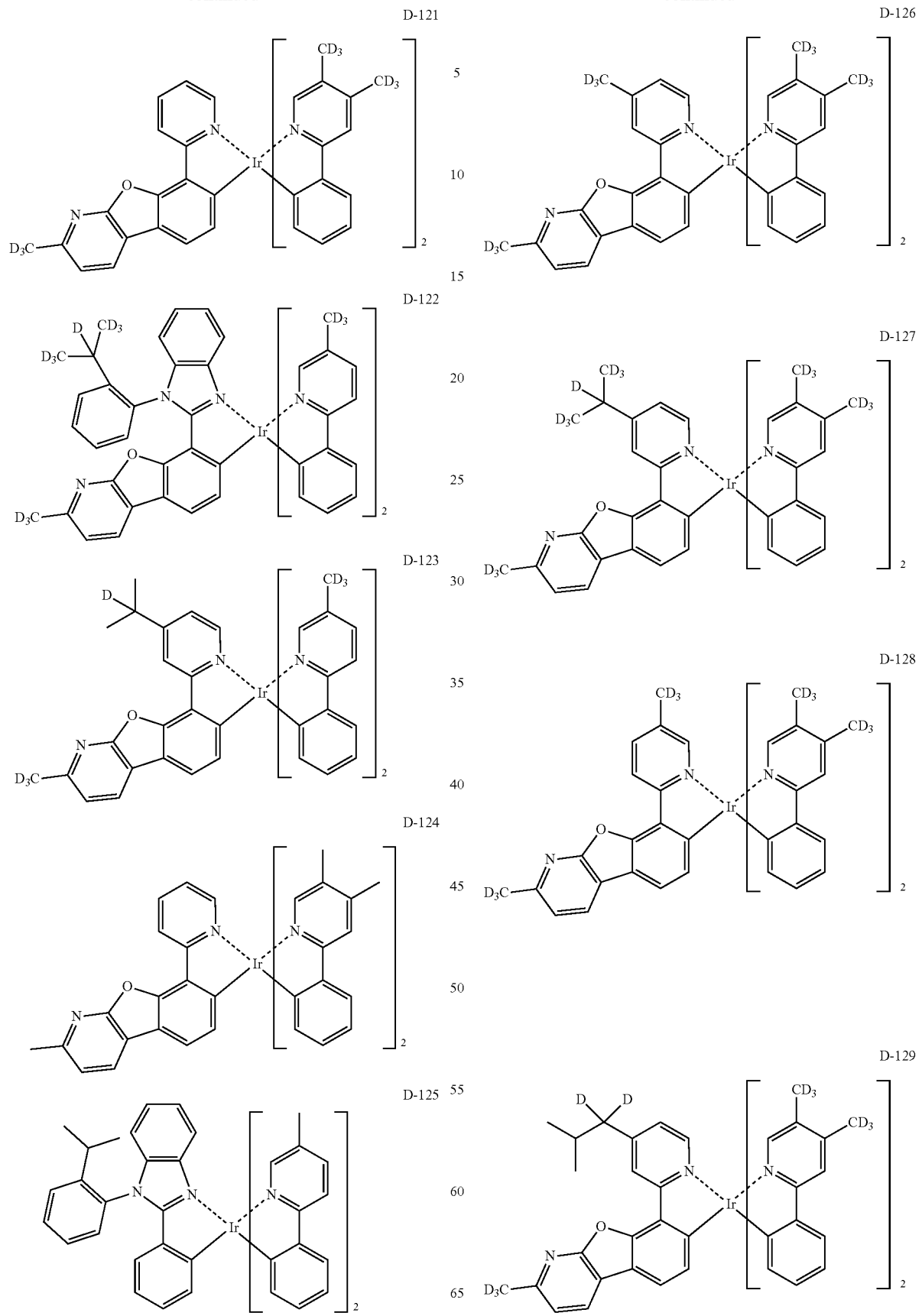

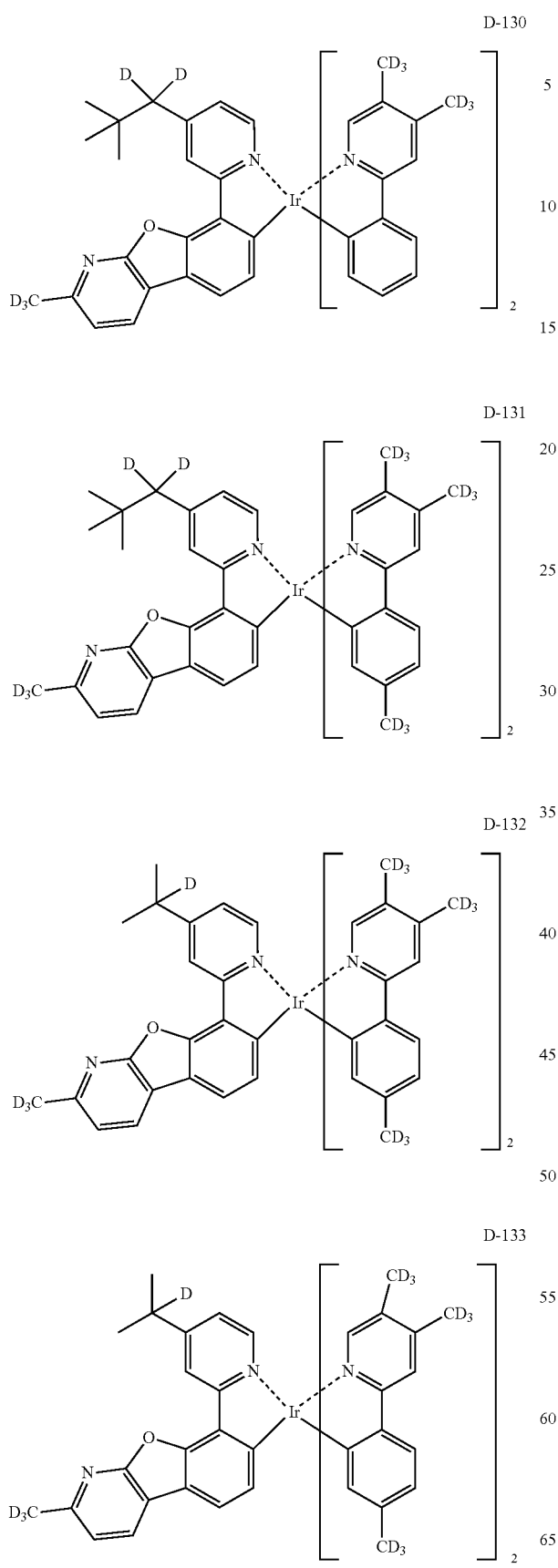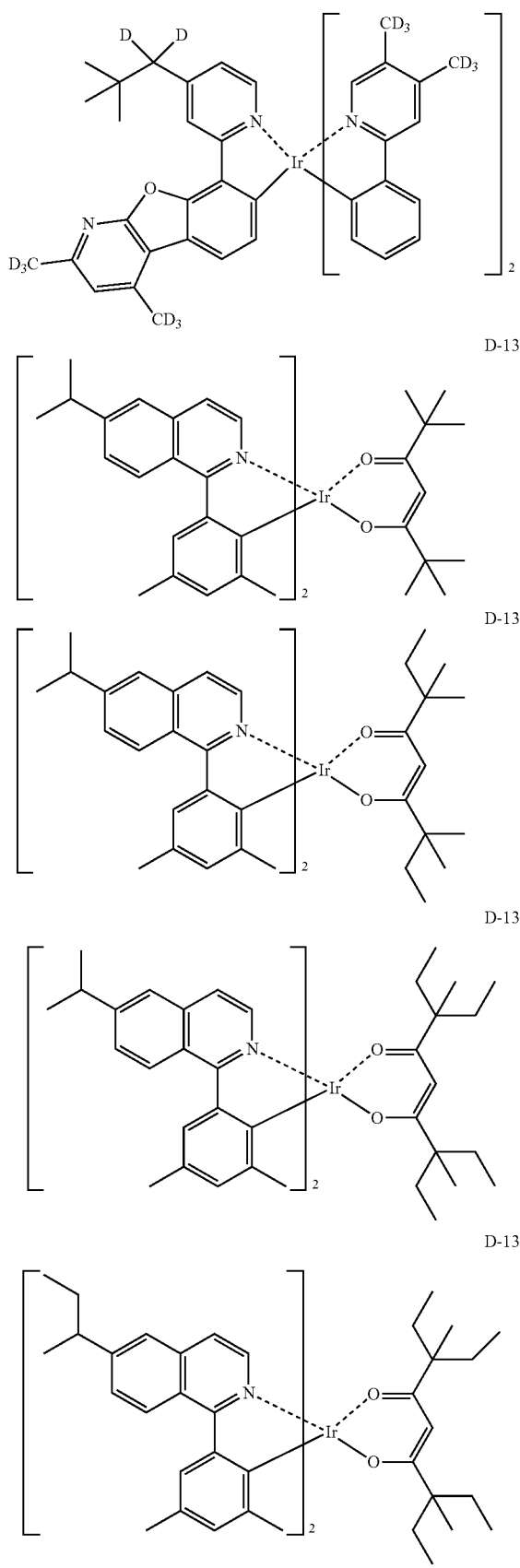

D-139
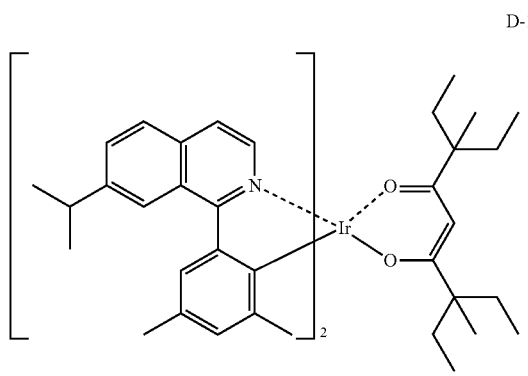
D-140
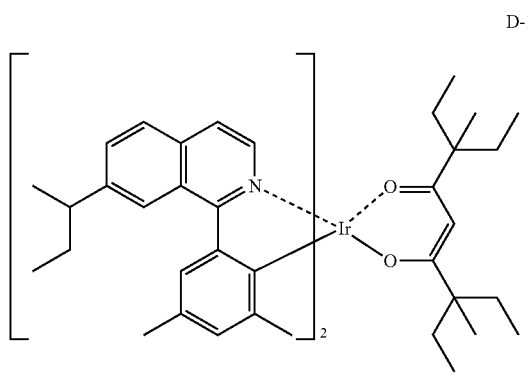
D-141
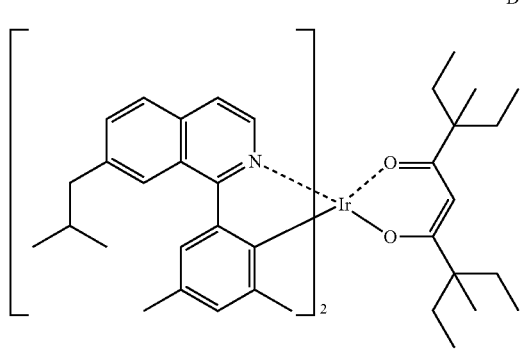
D-142
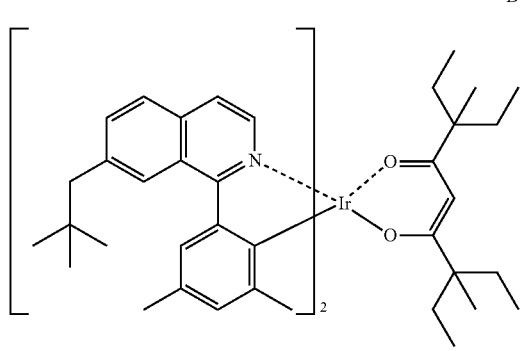
D-143
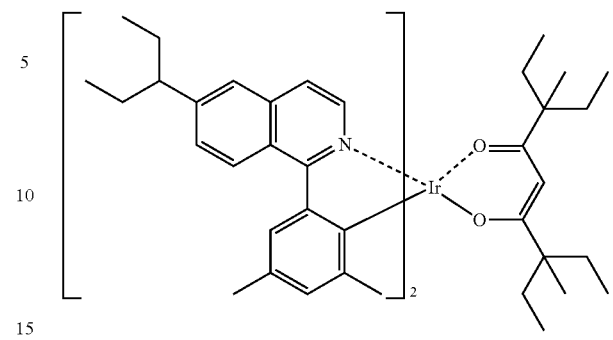
D-144
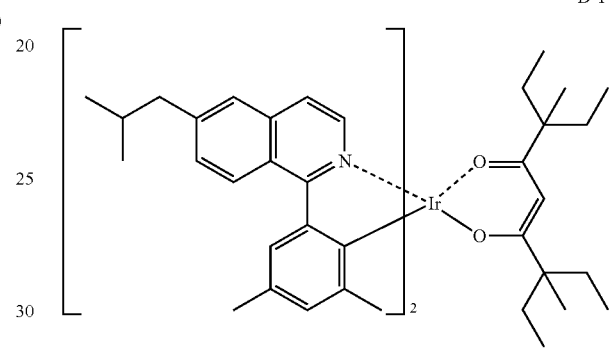
D-145
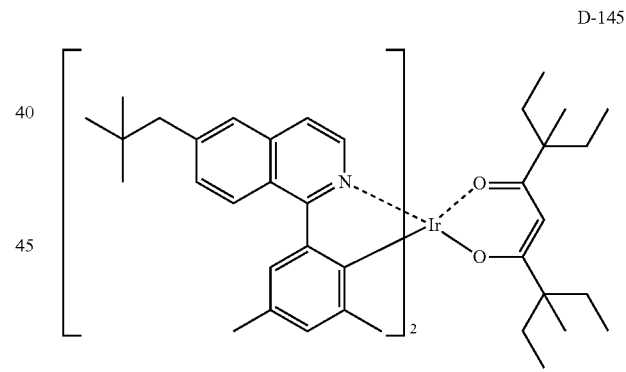
D-146
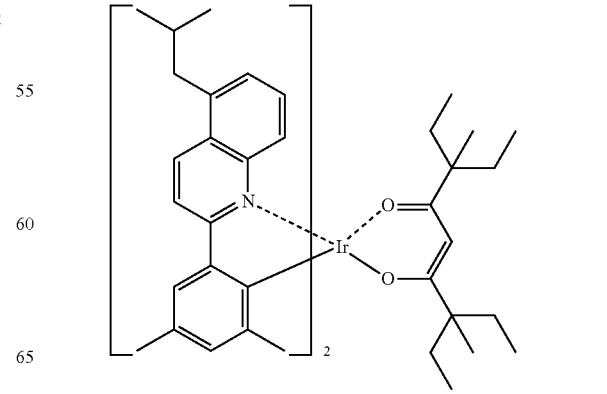

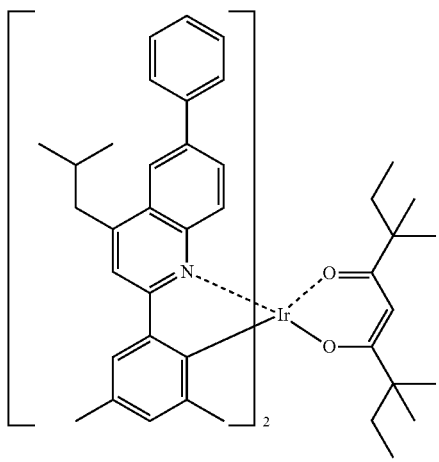

D-147

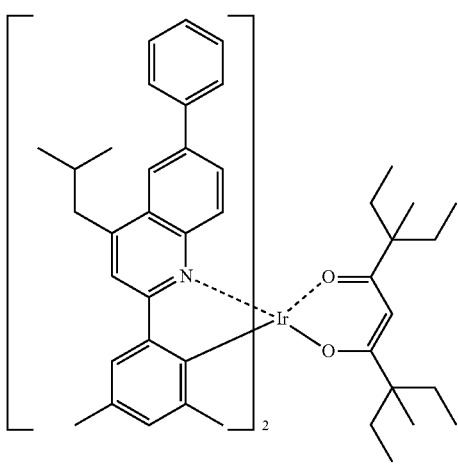

D-148

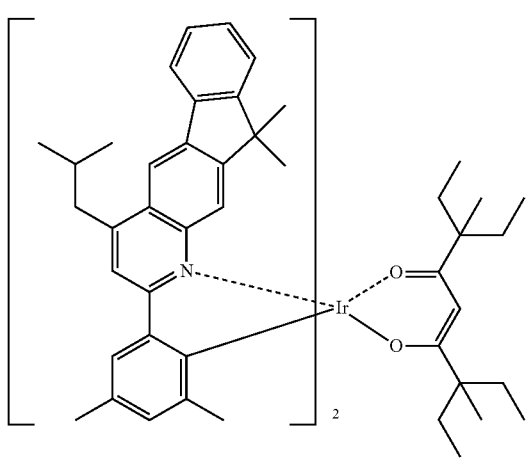

D-149

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the first host material and the second host material according to one embodiment, the layer can be formed by the above-listed methods, and can often be formed by co-deposition or mixture-deposition. The co-deposition is a mixed deposition method in which two or more materials are put into respective individual crucible sources and a current is applied to both cells simultaneously to evaporate the materials and to perform mixed deposition; and the mixed deposition is a mixed deposition method in which two or more materials are mixed in one crucible source before deposition, and then a current is applied to one cell to evaporate the materials.

According to one embodiment, when the first host material and the second host material exist in the same layer or different layers in the organic electroluminescent device, the layers by the two host compounds may be separately formed. For example, after depositing the first host material, a second host material may be deposited.

According to one embodiment, the present disclosure can provide display devices comprising a plurality of host materials including a first host material comprising the compound represented by formula 1 and a second host material comprising the compound represented by formula 2. In addition, by using the organic electroluminescent device of the present disclosure, display devices such as smartphones, tablets, notebooks, PCs, TVs, or display devices for vehicles, or lighting devices such as outdoor or indoor lighting can be prepared.

Hereinafter, the preparation method of compounds according to the present disclosure will be explained with reference to the synthesis method of a representative compound or intermediate compound in order to understand the present disclosure in detail.

[Example 1] Synthesis of Compound H1-76

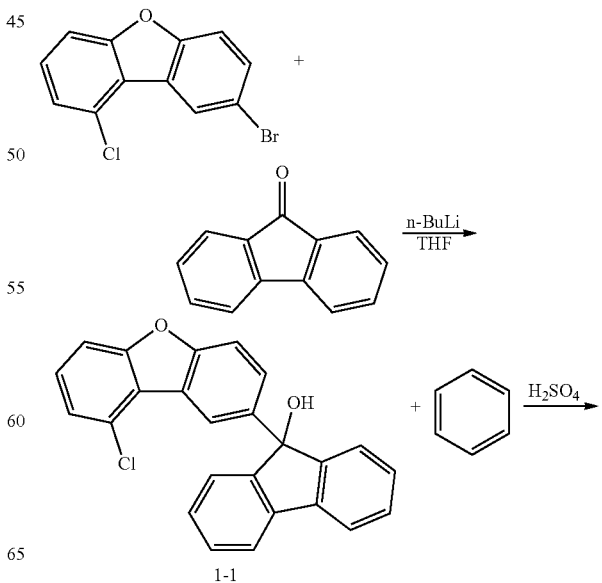

1-1

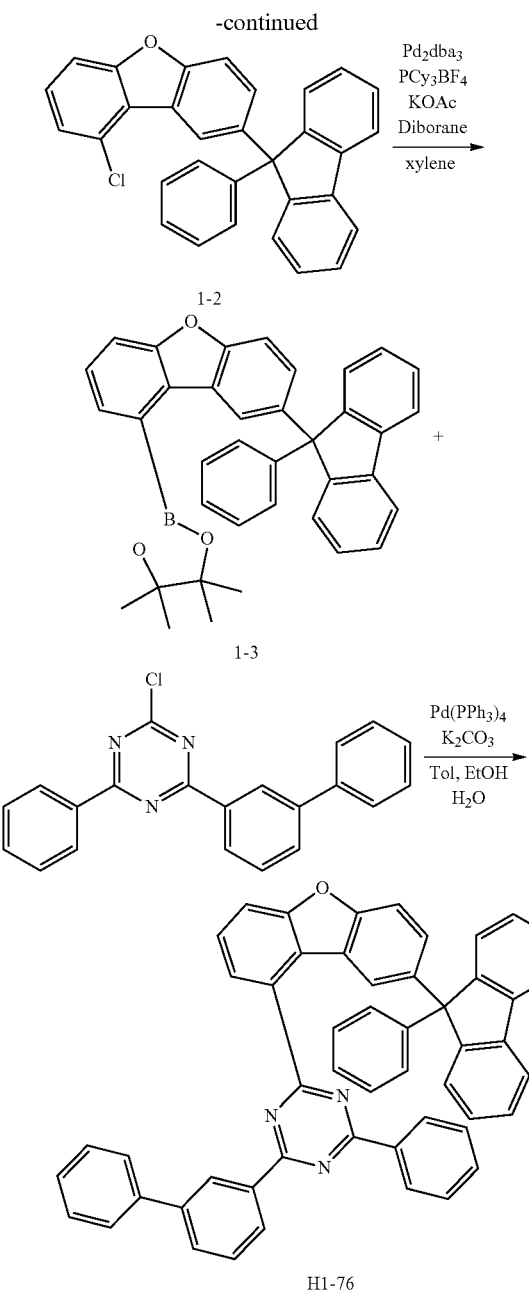

1) Synthesis of Compound 1-1

8-bromo-1-chloro-dibenzofuran (58 g, 208 mmol) and 1,000 mL of THF were added to the reaction vessel in a nitrogen atmosphere and then, cooled to −78° C. Next, n-BuLi (100 ml, 250 mmol) was slowly added dropwise thereto. Thereafter, fluorenone (37 g, 208 mmol) was added dropwise thereto, and stirred under reflux for 12 hours. After completion of the reaction, the reaction was stopped with water, and the organic layer was extracted with ethyl acetate, and the residual water was removed with magnesium sulfate followed by drying. Next, it separated by column chromatography to obtain compound 1-1 (55 g, yield: 70%).

2) Synthesis of Compound 1-2

Compound 1-1 (37 g, 98.4 mmol), 8 mL of sulfuric acid and 330 mL of benzene were added to the reaction vessel, and stirred under reflux for 2 hours. After completion of the reaction, the mixture was washed with distilled water, and the organic layer was extracted with ethyl acetate, and the residual water was removed with magnesium sulfate followed by drying. Next, it separated by column chromatography to obtain compound 1-2 (19 g, yield: 43%).

3) Synthesis of Compound 1-3

Compound 1-2 (8.2 g, 18.5 mmol), bis(pinacolato)diboron (5.6 g, 22.2 mmol), tris (dibenzylideneacetone)dipalladium(0) (0.84 g, 0.92 mmol), tricyclohexylphosphine tetrafluoroborate (PCy$_3$BF$_4$) (0.68 g, 1.85 mmol), KOAc (5.4 g, 55.5 mmol), and 95 mL of o-xylene were added to the reaction vessel, and stirred under reflux for 3 hours. After completion of the reaction, the mixture was washed with distilled water, and the organic layer was extracted with ethyl acetate, and then, the residual water was removed with magnesium sulfate followed by drying. Next, it separated by column chromatography to obtain compound 1-3 (9.5 g, yield: 88%).

4) Synthesis of Compound H1-76

Compound 1-3 (4 g, 7.48 mmol), 2-[1,1'-biphenyl]-3-yl-4-chloro-6-phenyl-1,3,5-triazine (2.7 g, 7.85 mmol), teterakis(trphenylphosphine)palladium(0) (Pd(PPh$_3$)$_4$) (0.43 g, 0.37 mmol), K$_2$CO$_3$ (2.6 g, 18.7 mmol), 40 mL of toluene (Tol), 10 mL of EtOH and 10 mL of distilled water were added to the reaction vessel, and stirred under reflux for 7 hours. After completion of the reaction, the mixture was washed with distilled water, and the organic layer was extracted with ethyl acetate, and then, the residual water was removed with magnesium sulfate followed by drying. Next, it separated by column chromatography to obtain compound H1-76 (4.6 g, yield: 86%).

|  | MW | UV | PL | M.P |
| --- | --- | --- | --- | --- |
| H1-76 | 713.86 | 328 nm | 417 nm | 191° C. |

[Example 2] Synthesis of Compound H1-84

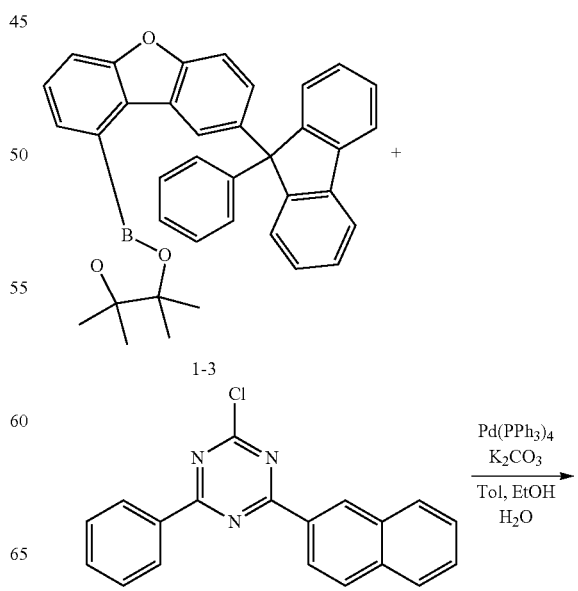

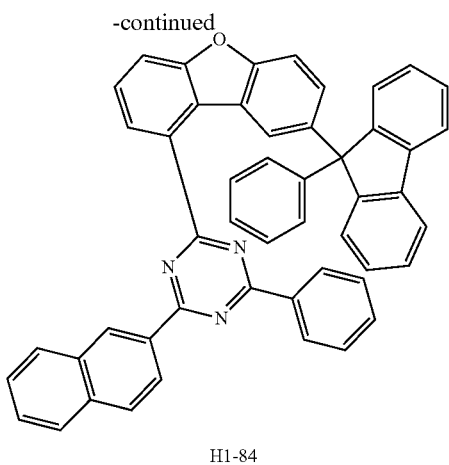

H1-84

Compound 1-3 (5 g, 9.35 mmol), 2-chloro-4-(2-naphthalenyl)-6-phenyl-1,3,5-triazine (3.1 g, 9.82 mmol), Pd(PPh$_3$)$_4$ (0.54 g, 0.46 mmol), K$_2$CO$_3$ (3.2 g, 23.3 mmol), 50 mL of toluene, 12 mL of EtOH, and 12 mL of distilled water were added to the reaction vessel, and stirred under reflux for 7 hours. After completion of the reaction, the mixture was washed with distilled water, and the organic layer was extracted with ethyl acetate and then, the residual water was removed with magnesium sulfate followed by drying. Next, it separated by column chromatography to obtain compound H1-84 (4.9 g, yield: 76%).

|       | MW    | UV     | PL     | M.P    |
|-------|-------|--------|--------|--------|
| H1-84 | 689.8 | 370 nm | 408 nm | 165° C.|

Hereinafter, the preparation method of an organic electroluminescent device comprising the plurality of host materials according to the present disclosure, and the property thereof will be explained in order to understand the present disclosure in detail.

[Device Example 1] Preparation of an OLED Comprising the Host Materials According to the Present Disclosure An OLED according to the present disclosure was produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and thereafter was stored in isopropanol and then used. Thereafter, the ITO substrate was mounted on a substrate holder of a vacuum vapor deposition apparatus. Then, compound HI-1 as a first hole injection compound was introduced into a cell of the vacuum vapor deposition apparatus, and compound HT-1 as a first hole transport compound was introduced into another cell of the vacuum vapor deposition apparatus. The two materials were evaporated at different rates and the first hole injection compound was deposited in a doping amount of 3 wt % based on the total amount of the first hole injection compound and the first hole transport compound to form a first hole injection layer having a thickness of 10 nm. Next, compound HT-1 was deposited as a first hole transport layer having a thickness of 80 nm on the first hole injection layer. Compound HT-2 was then introduced into another cell of the vacuum vapor deposition apparatus and was evaporated by applying an electric current to the cell, thereby forming a second hole transport layer having a thickness of 30 nm on the first hole transport layer. After forming the hole injection layer and the hole transport layers, a light-emitting layer was formed thereon as follows: Compounds H1-76 and H2-2 described in the following Table 1 were introduced into two cells of the vacuum vapor deposition apparatus as hosts, respectively, and compound D-50 was introduced into another cell as a dopant. The two host materials were evaporated at a different rate of 1:2 and the dopant material was evaporated at a different rate, simultaneously, and was deposited in a doping amount of 10 wt % based on the total amount of the hosts and dopant to form a light-emitting layer having a thickness of 40 nm on the hole transport layer. Next, compounds ETL-1 and EIL-1 as electron transport materials were deposited at a weight ratio of 40:60 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. Each compound used for all the materials was purified by vacuum sublimation under $10^8$ torr.

[Device Example 2] Preparation of an OLED Comprising the Host Materials According to the Present Disclosure An OLED was produced in the same manner as in Device Example 1, except that compound H1-84 was used as one of the host materials of the light-emitting layer.

[Device Example 3] Preparation of an OLED Comprising the Host Materials According to the Present Disclosure An OLED was produced in the same manner as in Device Example 1, except that compound H1-176 was used as one of the host materials of the light-emitting layer.

[Device Example 4] Preparation of an OLED Comprising the Host Materials According to the Present Disclosure An OLED was produced in the same manner as in Device Example 1, except that compound H1-176 was used as a single host of the light-emitting layer.

[Comparative Example 1] Preparation of an OLED Comprising a Conventional Compound as a Host An OLED was produced in the same manner as in Device Example 1, except that compound C-1 was used as a single host of the light-emitting layer.

The driving voltage, the luminous efficiency, and the light-emitting color at a luminance of 1,000 nits, and the time taken for luminance to decrease from 100% to 95% at a luminance of 20,000 nits (lifespan; T95) of the organic electroluminescent devices according to Device Examples 1 to 4 and Comparative Example 1 produced as described above, are measured, and the results thereof are shown in Table 1 below:

TABLE 1

|  | First host | Second host | Driving Voltage (V) | Luminous Efficiency (cd/A) | Light-Emitting Color | Lifespan (T95) (hr) |
|---|---|---|---|---|---|---|
| Device Example 1 | H1-76 | H2-2 | 3.1 | 93.0 | Green | 105 |
| Device Example 2 | H1-84 | H2-2 | 3.0 | 91.0 | Green | 20 |
| Device Example 3 | H1-176 | H2-2 | 3.1 | 91.0 | Green | 108 |
| Device Example 4 | H1-176 | — | 2.8 | 84.4 | Green | 7.4 |
| Comparative Example 1 | C-1 | — | 2.8 | 78.2 | Green | 2.2 |

Referring to Table 1 above, by comprising the organic electroluminescent compounds according to the present disclosure as host materials, an organic electroluminescent device having high luminous efficiency and significantly improved lifespan properties can be provided, compared to the organic electroluminescent device comprising a conventional host material.

The compounds used in Device Examples 1 to 4 and Comparative Example 1 above are shown in the following Table 2:

TABLE 2

| Hole Injection Layer/ Hole Transport Layer | 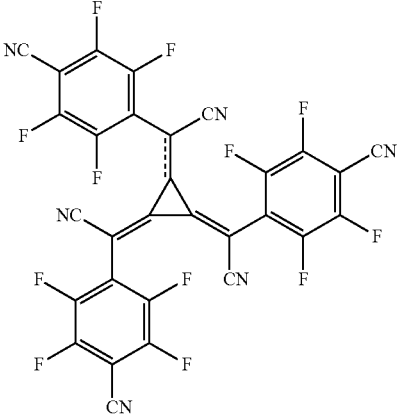 |
|---|---|

HI-1

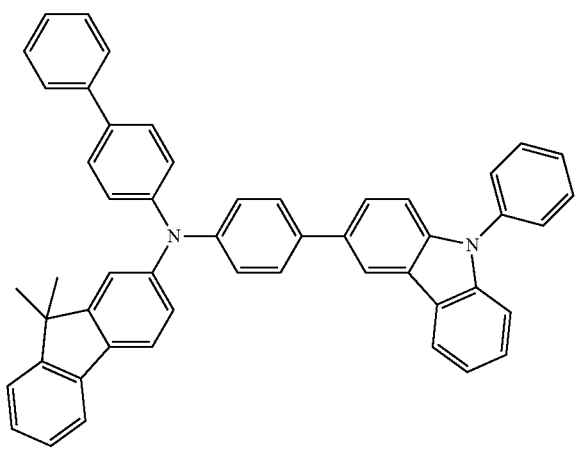

HT-1

TABLE 2-continued
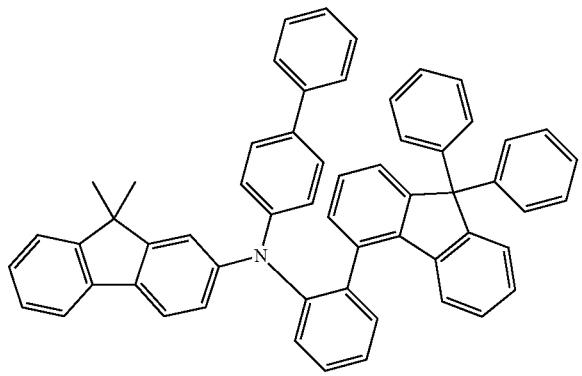
HT-2
Light-Emitting Layer
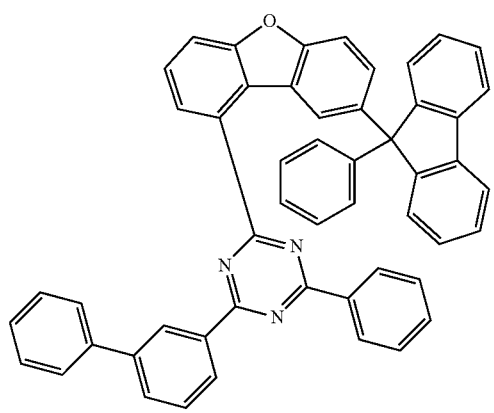
H1-76
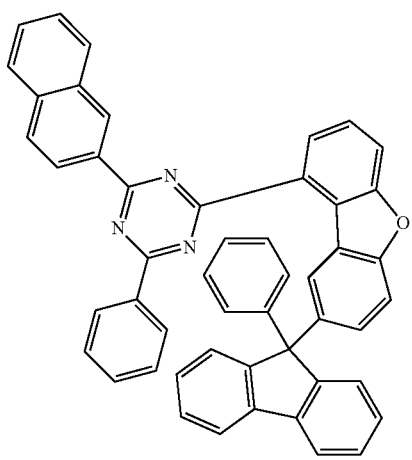
H1-84

TABLE 2-continued
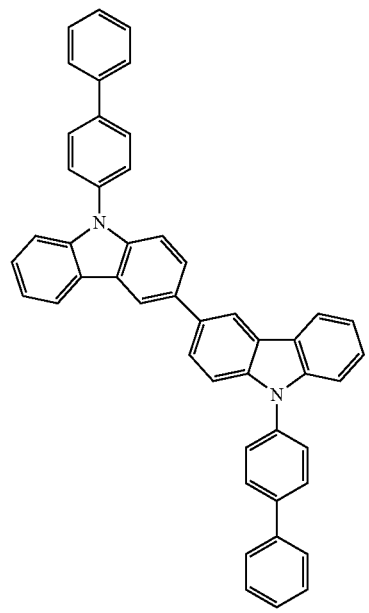
H2-2
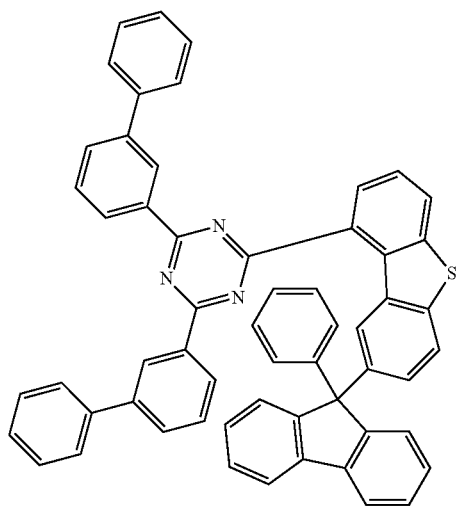
H1-176
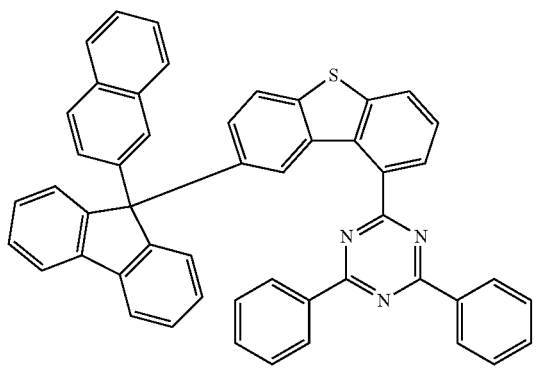
C-1

TABLE 2-continued
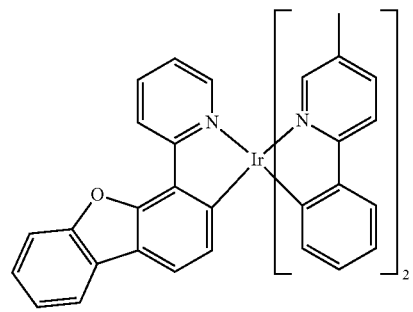
D-50
Electron
Transport
Layer/
Electron
Injection Layer
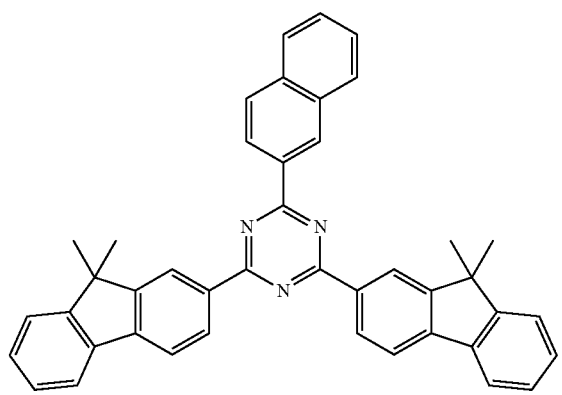
ETL-1
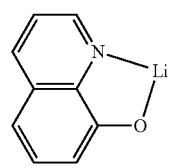
EIL-1

The invention claimed is:

1. A plurality of host materials comprising a first host material and a second host material, wherein the first host material comprises a compound represented by the following formulas 1-1 to 1-4 and the second host material comprises a compound represented by the following formula 2:

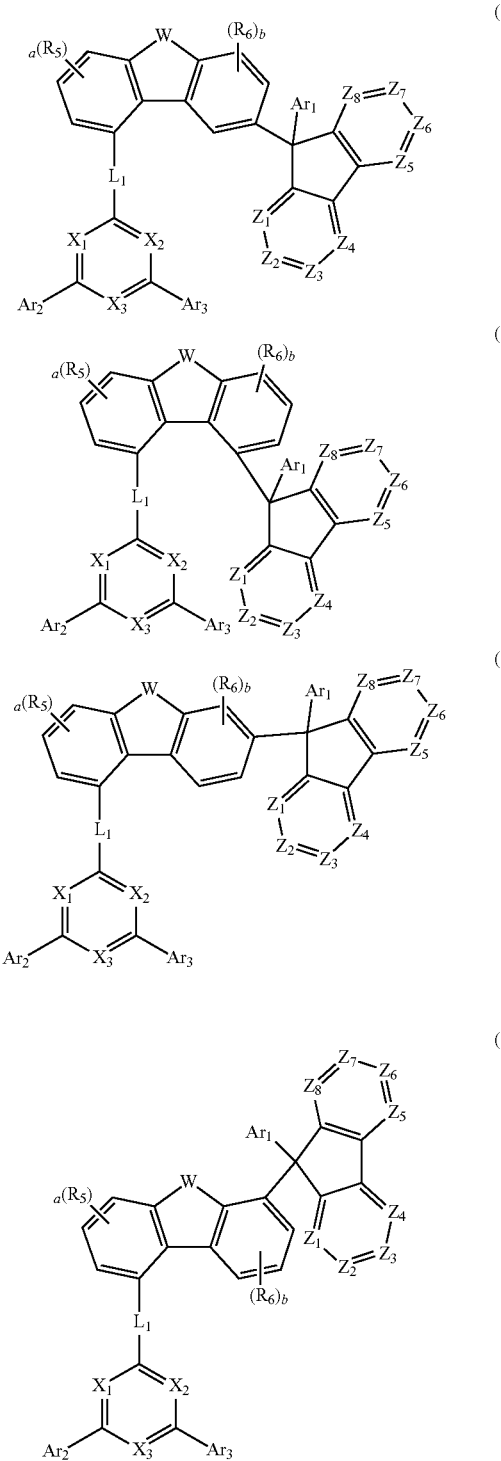

wherein,

W represents O or S;

$Z_1$ to $Z_8$ each independently represent, $CR_4$ or N;

$X_1$ to $X_3$ each independently represent, $CR_7$ or N;

$L_1$ represents, a single bond, a substituted or unsubstituted (C6-C30)arylene, or a substituted or unsubstituted (3- to 30-membered)heteroarylene;

$Ar_1$ represents a deuterium-substituted or unsubstituted phenyl, a deuterium-substituted or unsubstituted biphenyl, or a deuterium-substituted or an unsubstituted terphenyl;

$Ar_2$ and $Ar_3$ each independently represent, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl (C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

$R_4$ to $R_7$ each independently represent, hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30) alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino; or may be linked to the adjacent substituents to form a ring(s);

a and b each independently represent, an integer of 1 to 3; and when a and b are an integer of 2 or more, each of $R_5$ and each of $R_6$ may be the same or different;

(2)

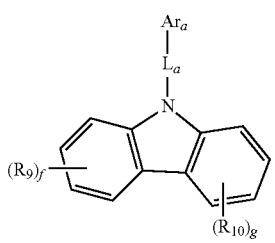

wherein,
- $L_a$ represents a single bond, a substituted or unsubstituted (C6-C30)arylene, or a substituted or unsubstituted (3- to 30-membered)heteroarylene;
- $Ar_a$ represents a substituted or unsubstituted (C6-C30) aryl, or a substituted or unsubstituted (3- to 30-membered)heteroaryl;
- $R_9$ and $R_{10}$ each independently represent, hydrogen, deuterium, halogen, cyano, a substituted or unsubstituted (C1-C30)alkyl, a substituted or unsubstituted (C6-C30) aryl, a substituted or unsubstituted (3- to 50-membered) heteroaryl, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30) alkenylamino, a substituted or unsubstituted (C1-C30) alkyl(C6-C30)arylamino, a substituted or unsubstituted (C1-C30)alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, a substituted or unsubstituted mono- or di-(C6-C30)arylamino, a substituted or unsubstituted mono- or di-(3- to 30-membered)heteroarylamino, or a substituted or unsubstituted (C6-C30)aryl(3- to 30-membered)heteroarylamino; or may be linked to the adjacent substituents to form a ring(s);
- f and g each independently represent, an integer of 1 to 4; and
- when f and g are an integer of 2 or more, each of $R_9$ and each of $R_{10}$ may be the same or different.

2. The plurality of host materials according to claim 1, wherein the substituent in the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted fused ring of aliphatic ring and aromatic ring, the substituted mono- or di-alkylamino, the substituted mono- or di-alkenylamino, the substituted alkylalkenylamino, the substituted mono- or di-arylamino, the substituted alkylarylamino, the substituted mono- or di-heteroarylamino, the substituted alkylheteroarylamino, the substituted alkenylarylamino, the substituted alkenylheteroarylamino, and the substituted arylheteroarylamino, each independently represents at least one selected from the group consisting of deuterium, halogen, cyano, carboxyl, nitro, hydroxy, (C1-C30)alkyl, halo(C1-C30)alkyl, (C2-C30)alkenyl, (C2-C30)alkynyl, (C1-C30) alkoxy, (C1-C30)alkylthio, (C3-C30)cycloalkyl, (C3-C30) cycloalkenyl, (3- to 7-membered)heterocycloalkyl, (C6-C30)aryloxy, (C6-C30)arylthio, (5- to 30-membered) heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30) arylsilyl, di(C1-C30)alkyl(C6-C30)arylsilyl, (C1-C30)alkyldi(C6-C30)arylsilyl, a fused ring of (C3-C30) aliphatic ring and (C6-C30) aromatic ring, amino, mono- or di-(C1-C30)alkylamino, mono- or di-(C2-C30)alkenylamino, (C1-C30)alkyl(C2-C30)alkenylamino, a substituted or unsubstituted mono- or di-(C6-C30)arylamino, (C1-C30)alkyl(C6-C30)arylamino, mono- or di-(3- to 30-membered) heteroarylamino, (C1-C30)alkyl(3- to 30-membered) heteroarylamino, (C2-C30)alkenyl(C6-C30)arylamino, (C2-C30)alkenyl(3- to 30-membered)heteroarylamino, (C6-C30)aryl(3- to 30-membered)heteroarylamino, (C1-C30) alkylcarbonyl, (C1-C30)alkoxycarbonyl, (C6-C30) arylcarbonyl, di(C6-C30)arylboronyl, di(C1-C30) alkylboronyl, (C1-C30)alkyl(C6-C30)arylboronyl, (C6-C30)ar(C1-C30)alkyl, and (C1-C30)alkyl(C6-C30)aryl.

3. The plurality of host materials according to claim 1, wherein the formula 2 is represented by the following formula 2-1 or 2-2:

(2-1)

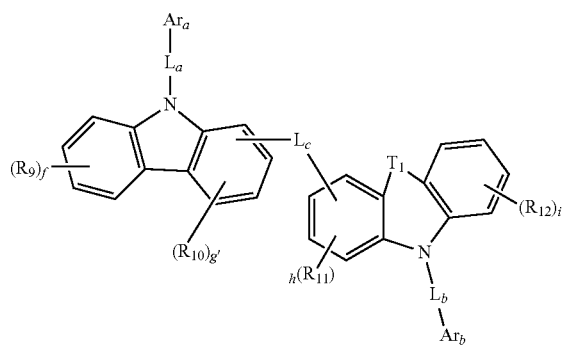

(2-2)

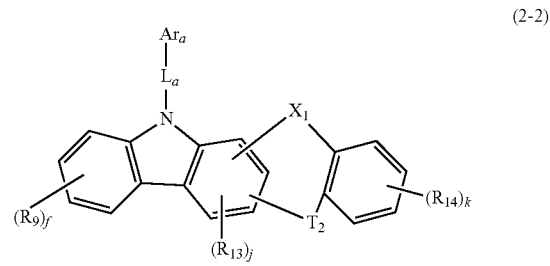

wherein,
- $L_a$, $Ar_a$, $R_9$, $R_{10}$, and f are as defined in claim 1;
- $T_1$ and $T_2$ each independently represent, a single bond, O, or S;
- $L_b$ and $L_c$ are as defined as $L_a$ in claim 1;
- $Ar_b$ is as defined as $Ar_a$ in claim 1;
- $R_{11}$ to $R_{14}$ each independently are as defined as $R_9$ in claim 1;
- $X_1$ represents O, S, or $NR_a$;
- $R_a$ represents a substituted or unsubstituted (C6-C30)aryl;
- g' and h each independently represent, an integer of 1 to 3, i and k each independently represent, an integer of 1 to 4, and j represents an integer of 1 or 2; and
- when g', h, i, j, and k are an integer of 2 or more, each of $R_{10}$, each of $R_{11}$, each of $R_{12}$, each of $R_{13}$, and each of $R_{14}$ may be the same or different.

4. The plurality of host materials according to claim 1, wherein the compound represented by the formula 1-1 to 1-4 is selected from the following compounds:
H1-28
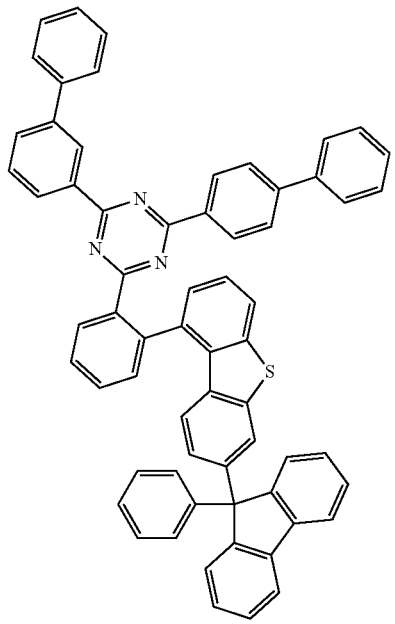
H1-35
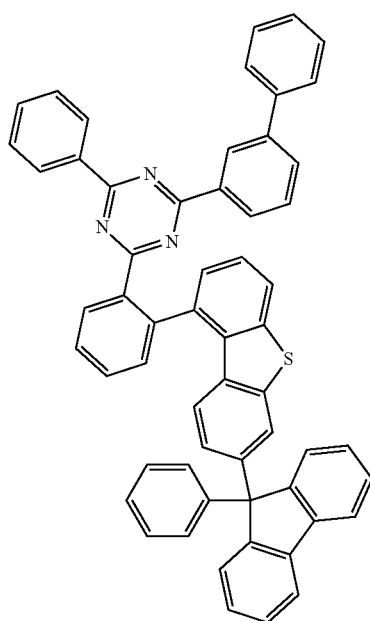
-continued
H1-40
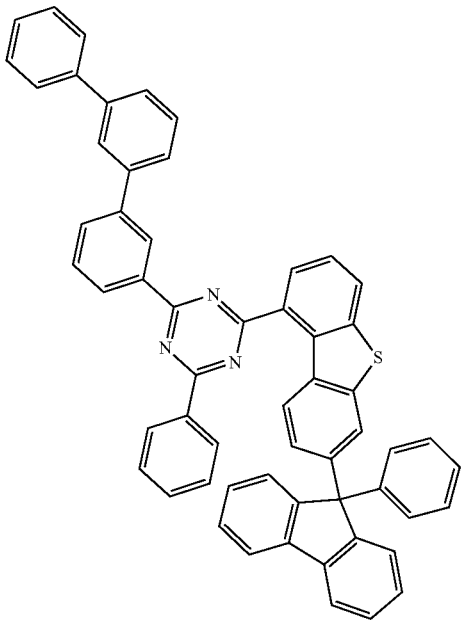
H1-41
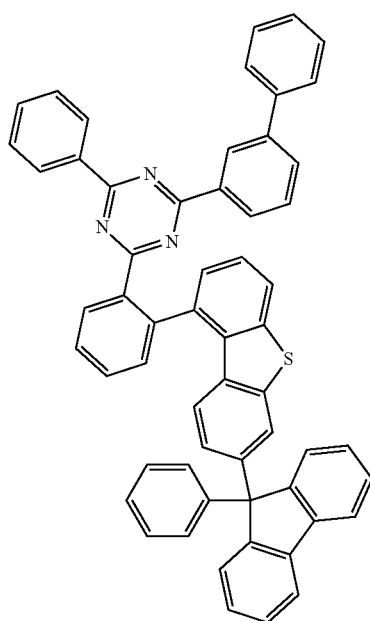

H1-44
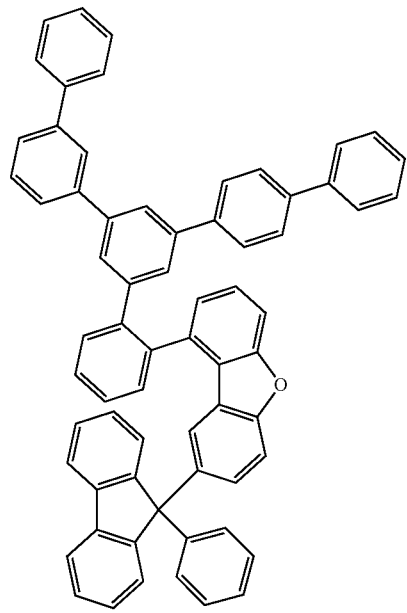
H1-53
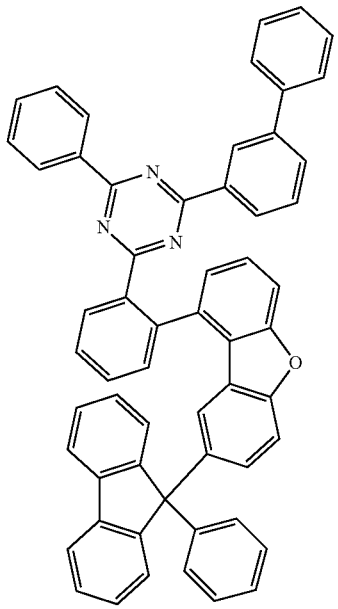
H1-45
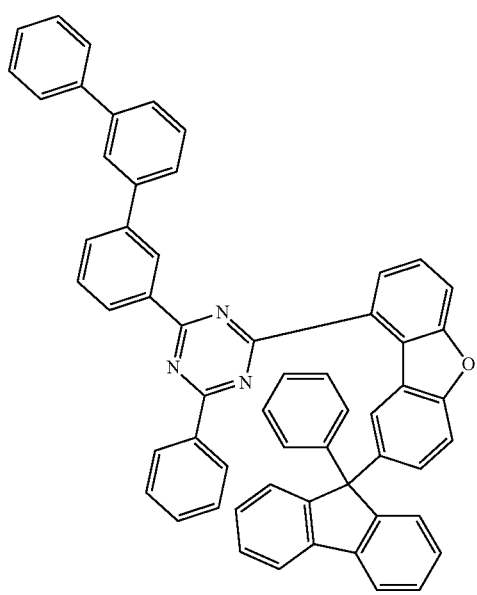
H1-54
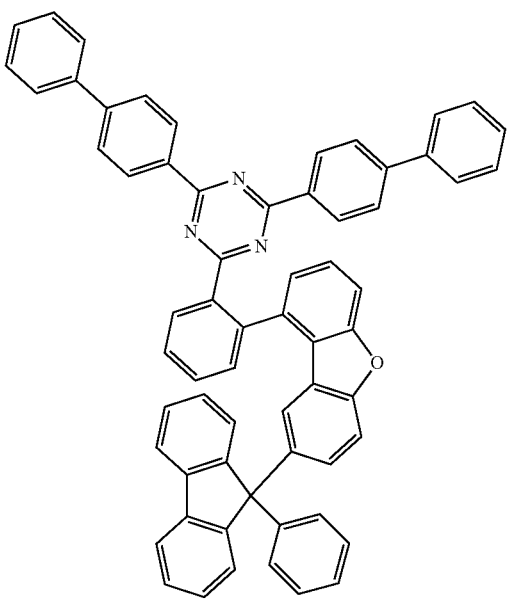

H1-55
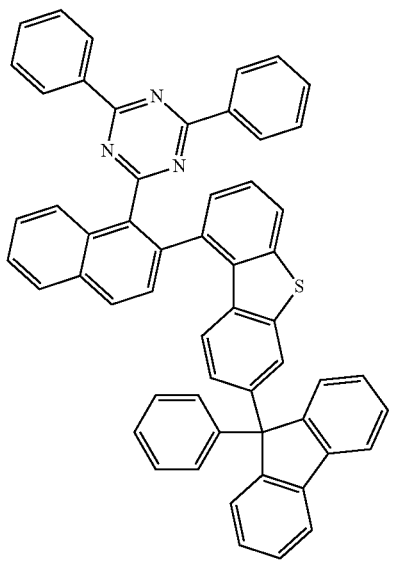
H1-56
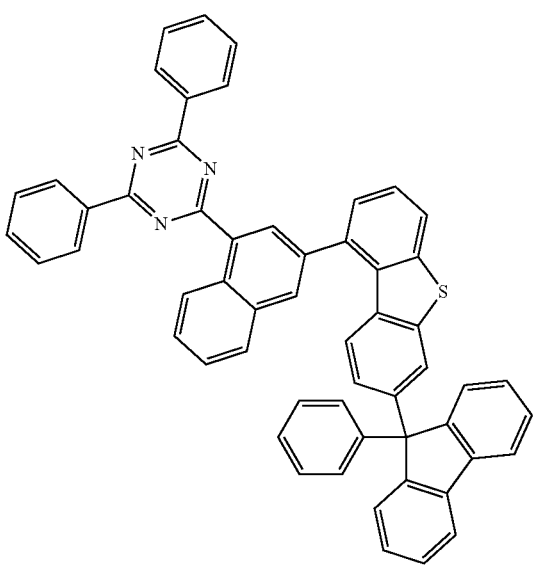
H1-57
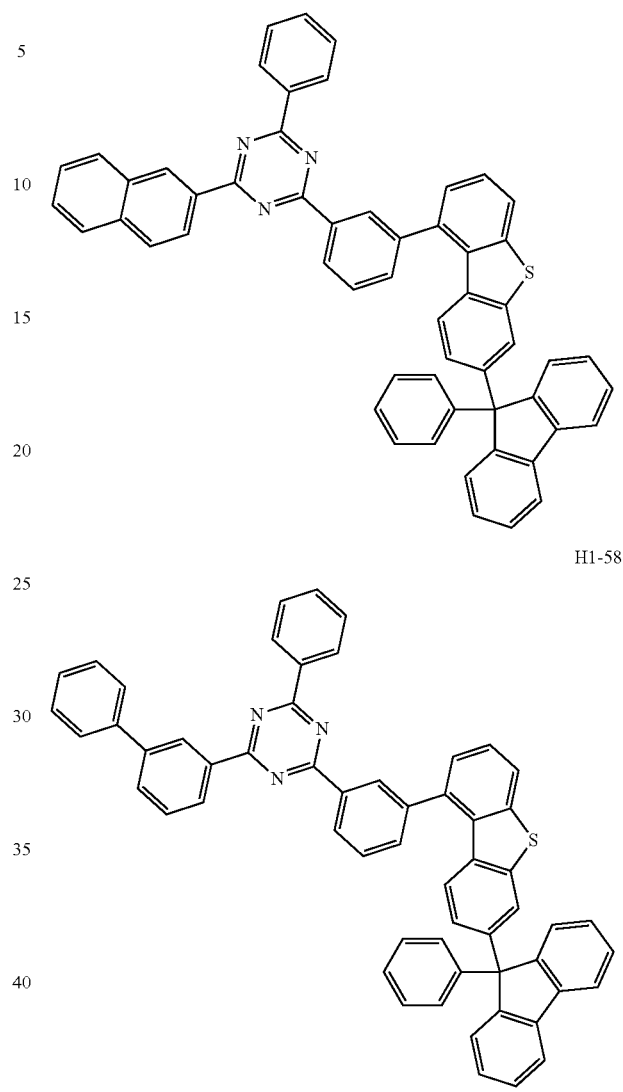
H1-58
H1-59

H1-60
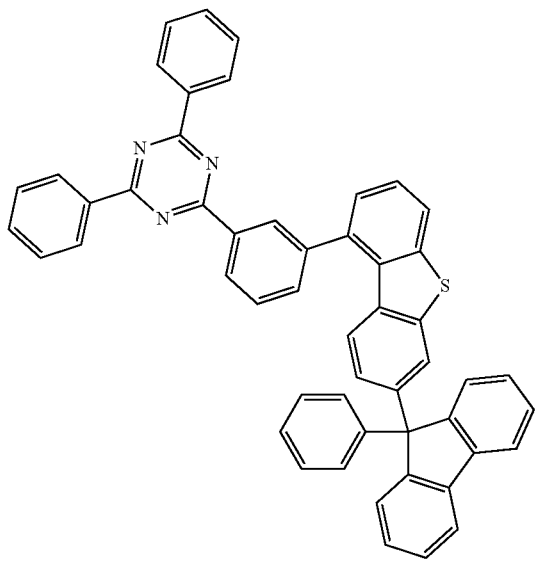
H1-61
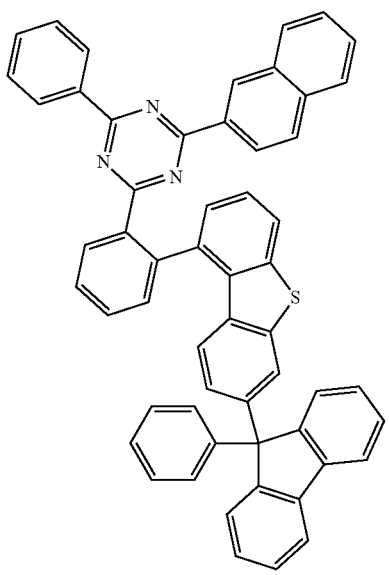
H1-62
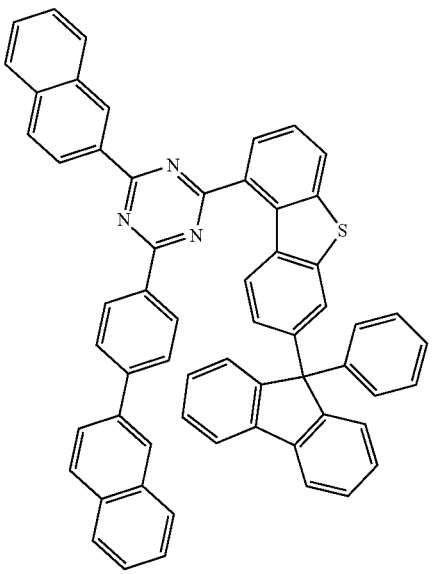
H1-63

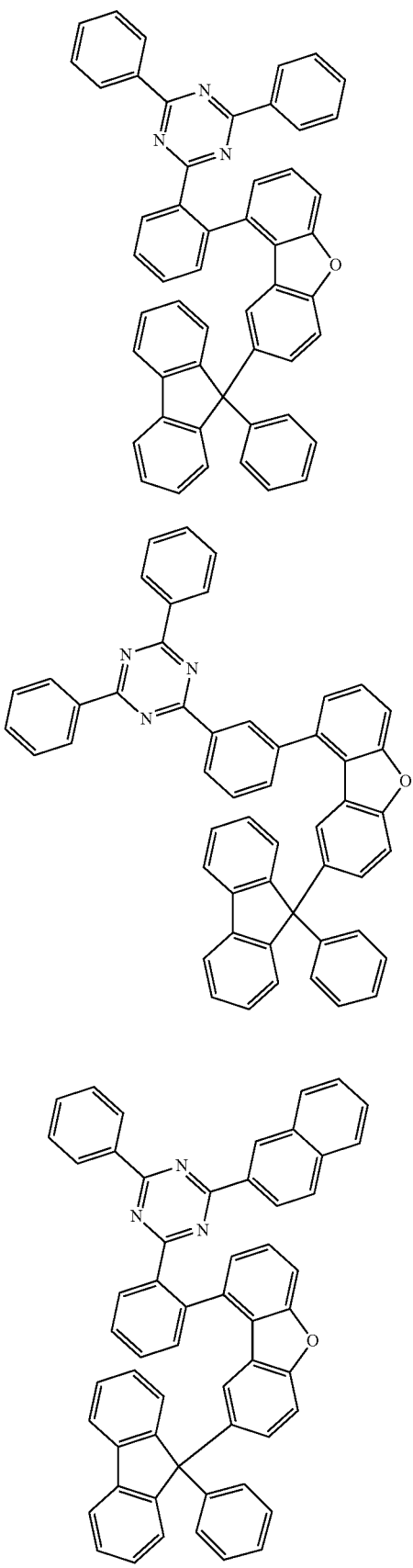
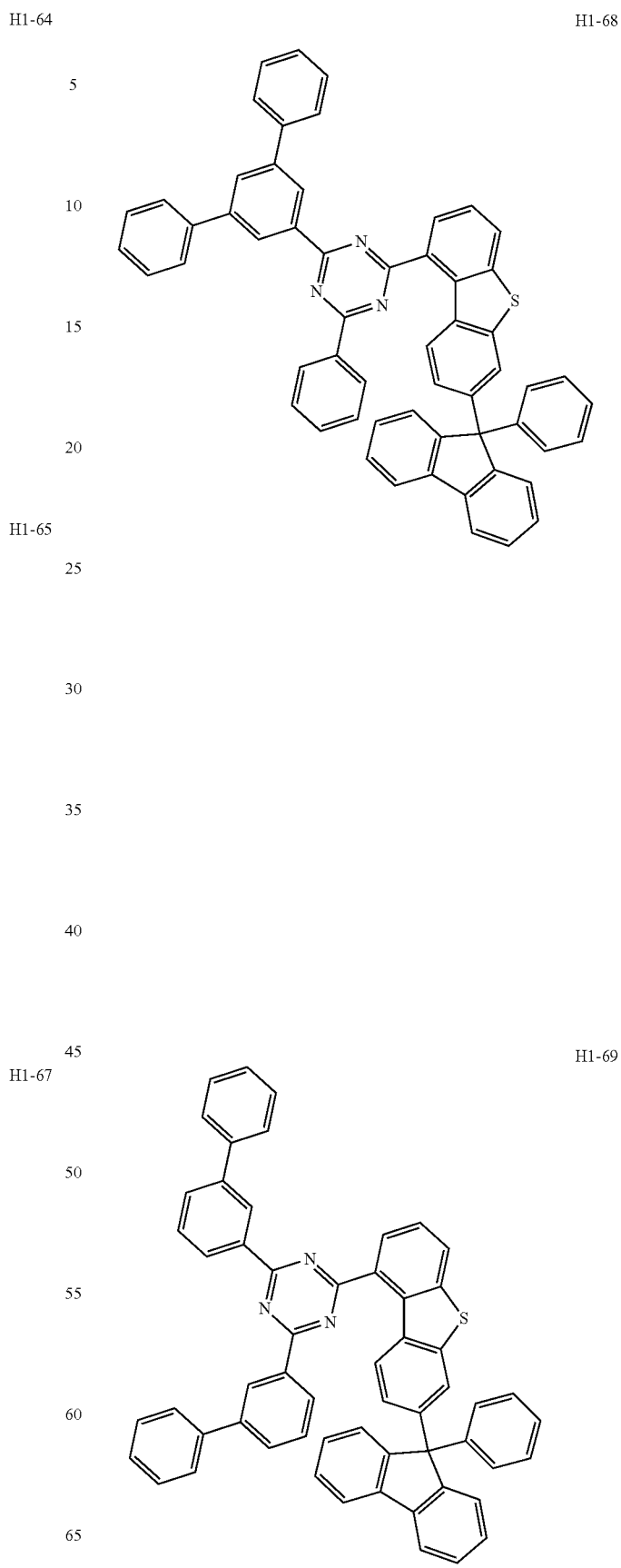

H1-70
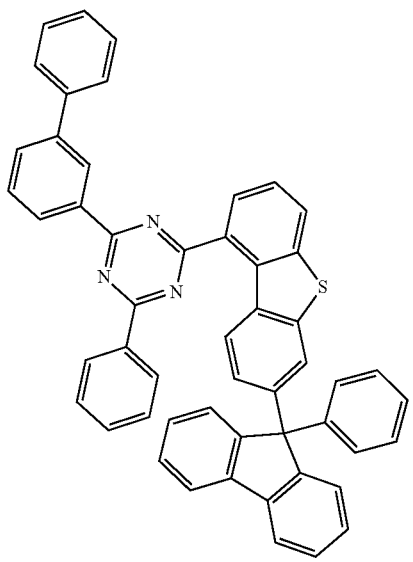
H1-71
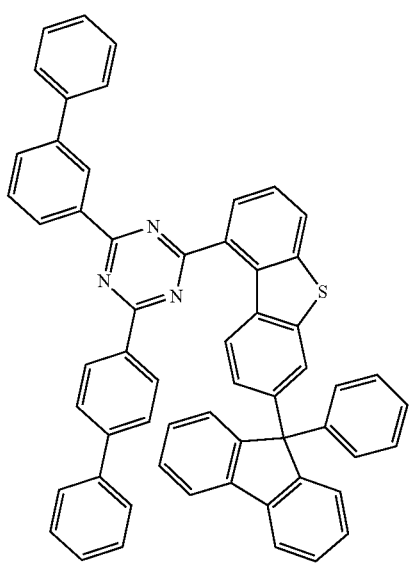
H1-72
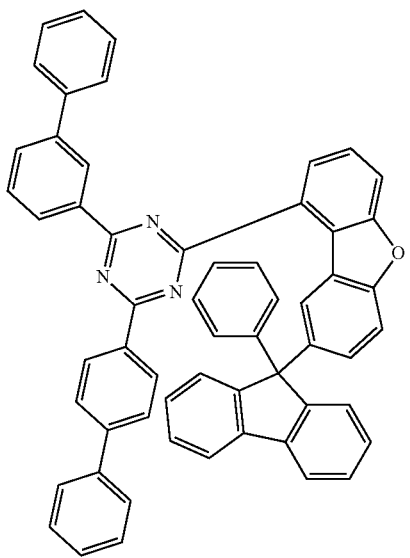
H1-74
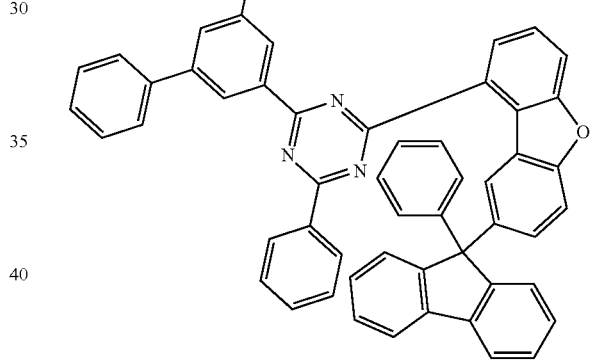
H1-75
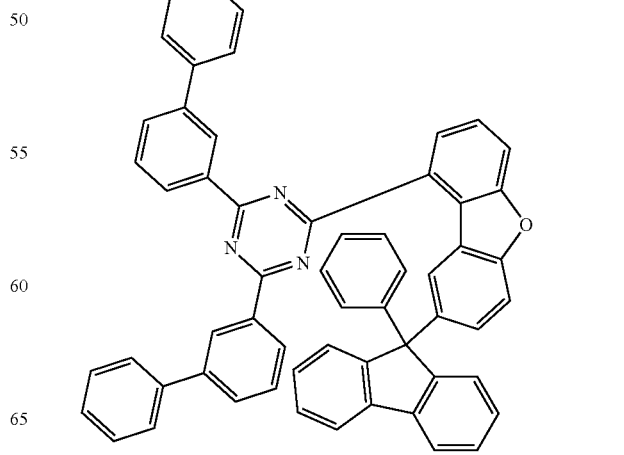

H1-76
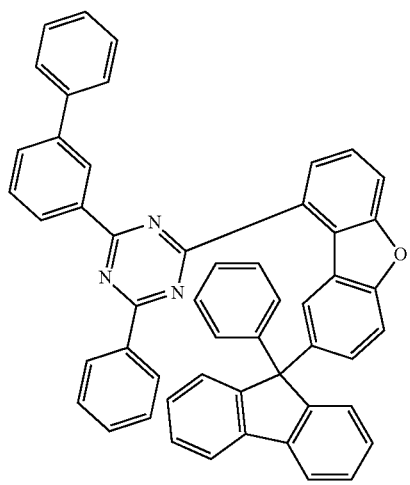
H1-77
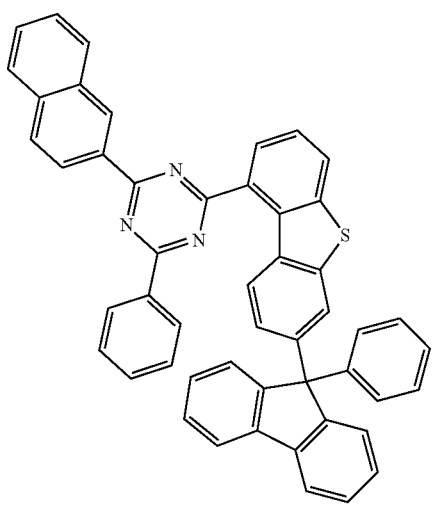
H1-78
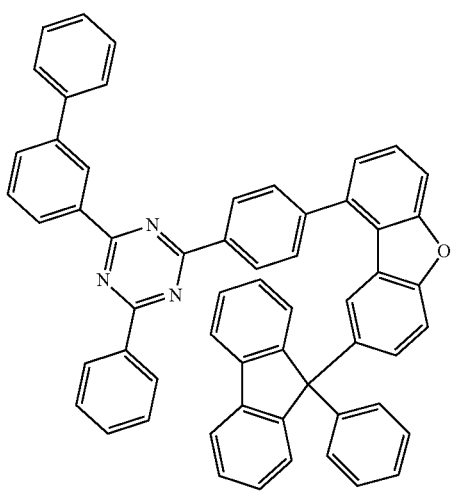
H1-79
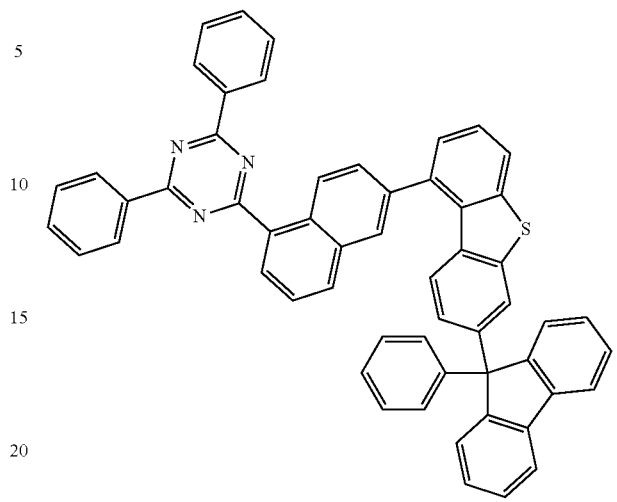
H1-80
H1-81
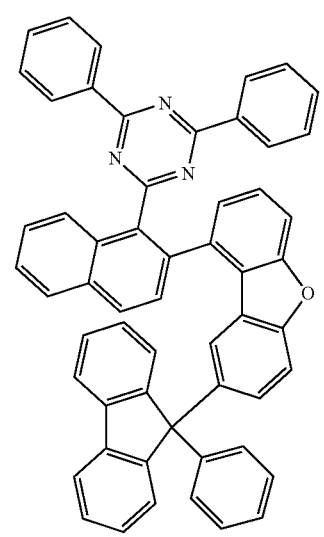

H1-82
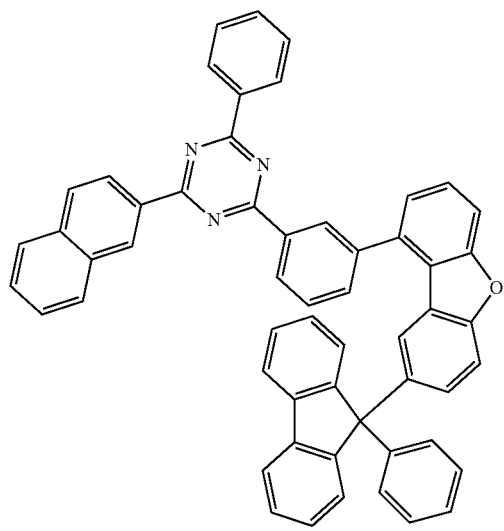
H1-83
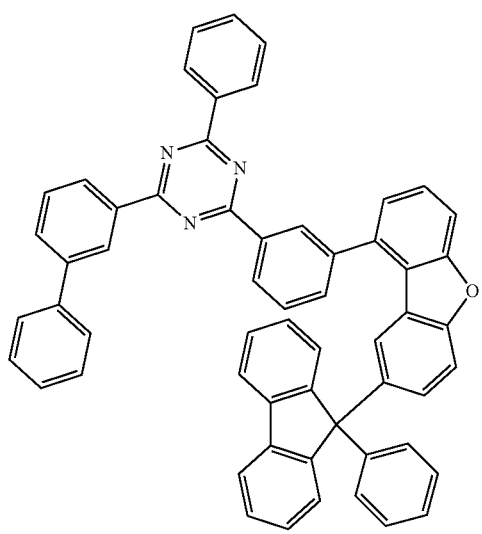
H1-84
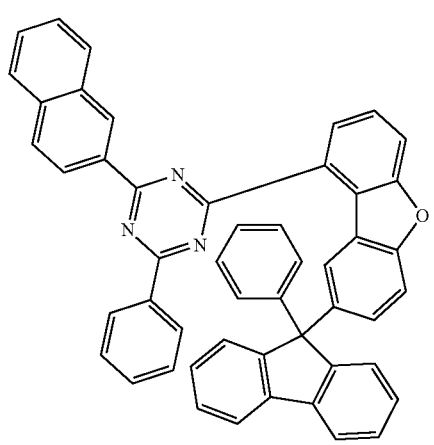
H1-85
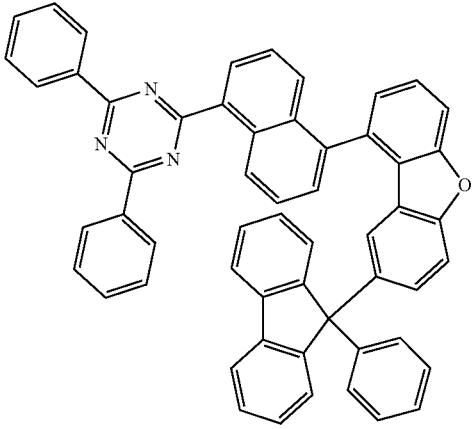
H1-86
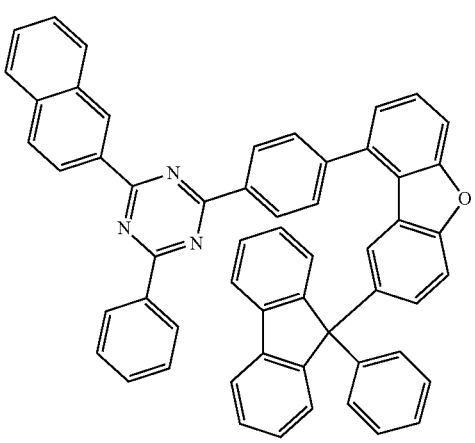
H1-87
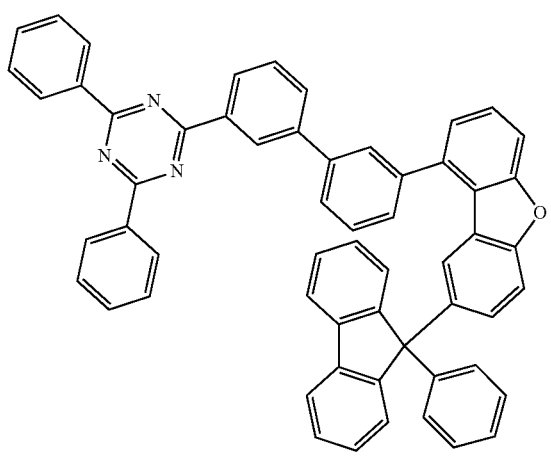

H1-88
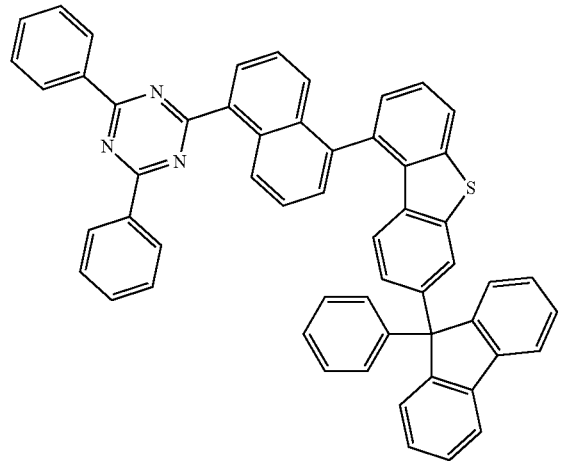
H1-89
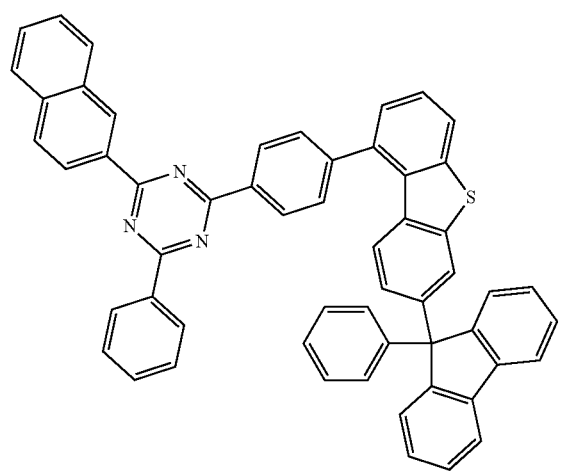
H1-90
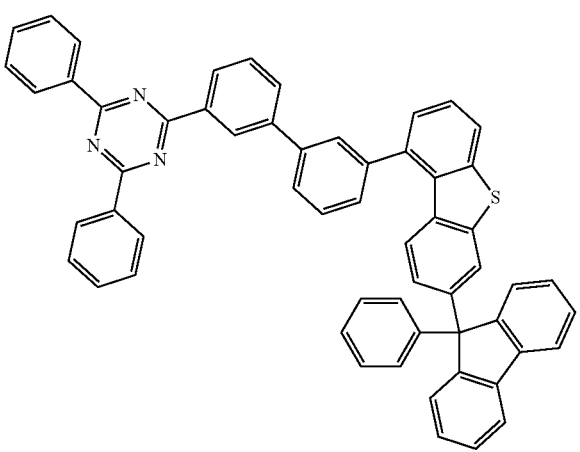
H1-91
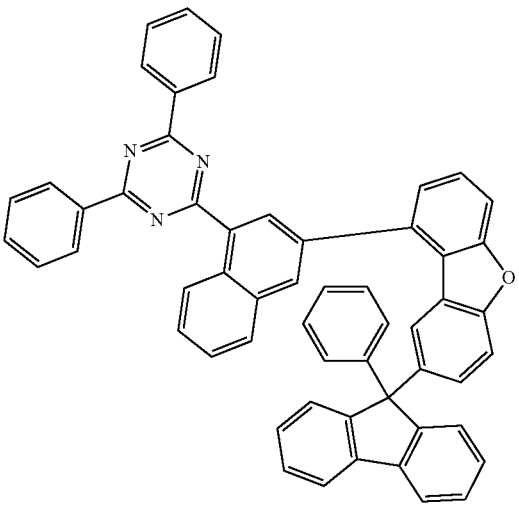
H1-92
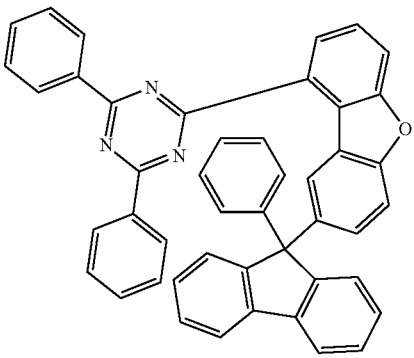
H1-93
H1-94
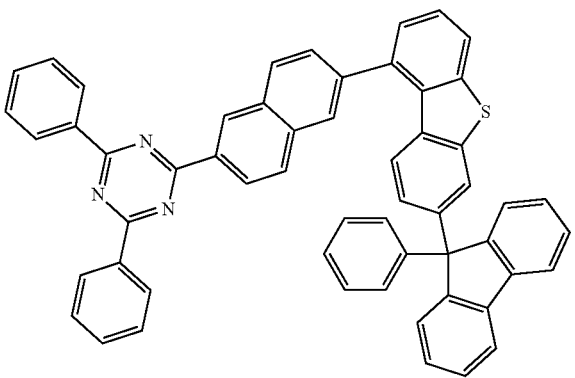

H1-95
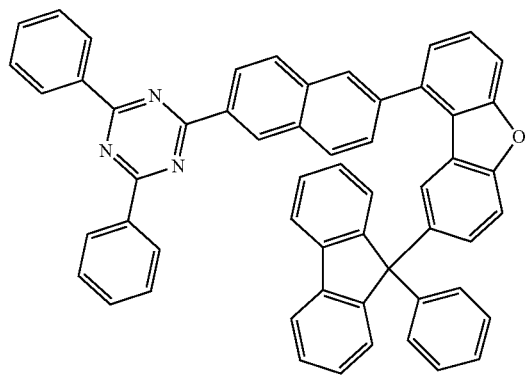
H1-96
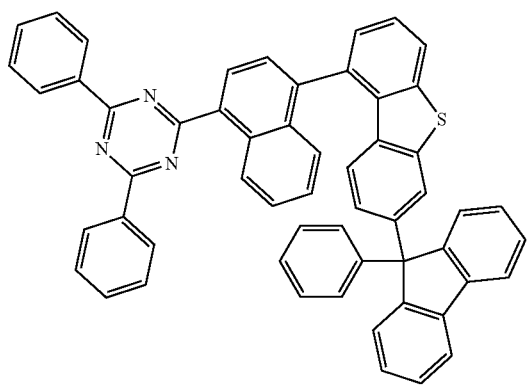
H1-97
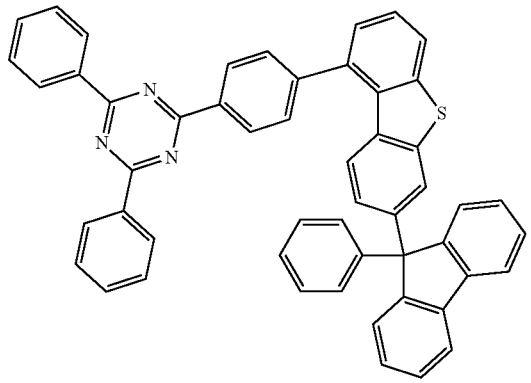
H1-98
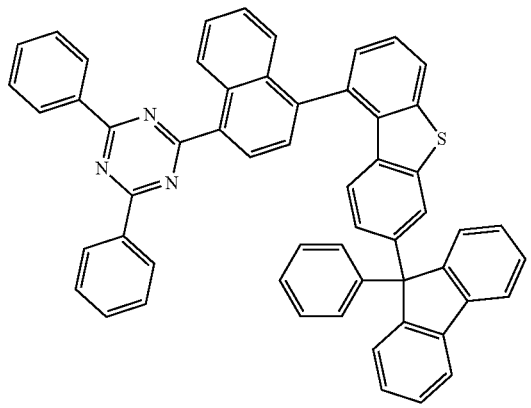
H1-99
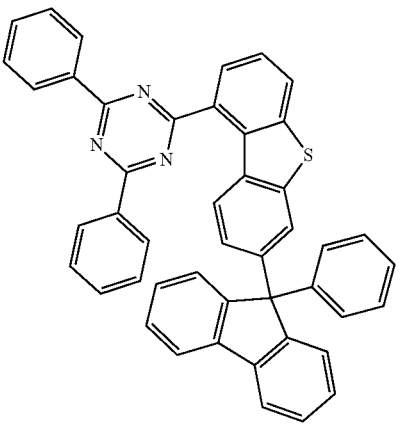
H1-100
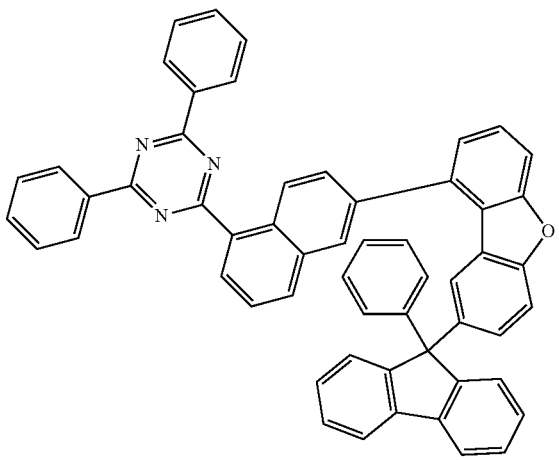
H1-115
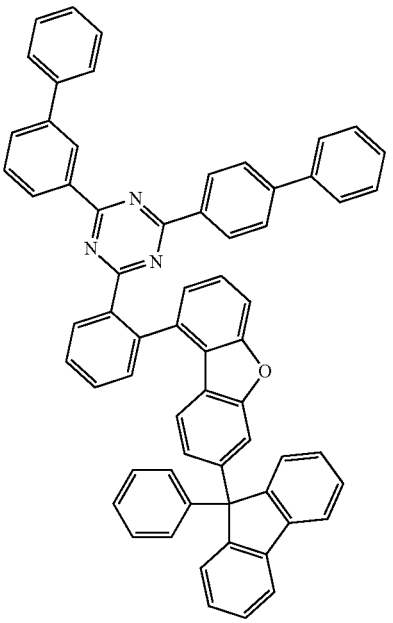

H1-116
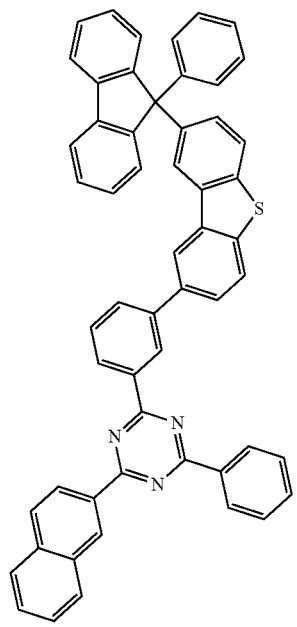
H1-129
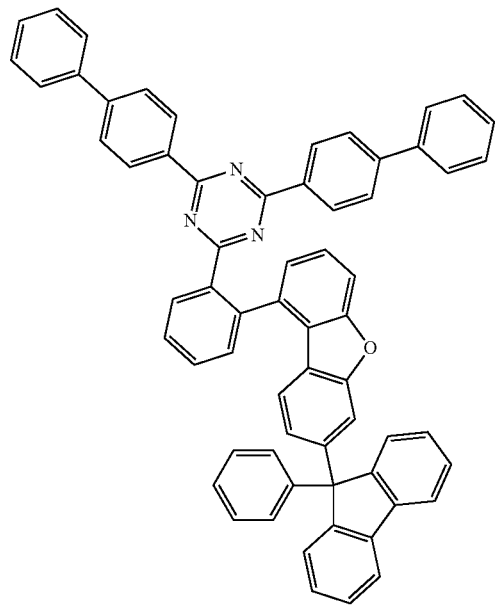
H1-127
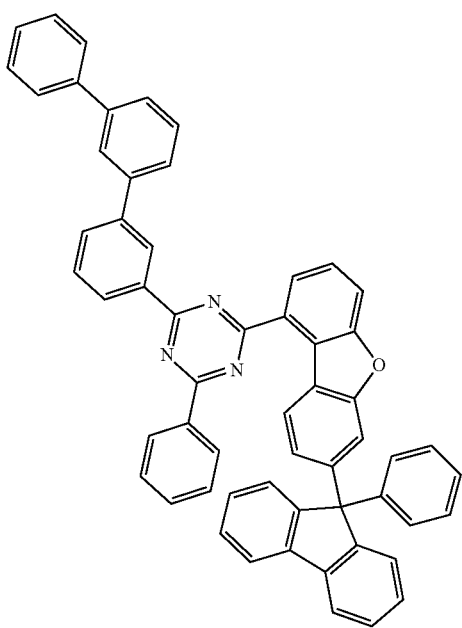
H1-133
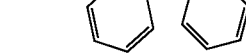

H1-137
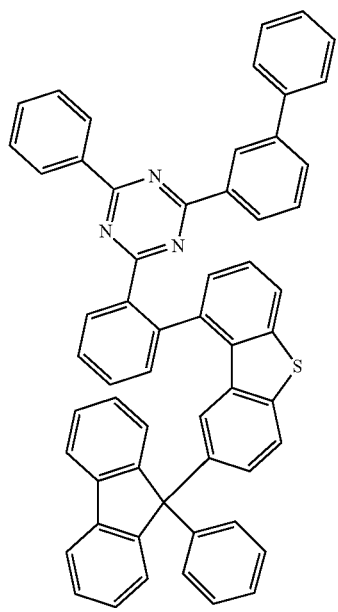
H1-141
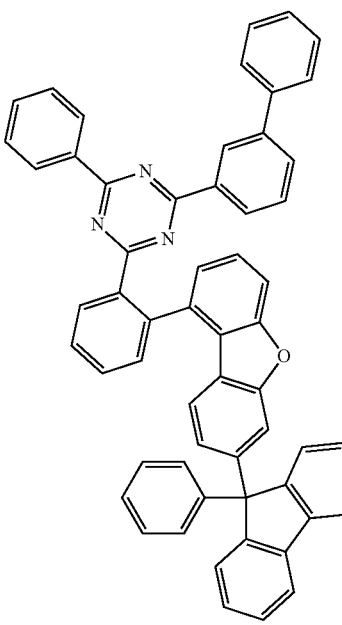
H-138
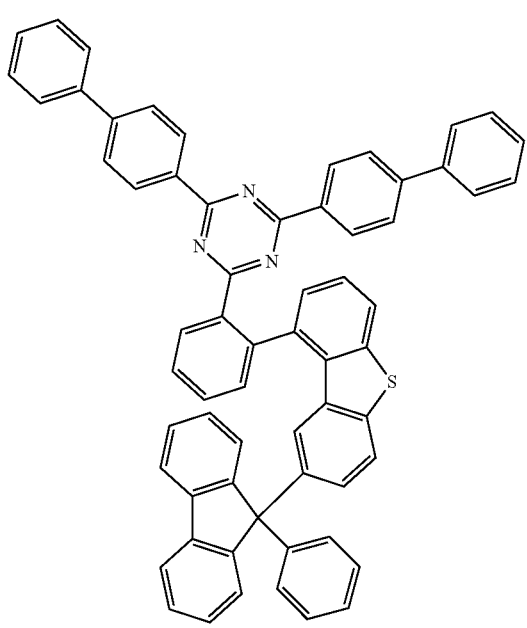
H1-145
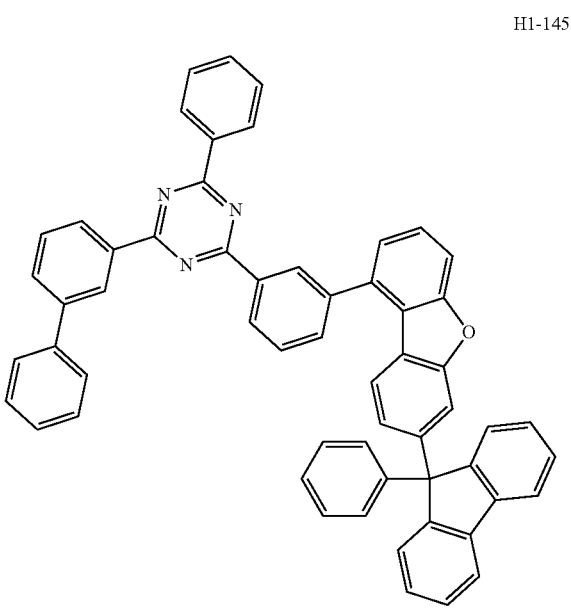

H1-146
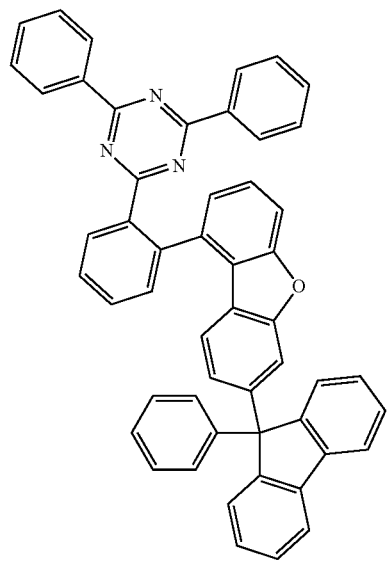
H1-147
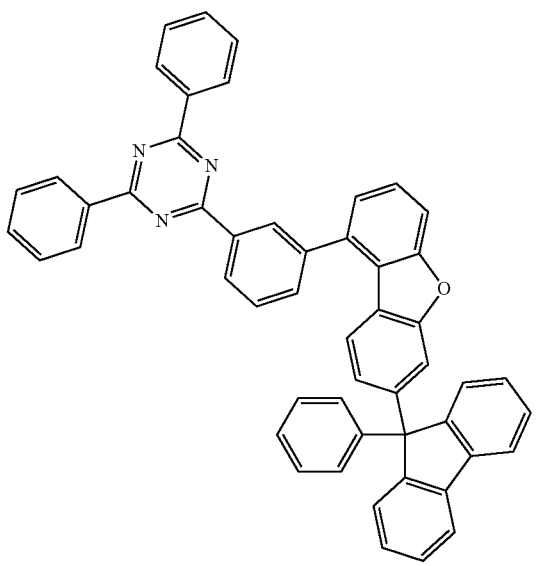
H1-148
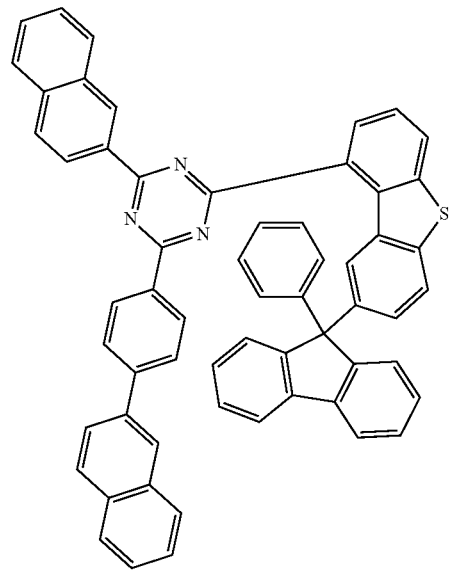
H1-149
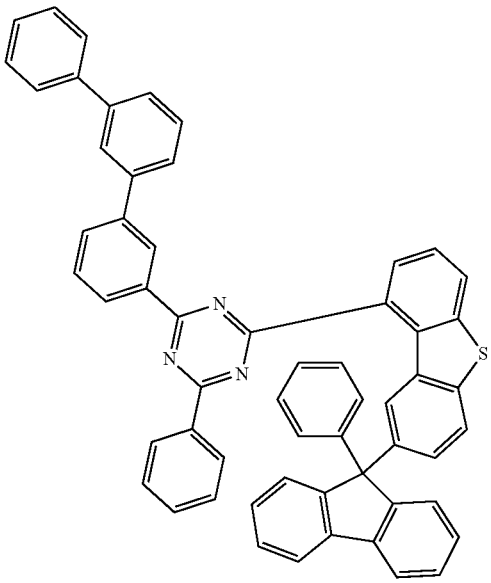

H1-150
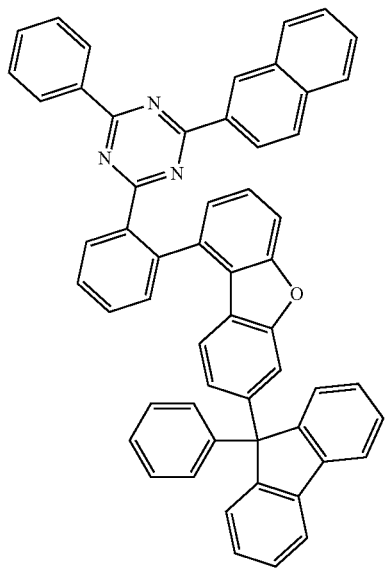
H1-151
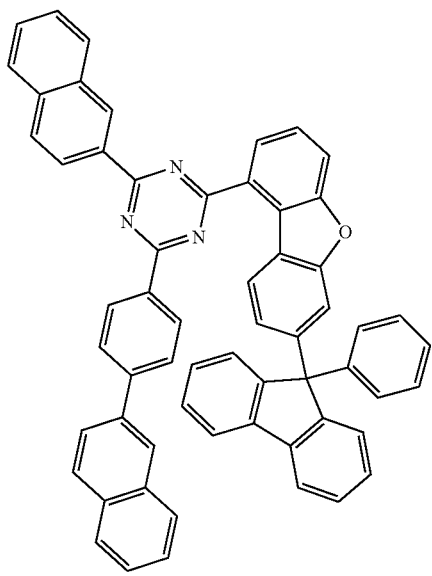
H1-159
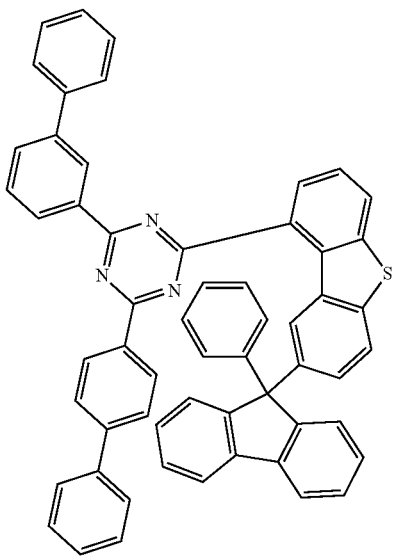
H1-160
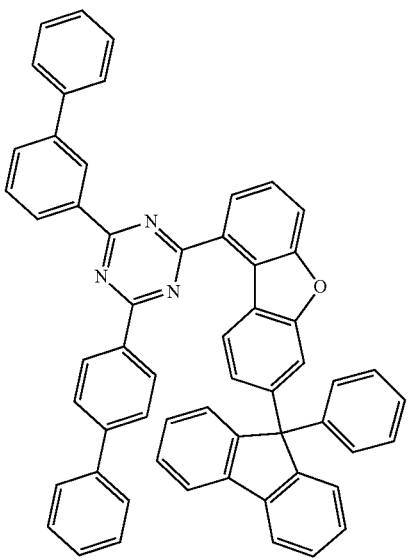

H1-162
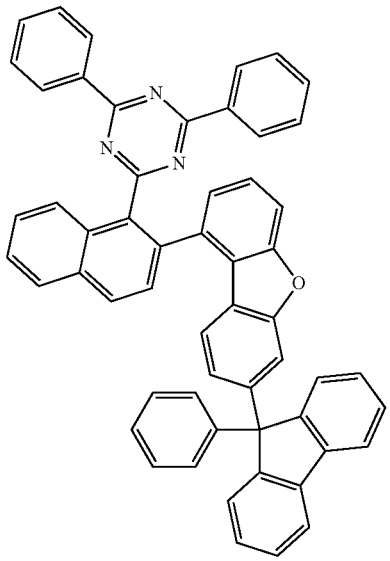
H1-163
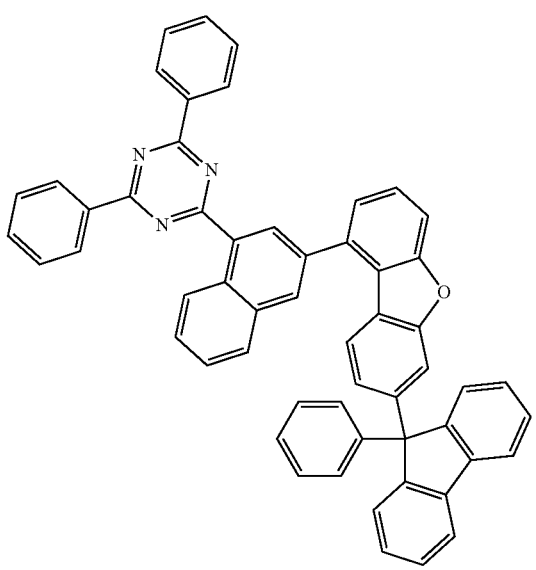
H1-164
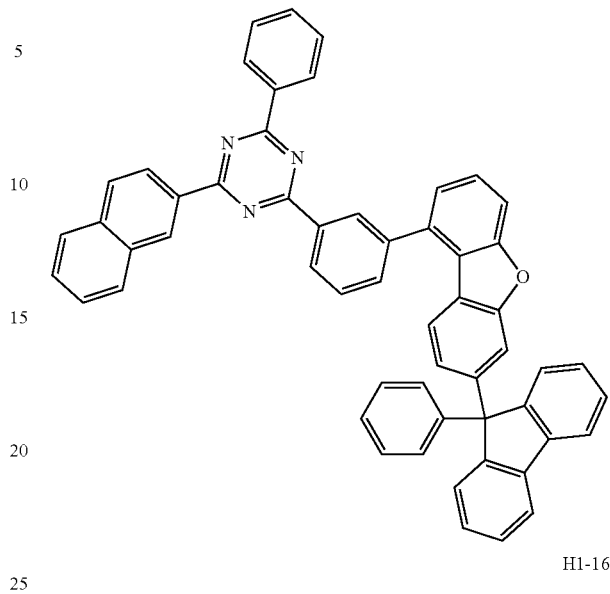
H1-165
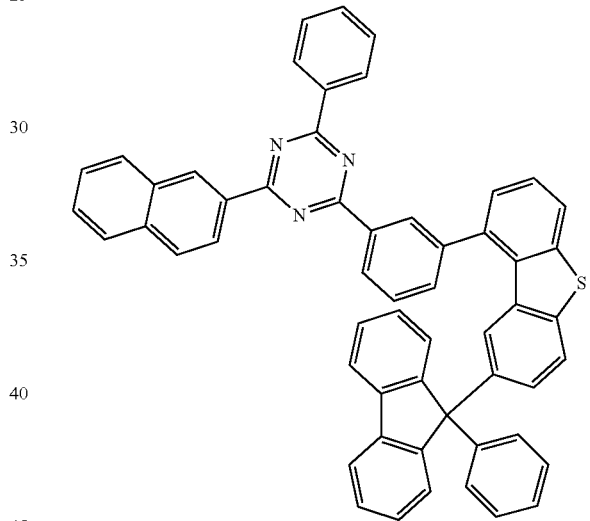
H1-166
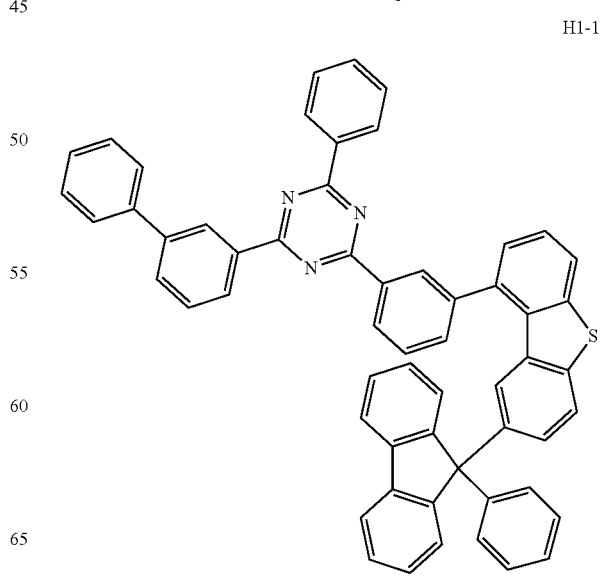

297
-continued
H1-167
H1-168
H1-170
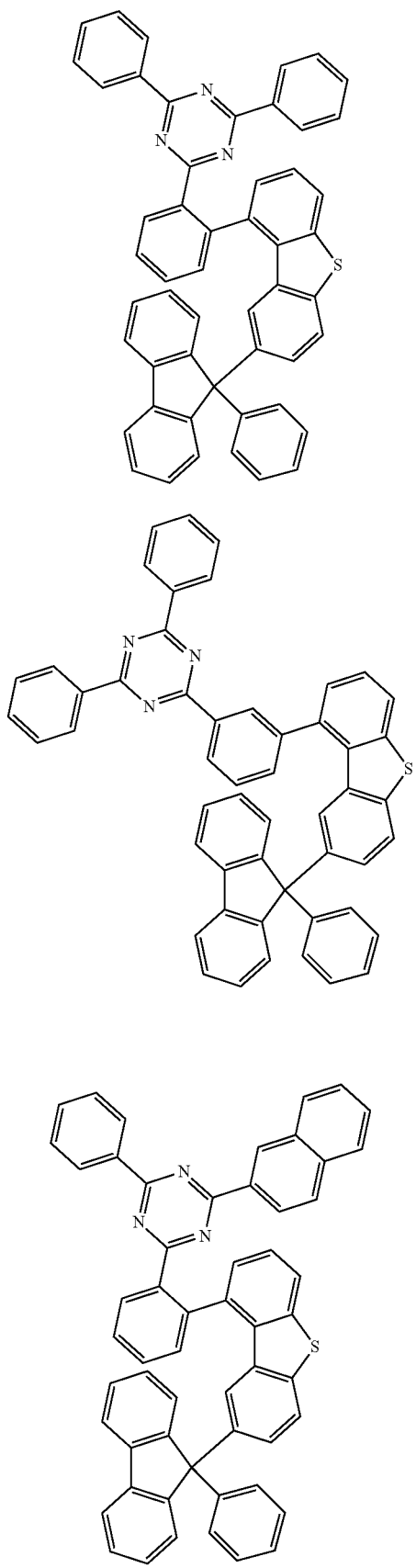
298
-continued
H1-171
H1-172
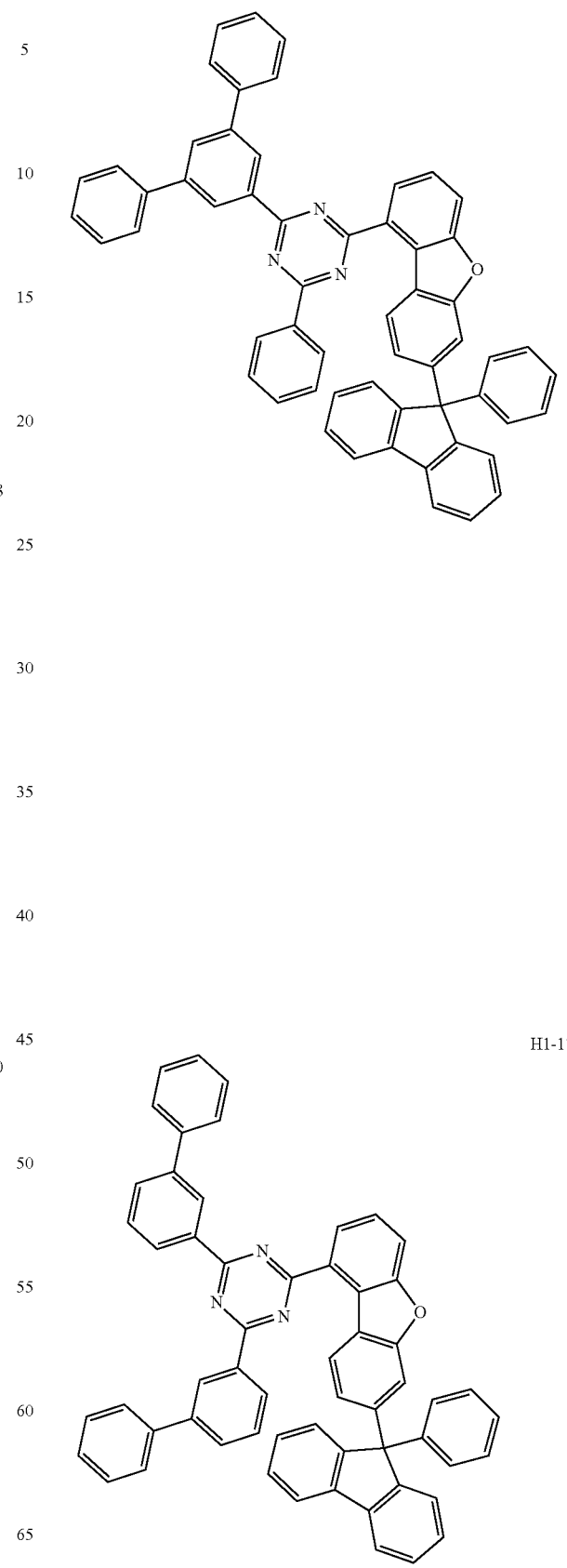

H1-173
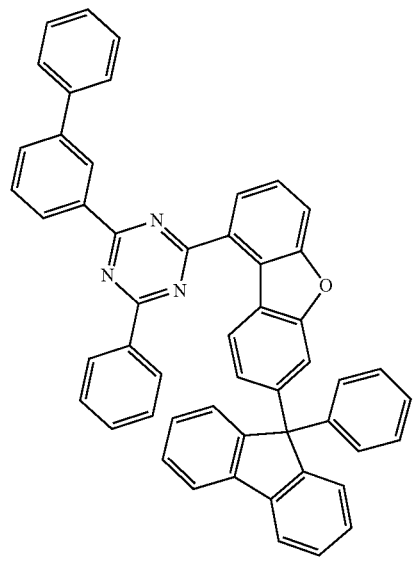
H1-175
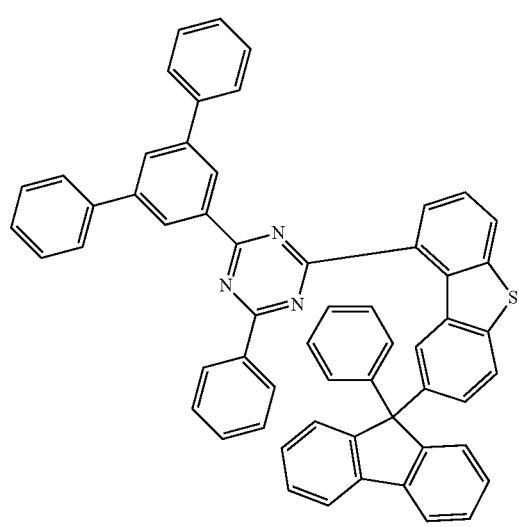
H1-176
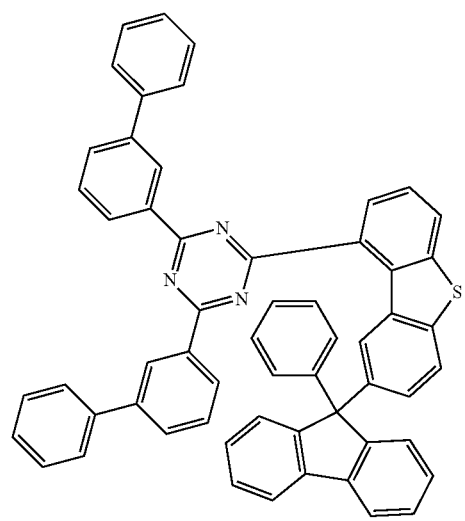
H1-177
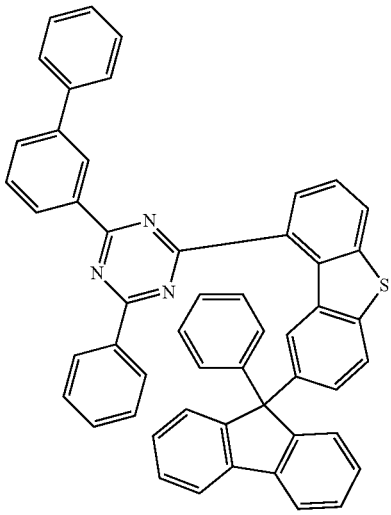
H1-179
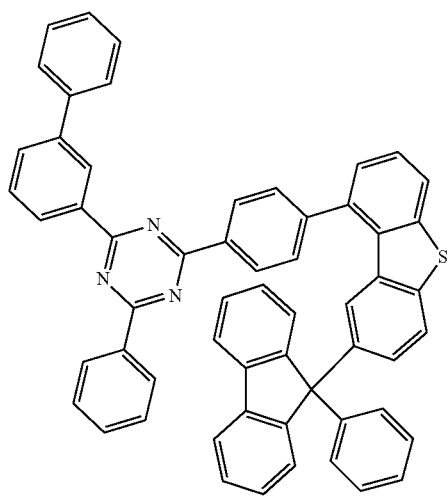
H1-180
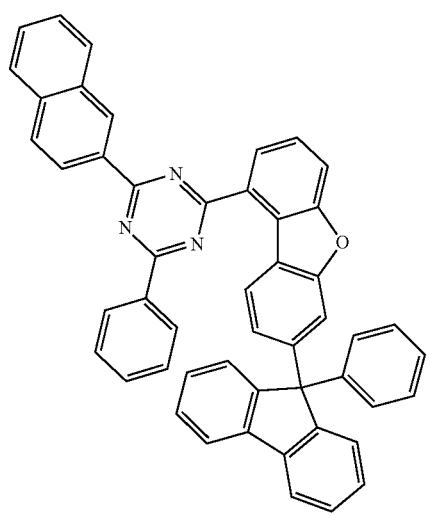

H1-181
H1-184
H1-182
H1-185
H1-183
H1-186
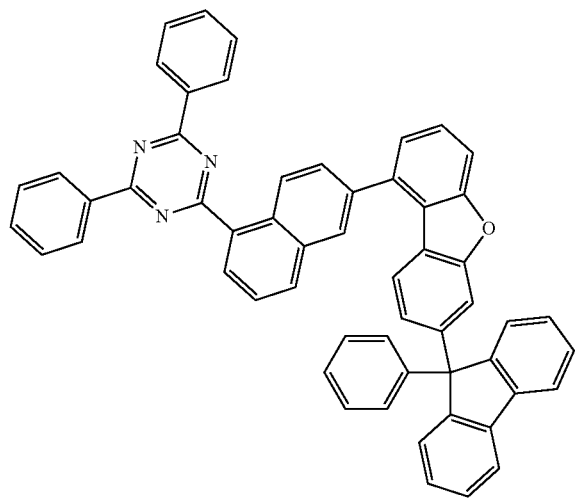
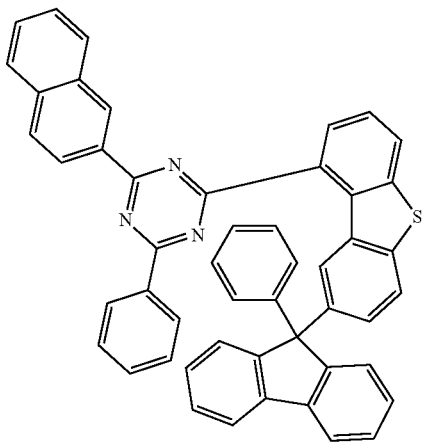
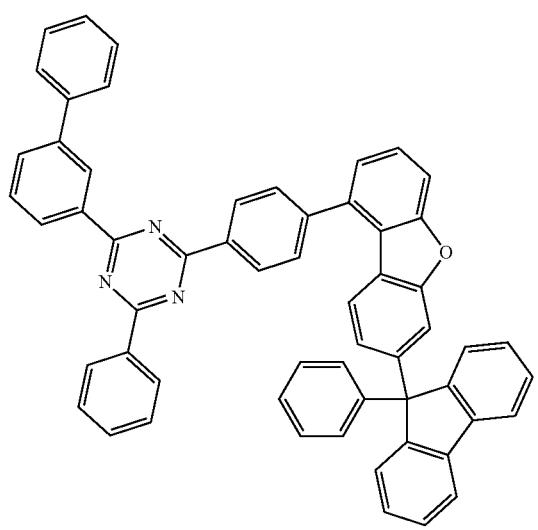
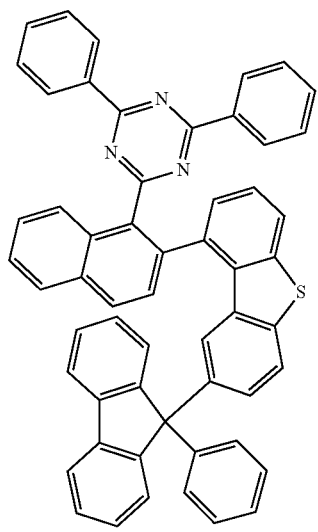

H1-187
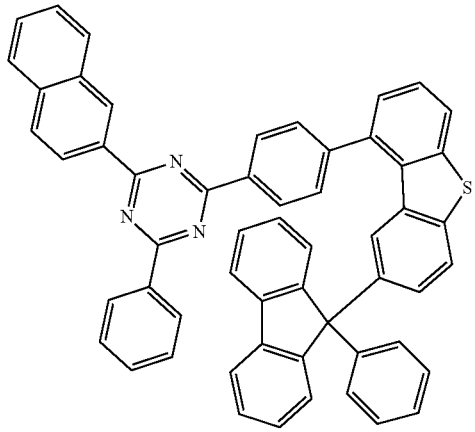
H1-190
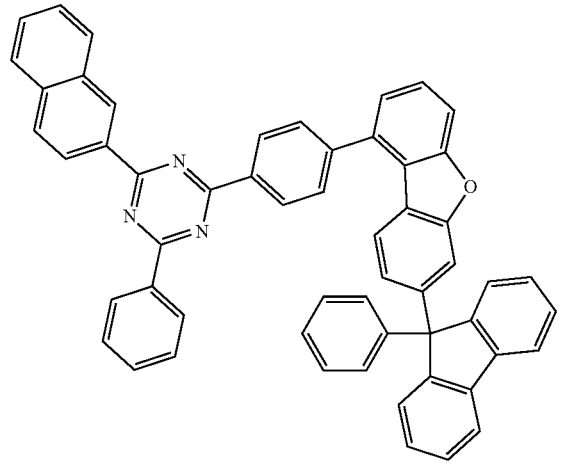
H1-188
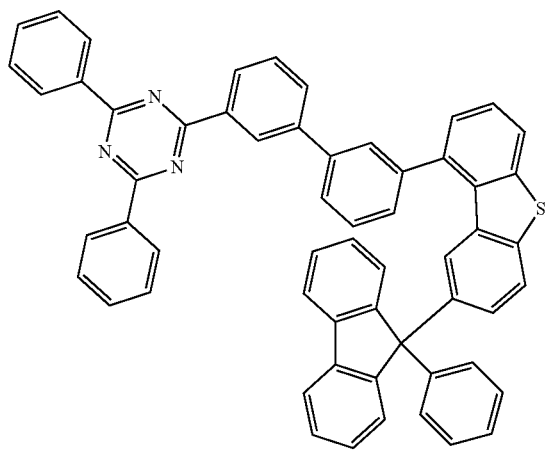
H1-191
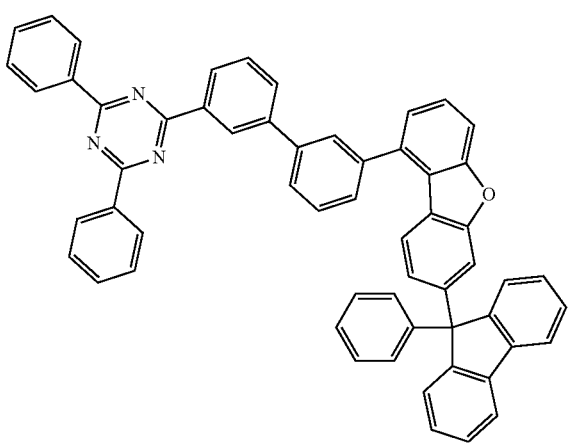
H1-189
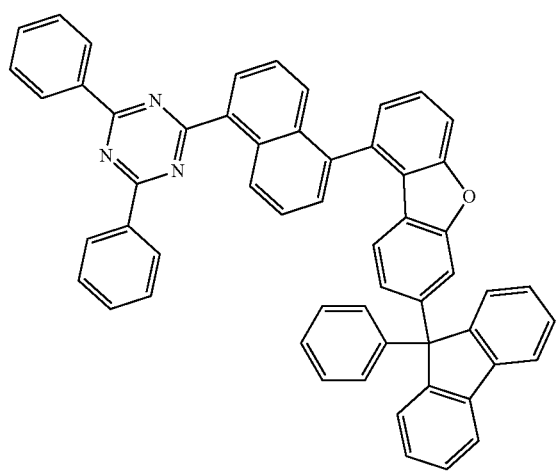
H1-192
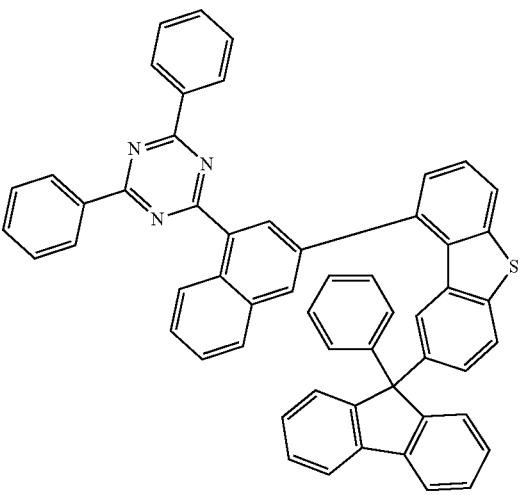

H1-193
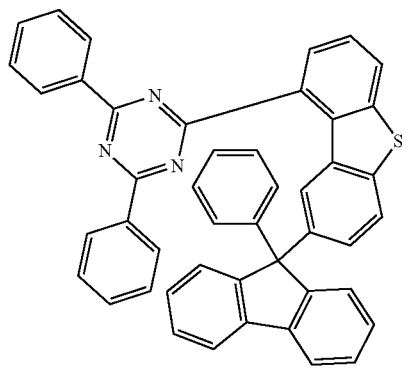
H1-194
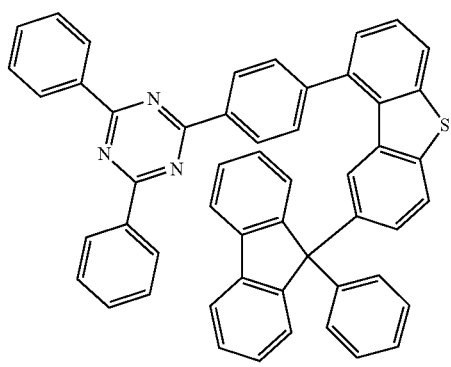
H1-195
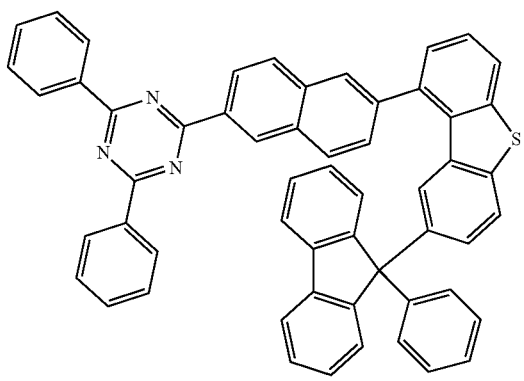
H1-196
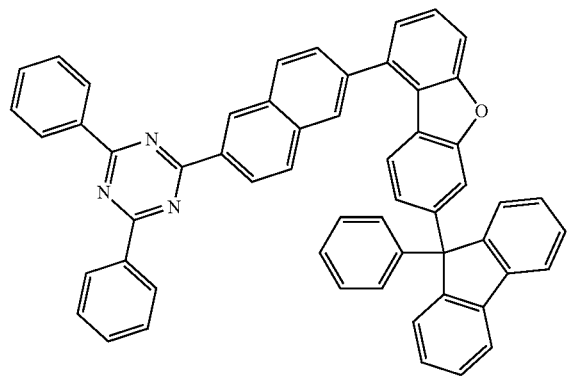
H1-197
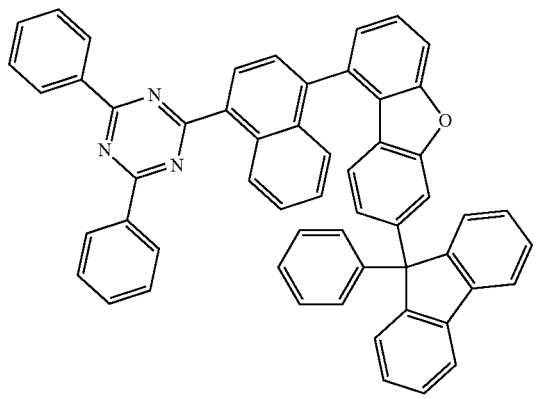
H1-198
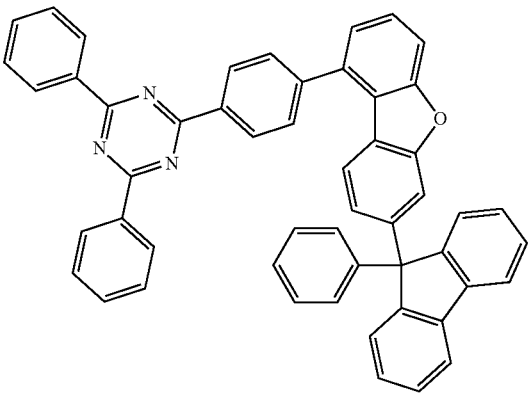
H1-199
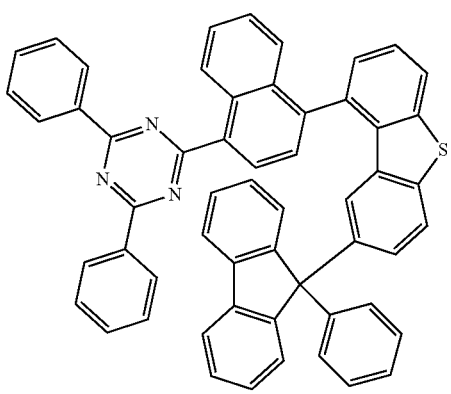

-continued
H1-200
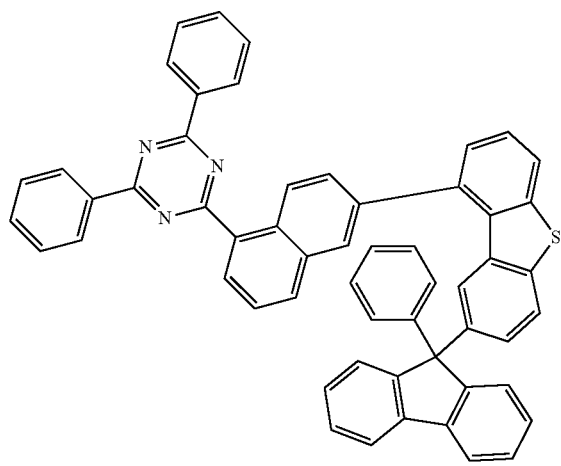
H1-243
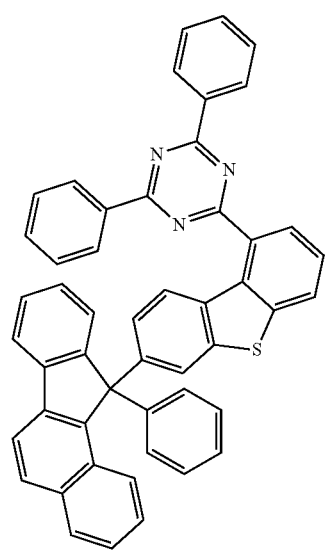
H1-244
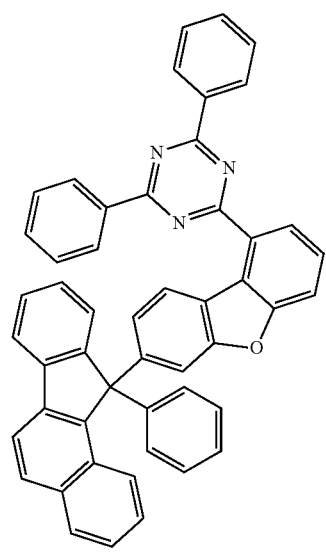
-continued
H1-257
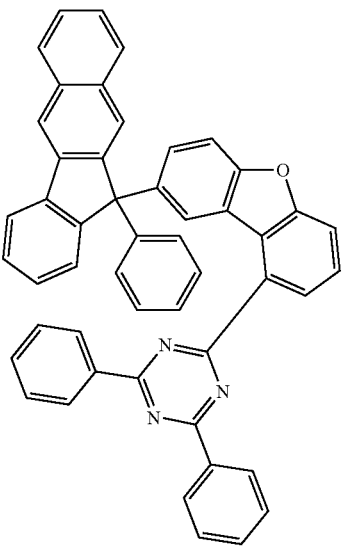
H1-258
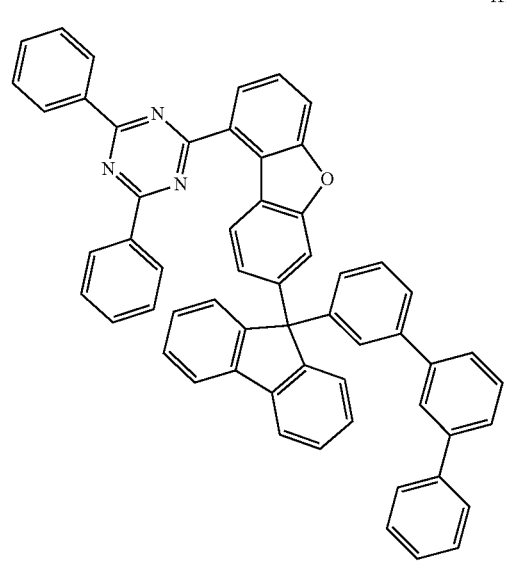
H1-264
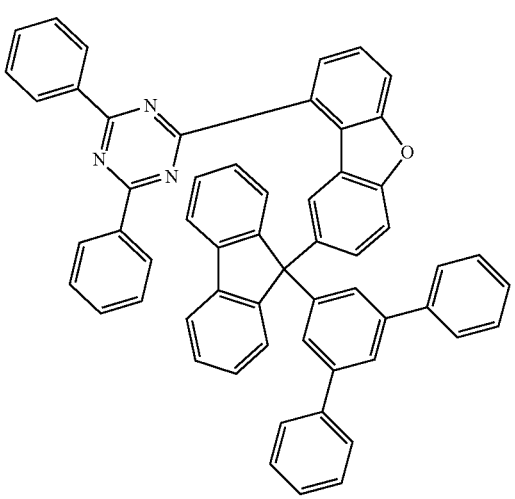

H1-270
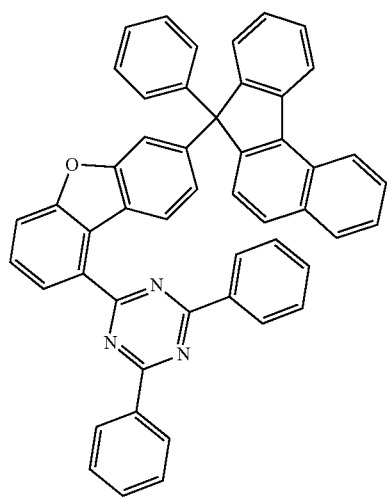
H1-281
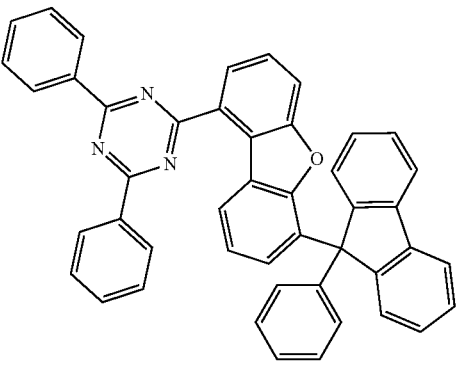
H1-277
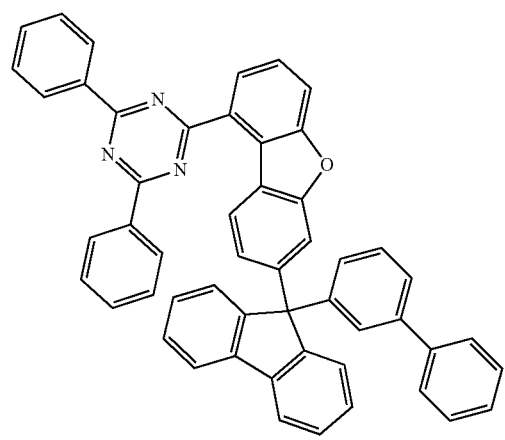
H1-284
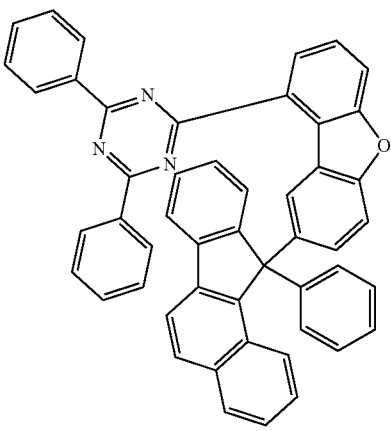
H1-279
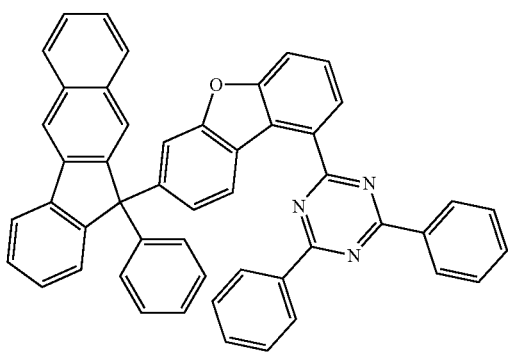
H1-285
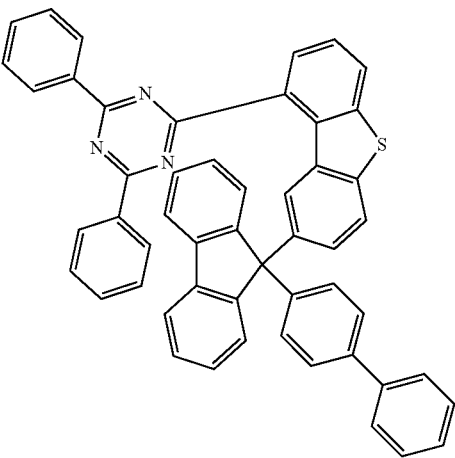

H1-286
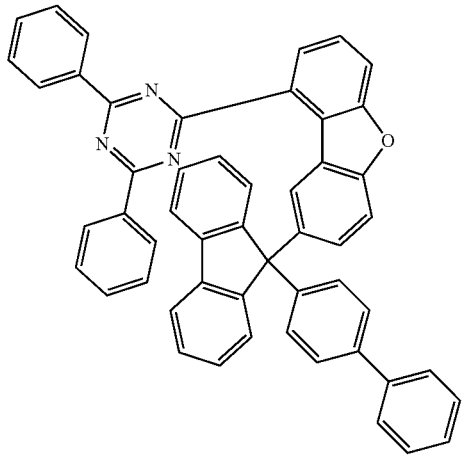
H1-288
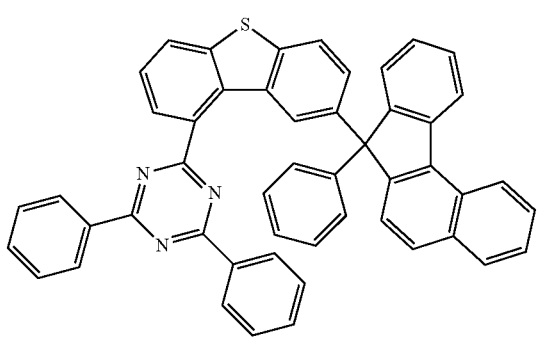
H1-289
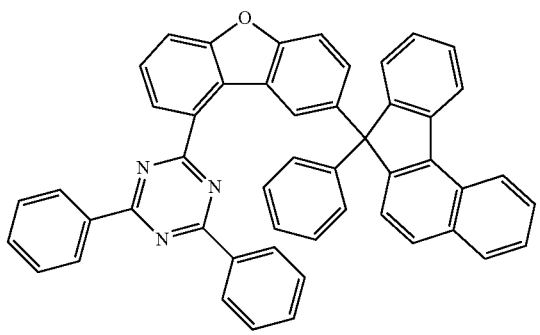
H1-290
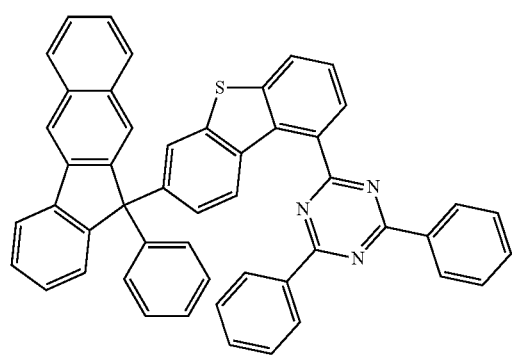
H1-291
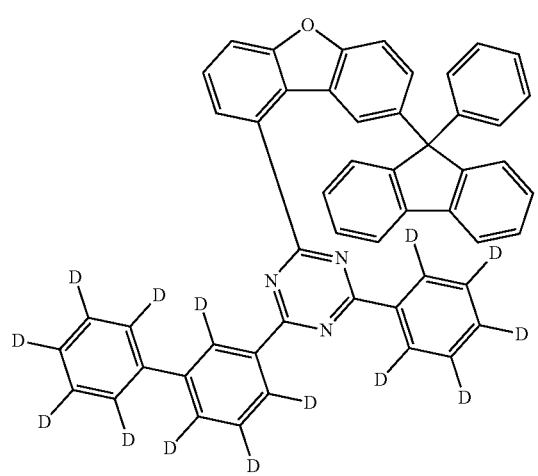
H1-292
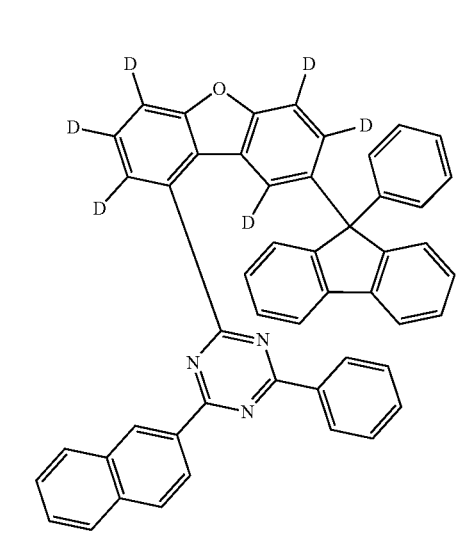
H2-293
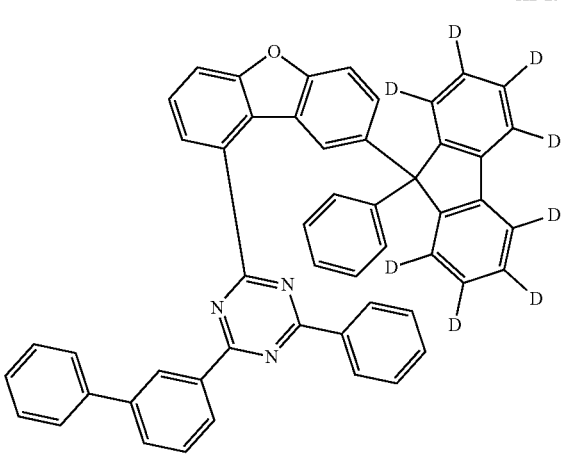

H1-294
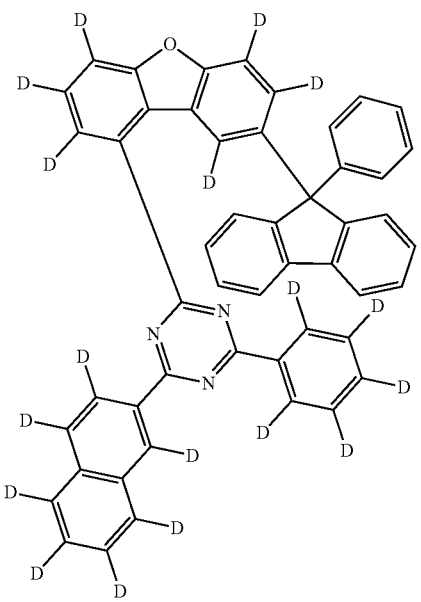
and
H1-295
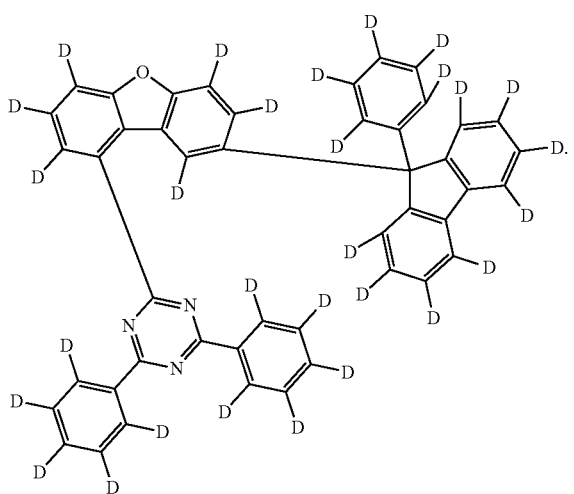
5. The plurality of host materials according to claim 1, wherein the compound represented by the formula 2 is selected from the following compounds:
H2-1
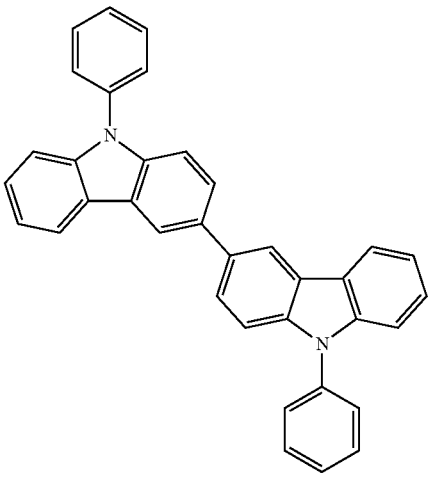
H2-2
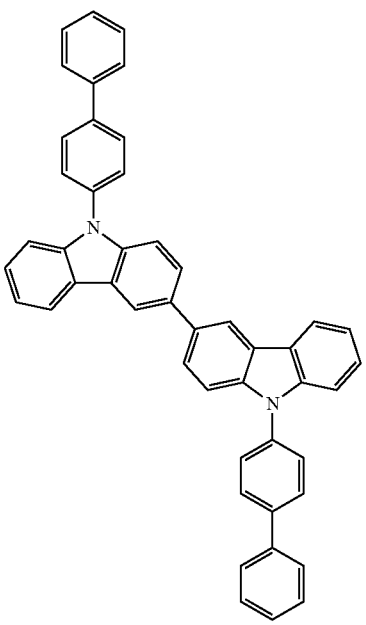

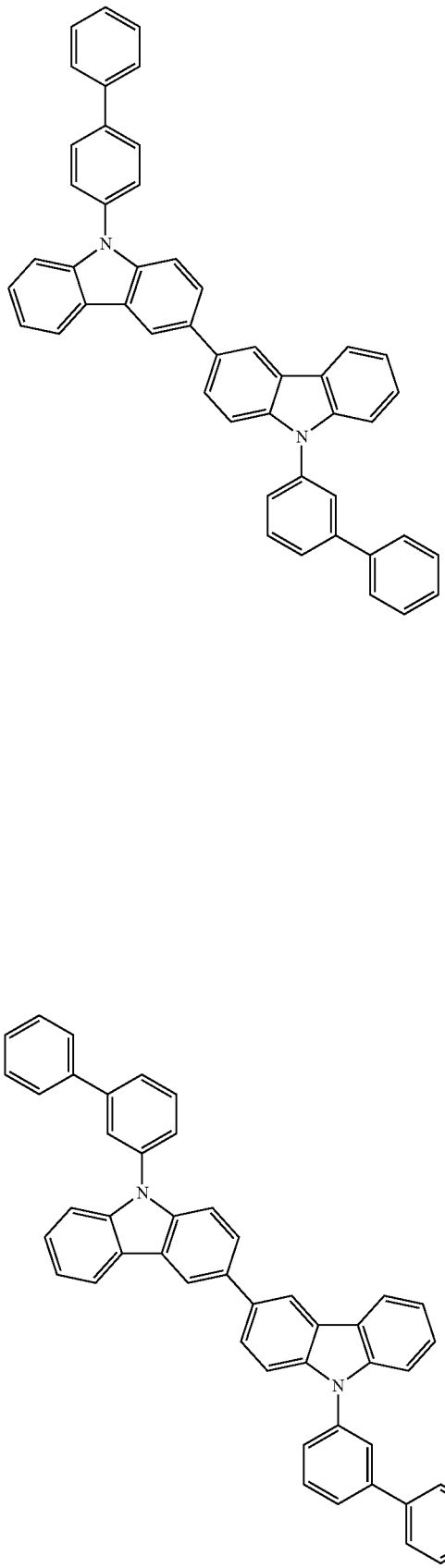
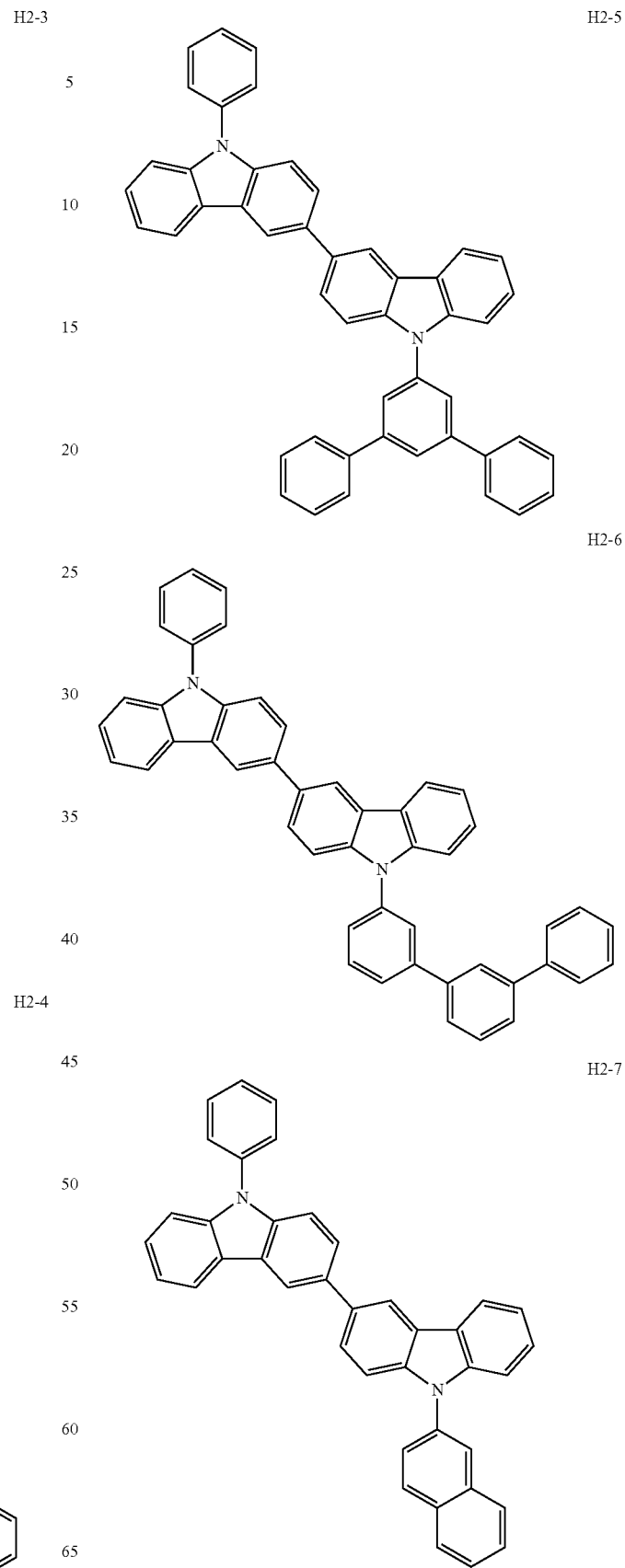

-continued
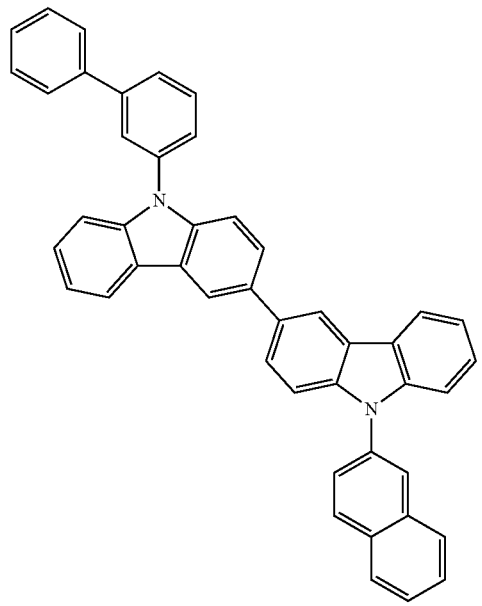
H2-8
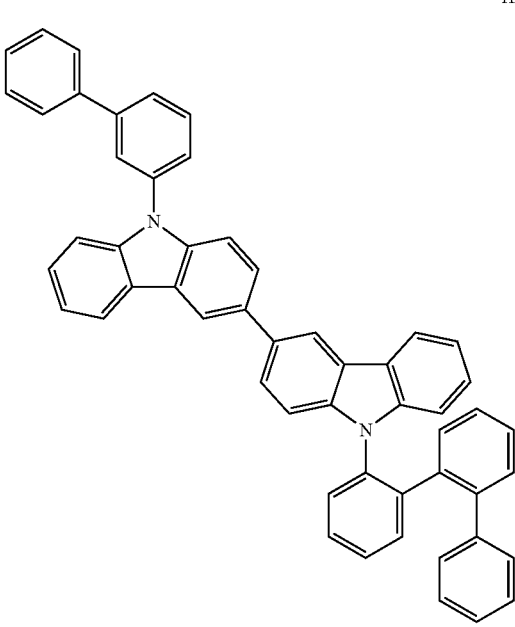
H2-11
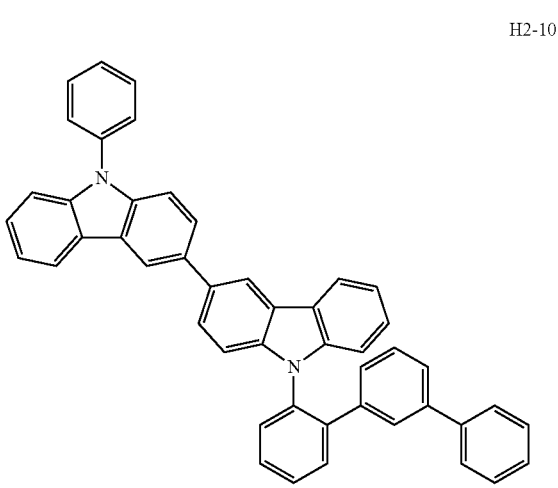
H2-9
H2-10
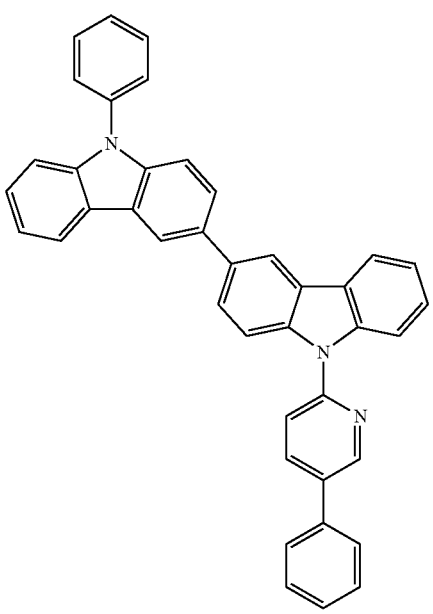
H2-12

-continued
H2-13
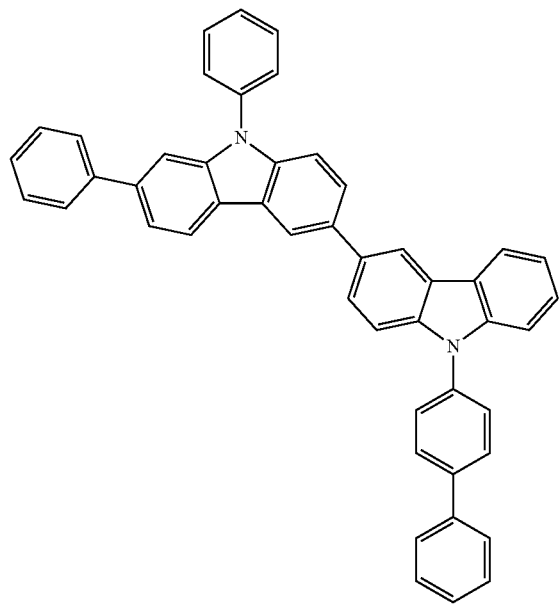
H2-14
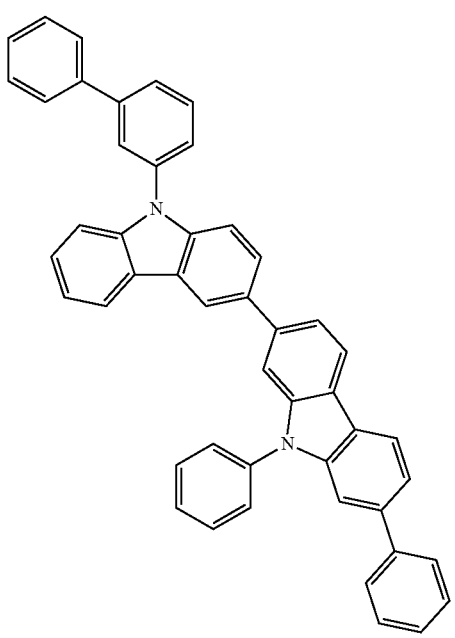
-continued
H2-15
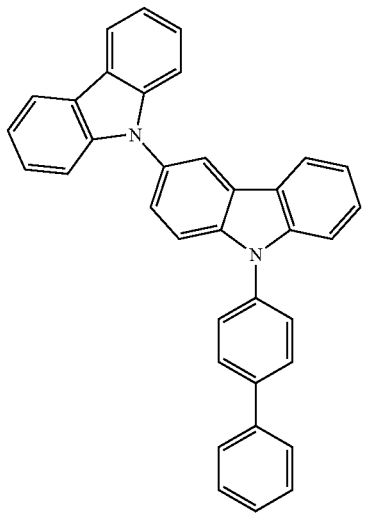
H2-16
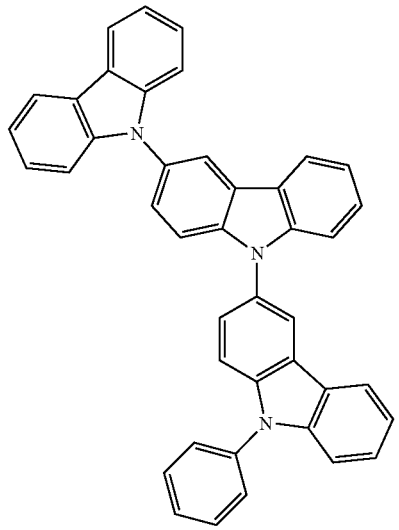
H2-17

H2-18
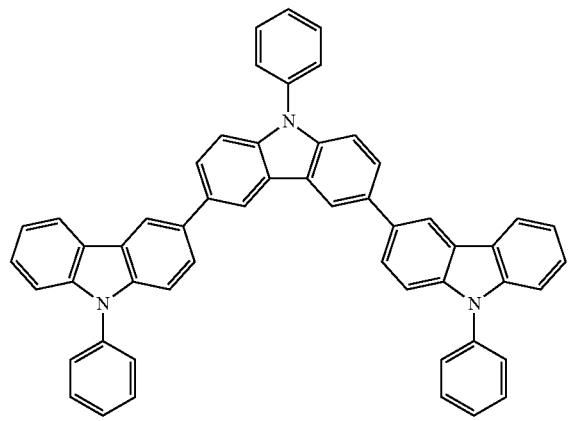
H2-21
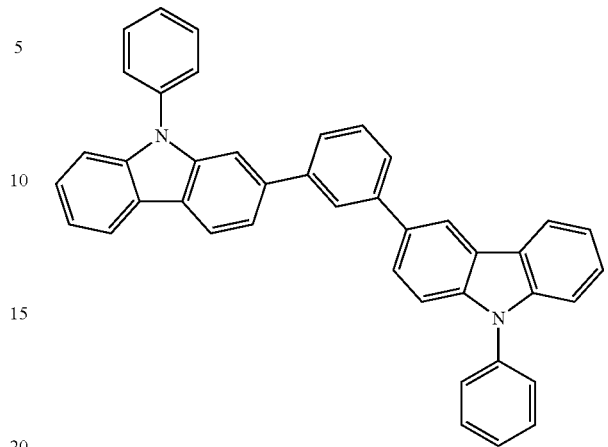
H2-19
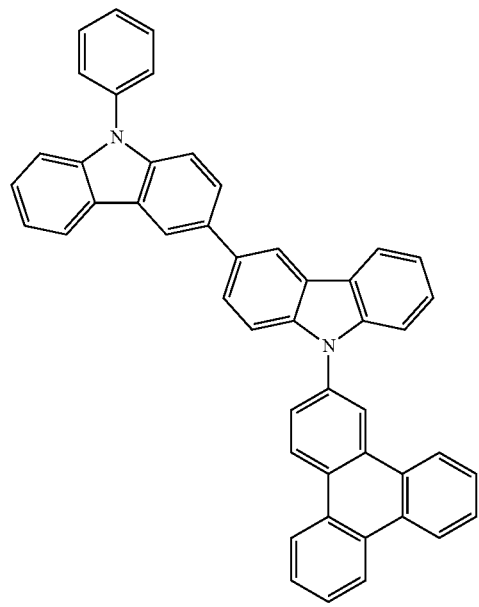
H2-23
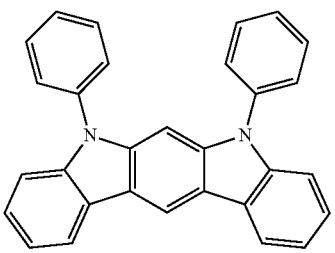
H2-24
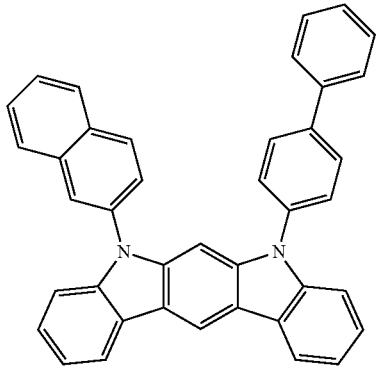
H2-20
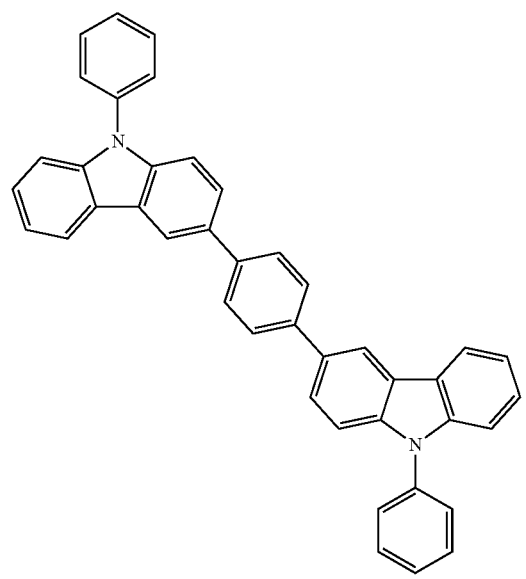
H2-25
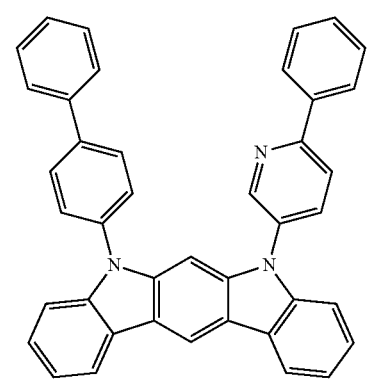

H2-26
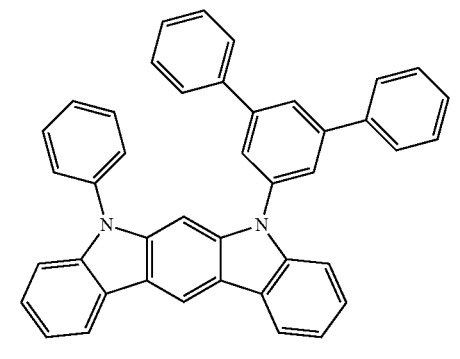
H2-27
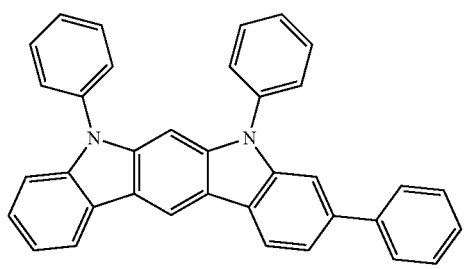
H2-28
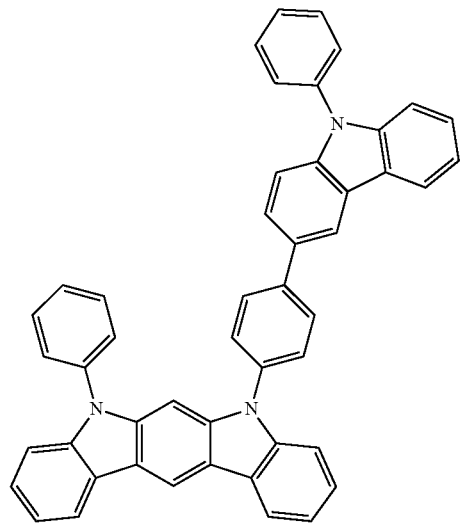
H2-29
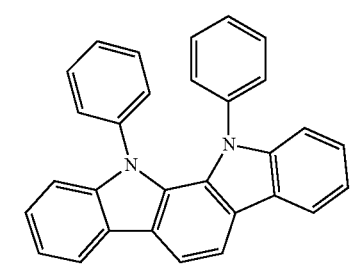
H2-30
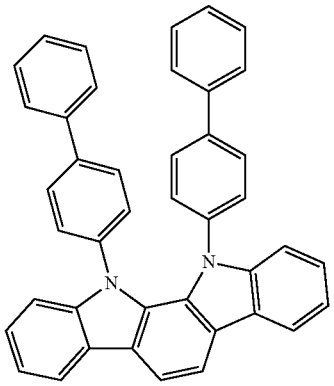
H2-31
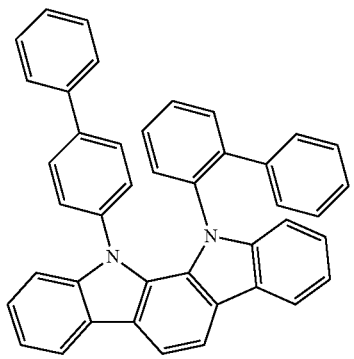
H2-32
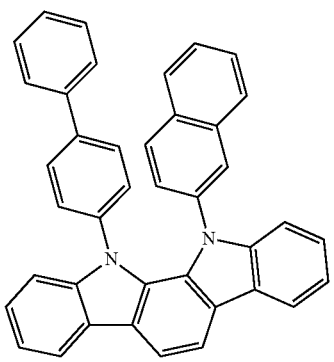
H2-33
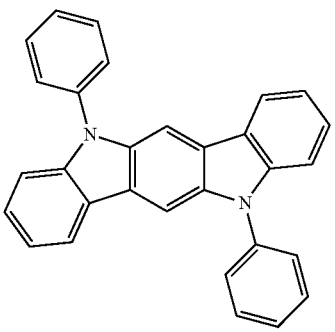

325
-continued
H2-34
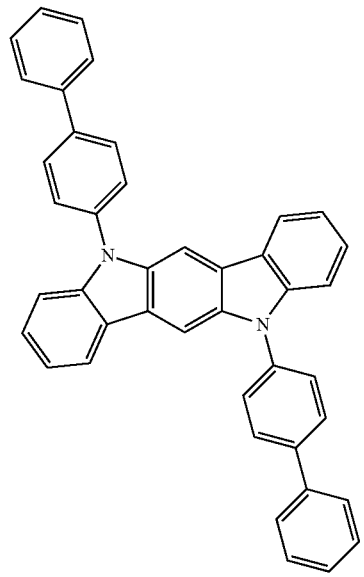
H2-35
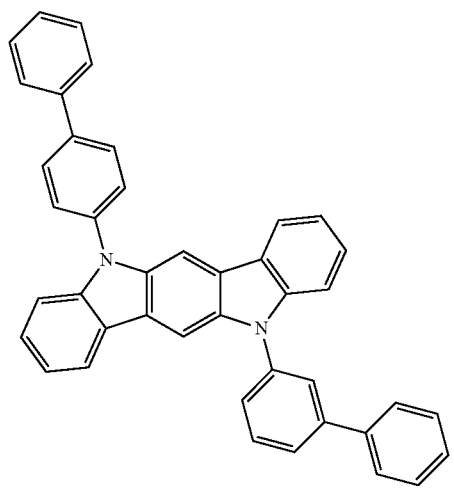
H2-36
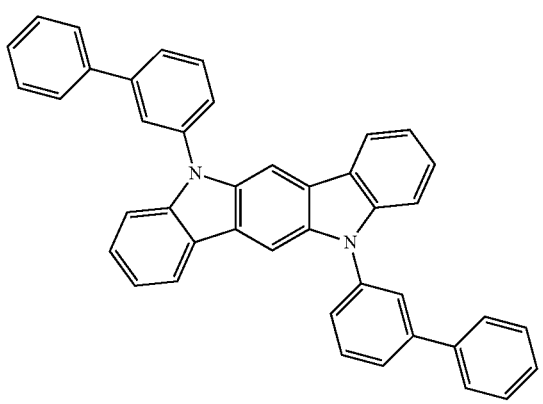
326
-continued
H2-37
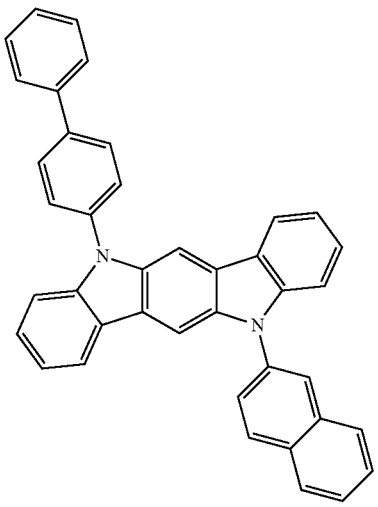
H2-38
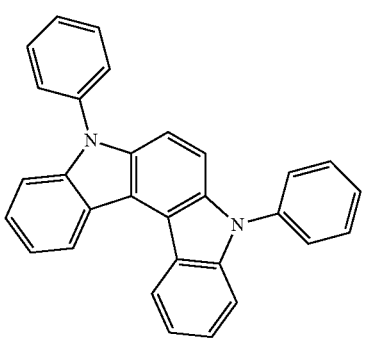
H2-39
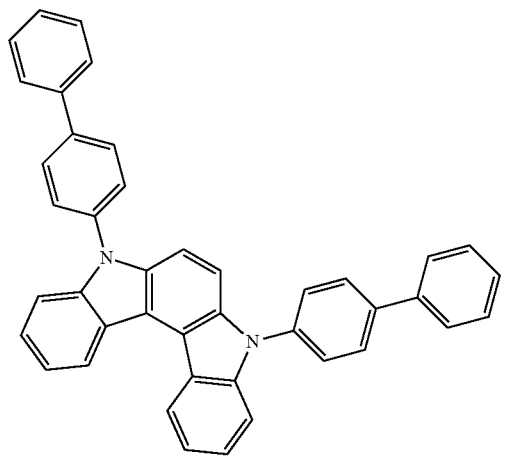

-continued
H2-40
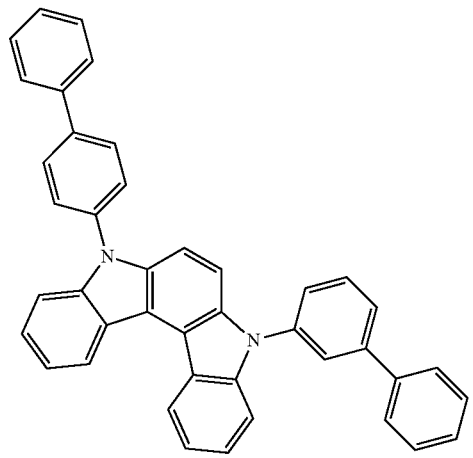
H2-41
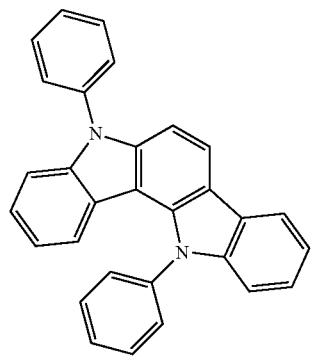
H2-42
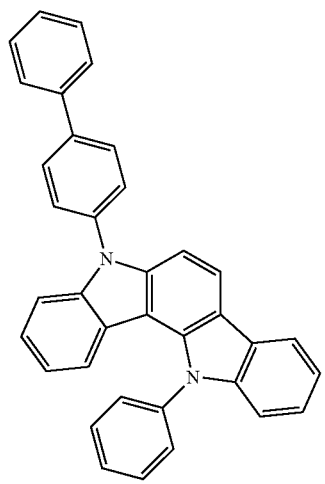
-continued
H2-43
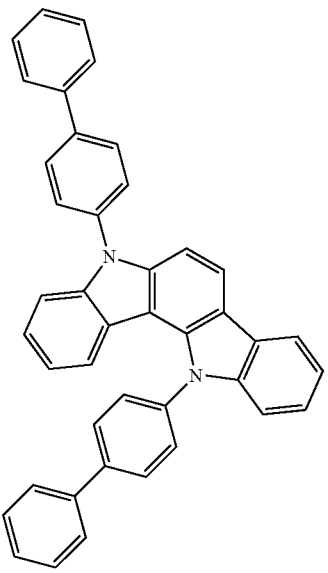
H2-44
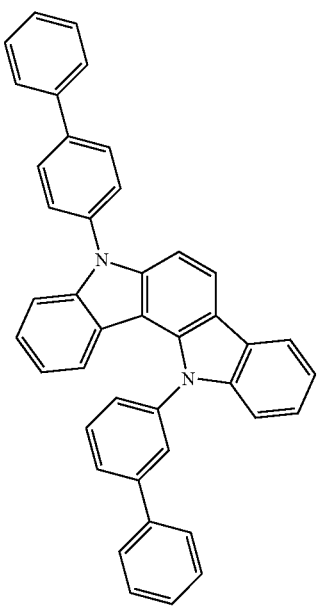

H2-45
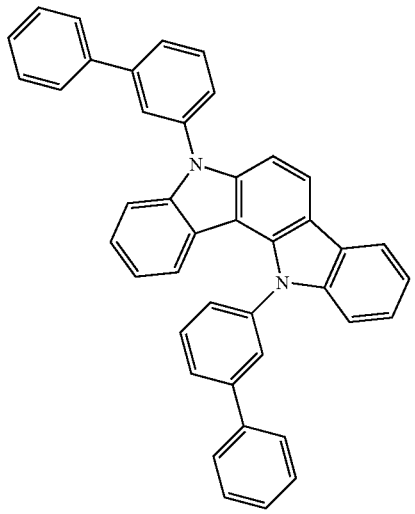
H2-46
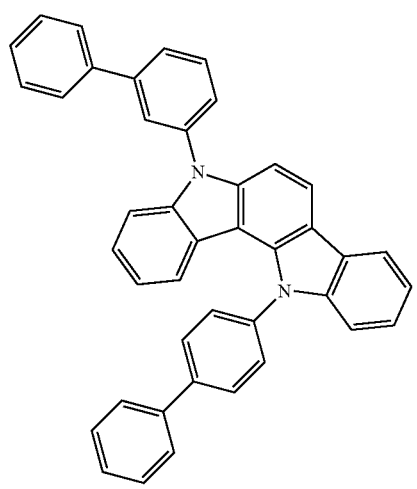
H2-47
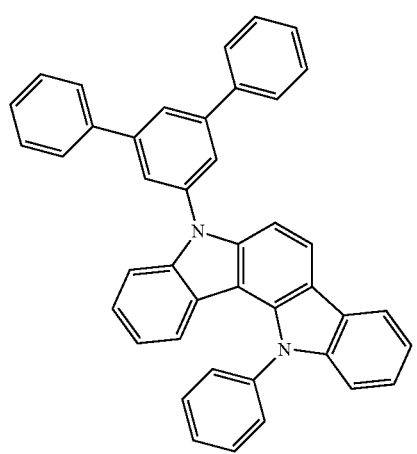
H2-48
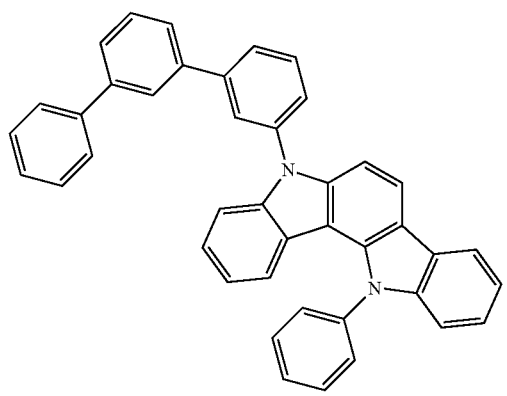
H2-49
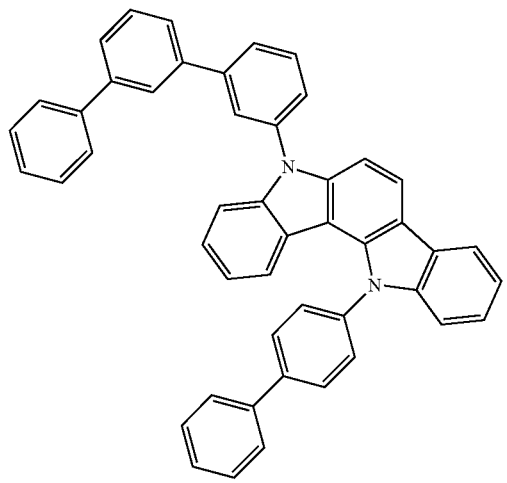
H2-50
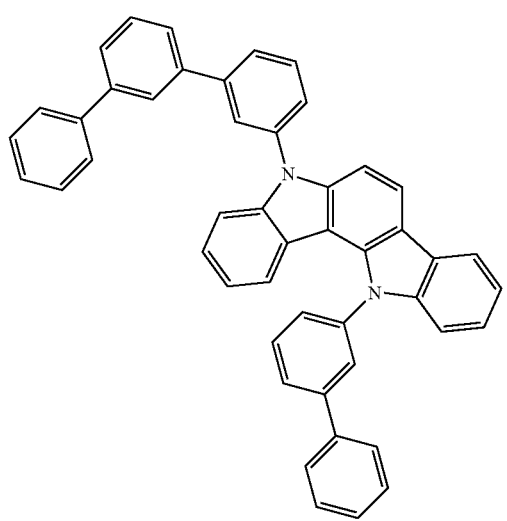

H2-51
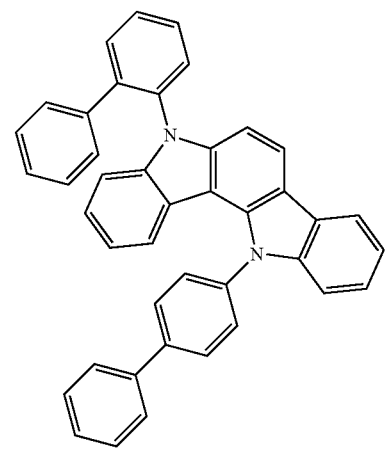
H2-52
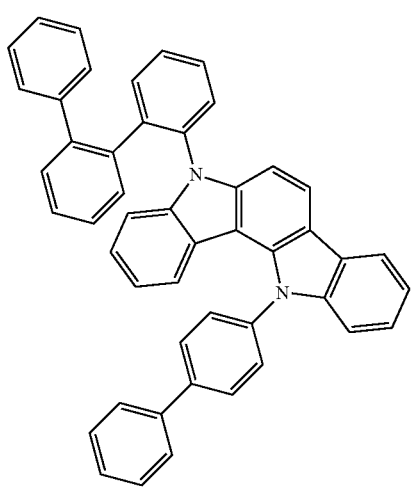
H2-53
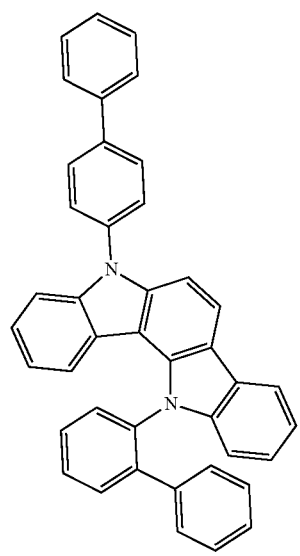
H2-54
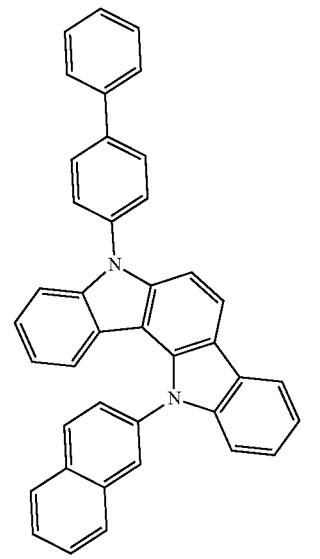
H2-55
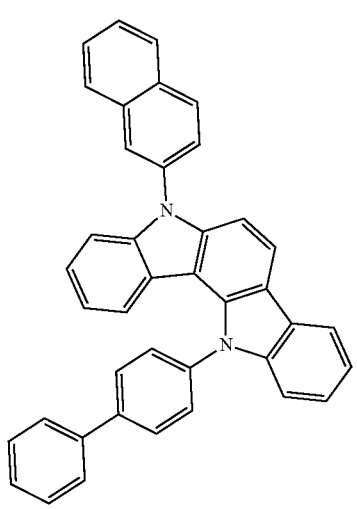
H2-56
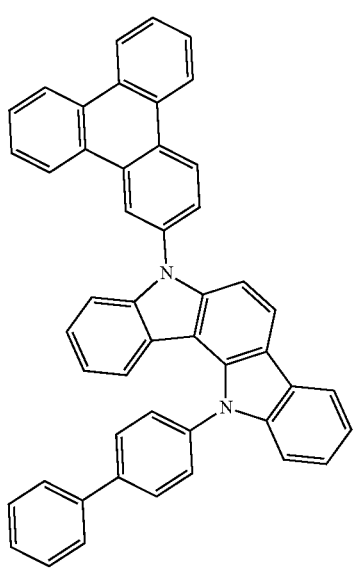

H2-57

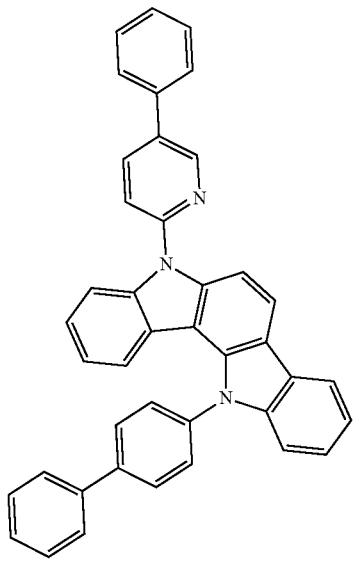

H2-59

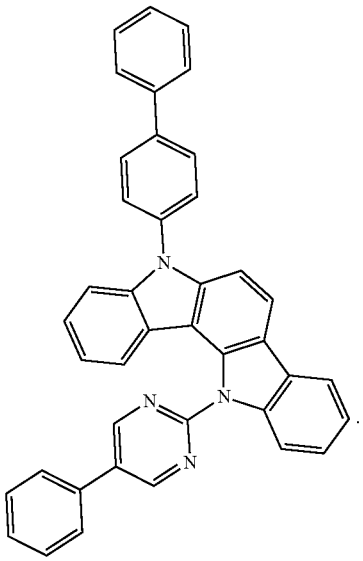

H2-58

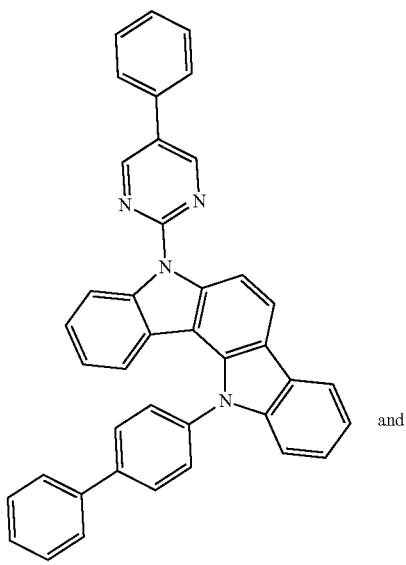 and

6. An organic electroluminescent device comprising: an anode; a cathode; and at least one light-emitting layer between the anode and the cathode, wherein the at least one light-emitting layer(s) comprises the plurality of host materials according to claim 1.

7. An organic electroluminescent compound represented by the following formula 1-1-1:

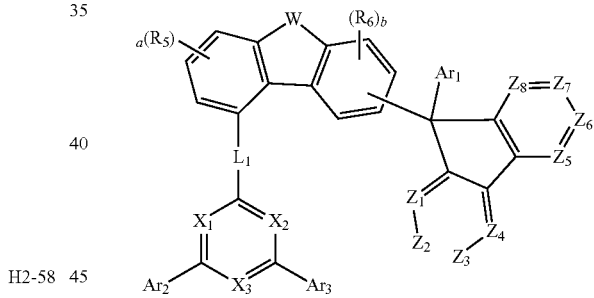

(1-1-1)

wherein,

W represents O or S;

$Z_1$ to $Z_8$ each independently represent, $CR_4$ or N;

$X_1$ to $X_3$ each independently represent, $CR_7$ or N;

$L_1$ represents a single bond or a substituted or unsubstituted (C6-C30)arylene;

$Ar_1$ represents an unsubstituted phenyl, an unsubstituted biphenyl, or an unsubstituted terphenyl;

$Ar_2$ and $Ar_3$ each independently represent, a substituted or unsubstituted (C6-C30)aryl or a substituted or unsubstituted (3- to 30-membered)heteroaryl;

$R_4$ to $R_7$ each independently represent, hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to the adjacent substituents to form a ring(s);

a and b each independently represent, an integer of 1 to 3; and when a and b are an integer of 2 or more, each of $R_5$ and each of $R_6$ may be the same or different.

8. The organic electroluminescent compound according to claim 7, wherein the compound represented by the formula 1-1-1 is selected from the following compounds:

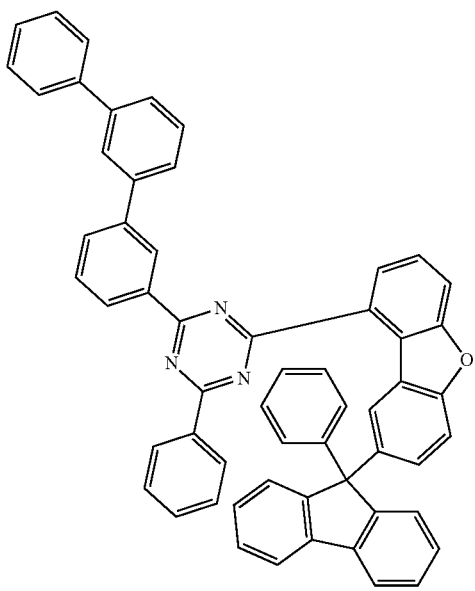

H1-45

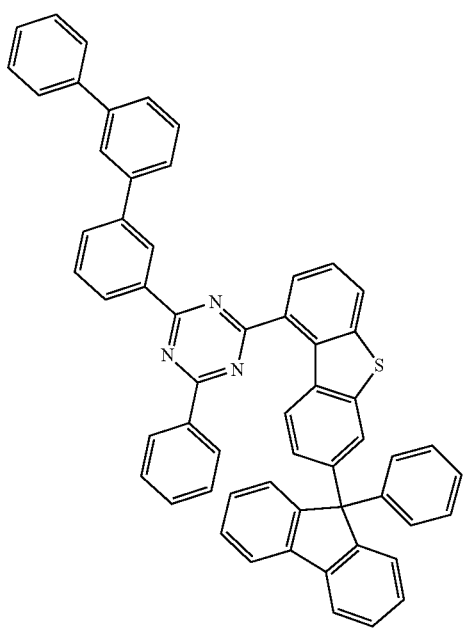

H1-40

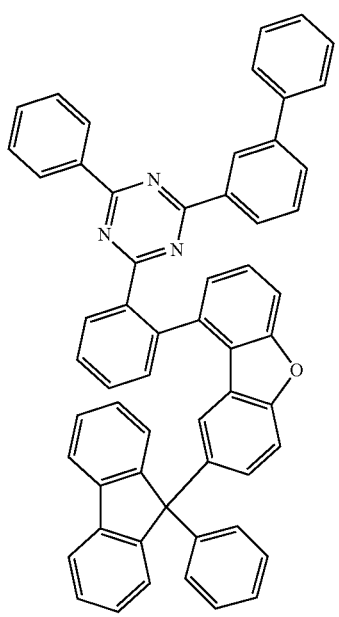

H1-53

H1-54
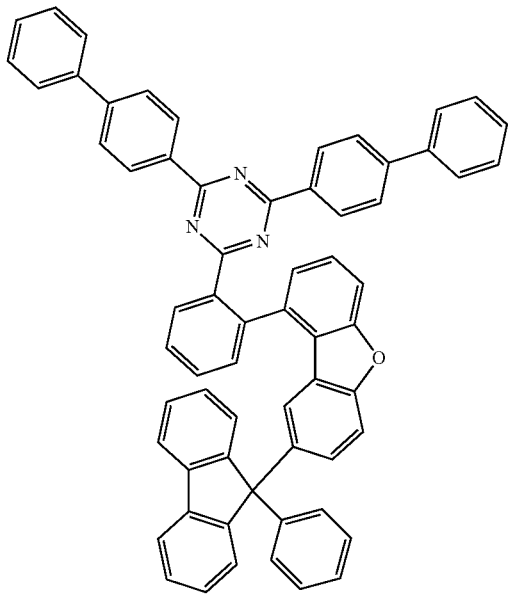
H1-55
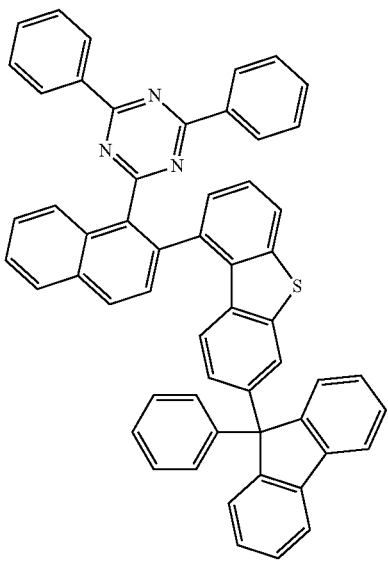
H1-56
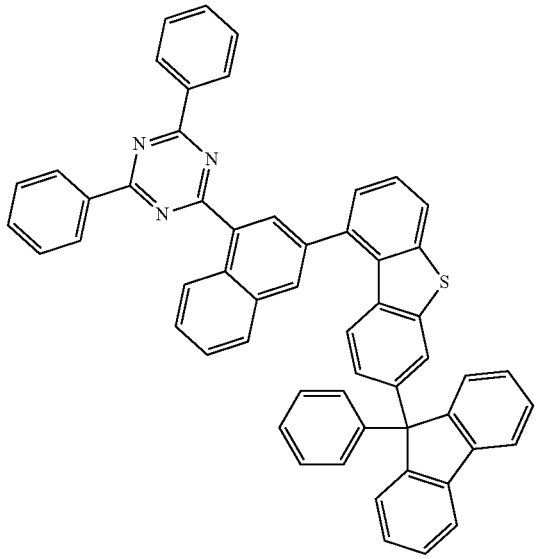
H1-57
H1-58
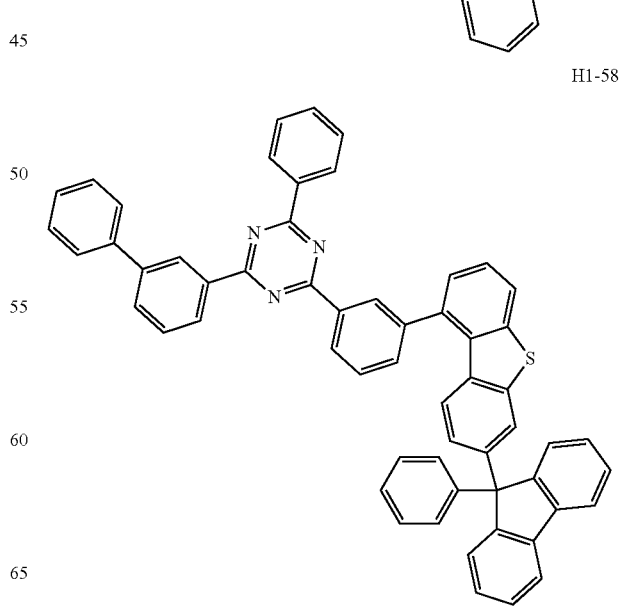

-continued
H1-59
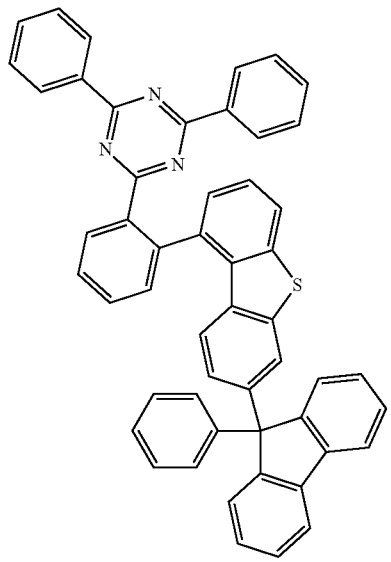
H1-60
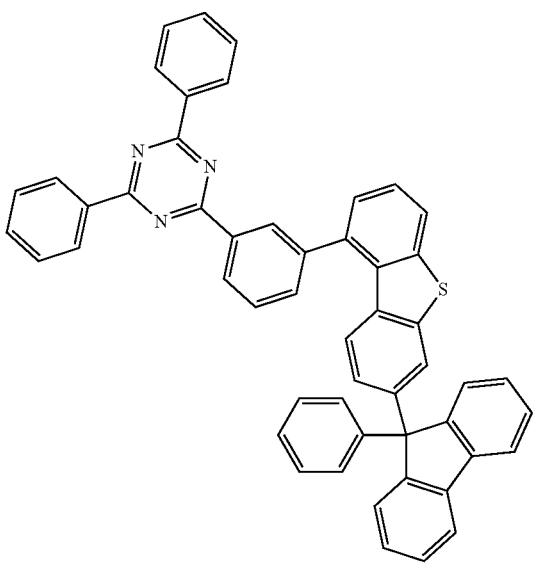
H1-61
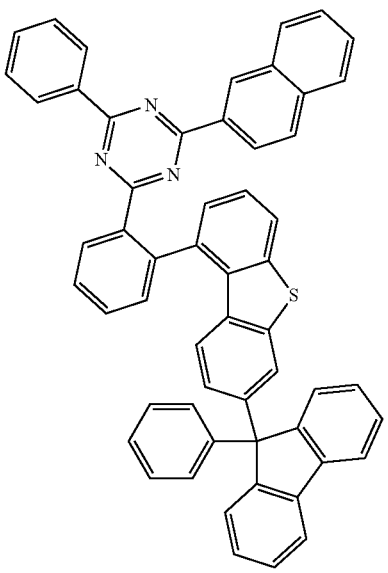
H1-62
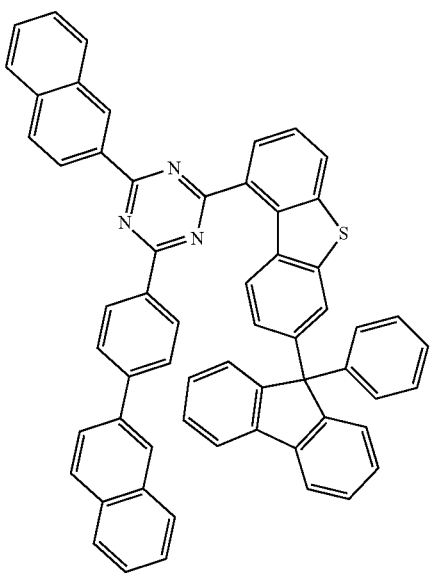

-continued
H1-63
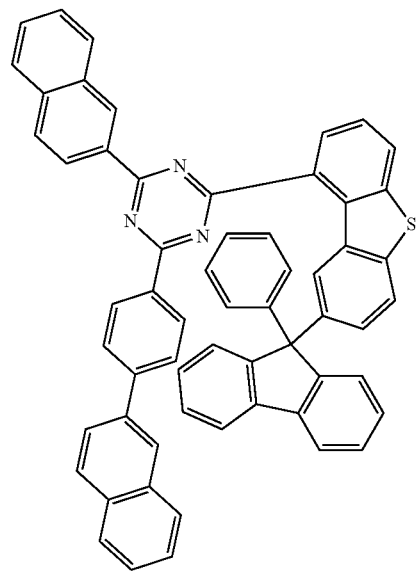
H1-64
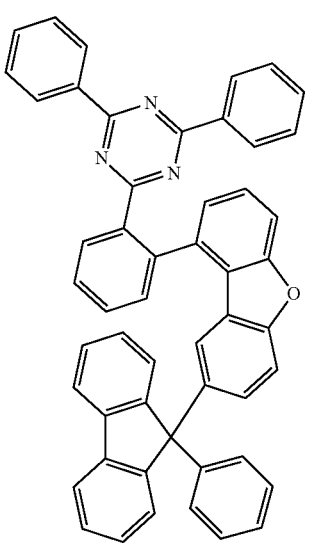
H1-65
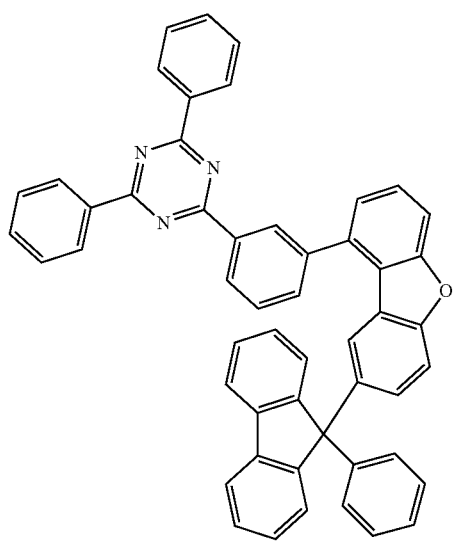
-continued
H1-67
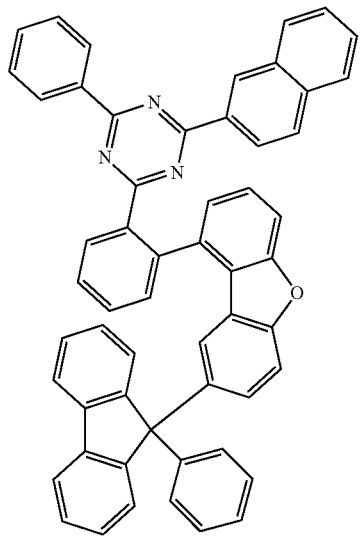
H1-68
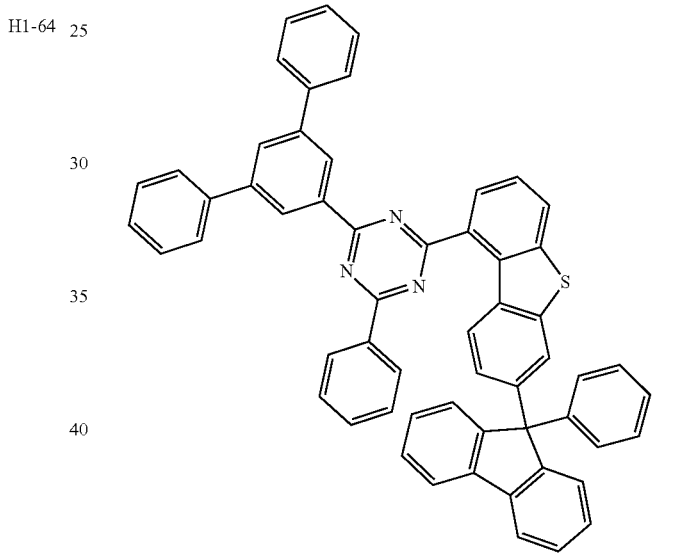
H1-69
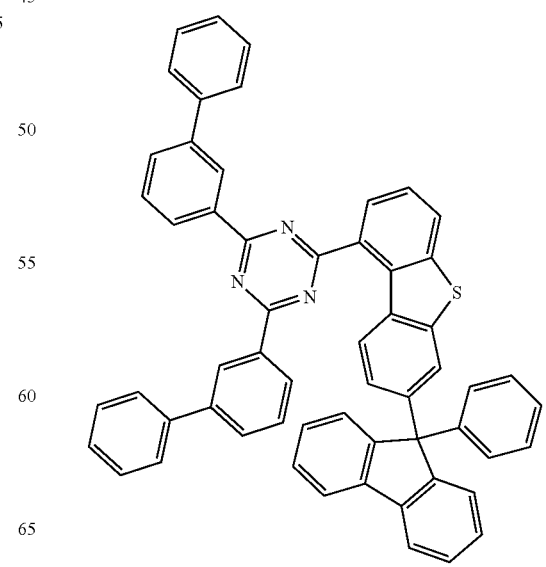

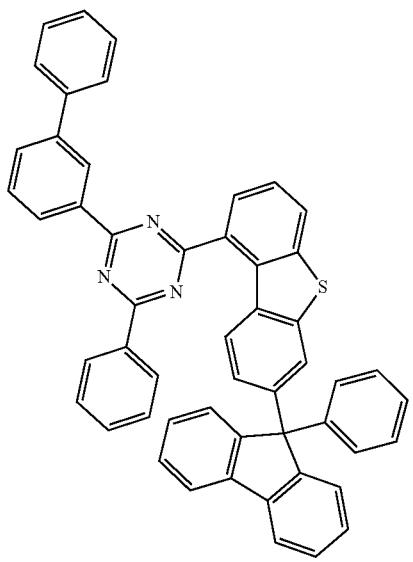
H1-70
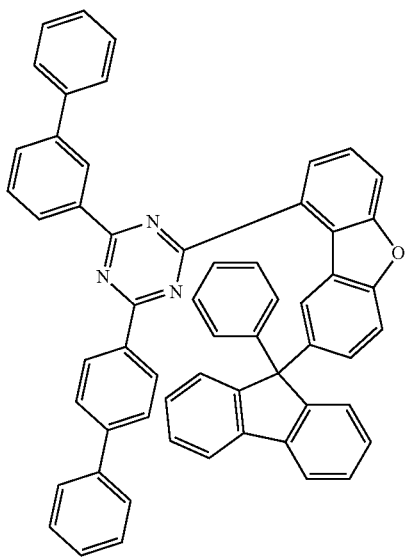
H1-72
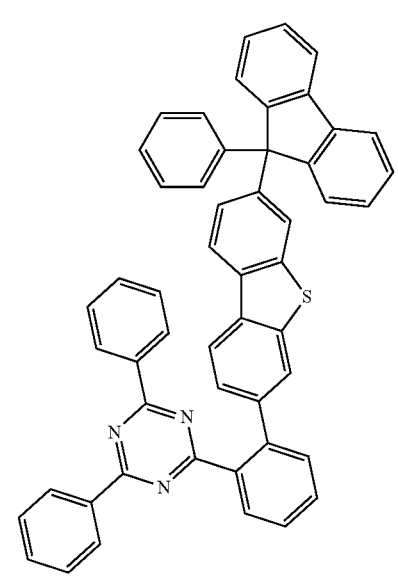
H1-73
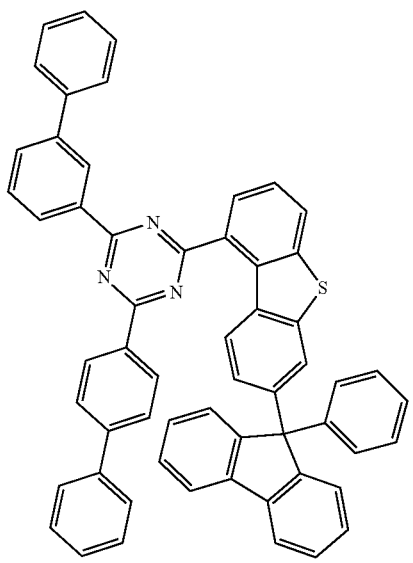
H1-71
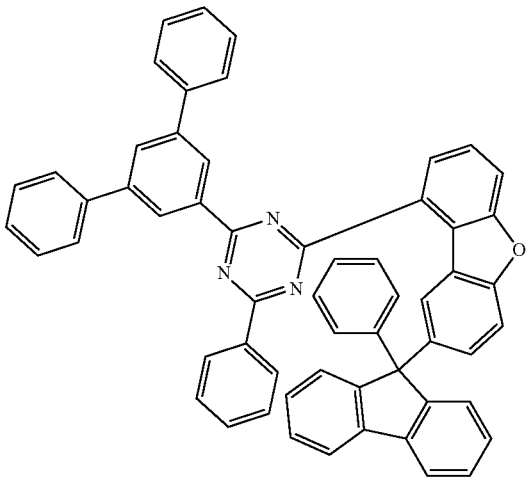
H1-74

-continued
H1-75
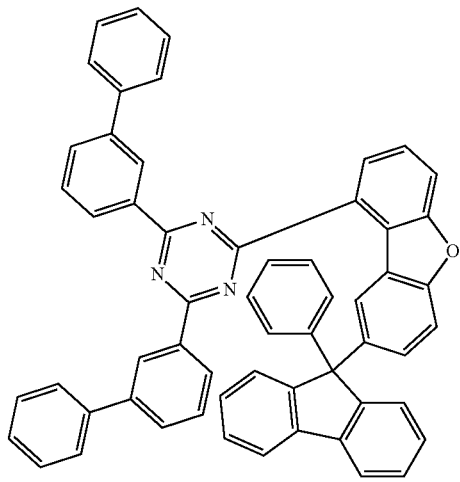
H1-76
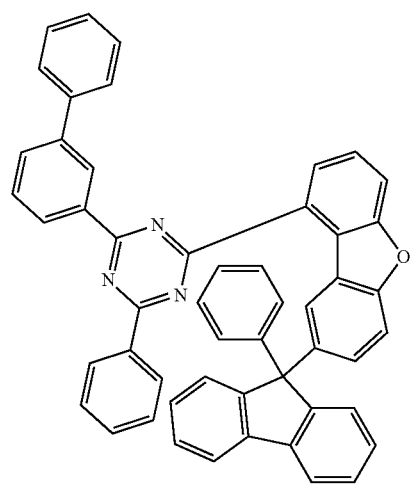
H1-77
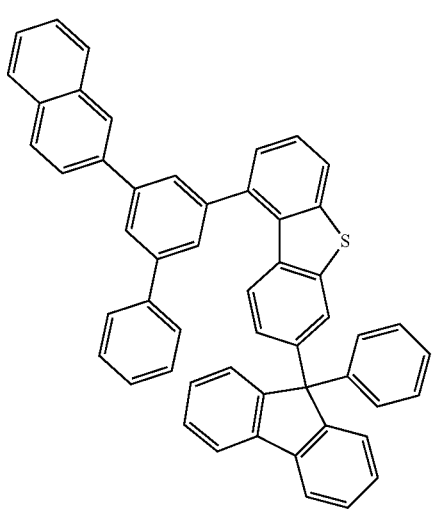
-continued
H1-78
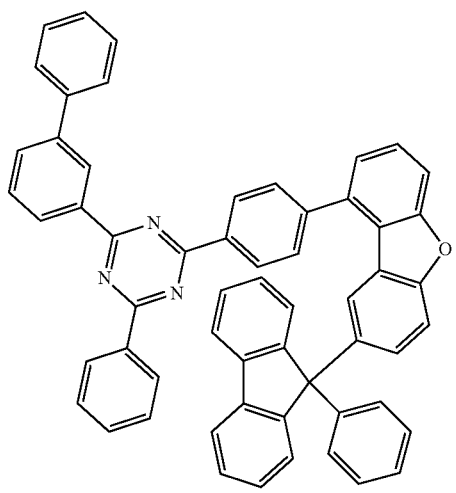
H1-79
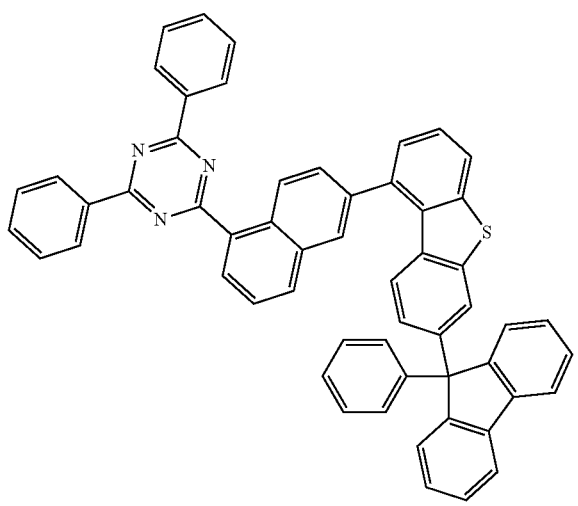
H1-80
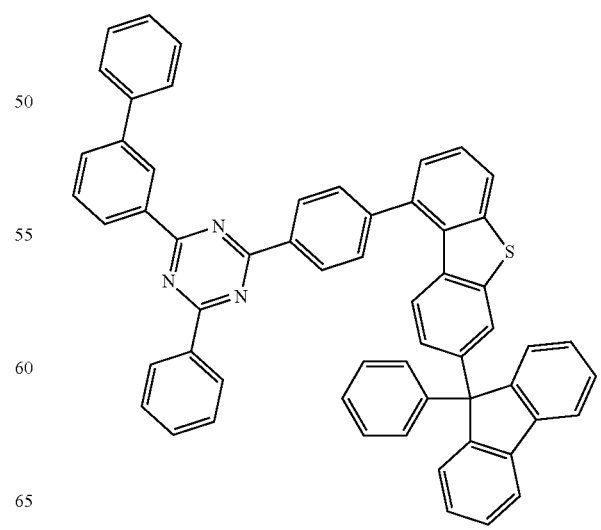

H1-81
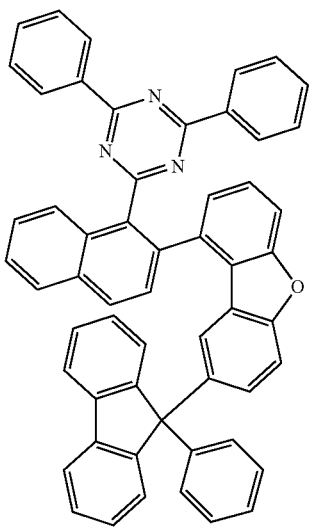
H1-82
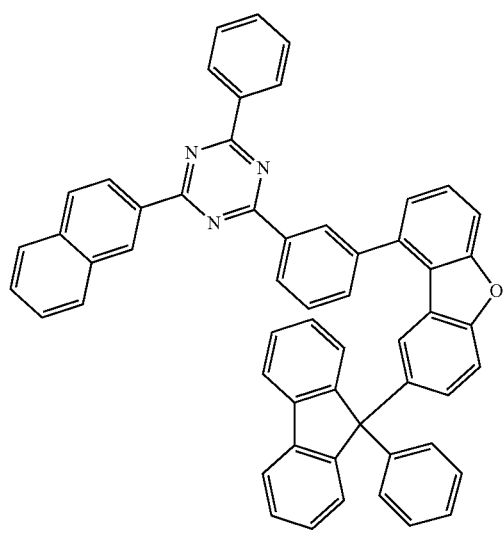
H1-83
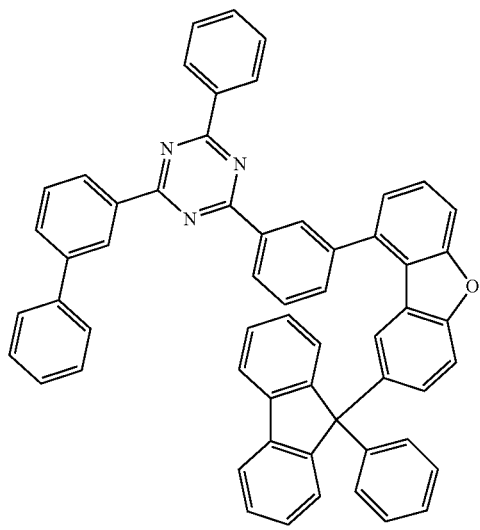
H1-84
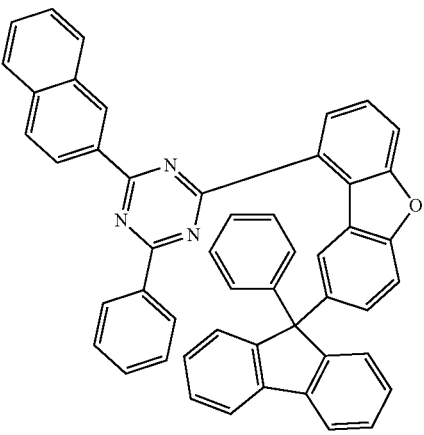
H1-85
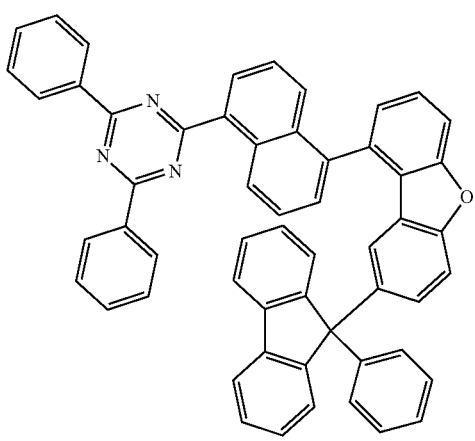
H1-86
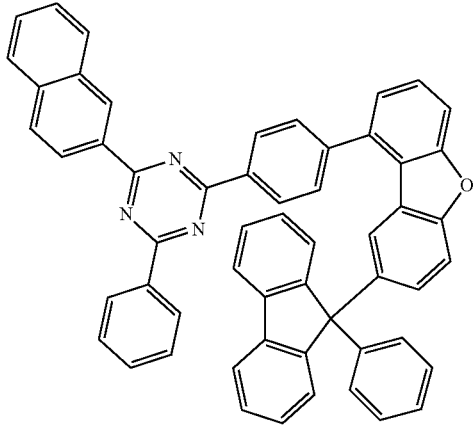

H1-87
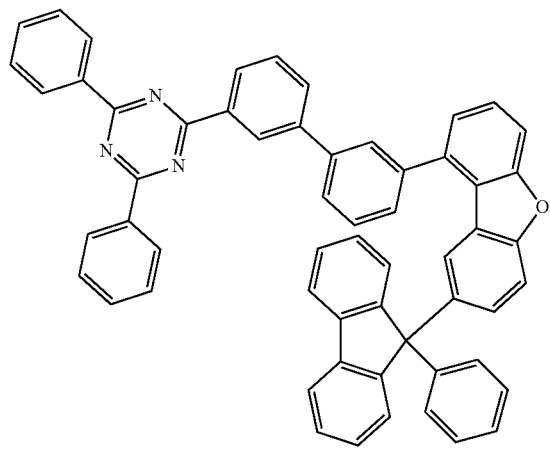
H1-88
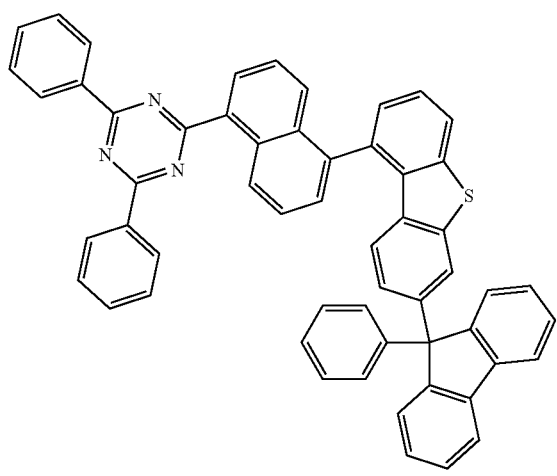
H1-89
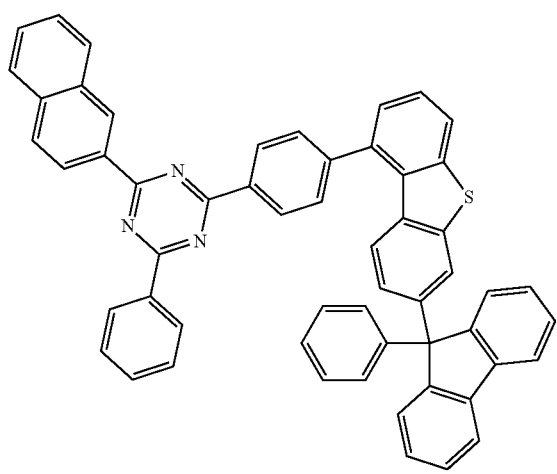
H1-90
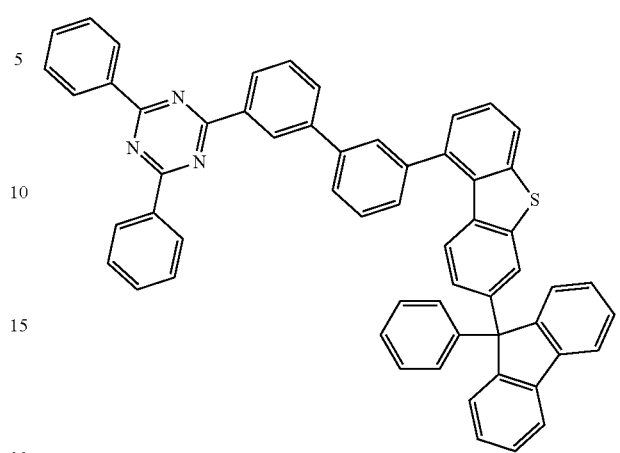
H1-91
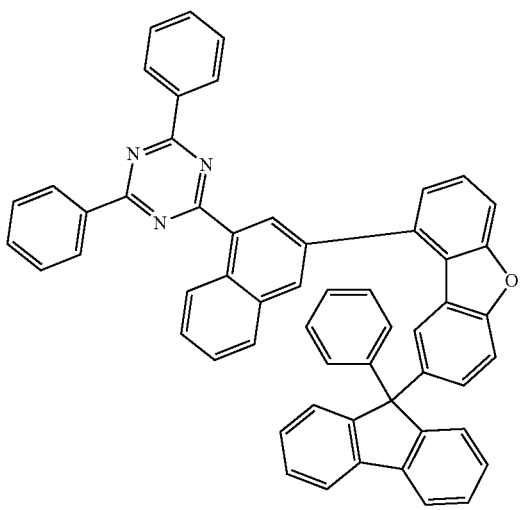
H1-92
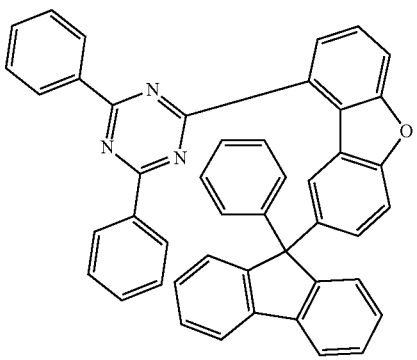

H1-93
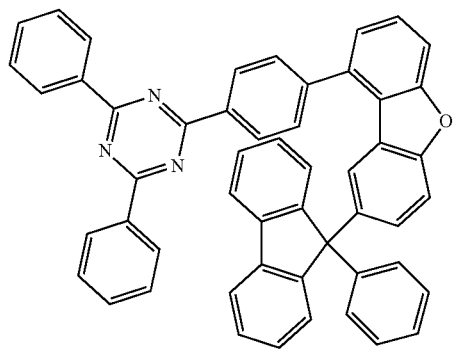
H1-94
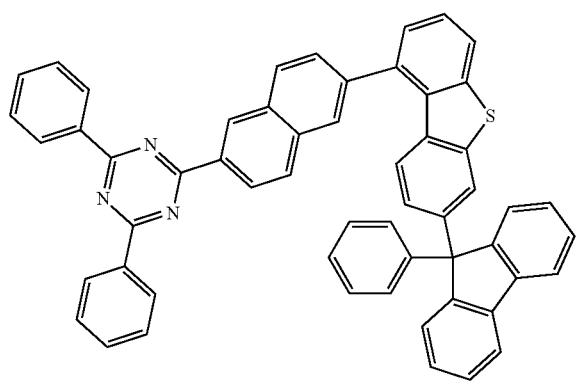
H1-95
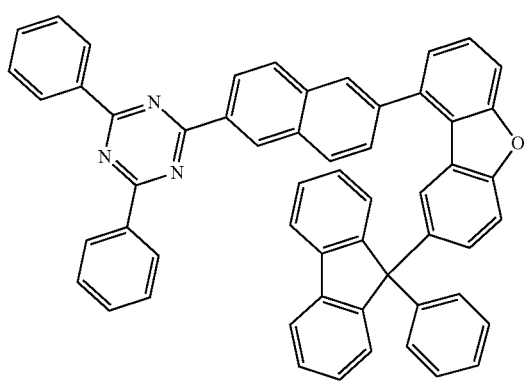
H1-96
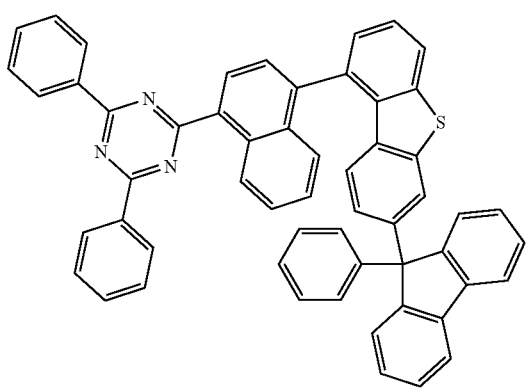
H1-97
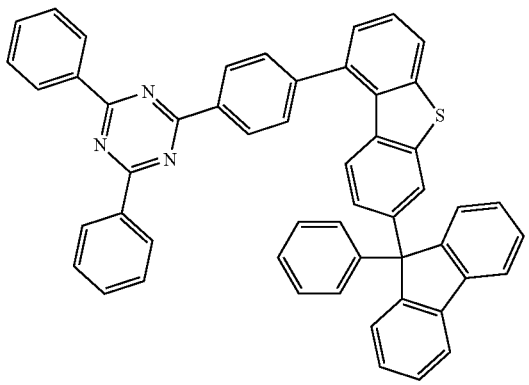
H1-98
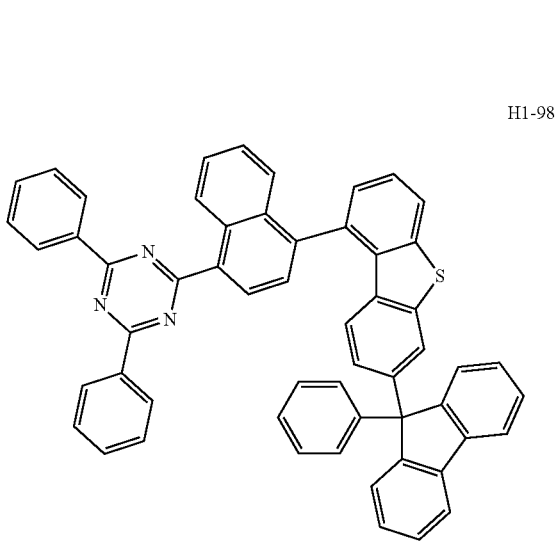
H1-99
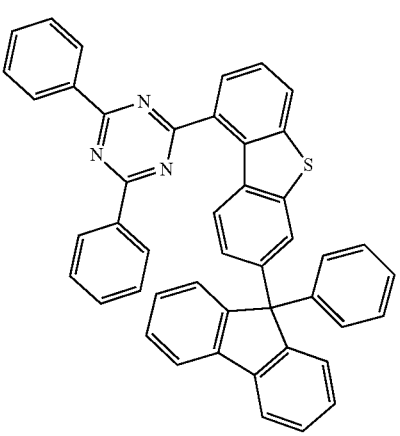

H1-100
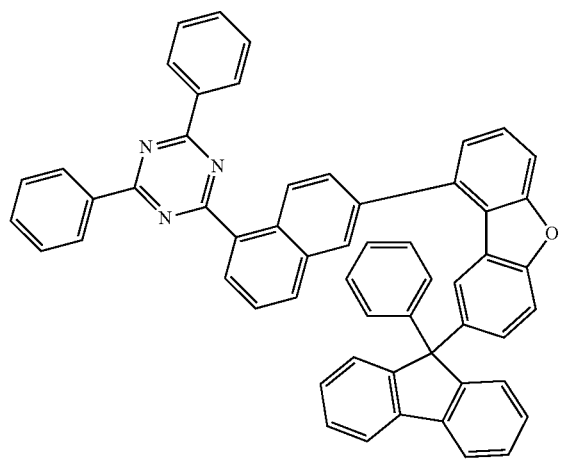
H1-115
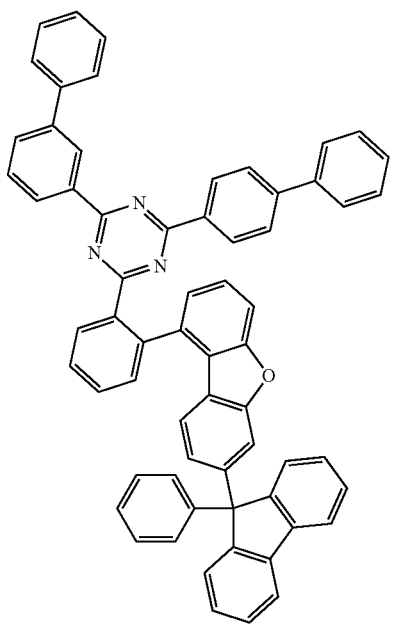
H1-127
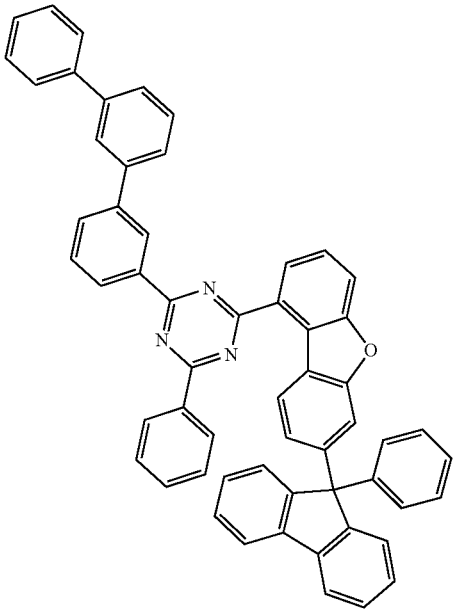
H1-128
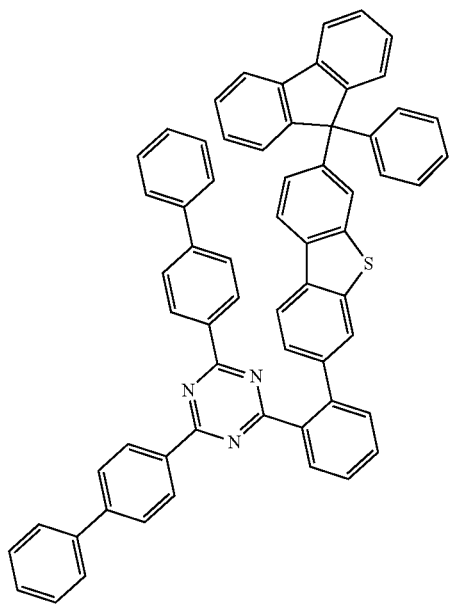

H1-129
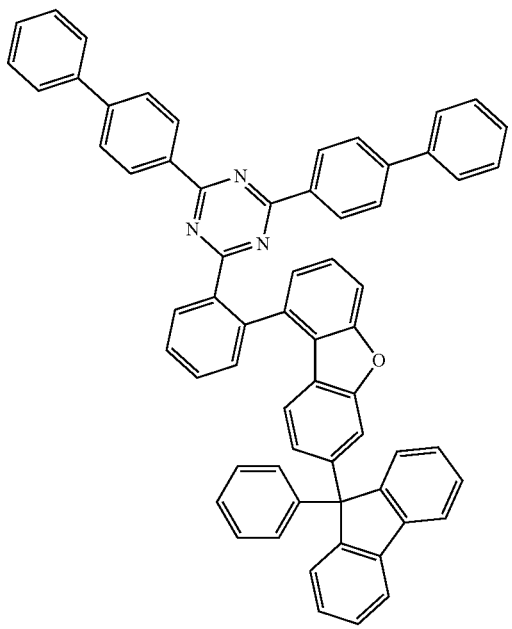
H1-141
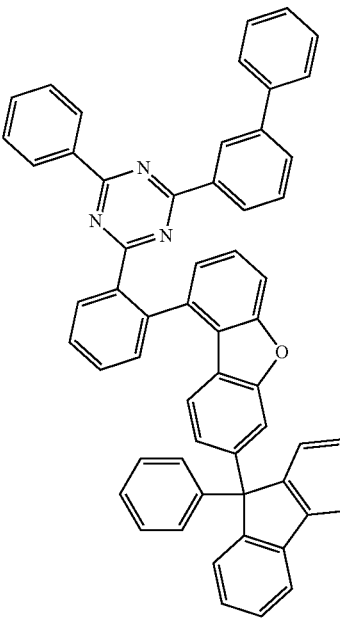
H1-133
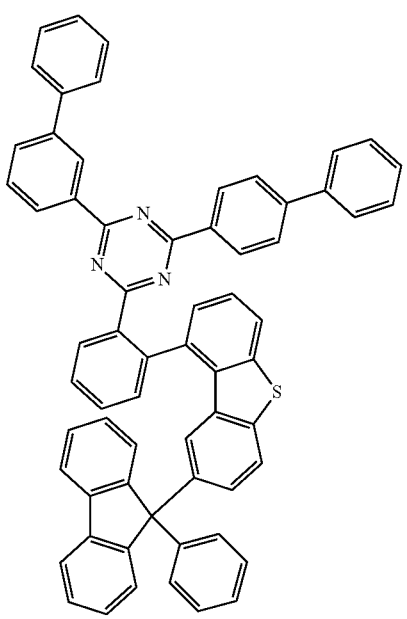
H1-145
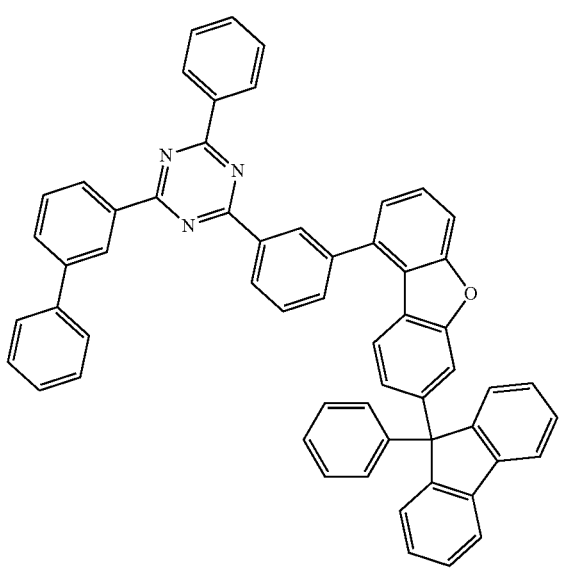

H1-146
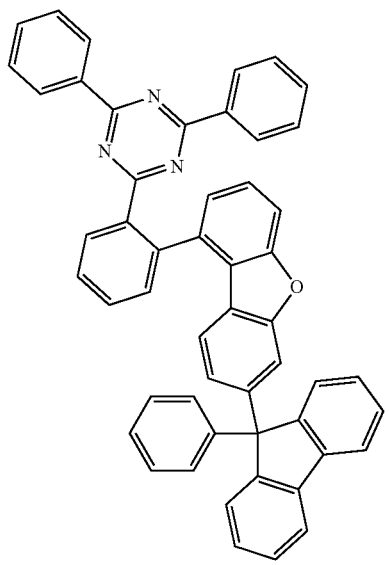
H1-147
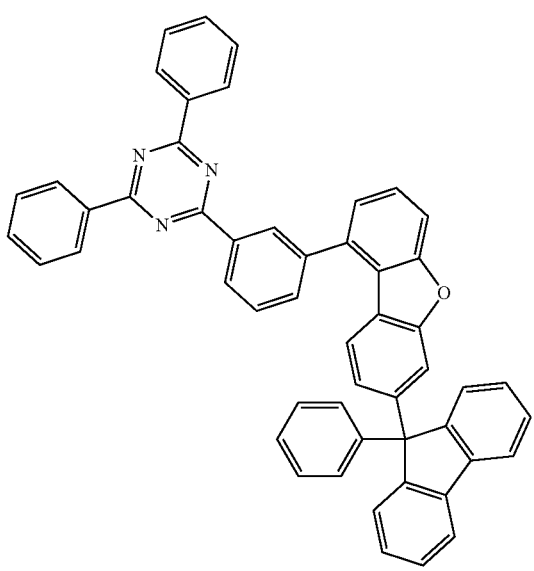
H1-148
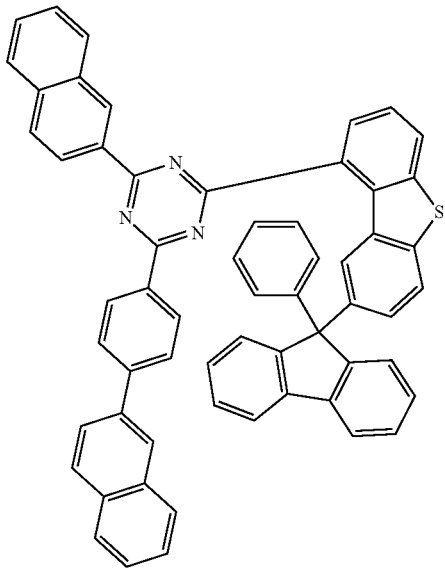
H1-149
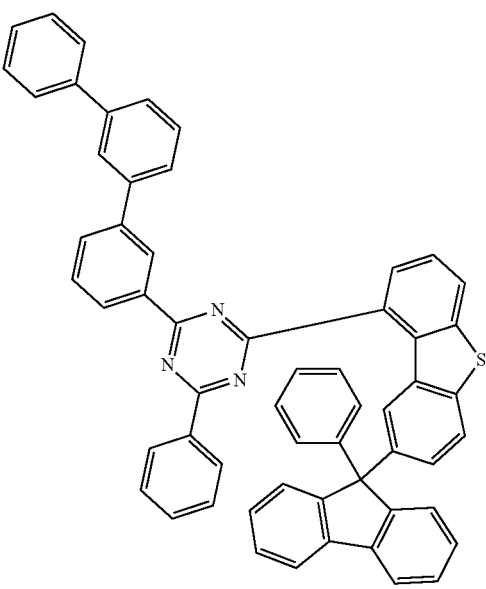

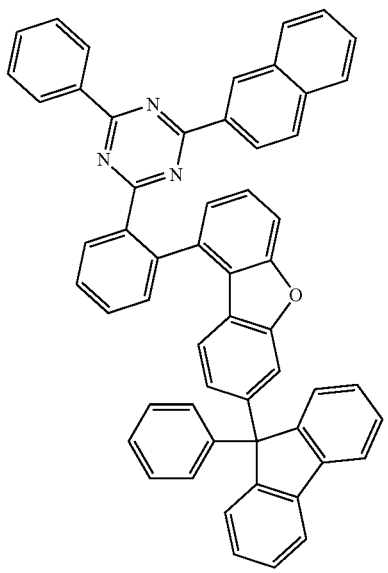
H1-150
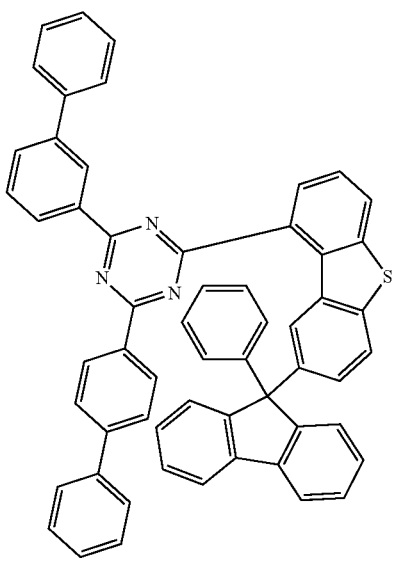
H1-159
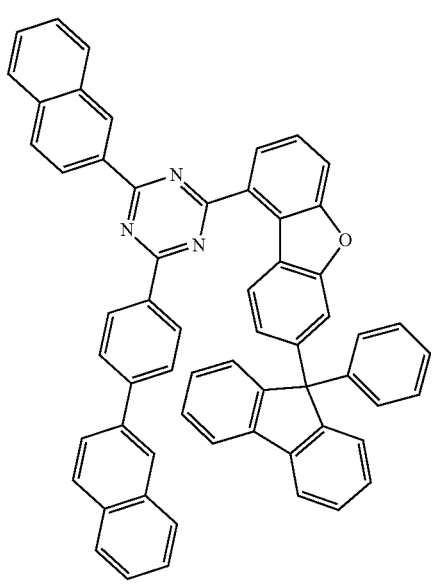
H1-151
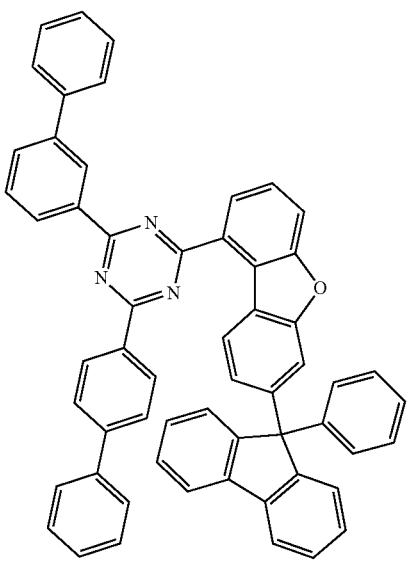
H1-160

-continued
H1-162
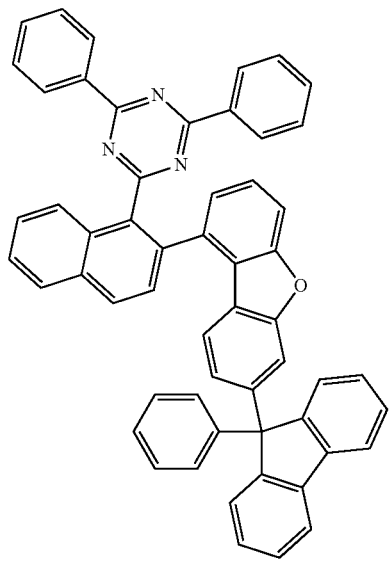
H1-164
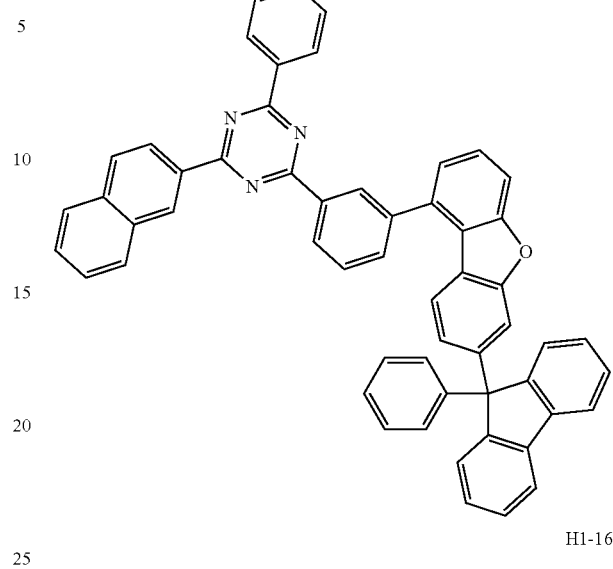
H1-165
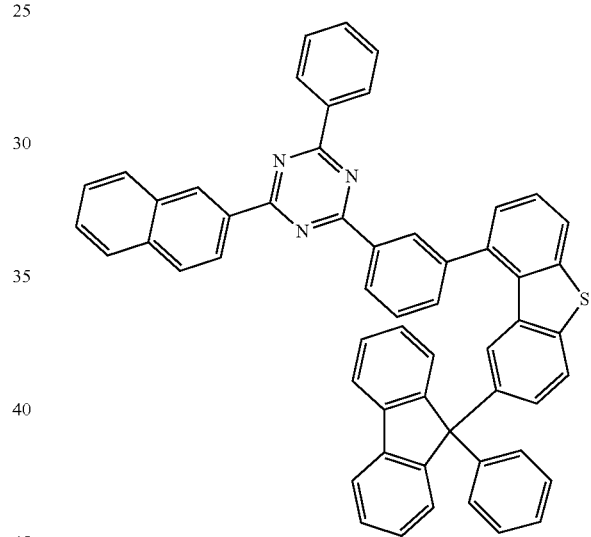
H1-163
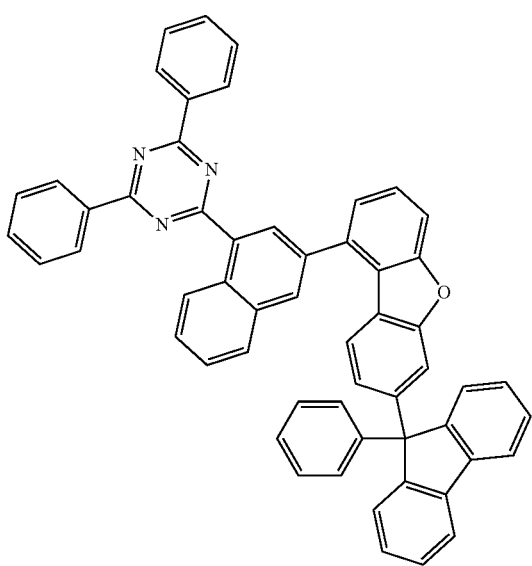
H1-166
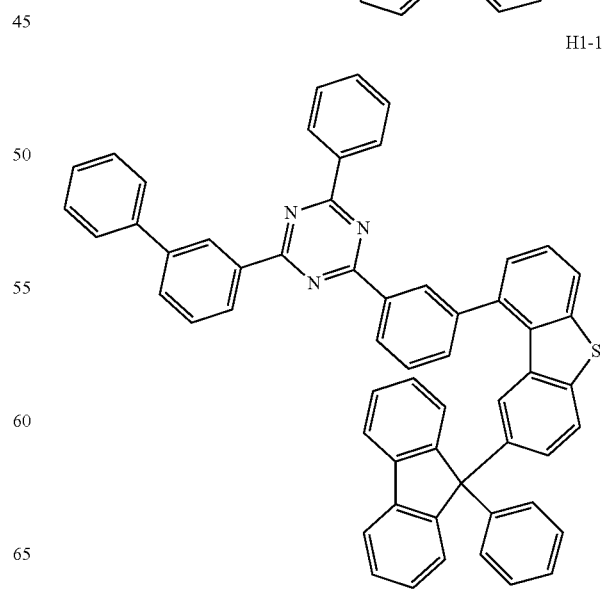

H1-167
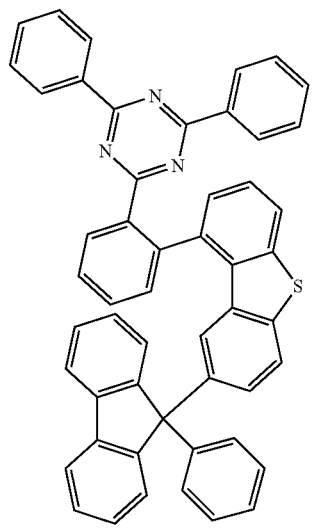
H1-168
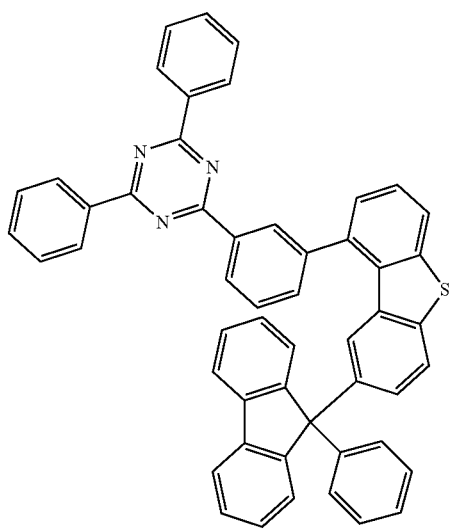
H1-170
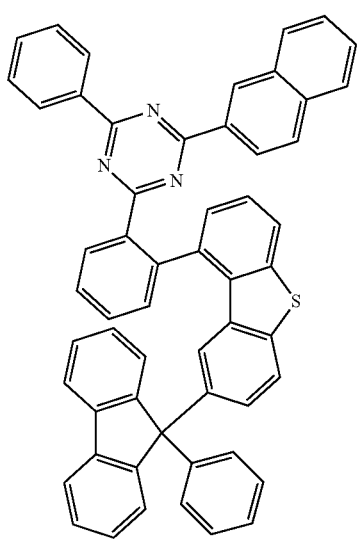
H1-171
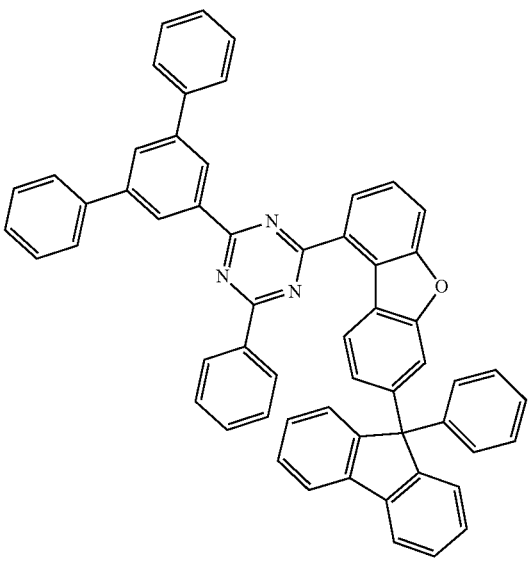
H1-172
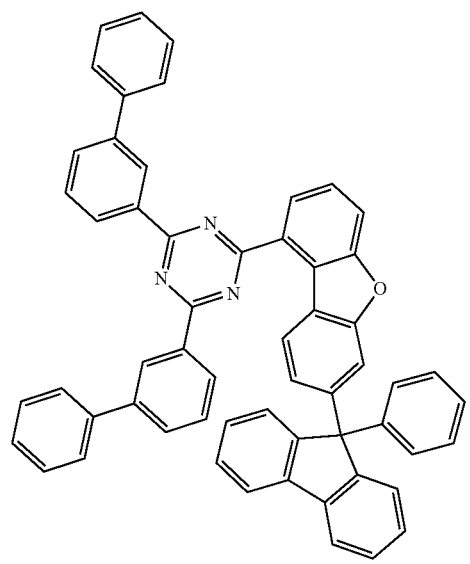

H1-173
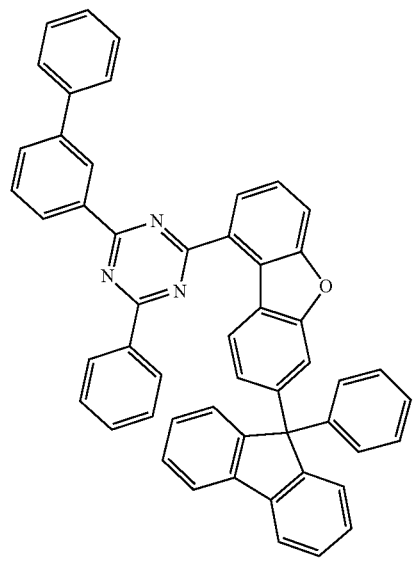
H1-175
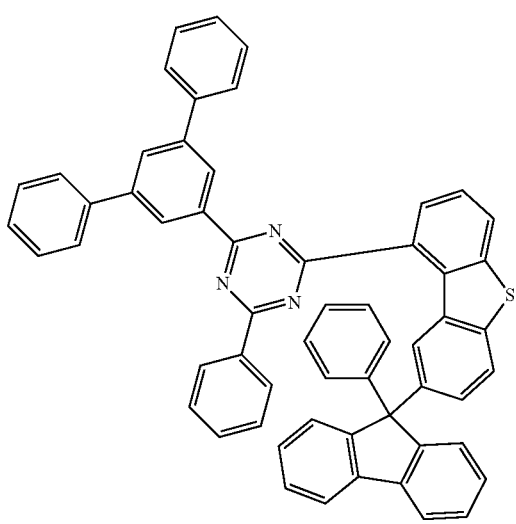
H1-176
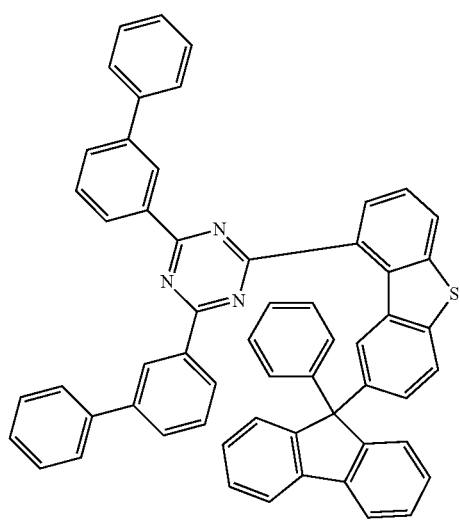
H1-177
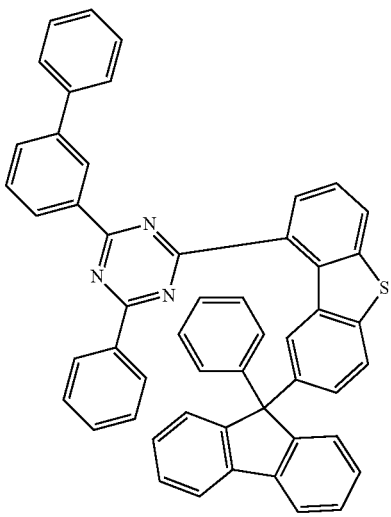
H1-179
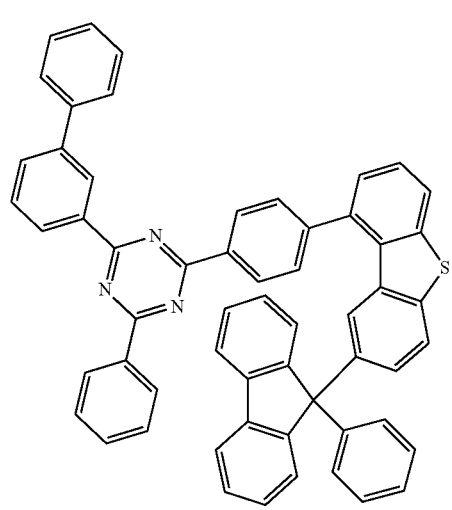
H1-180
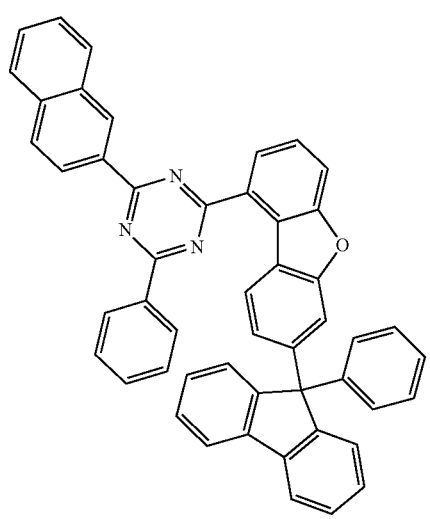

-continued
H1-181
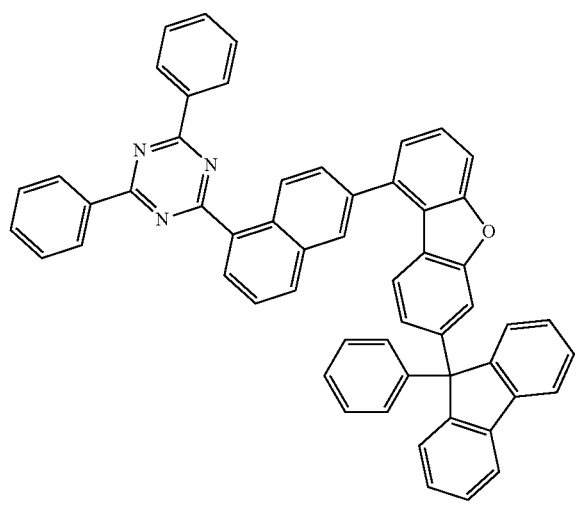
H1-182
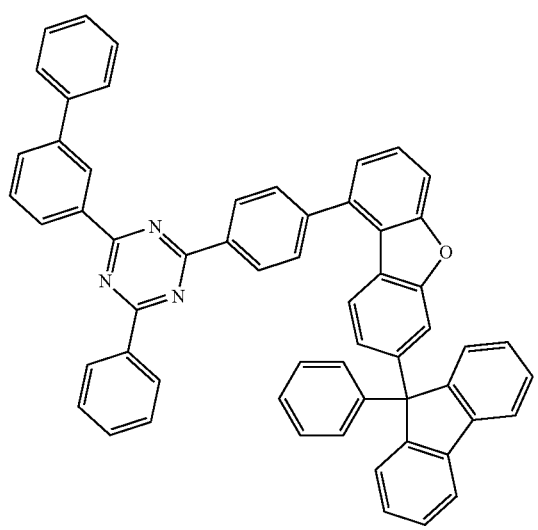
H1-183
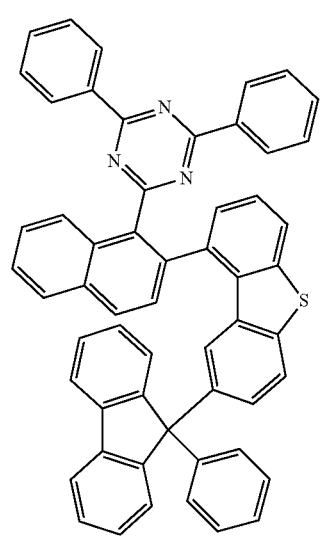
-continued
H1-184
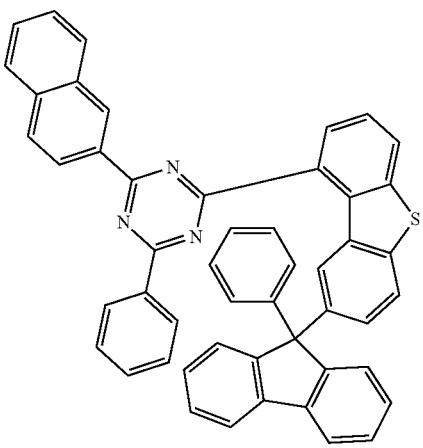
H1-186
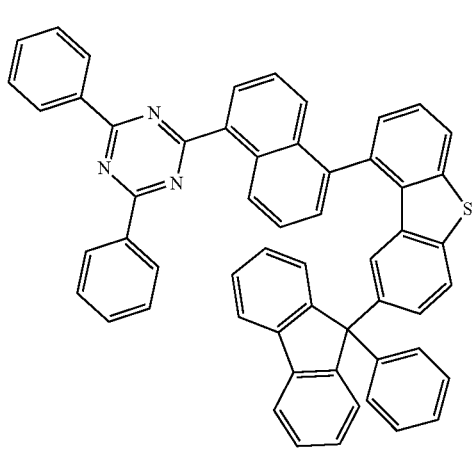
H1-187
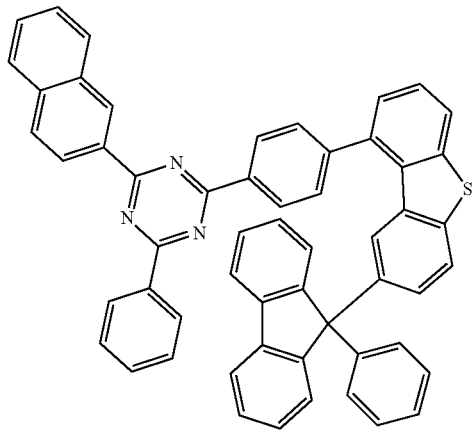

H1-188
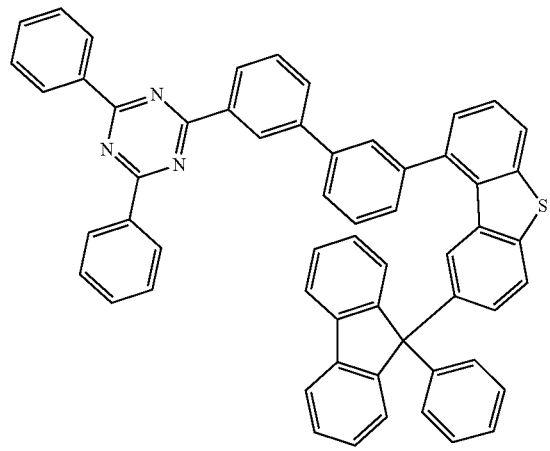
H1-189
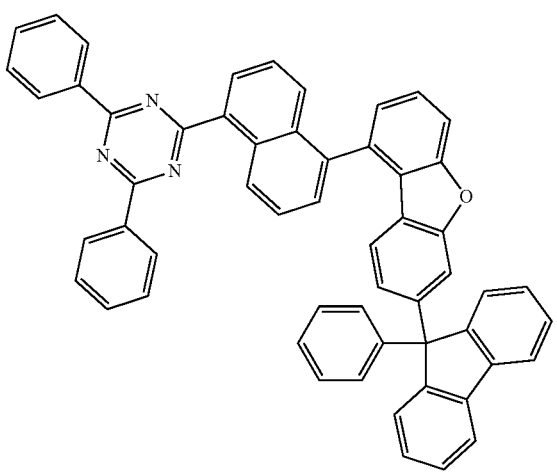
H1-190
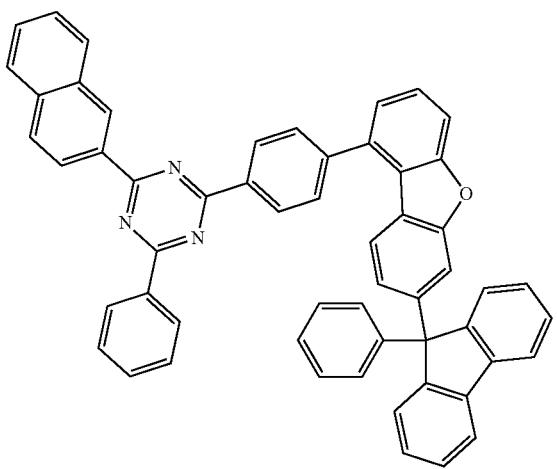
H1-191
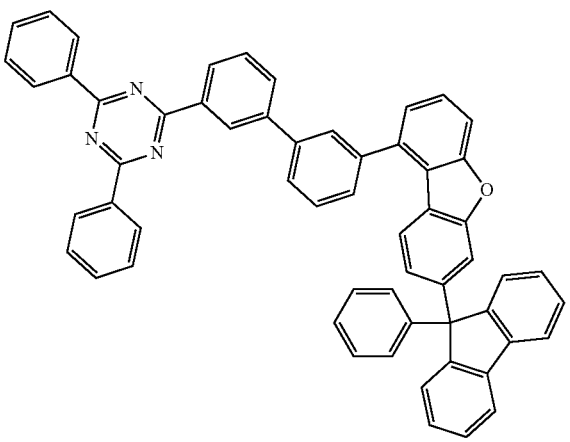
H1-192
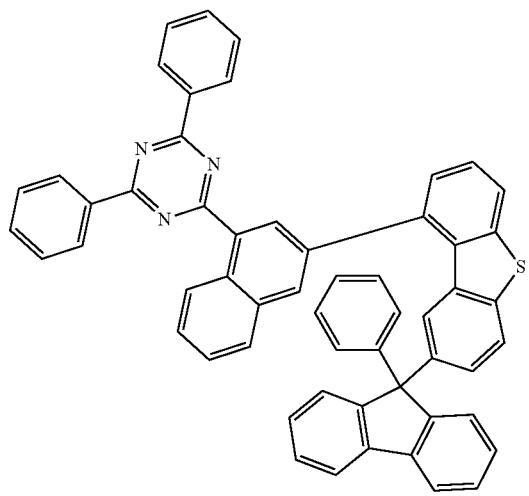
H1-193
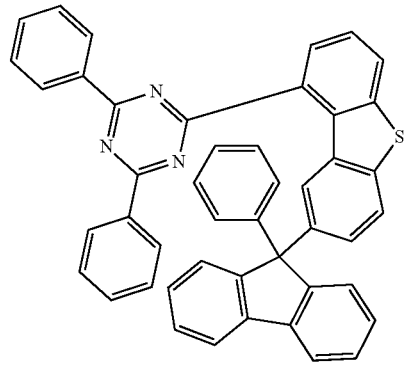

H1-194
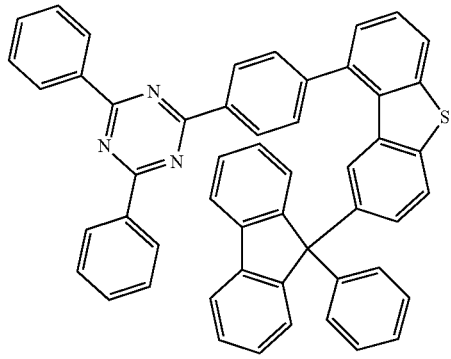
H1-195
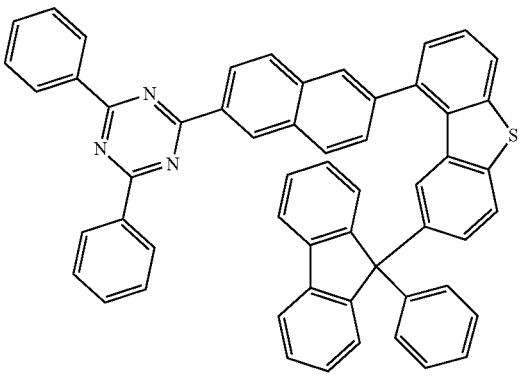
H1-196
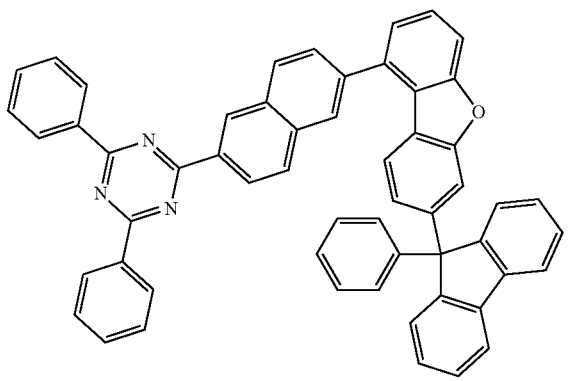
H1-197
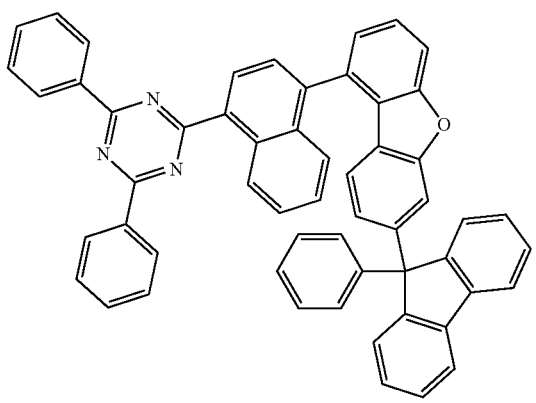
H1-198
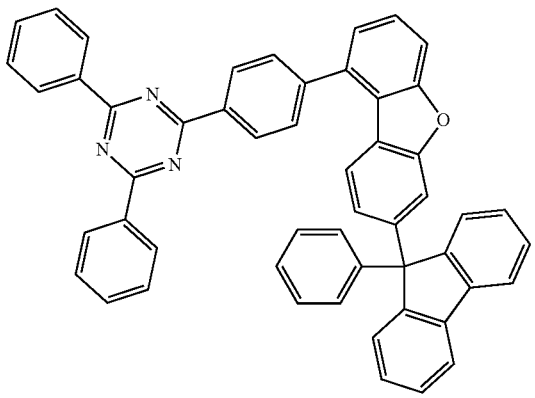
H1-199
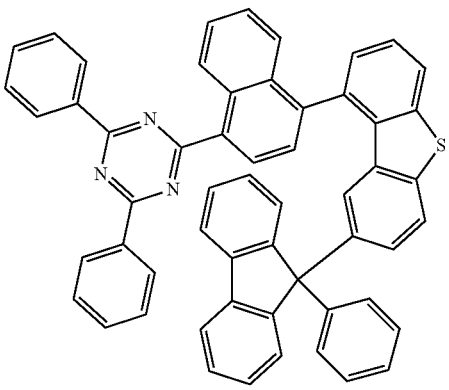
H1-200
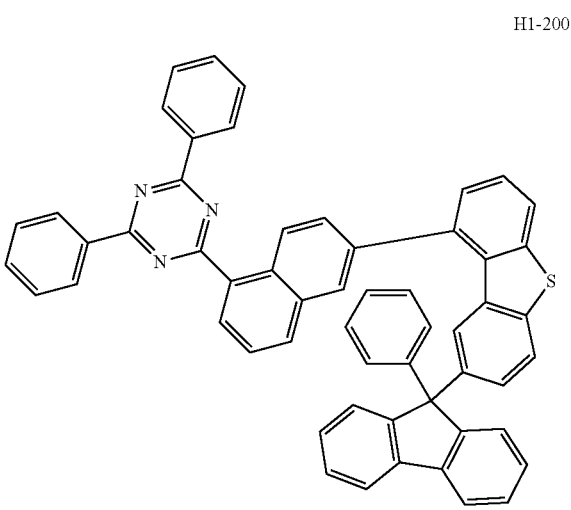

H1-243
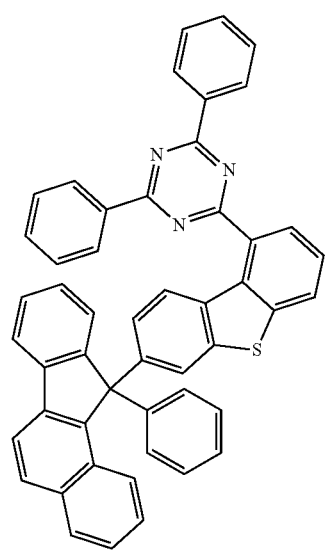
H1-244
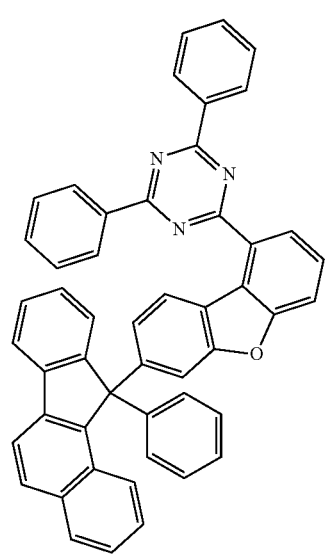
H1-257
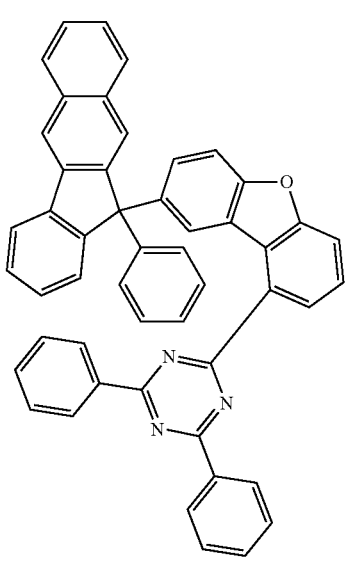
H1-258
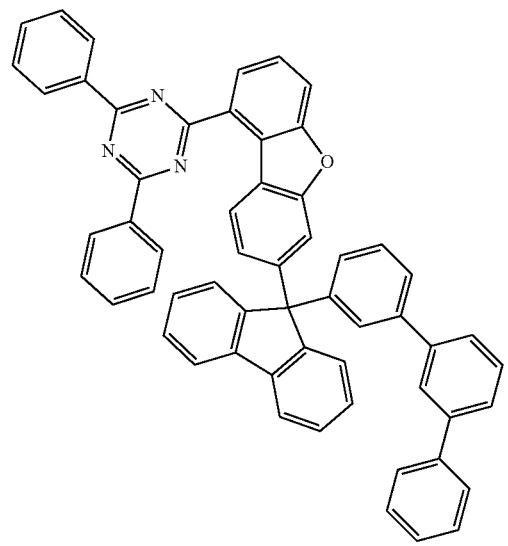
H1-264
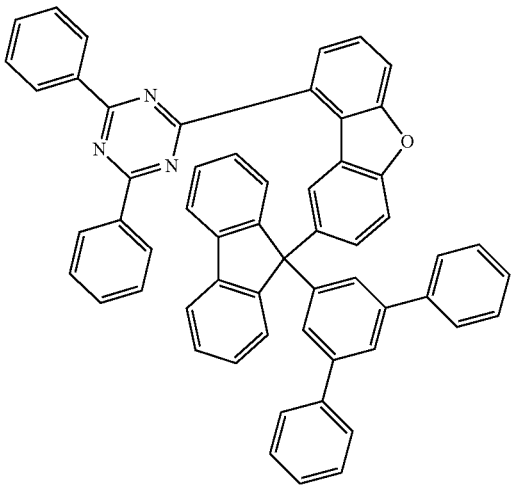
H1-270
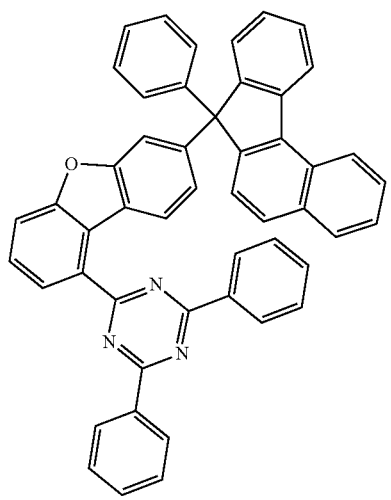

H1-277
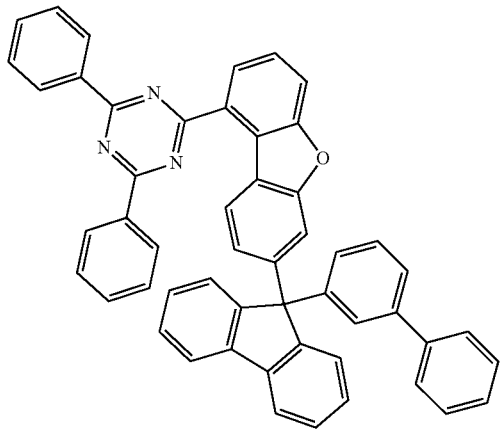
H1-279
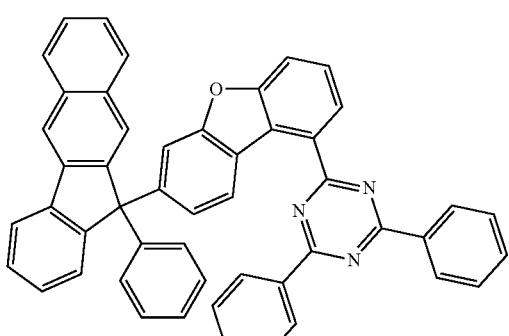
H1-281
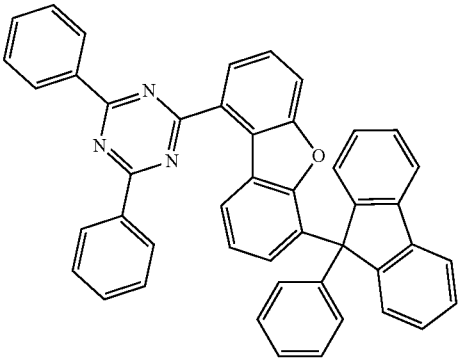
H1-284
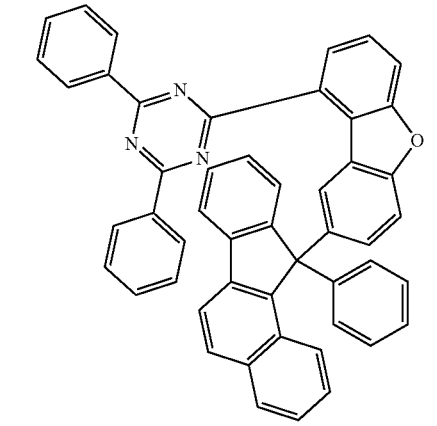
H1-285
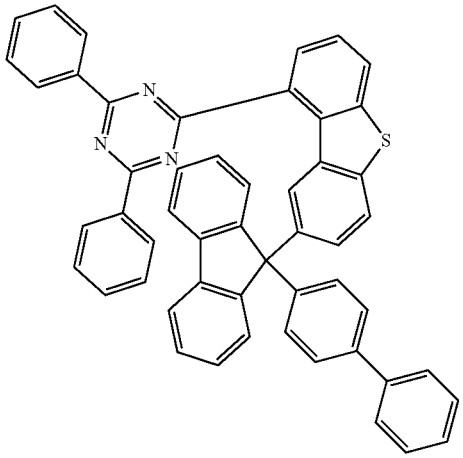
H1-286
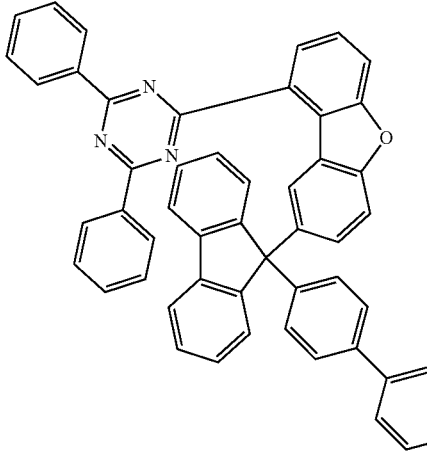
H1-288
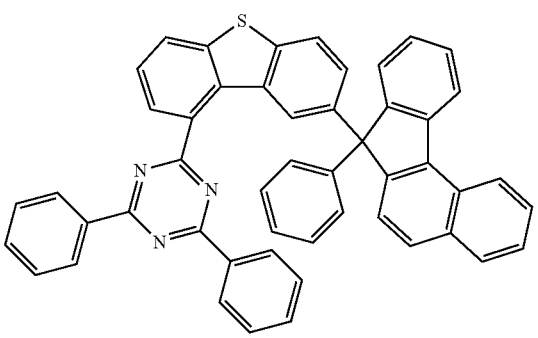
H1-289
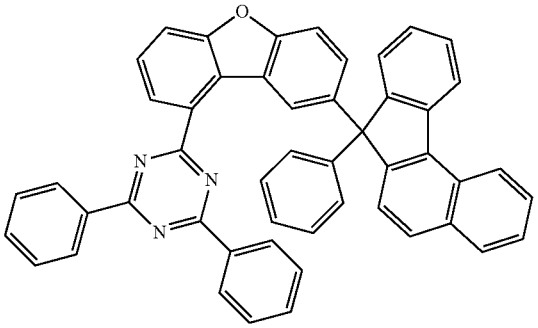

H1-290
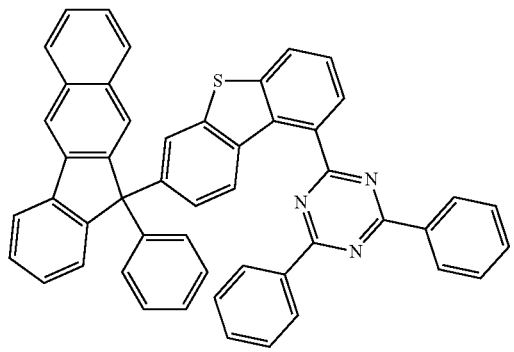
H1-291
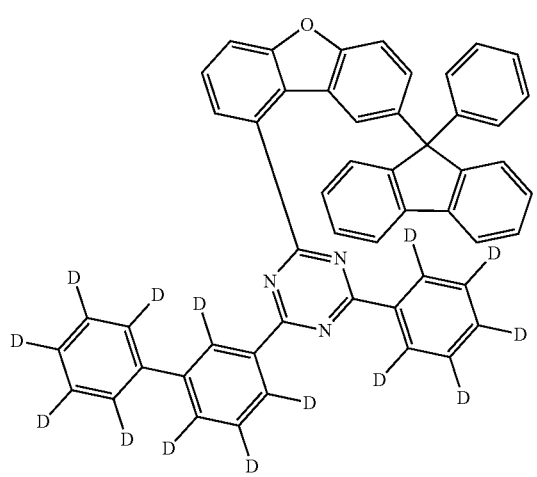
H1-292
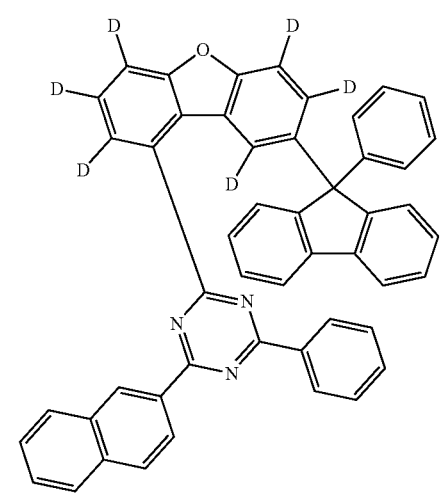
H2-293
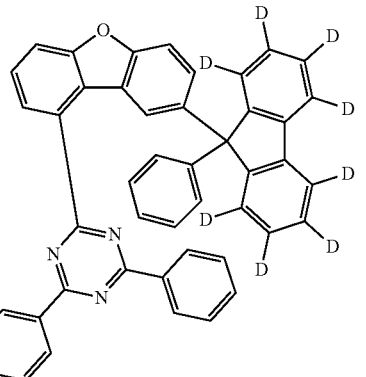
and
H1-294
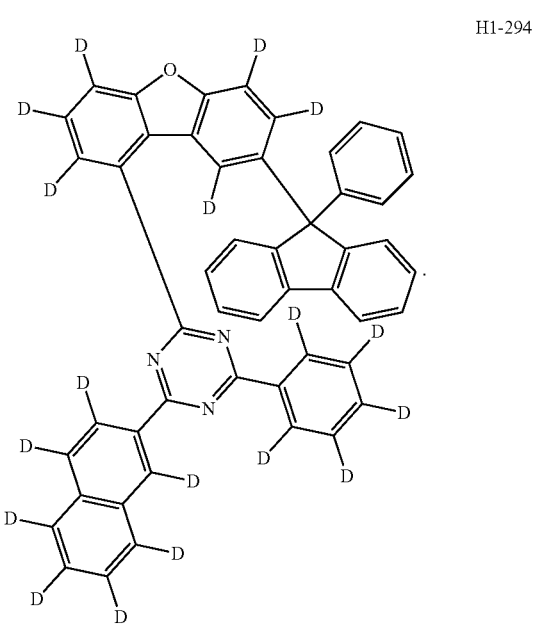 [SMILES: [2H]c1c([2H])c([2H])c(-c2nc(-c3c([2H])c([2H])c4c([2H])c([2H])c([2H])c([2H])c4c3[2H])nc(-c3c([2H])c([2H])c([2H])c4oc5c([2H])c([2H])c(C6(c7ccccc7)c7ccccc7-c7ccccc76)c([2H])c5c34)n2)c([2H])c1[2H]]
9. An organic electroluminescent material comprising an organic electroluminescent compound according to claim 7.
10. An organic electroluminescent device comprising an organic electroluminescent material according to claim 9.
* * * * *

UNITED STATES PATENT AND TRADEMARK OFFICE
CERTIFICATE OF CORRECTION

| | | |
|---|---|---|
| PATENT NO. | : 12,378,228 B2 | Page 1 of 1 |
| APPLICATION NO. | : 17/318973 | |
| DATED | : August 5, 2025 | |
| INVENTOR(S) | : Ji-Song Jun et al. | |

It is certified that error appears in the above-identified patent and that said Letters Patent is hereby corrected as shown below:

In the Claims

In Claim 4, the compound H1-116, represented by the formula 1-1 to 1-4, has inadvertent printing error. The compound appearing from Column 287, Line 1 to Line 27, requiring deletion is:

H1-116

"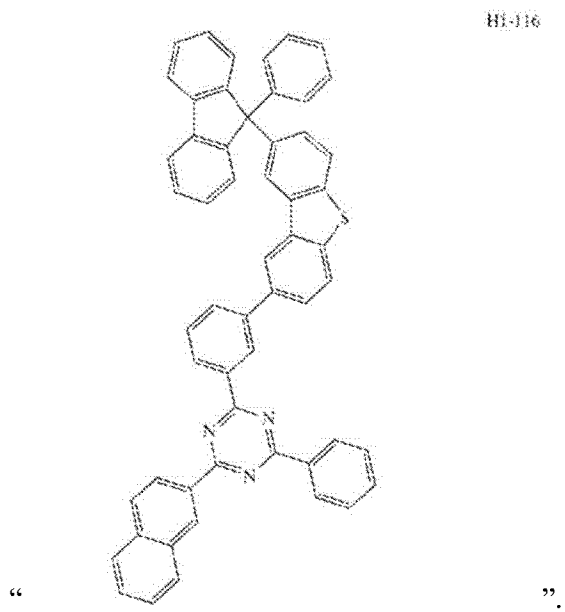".

Signed and Sealed this
Twenty-third Day of September, 2025

John A. Squires
*Director of the United States Patent and Trademark Office*